United States Patent
Kim et al.

(10) Patent No.: US 11,441,135 B2
(45) Date of Patent: Sep. 13, 2022

(54) TARGET-SPECIFIC CRISPR MUTANT

(71) Applicant: TOOLGEN INCORPORATED, Seoul (KR)

(72) Inventors: Young-Hoon Kim, Seoul (KR); Min Hee Jung, Seoul (KR); Joonsun Lee, Gangwon-Do (KR); Eunji Shin, Gyeonggi-do (KR); Kang In Lee, Seoul (KR); Seokjoong Kim, Seoul (KR); Jeongjoon Lee, Gyeonggi-do (KR)

(73) Assignee: TOOLGEN INCORPORATED, Seoul (KR)

(*) Notice: Subject to any disclaimer, the term of this patent is extended or adjusted under 35 U.S.C. 154(b) by 10 days.

(21) Appl. No.: 16/628,199

(22) PCT Filed: Jul. 6, 2018

(86) PCT No.: PCT/KR2018/007731
§ 371 (c)(1),
(2) Date: Jan. 2, 2020

(87) PCT Pub. No.: WO2019/009682
PCT Pub. Date: Jan. 10, 2019

(65) Prior Publication Data
US 2020/0149022 A1    May 14, 2020

Related U.S. Application Data

(60) Provisional application No. 62/529,601, filed on Jul. 7, 2017, provisional application No. 62/608,722, filed on Dec. 21, 2017.

(51) Int. Cl.
*C12N 9/22* (2006.01)
*C12N 9/78* (2006.01)
*C12N 15/86* (2006.01)

(52) U.S. Cl.
CPC ............ *C12N 9/22* (2013.01); *C12N 9/78* (2013.01); *C12N 15/86* (2013.01)

(58) Field of Classification Search
CPC . C12N 9/22; C12N 9/78; C12N 15/86; C12N 2310/20; C12N 15/102; C07K 2319/09; C07K 2319/01; C07K 2319/00
See application file for complete search history.

(56) References Cited

U.S. PATENT DOCUMENTS

| | | | |
|---|---|---|---|
| 10,494,620 B2 | 12/2019 | Doudna et al. | |
| 11,008,555 B2 | 5/2021 | Oakes et al. | |
| 2016/0312280 A1* | 10/2016 | May | A61K 47/6455 |
| 2016/0319260 A1 | 11/2016 | Joung et al. | |
| 2018/0080051 A1 | 3/2018 | Sheikh et al. | |
| 2018/0237771 A1 | 8/2018 | Kim et al. | |
| 2018/0296603 A1 | 10/2018 | Gori et al. | |
| 2019/0185860 A1 | 6/2019 | Kim et al. | |

FOREIGN PATENT DOCUMENTS

| | | |
|---|---|---|
| EP | 3 498 846 A1 | 6/2019 |
| KR | 10-2018-0031671 A | 3/2018 |
| WO | WO-2015-052231 A2 | 4/2015 |
| WO | WO-2015/089277 A1 | 6/2015 |
| WO | WO-2016-115355 A1 | 7/2016 |
| WO | WO-2016/161207 A1 | 10/2016 |
| WO | WO-2016-205613 A1 | 12/2016 |
| WO | WO-2017-040348 A1 | 3/2017 |
| WO | WO-2017/048969 A1 | 3/2017 |
| WO | WO-2018-034554 A1 | 2/2018 |

OTHER PUBLICATIONS

Goeker, M., Gen Bank accession No. PXW91788, Jun. 7, 2018.*
Sabharwal et al., Gen Bank accession No. KJQ69483, Mar. 23, 2015.*
Nishiki et al., Gen Bank accession No. BBE40087, Jul. 7, 2018.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
International Search Report from corresponding PCT Application No. PCT/KR2018/005110, dated Jan. 23, 2020.
Tycko, J., et al.; "Methods for Optimizing CRISPR-Cas9 Genome Editing Specificity", Mol Cell. Aug. 4, 2016; 63(3): 355-370.
Vakulskas, C. A., et al.; "A high-fidelity Cas9 mutant delivered as a ribonucleoprotein complex enables efficient gene editing in human haematopoietic stem and progenitor cells", Nat Med. Aug. 2018 ; 24(8): 1216-1224.
Written Opinion of the International Searching Authority from corresponding PCT Application No. PCT/KR2019/005110, dated Jan. 23, 2020.
Lee, J. K., et al.; "Directed evolution of CRISPR-Cas9 to increase its specificity", Nature Communications (2018) 9:3048, p. 1-11.
NCBI, NCBI Reference Sequence: WP_010922251.1, Oct. 7, 2015.
International Search Report from corresponding PCT Application No. PCT/KR2018/007731, dated Feb. 8, 2019.
Kim, D. et al. Nat Methods 12, 237-243, 231 p following 243 (2015).
Tsai, S.Q. et al. Nat Biotechnol 33, 187-197 (2015).
Kim, S., Kim, D., Cho, S.W., Kim, J. & Kim, J.S. Genome Res 24, 1012-1019 (2014).
Cho, S.W. et al. Genome Res 24, 132-141 (2014).
Mali, P. et al. Nat Biotechnol 31, 833-838 (2013).
Ran, F.A. et al. Cell 154, 1380-1389 (2013).

(Continued)

*Primary Examiner* — Delia M Ramirez
(74) *Attorney, Agent, or Firm* — Harness, Dickey & Pierce, P.L.C.

(57) ABSTRACT

The present invention relates to an artificially engineered CRISPR/Cas9 system. More particularly, the present invention relates to an artificially engineered CRISPR enzyme having enhanced target specificity and a use of an artificially engineered CRISPR/Cas9 system including the same enzyme in genome and/or epigenome manipulation or modification, genome targeting, genome editing, and in vitro diagnosis, etc.

6 Claims, 23 Drawing Sheets
Specification includes a Sequence Listing.

(56) References Cited

OTHER PUBLICATIONS

Fu, Y., Sander, J.D., Reyon, D., Cascio, V.M. & Joung, J.K. Nat Biotechnol 32, 279-284 (2014).
Nishimasu, H. et al. Cell 156, 935-949 (2014).
Kleinstiver, B.P. et al. Nature 529, 490-495 (2016).
Slaymaker, I.M. et al. Science 351, 84-88 (2016).
Chen, J.S. et al. Nature (2017).
Kleinstiver, B.P. et al. Nat Biotechnol 33, 1293-1298 (2015).
Kleinstiver, B.P. et al. Nature 523, 481-485 (2015).
Chen, Z. & Zhao, H. Nucleic Acids Res 33, e154 (2005).
Hsu, P.D. et al. Nat Biotechnol 31, 827-832 (2013).
McKenzie, G.J. & Craig, N.L. BMC Microbiol 6, 39 (2006).
Kulcsar, P.I. et al. Genome Biol 18, 190 (2017).
Zhang, D. et al. Genome Biol 18, 191 (2017).
Komor, A.C., Kim, Y.B., Packer, M.S., Zuris, J.A. & Liu, D.R. Nature 533, 420-424 (2016).
Kim, D., Kim, S., Park, J. & Kim, J.S. Genome Res 26, 406-415 (2016).
Geissmann, Q. PLoS One 8, e54072, (2013).
EESR from corresponding European Patent Application No. 18829020.9, dated Feb. 26, 2021.
Office Action from corresponding Japanese Patent Application No. 2020-500033, dated May 11, 2021.
Written Opinion of the International Searching Authority from corresponding PCT Application No. PCT/KR2018/007731, dated Feb. 8, 2019.
Office Action from corresponding Australian Patent Application No. 2018295992, dated Apr. 7, 2021.
Notice of Allowance from corresponding Australian Patent Application No. 2018295992, dated Oct. 9, 2021.
Office Action from corresponding Japanese Patent Application No. 2020-500033, dated Jan. 26, 2022.
Lee, J. K., et al.; "Directed evolution of CRISPR-Cas9 to increase its specificity", Nat. Commun., 2018, vol. 9, No. 3048, pp. 1-10.
Liu, H.., et al.; "Blossom of CRISPR technologies and applications in disease treatment", Synth. Syst. Biotechnol., 2018, vol. 3, pp. 217-228.
Office Action from corresponding Japanese Patent Application No. 2020-500033, dated Apr. 26, 2021.
Extended European Search Report from corresponding European Patent Application No. 18829020.9, dated Feb. 26, 2021.

* cited by examiner

TARGET-SPECIFIC CRISPR MUTANT

CROSS REFERENCE TO RELATED APPLICATIONS

This application is a national phase application of PCT Application No. PCT/KR2018/007731, filed on Jul. 6, 2018, which claims priority to U.S. Patent Application Nos. 62/529,601, filed on Jul. 7, 2017 and 62/608,722, filed on Dec. 21, 2017. The entire disclosures of the applications identified in this paragraph are incorporated herein by references.

FIELD

The present invention relates to an artificially engineered CRISPR/Cas9 system. More particularly, the present invention relates to an artificially engineered CRISPR enzyme having improved target specificity, and a use for genome and/or epigenome manipulation or modification, genome targeting, genome editing and in vitro diagnostics, etc. using an artificially engineered CRISPR/Cas9 system including the CRISPR enzyme.

BACKGROUND

The CRISPR-Cas system consists of a guide RNA (gRNA) having a complementary sequence to a target gene or nucleic acid and a CRISPR enzyme which is a nuclease that can cleave a target gene or nucleic acid, wherein the gRNA and the CRISPR enzyme form a CRISPR complex, and the target gene or nucleic acid is cleaved or modified by the formed CRISPR complex.

However, as well as the effect of modifying a target gene or nucleic acid, the modification of an undesired non-target gene or nucleic acid has not been solved yet. The non-target gene or nucleic acid is a gene site having a partially complementary sequence with gRNA and can form partially complementary bonds with the gRNA, wherein due to the partial complementary binding, the CRISPR complex can cleave or modify a corresponding gene site, which is a non-target gene or nucleic acid which is not subjected to modification.

Therefore, to increase efficiency of specifically modifying a target gene or nucleic acid using the CRISPR-Cas system, or to solve a problem such as genetic binding which can cause the modification of a non-target gene or nucleic acid, it is important to increase the target specificity of the CRISPR-Cas system. To increase the target specificity of the CRISPR-Cas system, a variety of research on selection of gRNA with a low amount of non-target gene candidates and adjustment of activity and/or specificity of the CRISPR enzyme has been tried.

PRIOR ART DOCUMENT

Non-Patent Document (Non-patent document 0001) Kim, D. et al. Nat Methods 12, 237-243, 231 p following 243 (2015)
(Non-patent document 0002) Tsai, S. Q. et al. Nat Biotechnol 33, 187-197 (2015)
(Non-patent document 0003) Kim, S., Kim, D., Cho, S. W., Kim, J. & Kim, J. S. Genome Res 24, 1012-1019 (2014)
(Non-patent document 0004) Cho, S. W. et al. Genome Res 24, 132-141 (2014)
(Non-patent document 0005) Mali, P. et al. Nat Biotechnol 31, 833-838 (2013)
(Non-patent document 0006) Ran, F. A. et al. Cell 154, 1380-1389 (2013)
(Non-patent document 0007) Fu, Y., Sander, J. D., Reyon, D., Cascio, V. M. & Joung, J. K. Nat Biotechnol 32, 279-284 (2014)
(Non-patent document 0008) Nishimasu, H. et al. Cell 156, 935-949 (2014)
(Non-patent document 0009) Kleinstiver, B. P. et al. Nature 529, 490-495 (2016)
(Non-patent document 0010) Slaymaker, I. M. et al. Science 351, 84-88 (2016)
(Non-patent document 0011) Chen, J. S. et al. Nature (2017)
(Non-patent document 0012) Kleinstiver, B. P. et al. Nat Biotechnol 33, 1293-1298 (2015)
(Non-patent document 0013) Kleinstiver, B. P. et al. Nature 523, 481-485 (2015)
(Non-patent document 0014) Chen, Z. & Zhao, H. Nucleic Acids Res 33, e154 (2005)
(Non-patent document 0015) Hsu, P. D. et al. Nat Biotechnol 31, 827-832 (2013)
(Non-patent document 0016) McKenzie, G. J. & Craig, N. L. BMC Microbiol 6, 39 (2006)
(Non-patent document 0017) Kulcsar, P. I. et al. Genome Biol 18, 190 (2017)
(Non-patent document 0018) Zhang, D. et al. Genome Biol 18, 191 (2017)
(Non-patent document 0019) Komor, A. C., Kim, Y. B., Packer, M. S., Zuris, J. A. & Liu, D. R. Nature 533, 420-424 (2016)
(Non-patent document 0020) Kim, D., Kim, S., Park, J. & Kim, J. S. Genome Res 26, 406-415 (2016)
(Non-patent document 0021) Geissmann, Q. PLoS One 8, e54072

SUMMARY

Technical Problem

In one aspect, the present invention is directed to providing an artificially engineered CRISPR enzyme having improved target specificity.

Technical Solution

To solve the problem, the present invention relates to an artificially engineered CRISPR enzyme. More particularly, the present invention relates to a Cas9 having improved target specificity for a target gene or nucleic acid and a CRISPR/Cas9 system using the same.

The present invention provides an artificially engineered CRISPR enzyme for a specific purpose.

In one aspect, the artificially engineered CRISPR enzyme may be a SpCas9 variant (mutant) with improved target specificity comprising an artificial manipulation, wherein the artificial manipulation may comprise an artificial manipulation (modification) of one or more amino acids present in one or more regions selected from a first region, a second region, a third region and a fourth region of a wild-type *Streptococcus pyogenes* Cas9 (SpCas9).

The first region of the wild-type SpCas9 may be one or more parts selected from the group consisting of a part of the wild-type SpCas9 interacting with a gRNA, a part of the wild-type SpCas9 interacting with a target sequence, a part of the wild-type SpCas9 interacting with a gRNA-target sequence heteroduplex, and a part of the wild-type SpCas9 interacting with PAM (Protospacer adjacent motif) distal end of the gRNA-target sequence heteroduplex.

Here, the PAM distal end of the gRNA-target sequence heteroduplex may be 6 to 10 base pairs at the end of the gRNA-target sequence heteroduplex far from the PAM location.

Here, the PAM may be 5'-NGG-3'.

The second region of the wild-type SpCas9 may be a part of the wild-type SpCas9 performing a function of cleaving a nucleic acid.

The third region of the wild-type SpCas9 may be a part of the wild-type SpCas9 performing a function of cleaving a nucleic acid.

The fourth region of the wild-type SpCas9 may be one or more parts selected from the group consisting of a part of the wild-type SpCas9 recognizing or interacting with a PAM sequence in a target gene or nucleic acid, and a part of the wild-type SpCas9 interacting with a part of a nucleotide sequence of a gRNA.

The first region of the wild-type SpCas9 may be one or more regions selected from the group consisting of a region located in a REC lobe of the wild-type SpCas9, a whole REC domain of the wild-type SpCas9, and a part of a REC domain of the wild-type SpCas9.

The second region of the wild-type SpCas9 may be one or more regions selected from the group consisting of a region located in a NUC lobe of the wild-type SpCas9, a whole RuvC domain of the wild-type SpCas9, a part of a RuvC domain of the wild-type SpCas9, and a part including a metal dependent nucleic acid cleaving region of a RuvC domain of the wild-type SpCas9.

Here, the metal dependent nucleic acid cleaving region of the RuvC domain may be a region capable of cleaving a binding between nucleic acids at target location by interacting with a metal in the RuvC domain.

The third region of the wild-type SpCas9 may be one or more regions selected from the group consisting of a region located in a NUC lobe of the wild-type SpCas9, a whole HNH domain of the wild-type SpCas9, a part of a HNH domain of the wild-type SpCas9, and a part including a metal dependent nucleic acid cleaving region of a HNH domain of the wild-type SpCas9.

Here, the metal dependent nucleic acid cleaving region of the HNH domain may be a region capable of cleaving a binding between nucleic acids at target location by interacting with a metal in the HNH domain.

The fourth region of the wild-type SpCas9 may be one or more regions selected from the group consisting of a region located in a NUC lobe of the wild-type SpCas9, a whole PI domain of the wild-type SpCas9, and a part of a PI domain of the wild-type SpCas9.

The first region may comprise one or more regions selected from the group consisting of a region 1-1 composed of an amino acid sequence from phenylalanine at 196th position (F196) to isoleucine at $282^{th}$ position (I282) of the wild-type SpCas9, a region 1-2 composed of an amino acid sequence from proline at $316^{th}$ position (P316) to asparagine at 394th position (N394) of the wild-type SpCas9, a region 1-3 composed of an amino acid sequence from lysine at $510^{th}$ position (K510) to asparagine at $612^{th}$ position (N612) of the wild-type SpCas9, and a region 1-4 composed of an amino acid sequence from threonine at $678^{th}$ position (T678) to histidine at $698^{th}$ position (H698) of the wild-type SpCas9.

The first region may comprise N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9.

Here, the second region may comprise one or more regions selected from the group consisting of a region 2-1 composed of an amino acid sequence from methionine at $1^{st}$ position (M1) to threonine at $22^{th}$ position (T22) of the wild-type SpCas9, a region 2-2 composed of an amino acid sequence from proline at $731^{th}$ position (P731) to threonine at $770^{th}$ position (T770) of the wild-type SpCas9, and a region 2-3 composed of an amino acid sequence from glutamine at $926^{th}$ position (Q926) to serine at $1040^{th}$ position (S1040) of the wild-type SpCas9.

The second region may comprise I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 of the wild-type SpCas9.

Here, the third region may comprise a region 3-1 composed of an amino acid sequence from lysine at $775^{th}$ position (K775) to leucine at $900^{th}$ position (L900) of the wild-type SpCas9.

The third region may comprise K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 of the wild-type SpCas9.

Here, the fourth region may comprise a region 4-1 composed of an amino acid sequence from glutamic acid at $1099^{th}$ position (E1099) to valine at $1139^{th}$ position (V1139) of the wild-type SpCas9.

The fourth region may comprise T1102, S1106, E1108, S1116, D1117, D1125, D1127, D1135, S1136 and T1138 of the wild-type SpCas9.

In an exemplary embodiment, the one or more amino acids present in one or more regions selected from the first region, the second region, the third region and the fourth region of the wild-type SpCas9 may be one or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9.

In one exemplary embodiment, the one or more amino acids present in one or more regions selected from the first region, the second region, the third region and the fourth region of the wild-type SpCas9 may be one or more amino acids selected from the group consisting of A203, N277, G366, F539, I601, M763, K890, D965, F1038, T1102 and D1127 of the wild-type SpCas9.

The artificial manipulation may be a deletion of the one or more amino acids present in one or more regions selected from the first region, the second region, the third region and the fourth region of the wild-type SpCas9.

The artificial manipulation may be a substitution of the one or more amino acids present in one or more regions selected from the first region, the second region, the third region and the fourth region of the wild-type SpCas9 with a different amino acid.

Here, the different amino acid may be an amino acid having a smaller functional group than the one or more amino acids present in one or more regions selected from the first region, the second region, the third region and the fourth region of the wild-type SpCas9.

Here, the different amino acid may be an amino acid having a larger functional group than the one or more amino acids present in one or more regions selected from the first region, the second region, the third region and the fourth region of the wild-type SpCas9.

Here, the different amino acid may be an amino acid having a higher hydropathy index than the one or more amino acids present in one or more regions selected from the first region, the second region, the third region and the fourth region of the wild-type SpCas9.

Here, the different amino acid may be an amino acid having a lower hydropathy index than the one or more amino acids present in one or more regions selected from the first region, the second region, the third region and the fourth region of the wild-type SpCas9.

In one aspect, the SpCas9 variant may be a target specific SpCas9 (TS-SpCas9) variant comprising an artificial manipulation of one or more amino acids selected from the group consisting of A203, N277, G366, F539, I601, M763, K890, D965, F1038, T1102 and D1127 of the wild-type SpCas9.

The artificial manipulation may be a deletion or a substitution of one or more amino acids selected from the group consisting of A203, N277, G366, F539, I601, M763, K890, D965, F1038, T1102 and D1127 of the wild-type SpCas9 with a different amino acid.

Here, the different amino acid may be an amino acid having a larger or smaller functional group than the one or more amino acids selected from the group consisting of A203, N277, G366, F539, I601, M763, K890, D965, F1038, T1102 and D1127 of the wild-type SpCas9.

Here, the different amino acid may be an amino acid having a higher or lower hydropathy index than the one or more amino acids selected from the group consisting of A203, N277, G366, F539, I601, M763, K890, D965, F1038, T1102 and D1127 of the wild-type SpCas9.

The TS-SpCas9 variant may comprise an artificial manipulation of F539 of the wild-type SpCas9.

The TS-SpCas9 variant may comprise an artificial manipulation of M763 of the wild-type SpCas9.

The TS-SpCas9 variant may comprise an artificial manipulation of K890 of the wild-type SpCas9.

The TS-SpCas9 variant may comprise an artificial manipulation of F539/M763(F539 and M763), F539/K890 or M763/K890 of the wild-type SpCas9.

The TS-SpCas9 variant may comprise an artificial manipulation of F539, M763 and K890 of the wild-type SpCas9.

In one aspect, the artificially engineered CRISPR enzyme may be a fusion protein comprising the TS-SpCas9 variant.

The fusion protein may comprise one or more functional domains.

Here, the functional domain may be one or more domains selected from the group consisting of a domain having methylase activity, demethylase activity, transcription activation activity, transcription repression activity, transcription release factor activity, histone modification activity, RNA cleavage activity or nucleic acid binding activity, a tag for isolation and purification of a protein (including a peptide), a report gene, a NLS (nuclear localization sequence or signal), a NES (nuclear export sequence or signal), and a deaminase.

In one aspect, the artificially engineered CRISPR enzyme may be a form of a nucleic acid encoding the SpCas9 variant, the TS-SpCas9 variant and/or the fusion protein.

In one aspect, the nucleic acid may be included in a vector.

In one aspect, the nucleic acid encoding the SpCas9 variant, the TS-SpCas9 variant and/or the fusion protein; and/or the vector may be introduced in a cell.

In one aspect, a genome of a cell may be artificially manipulated using the SpCas9 variant, the TS-SpCas9 variant, and/or the fusion protein, with a gRNA.

The gRNA may be a nucleic acid comprising a nucleotide sequence complementary binding to a target sequence of a target gene present in the genome of the cell.

Advantageous Effects

According to the present invention, a CRISPR-Cas system having improved target specificity using an artificially manipulated CRISPR enzyme can be used in genome and/or epigenome manipulation or modification, genome targeting, genome editing and in vitro diagnostics.

DETAILED DESCRIPTION

Figure 1:
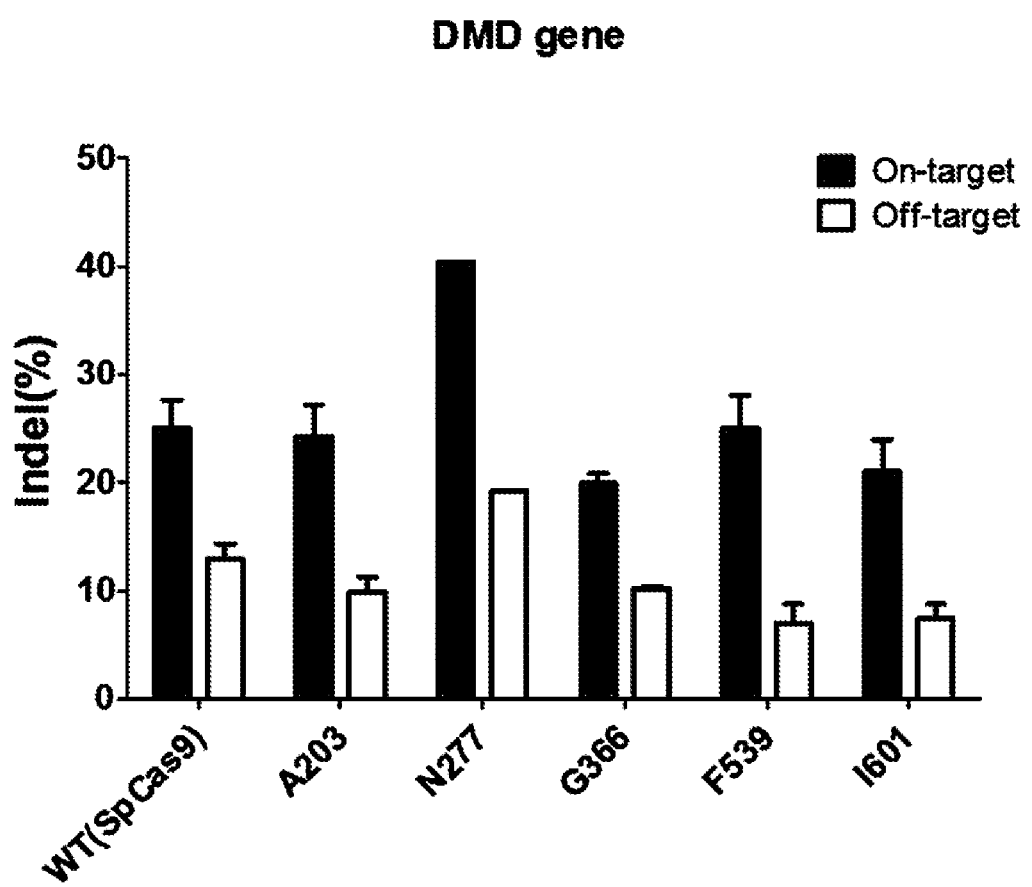
FIG. 1 is a graph showing indel (insertion and deletion) frequencies (%), which represents the manipulation effect of a target gene (DMD gene) by first region variants of SpCas9.

Unless defined otherwise, all technical and scientific terms used in the specification have the same meanings as conventionally understood by those of ordinary skill in the art to which the present invention belongs. Although methods and materials similar or identical to those described herein can be used in practice or testing of the present invention, suitable methods and materials are described below. All publications, patent applications, patents and other references mentioned herein are incorporated by reference in their entirety. In addition, the materials, methods and examples are merely illustrative, but are not intended to be limited.

One aspect of the disclosure disclosed herein relates to a CRISPR enzyme.

The "CRISPR enzyme" is a major protein component of a clustered regularly interspaced short palindromic repeats (CRISPR)-CRISPR-associated protein (Cas) system, and forms a complex with a guide RNA (gRNA), thereby forming a CRISPR-Cas system.

The "gRNA" refers to an RNA capable of specifically targeting a CRISPR complex, that is, a gRNA-CRISPR enzyme complex, with respect to a target gene or nucleic acid. The gRNA is specific RNA for a target sequence, which may bind to the CRISPR enzyme, and guide the CRISPR enzyme to the target gene or nucleic acid. Here, the "target sequence" is a nucleotide sequence present in a target gene or nucleic acid, and specifically, a partial nucleotide sequence of a target region in the target gene or nucleic acid. The "target region" used herein is a site that can be modified by a guide nucleic acid-editor protein in the target gene or nucleic acid.

The gRNA may include multiple domains. Due to each domain, interactions may occur in a strand or between strands of a three-dimensional structure or an active form of the gRNA.

The gRNA may be called single-stranded gRNA (single RNA molecule; single gRNA; sgRNA); or double-stranded gRNA (including more than one, generally, two discrete RNA molecules).

In one exemplary embodiment, the single-stranded gRNA may include a guide domain, that is, a domain including a guide sequence capable of forming a complementary bond with a target gene or nucleic acid; a first complementary domain; a linker domain; a second complementary domain which has a complementary sequence to the first complementary domain sequence and may form with the first complementary domain sequence; a proximal domain; and optionally a tail domain in the 5' to 3' direction.

In another embodiment, the double-stranded gRNA may include a first strand which includes a guide domain, that is, a domain including a guide sequence capable of forming a complementary bond with a target gene or nucleic acid, and a first complementary domain; and a second strand which includes a second complementary domain, which has a complementary sequence to the first complementary domain sequence and may form with the first complementary domain sequence, a proximal domain, and optionally a tail domain in the 5' to 3' direction.

Here, the first strand may be referred to as crRNA, and the second strand may be referred to as tracrRNA. The crRNA may include a guide domain and a first complementary domain, and the tracrRNA may include a second complementary domain, a proximal domain and optionally a tail domain.

In still another embodiment, the single-stranded gRNA may include a guide domain, that is, a domain including a guide sequence capable of forming a complementary bond with a target gene or nucleic acid; a first complementary domain; and a second complementary domain, which has a complementary sequence to the first complementary domain sequence and may form with the first complementary domain sequence, in the 5' to 3' direction.

The CRISPR enzyme is a nucleic acid or polypeptide (or a protein) having a sequence encoding the CRISPR enzyme, and representatively, a Type II CRISPR enzyme or Type V CRISPR enzyme is widely used.

The CRISPR enzyme may be a Type II CRISPR enzyme.

The Type II CRISPR enzyme may be a Cas9.

Here, the Cas9 may be derived from various microorganisms such as Streptococcus pyogenes, Streptococcus thermophilus, Streptococcus sp., Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas sp., Crocosphaera watsonii, Cyanothece sp., Microcystis aeruginosa, Synechococcus sp., Acetohalobium arabaticum, Ammonifex degensii, Caldicelulosiruptor bescil, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter sp., Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc sp., Arthrospira maxima, Arthrospira platensis, Arthrospira sp., Lyngbya sp., Microcoleus chthonoplastes, Oscillatoria sp., Petrotoga mobilis, Thermosipho africanus and Acaryochloris marina, etc.

Here, the Cas9 may be isolated from a naturally-occurring microorganism, or produced unnaturally by a recombinant method or synthetic method.

The crystal structure of the type II CRISPR enzyme was determined according to studies on two or more types of natural microbial type II CRISPR enzyme molecules (Jinek et al., Science, 343(6176):1247997, 2014) and studies on Streptococcus pyogenes Cas9 (SpCas9) complexed with gRNA (Nishimasu et al., Cell, 156:935-949, 2014; and Anders et al., Nature, 2014, doi: 10.1038/nature13579).

The type II CRISPR enzyme includes two lobes, that is, recognition (REC) and nuclease (NUC) lobes, and each lobe includes several domains.

The REC lobe includes an arginine-rich bridge helix (BH) domain, an REC1 domain and an REC2 domain.

Here, the BH domain is a long α-helix and arginine-rich region, and the REC1 domain and REC2 domain play an important role in recognizing a double strand formed in gRNA, for example, single-stranded gRNA, double-stranded gRNA or tracrRNA.

The NUC lobe includes an RuvC domain, an HNH domain and a PAM-interaction (PI) domain. Here, the RuvC domain encompasses RuvC-like domains, and the HNH domain encompasses HNH-like domains.

Here, the RuvC domain shares structural similarity with members of the microorganism family existing in nature having the type II CRISPR enzyme, and cleaves a single strand, for example, a non-complementary strand of a target gene or nucleic acid, that is, a strand not forming a complementary bond with gRNA. The RuvC domain is sometimes referred to as an RuvCI domain, RuvCII domain or RuvCIII domain in the art, and generally called an RuvC I, RuvCII or RuvCIII.

The HNH domain shares structural similarity with the HNH endonuclease, and cleaves a single strand, for example, a complementary strand of a target nucleic acid molecule, that is, a strand forming a complementary bond with gRNA. The HNH domain is located between RuvC II motif and RuvC III motif.

The PI domain recognizes a specific nucleotide sequence in a target gene or nucleic acid, that is, a protospacer adjacent motif (PAM) or interacts with PAM. Here, the PAM may vary according to the origin of the type II CRISPR enzyme. For example, when the CRISPR enzyme is SpCas9, the PAM may be 5'-NGG-3', when the CRISPR enzyme is Streptococcus thermophilus Cas9 (StCas9), the PAM may be 5'-NNAGAAW-3' (W=A or T), when the CRISPR enzyme is Staphylococcus aureus Cas9 (SaCas9), the PAM may be 5'-NNGRR-3' (R=A or G), when the CRISPR enzyme is Neisseria meningitides Cas9 (NmCas9), the PAM may be 5'-NNNNGATT-3', and when the CRISPR enzyme is Campylobacter jejuni Cas9 (CjCas9), the PAM may be 5'-NNNVRYAC-3' (V=G, C or A, R=A or G, Y=C or T), where the N may be A, T, G or C; or A, U, G or C. While it is generally understood that PAM is determined according to the origin of the above-described enzyme, according to the progression of research on mutants of the enzyme derived from the above-described origins, the PAM may vary.

The CRISPR enzyme may be a nuclease or restriction enzyme which has a function of cleaving the double strands of a target gene or nucleic acid.

The CRISPR enzyme may be a fully active CRISPR enzyme.

The "fully active" refers to having the same function as the function of a wild-type CRISPR enzyme, and the CRISPR enzyme in such a state is called a fully active CRISPR enzyme. Here, the "function of a wild-type CRISPR enzyme" refers to the state of a wild-type CRISPR enzyme having functions of cleaving the double strands of DNA, that is, a first function of cleaving the first strand of the double strands of DNA and a second function of cleaving the second strand thereof.

The fully active CRISPR enzyme may be a wild-type CRISPR enzyme that cleaves the double strands of DNA.

The fully active CRISPR enzyme may be a CRISPR enzyme variant formed by modifying or manipulating a wild-type CRISPR enzyme that cleaves the double strands of DNA.

The CRISPR enzyme variant may be an enzyme formed by substituting one or more amino acids with different amino acids, or removing one or more amino acids in the amino acid sequence of the wild-type CRISPR enzyme.

The CRISPR enzyme variant may be an enzyme produced by adding one or more amino acids to the amino acid sequence of the wild-type CRISPR enzyme. Here, the added amino acid may be located at the N-terminus or C-terminus of the wild-type enzyme, or in the amino acid sequence thereof.

The CRISPR enzyme variant may be a fully active enzyme having an improved function compared to the wild-type CRISPR enzyme.

For example, a specifically modified or engineered form of the wild-type CRISPR enzyme, that is, a CRISPR enzyme variant may cleave a double-stranded DNA in a state which does not bind to the double-stranded DNA to be cleaved or keep a constant distance thereto. In this case, the modified or engineered form may be a fully active CRISPR enzyme having an improved functional activity, compared to the wild-type CRISPR enzyme.

The CRISPR enzyme variant may be a fully active CRISPR enzyme having a reduced function compared to the wild-type CRISPR enzyme.

For example, a specifically modified or engineered form of the wild-type CRISPR enzyme, that is, a CRISPR enzyme variant may cleave a double-stranded DNA in a state which is closing to a certain distance from or is forming a specific binding to the double-stranded DNA to be cleaved. Here, the specific binding may be, for example, a bond between an amino acid at a specific site of the CRISPR enzyme variant and a DNA nucleotide sequence at a cleavage site. In this case, the modified or engineered form may be a fully active CRISPR enzyme having a reduced functional activity, compared to the wild-type CRISPR enzyme.

The CRISPR enzyme may be an incomplete or partially-active CRISPR enzyme.

The "incomplete or partially active" means a state having one selected from functions of the wild-type CRISPR enzyme, that is, a first function of cleaving the first strand of the double strands of DNA and a second function of cleaving the second strand of the double strands of DNA. The CRISPR enzyme in such a state is referred to as an incomplete or partially-active CRISPR enzyme. In addition, the incomplete or partially-active CRISPR enzyme may be referred to as a nickase.

The term "nickase" refers to a CRISPR enzyme engineered or modified to cleave only one strand of the double strand of the target gene or nucleic acid, and the nickase has nuclease activity of cleaving a single strand, for example, a strand that is non-complementary or complementary to gRNA of the target gene or nucleic acid. Therefore, to cleave the double strand, nuclease activity of the two nickases is needed.

The nickase may have a nuclease activity caused by a RuvC domain of the CRISPR enzyme. That is, the nickase may not include a nuclease activity caused by an HNH domain of the CRISPR enzyme, and to this end, the HNH domain may be manipulated or modified.

In one example, when the CRISPR enzyme is a Type II CRISPR enzyme, the nickase may be a Type II CRISPR enzyme including a modified HNH domain.

For example, when the Type II CRISPR enzyme is wild-type SpCas9, the nickase may be a SpCas9 variant having an inactivated nuclease activity of the HNH domain due to a mutation of histidine to alanine at position 840 in the amino acid sequence of the wild-type SpCas9. Since the nickase produced thereby, that is, the SpCas9 variant has a nuclease activity caused by a RuvC domain, a non-complementary strand of a target gene or nucleic acid, that is, a strand that does not complementarily bind with gRNA may be cleaved.

For another example, when the Type II CRISPR enzyme is wild-type CjCas9, the nickase may be a CjCas9 variant having an inactivated nuclease activity of a HNH domain due to a mutation of histidine to alanine at position 559 in the amino acid sequence of the wild-type CjCas9. Since the nickase produced thereby, that is, the CjCas9 variant has a nuclease activity caused by a RuvC domain, a non-complementary strand of a target gene or nucleic acid, that is, a strand that does not complementarily bind with gRNA may be cleaved.

In addition, the nickase may have a nuclease activity caused by the HNH domain of the CRISPR enzyme. That is, the nickase may not include a nuclease activity caused by the RuvC domain of the CRISPR enzyme, and to this end, the RuvC domain may be manipulated or modified.

In one example, when the CRISPR enzyme is a Type II CRISPR enzyme, the nickase may be a Type II CRISPR enzyme including the modified RuvC domain.

For example, when the Type II CRISPR enzyme is wild-type SpCas9, the nickase may be a SpCas9 variant having an inactivated nuclease activity of the RuvC domain due to a mutation of aspartic acid to alanine at position 10 in the amino acid sequence of the wild-type SpCas9. Since the nickase produced thereby, that is, the SpCas9 variant has a nuclease activity caused by an HNH domain, a complementary strand of a target gene or nucleic acid, that is, a strand complementarily binding to gRNA may be cleaved.

For another example, when the Type II CRISPR enzyme is wild-type CjCas9, the nickase may be a CjCas9 variant having an inactivated nuclease activity of the RuvC domain due to a mutation of aspartic acid to alanine at position 8 in the amino acid sequence of the wild-type CjCas9. Since the nickase produced thereby, that is, the CjCas9 variant has a nuclease activity caused by an HNH domain, a complementary strand of a target gene or nucleic acid, that is, a strand complementarily binding to gRNA may be cleaved.

The CRISPR enzyme may be an inactive CRISPR enzyme.

The "inactive" may mean a state of losing functions of the wild-type CRISPR enzyme, that is, both of a first function of cleaving the first strand of the double-stranded DNA and a second function of cleaving the second strand of the double-stranded DNA. The CRISPR enzyme in such a state is referred to as an inactive CRISPR enzyme.

The inactive CRISPR enzyme may have nuclease inactivity due to a mutation in a domain having a nuclease activity of the wild-type CRISPR enzyme.

The inactive CRISPR enzyme may have nuclease inactivity due to mutations in the RuvC domain and the HNH domain. That is, the inactive CRISPR enzyme may not include a nuclease activity caused by the RuvC domain and the HNH domain of the CRISPR enzyme, and to this end, the RuvC domain and the HNH domain may be manipulated or modified.

In one example, when the CRISPR enzyme is a Type II CRISPR enzyme, the inactive CRISPR enzyme may be a Type II CRISPR enzyme including the modified RuvC domain and the modified HNH domain.

For example, when the Type II CRISPR enzyme is a wild-type SpCas9, the inactive CRISPR enzyme may be a SpCas9 variant having an inactivated nuclease activity of the RuvC domain and the HNH domain by alanine mutations of both of aspartic acid at position 10 and histidine at position 840 in the amino acid sequence of the wild-type SpCas9. Since the inactive CRISPR enzyme produced thereby, that is, the SpCas9 variant has an inactivated nuclease activity of the RuvC domain and the HNH domain, none of the double strands of the target gene or nucleic acid may be cleaved.

For another example, when the Type II CRISPR enzyme is wild-type CjCas9, the inactive CRISPR enzyme may be a CjCas9 variant having an inactivated nuclease activity of the RuvC domain and the HNH domain by alanine mutations of both of aspartic acid at position 8 and histidine at position 559 in the amino acid sequence of the wild-type CjCas9. Since the inactive CRISPR enzyme produced thereby, that is, the CjCas9 variant has an inactivated nuclease activity of the RuvC domain and the HNH domain, none of the double strands of the target gene or nucleic acid may be cleaved.

The CRISPR enzyme may have a helicase activity, that is, a function of unwinding the helical structure of a double-stranded nucleic acid, in addition to the above-described nuclease activity.

In addition, the CRISPR enzyme may be modified to have a fully active, incomplete or partially-active, or inactive helicase activity.

According to an exemplary embodiment of the disclosure of the specification, the CRISPR enzyme may be an artificially engineered CRISPR enzyme.

The term "artificially engineered (artificially modified or manipulated)" means a state formed by artificial modification, not a naturally-occurring state. Here, the artificial modification may occur in a nucleic acid encoding the CRISPR enzyme, and/or protein thereof. In addition, the artificial modification includes all modifications which are possible artificial manipulations occurring in a process of producing a protein from a nucleic acid encoding the CRISPR enzyme, that is, the entire process including transcription, post-transcriptional modification, translation and post-translational modification. Hereinafter, an unnatural, artificially engineered or modified CRISPR enzyme may be used interchangeably with an artificial CRISPR enzyme or CRISPR enzyme variant (CRISPR enzyme mutant).

The artificially engineered CRISPR enzyme may be a CRISPR enzyme variant having modified functions of the wild-type CRISPR enzyme, that is, a first function of cleaving a first strand of the double-stranded DNA and/or a second function of cleaving a second strand of the double-stranded DNA.

For example, the CRISPR enzyme variant may be in a form in which the first function of the functions of the wild-type CRISPR enzyme is lost.

Alternatively, the CRISPR enzyme variant may be in a form in which the first function of the functions of the wild-type CRISPR enzyme is improved.

For example, the CRISPR enzyme variant may be in a form in which the second function of the functions of the wild-type CRISPR enzyme is lost.

Alternatively, the CRISPR enzyme variant may be in a form in which the second function of the functions of the wild-type CRISPR enzyme is improved.

For example, the CRISPR enzyme variant may be in a form in which all of the functions, that is, the first and second functions, of the wild-type CRISPR enzyme are lost.

Alternatively, the CRISPR enzyme variant may be in a form in which all of the functions, that is, the first and second functions, of the wild-type CRISPR enzyme are improved.

Alternatively, the CRISPR enzyme variant may be in a form in which, among the functions of the wild-type CRISPR enzyme, the first function is lost and the second function is improved.

Alternatively, the CRISPR enzyme variant may be in a form in which, among the functions of the wild-type CRISPR enzyme, the first function is improved and the second function is lost.

The artificially engineered CRISPR enzyme may form a gRNA-CRISPR enzyme complex by an interaction with gRNA.

Here, the artificially engineered CRISPR enzyme may be a CRISPR enzyme variant modified a function of interacting with gRNA of the wild-type CRISPR enzyme.

For example, the CRISPR enzyme variant may be in a form with reduced interaction with gRNA, compared to the wild-type CRISPR enzyme.

Alternatively, the CRISPR enzyme variant may be in a form with increased interaction with gRNA, compared to the wild-type CRISPR enzyme.

For example, the CRISPR enzyme variant may be in a form with reduced interaction with gRNA while having a first function of the wild-type CRISPR enzyme.

Alternatively, the CRISPR enzyme variant may be in a form with increased interaction with gRNA while having a first function of the wild-type CRISPR enzyme.

For example, the CRISPR enzyme variant may be in a form with reduced interaction with gRNA while having second function of the wild-type CRISPR enzyme.

Alternatively, the CRISPR enzyme variant may be in a form with increased interaction with gRNA while having a second function of the wild-type CRISPR enzyme.

For example, the CRISPR enzyme variant may be in a form with reduced interaction with gRNA while not having a first function and a second function of the wild-type CRISPR enzyme.

Alternatively, the CRISPR enzyme variant may be in a form with increased interaction with gRNA while not having a first function and a second function of the wild-type CRISPR enzyme.

Here, various gRNA-CRISPR enzyme complexes may be formed according to the interaction strength between gRNA and a CRISPR enzyme variant, and have a difference in function of accessing or cleaving a target sequence according to the CRISPR enzyme variant.

For example, only when the gRNA-CRISPR enzyme complex formed by the CRISPR enzyme variant having a reduced interaction with gRNA becomes very close or localized to a target sequence completely complementary binding to gRNA, the double or single strand(s) of the target sequence may be cleaved.

The artificially engineered CRISPR enzyme disclosed herein may be a CRISPR enzyme variant formed by modifying at least one amino acid of the amino acid sequence of the wild-type CRISPR enzyme.

The CRISPR enzyme variant may be in a form in which at least one amino acid is removed from the amino acid sequence of the wild-type CRISPR enzyme.

In one example, the CRISPR enzyme variant may be in a form in which one or more amino acids are removed from positively-charged amino acids of the wild-type CRISPR enzyme.

In another example, the CRISPR enzyme variant may be in a form in which one or more amino acids are removed from negatively-charged amino acids of the wild-type CRISPR enzyme.

In still another example, the CRISPR enzyme variant may be in a form in which one or more amino acids are removed from uncharged amino acids (or non-charged amino acids) of the wild-type CRISPR enzyme.

In yet another example, the CRISPR enzyme variant may be in a form in which one or more amino acids are removed from the positively charged amino acids, the negatively charged amino acids, and non-charged amino acids of the wild-type CRISPR enzyme.

The CRISPR enzyme variant may be in a form in which at least one amino acid selected from the amino acid sequence of the wild-type CRISPR enzyme is substituted with a different amino acid.

Here, the different amino acid, that is, the substituted amino acid may be one amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

Here, the alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine may be used as itself or as chemically modified forms thereof including methylation, acetylation, and phosphorylation.

In one example, the CRISPR enzyme variant may be in a form in which one or more amino acid selected from the positively charged amino acids of the wild-type CRISPR enzyme are substituted with a different amino acid. Here, the different amino acid may be one or more amino acids selected from stereoisomers of the selected one or more amino acids, other positively charged amino acids, negatively charged amino acids and non-charged amino acids.

In another example, the CRISPR enzyme variant may be in a form in which one or more amino acids of the negatively charged amino acids of the wild-type CRISPR enzyme are substituted with a different amino acid. Here, the different amino acid may be one or more amino acids selected from stereoisomers of the selected one or more amino acids, positively charged amino acids, other negatively charged amino acids and non-charged amino acids.

In still another example, the CRISPR enzyme variant may be in a form in which one or more amino acids of the non-charged amino acids of the wild-type CRISPR enzyme are substituted with a different amino acid. Here, the different amino acid may be one or more amino acids selected from stereoisomers of the selected one or more amino acids, other non-charged amino acids, positively charged amino acids and negatively charged amino acids.

In yet another example, the CRISPR enzyme variant may be in a form in which one or more amino acids of the positively charged, negatively charged and non-charged amino acids of the wild-type CRISPR enzyme are substituted with a different amino acid. Here, the different amino acid may be one or more amino acids selected from stereoisomers of the selected one or more amino acids, positively charged amino acids, negatively charged amino acids and non-charged amino acids.

The CRISPR enzyme variant may be in a form in which at least one amino acid is substituted or removed from the amino acid sequence of the wild-type CRISPR enzyme.

The artificially engineered CRISPR enzyme disclosed herein may be a CRISPR enzyme variant formed by adding at least one amino acid to the amino acid sequence of the wild-type CRISPR enzyme.

The CRISPR enzyme variant may be in a form in which at least one amino acid is added, compared to the amino acid sequence of the wild-type CRISPR enzyme.

Alternatively, the CRISPR enzyme variant may be in a form in which at least one functional domain is added to the amino acid sequence of the wild-type CRISPR enzyme.

Here, the functional domain may consist of one or more amino acids, and may be a peptide or polypeptide.

Here, the functional domain may be a domain having an additional function, in addition to the original functions of the wild-type CRISPR enzyme, such as the first function of cleaving the first strand of the double-stranded DNA and the second function of cleaving the second strand thereof.

Alternatively, the functional domain may be a domain having a function similar to the original functions of the wild-type CRISPR enzyme, such as the first function of cleaving the first strand of the double-stranded DNA and the second function of cleaving the second strand thereof.

In one example, the functional domain may be a domain having methylase activity, demethylase activity, transcription activation activity, transcription repression activity, transcription release factor activity, histone modification activity, RNA cleavage activity or nucleic acid binding activity.

In another example, the functional domain may be a tag or reporter gene for isolation and purification of a protein (including a peptide). Here, the tag includes a histidine (His) tag, a V5 tag, a FLAG tag, an influenza hemagglutinin (HA) tag, a Myc tag, a VSV-G tag and a thioredoxin (Trx) tag, etc., and the reporter gene includes glutathione-S-transferase (GST), horseradish peroxidase (HRP), chloramphenicol acetyltransferase (CAT), β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In still another example, the functional domain may be a deaminase.

For example, an incomplete or partial CRISPR enzyme may additionally include a cytidine deaminase as a functional domain. Alternatively, an incomplete or partial CRISPR enzyme may additionally include an adenine deaminase as a functional domain.

In yet another example, the functional domain may be a nuclear localization sequence or signal (NLS) or a nuclear export sequence or signal (NES).

For example, the CRISPR enzyme may include one or more NLSs. Here, one or more NLSs may be included at an N-terminus of the CRISPR enzyme or the proximity thereof; a C-terminus of the CRISPR enzyme or the proximity thereof; or a combination thereof. The NLS may be an NLS sequence derived from the following NLSs, but the present invention is not limited thereto: NLS of a SV40 virus large T-antigen having the amino acid sequence PKKKRKV (SEQ ID NO: 12); NLS from nucleoplasmin (e.g., nucleoplasmin bipartite NLS having the sequence KRPAATKKAGQAKKKK (SEQ ID NO: 13)); c-myc NLS having the amino acid sequence PAAKRVKLD (SEQ ID NO: 14) or RQRRNELKRSP (SEQ ID NO: 15); hRNPA1 M9 NLS having the sequence NQSSNFGPMKGGNFGGRSSGPYGGGGQYFAKPRNQGGY (SEQ ID NO: 16); the sequence RMRIZFKNKGKDTAELRRRRVEVSVELRKAKKDEQILKRRNV (SEQ ID NO: 17) of the IBB domain from importin-α; the sequences VSRKRPRP (SEQ ID NO: 18) and PPKKARED (SEQ ID NO: 19) of a myoma T protein; the sequence PQPKKKPL (SEQ ID NO: 20) of human p53; the sequence SALIKKKKKMAP (SEQ ID NO: 21) of mouse c-abl IV; the sequences DRLRR (SEQ ID NO: 22) and PKQKKRK (SEQ ID NO: 23) of influenza virus NS1; the sequence RKLKKKIKKL (SEQ ID NO: 24) of a hepatitis delta virus antigen; the sequence REKKKFLKRR (SEQ ID NO: 25) of a mouse Mx1 protein; the sequence KRKGDEVDGVDEVAKKKSKK (SEQ ID NO: 26) of a human poly (ADP-ribose) polymerase; or the sequence RKCLQAGMNLEARKTKK (SEQ ID NO: 27) of a steroid hormone receptor (human) glucocorticoid.

The artificially engineered CRISPR enzyme may be a CRISPR enzyme variant formed by modifying at least one amino acid in the amino acid sequence of a specific region of the wild-type CRISPR enzyme.

The artificially engineered CRISPR enzyme may be a CRISPR enzyme variant formed by adding one or more amino acids to a specific region of the wild-type CRISPR enzyme.

Here, the specific region of the wild-type CRISPR enzyme may be one or more regions selected from a first region, a second region, a third region and a fourth region.

The first region may be a part of the wild-type CRISPR enzyme interacting with a gRNA.

The first region may be a part of the wild-type CRISPR enzyme interacting with a target sequence.

The first region may be a part of the wild-type CRISPR enzyme interacting with a gRNA-target sequence heteroduplex.

The first region may be a part of the wild-type CRISPR enzyme interacting with a PAM distal end of the gRNA-target sequence heteroduplex.

Here, the PAM distal end of the gRNA-target sequence heteroduplex may mean 6 to 10 base pairs at the end of the gRNA-target sequence heteroduplex far from the PAM location, which is a sequence of 6 to 10 bases of the gRNA and a 6 to 10 bases sequence of the target sequence complementarily binding thereto.

The first region may be a region located in a REC lobe of the wild-type CRISPR enzyme.

The first region may be all or a part of a REC domain of the wild-type CRISPR enzyme.

The second region may be a part of the wild-type CRISPR enzyme having the first function or the second function of the wild-type CRISPR enzyme.

The second region may be a region located in an NUC lobe of the wild-type CRISPR enzyme.

The second region may be all or a part of a wild-type RuvC domain of the CRISPR enzyme.

The second region may be a part of a RuvC domain including a metal dependent nucleic acid cleaving region of the wild-type RuvC domain of the CRISPR enzyme.

Here, the metal dependent nucleic acid cleaving region of the RuvC domain may mean a region capable of cleaving the binding between nucleic acids at a target location by interacting with the metal in the RuvC domain.

The metal dependent nucleic acid cleaving region may consist of a part interacting with a metal and a part capable of cleaving the binding between nucleic acids at a target location.

The third region may be a part of the wild-type CRISPR enzyme having the first function or the second function of the wild-type CRISPR enzyme.

The third region may be a region located in an NUC lobe of the wild-type CRISPR enzyme.

The third region may be all or a part of an HNH domain of the wild-type CRISPR enzyme.

The third region may be a part of an HNH domain including a metal dependent nucleic acid cleaving region of the HNH domain of the wild-type CRISPR enzyme.

Here, the metal dependent nucleic acid cleaving region of the HNH domain may mean a region capable of cleaving the binding between nucleic acids at a target location by interacting with a metal in the HNH domain.

The fourth region may be a part of the wild-type CRISPR enzyme that can recognize a specific nucleotide sequence, that is, a protospacer adjacent motif (PAM), in a target gene or nucleic acid.

The fourth region may be a part of the wild-type CRISPR enzyme, which interacts with a specific nucleotide sequence, that is, PAM, in a target gene or nucleic acid.

The fourth region may be a part of the wild-type CRISPR enzyme, which interacts with a part of the nucleotide sequence of gRNA.

The fourth region may be a region located in a NUC lobe of the wild-type CRISPR enzyme.

The fourth region may be all or a part of a PI domain of the wild-type CRISPR enzyme.

The artificially engineered CRISPR enzyme may be a CRISPR enzyme variant formed by modifying at least one amino acid in the amino acid sequence of one or more regions selected from the first region, the second region, the third region and the fourth region of the wild-type CRISPR enzyme.

The CRISPR enzyme variant may be in a form in which at least one amino acid in the amino acid sequence of the first region of the wild-type CRISPR enzyme is modified.

The CRISPR enzyme variant may be in a form in which at least one amino acid in the amino acid sequence of the second region of the wild-type CRISPR enzyme is modified.

The CRISPR enzyme variant may be in a form in which at least one amino acid in the amino acid sequence of the third region of the wild-type CRISPR enzyme is modified.

The CRISPR enzyme variant may be in a form in which at least one amino acid in the amino acid sequence of the fourth region of the wild-type CRISPR enzyme is modified.

The CRISPR enzyme variant may be in a form in which at least two amino acids in the amino acid sequences of the first region and the second region of the wild-type CRISPR enzyme are modified. Here, two or more amino acids may be present in different regions, respectively.

The CRISPR enzyme variant may be in a form in which at least two amino acids in the amino acid sequences of the first region and the third region of the wild-type CRISPR enzyme are modified. Here, two or more amino acids may be present in different regions, respectively.

The CRISPR enzyme variant may be in a form in which at least two amino acids in the amino acid sequences of the first region and the fourth region of the wild-type CRISPR enzyme are modified. Here, two or more amino acids may be present in different regions, respectively.

The CRISPR enzyme variant may be in a form in which at least two amino acids in the amino acid sequences of the second region and the third region of the wild-type CRISPR enzyme are modified. Here, two or more amino acids may be present in different regions, respectively.

The CRISPR enzyme variant may be in a form in which at least two amino acids in the amino acid sequences of the second region and the fourth region of the wild-type CRISPR enzyme. Here, the two or more amino acids may be present in different regions, respectively.

The CRISPR enzyme variant may be in a form in which at least two amino acids in the amino acid sequences of the third region and the fourth region of the wild-type CRISPR enzyme are modified. Here, the two or more amino acids may be present in different regions, respectively.

The CRISPR enzyme variant may be in a form in which at least three amino acids in the amino acid sequences of the first region, the second region and the third region of the wild-type CRISPR enzyme are modified. Here, the three or more amino acids may be present in different regions, respectively.

The CRISPR enzyme variant may be in a form in which at least three amino acids in the amino acid sequences of the first region, the second region and the fourth region of the wild-type CRISPR enzyme are modified. Here, the three or more amino acids may be present in different regions, respectively.

The CRISPR enzyme variant may be in a form in which at least three amino acids in the amino acid sequences of the first region, the third region and the fourth region of the wild-type CRISPR enzyme are modified. Here, the three or more amino acids may be present in different regions, respectively.

The CRISPR enzyme variant may be in a form in which at least three amino acids in the amino acid sequences of the second region, the third region and the fourth region of the wild-type CRISPR enzyme are modified. Here, the three or more amino acids may be present in different regions, respectively.

The CRISPR enzyme variant may be in a form in which at least four amino acids in the amino acid sequences of the first region, the second region, the third region and the fourth region of the wild-type CRISPR enzyme are modified. Here, the four or more amino acids may be present in different regions, respectively.

The CRISPR enzyme variant may include the modification of at least one amino acid selected from the one or more regions.

Here, the modification may be a deletion of the selected one or more amino acid.

Here, the modification may be a substitution of the selected one or more amino acids with different amino acids.

In one example, the different amino acid may be a stereoisomer of the selected amino acid.

For example, the modification may be a substitution of L-glutamine located in the first region of the wild-type CRISPR enzyme, with D-glutamine.

In another example, the different amino acid may be an amino acid having a lower hydropathy index than that of the selected amino acid.

For example, the modification may be a substitution of phenylalanine (hydropathy index: 2.8) located in the second region of the wild-type CRISPR enzyme, with glycine having a lower hydropathy index (−0.4).

In still another example, the different amino acid may be an amino acid having a higher hydropathy index than that of the selected amino acid.

For example, the modification may be a substitution of serine (hydropathy index: −0.8) located in the first region of the wild-type CRISPR enzyme, with leucine having a higher hydropathy index (3.8).

In one example, the different amino acid may be an amino acid having a smaller functional group than that of the selected amino acid.

For example, the modification may be a substitution of valine located in the third region of the wild-type CRISPR enzyme, with alanine having a smaller functional group than that of the valine.

In another example, the different amino acid may be an amino acid having a larger functional group than that of the selected amino acid.

For example, the modification may be a substitution of glycine located in the second region of the wild-type CRISPR enzyme, with histidine having a larger functional group than that of the glycine.

In one example, the different amino acid may be an amino acid having higher hydrophobicity than that of the selected amino acid.

For example, the modification may be a substitution of asparagine (Kyte-Doolittle hydrophobicity: −3.5) located in the first region of the wild-type CRISPR enzyme, with threonine (Kyte-Doolittle hydrophobicity: −0.7).

In another example, the different amino acid may be an amino acid having lower hydrophobicity than that of the selected amino acid.

For example, the modification may be a substitution of cysteine (Kyte-Doolittle hydrophobicity: 2.5) located in the fourth region of the wild-type CRISPR enzyme, with proline (Kyte-Doolittle hydrophobicity: −1.6).

In one example, the different amino acid may be an amino acid larger than the selected amino acid.

For example, the modification may be a substitution of lysine (molecular weight (m.w.): 146.189) located in the third region of the wild-type CRISPR enzyme, with tryptophan (m.w.: 204.228).

In another example, the different amino acid may be an amino acid smaller than the selected amino acid.

For example, the modification may be a substitution of phenylalanine (m.w.: 165.192) located in the second region of the wild-type CRISPR enzyme, with glutamic acid (m.w.: 147.131).

The modification may be a substitution of the selected one or more amino acids with the same number of other amino acids.

For example, the modification may be a substitution of one alanine located in the first region of the wild-type CRISPR enzyme, with one glycine. Alternatively, the modification may be a substitution of one arginine located in the first region and one histidine located in the fourth region of the wild-type CRISPR enzyme, with one leucine (the first region) and one serine (the fourth region), respectively. Alternatively, the modification may be a substitution of one arginine and one valine located in the second region and one leucine located in the third region of the wild-type CRISPR enzyme, with respective one phenylalanine, that is, a total of three phenylalanines.

The modification may be a substitution of the selected one or more amino acids with a different number of other amino acids.

For example, the modification may be a substitution of one leucine located in the second region of the wild-type CRISPR enzyme with cysteine-alanine-alanine, that is, a total of three amino acids. Alternatively, the modification may be a substitution of one histidine located in the first region and two contiguous amino acids, alanine-glutamine, located in the third region of the wild-type CRISPR enzyme, with methionine-valine (the first region) and proline (the third region), respectively. Alternatively, the modification may be a substitution of one glutamic acid located in the first region, three contiguous amino acids, alanine-leucine-histidine, located in the second region and two contiguous amino acids, tryptophan-serine, located in the third region of the wild-type CRISPR enzyme, with alanine (the first region), methionine-proline (the second region) and cysteine-alanine-threonine-valine (the third region), respectively.

The artificially engineered CRISPR enzyme may be a CRISPR enzyme variant formed by adding at least one amino acid into one or more regions selected from the first region, the second region, the third region and the fourth region of the wild-type CRISPR enzyme.

Here, the addition may be an addition of one or more amino acids to the N-terminal and/or C-terminal position(s) of one or more amino acids present in the selected one or more regions.

In one example, the addition may be an addition of one or more amino acids having a positively charge to the N-terminal and/or C-terminal position(s) of one or more amino acids present in the selected one or more regions.

For example, the addition may be to add one arginine to the C-terminus of the selected one alanine located in the first region. Alternatively, the addition may be to add two amino acids, histidine-lysine, to the N-terminus of the selected glutamic acid located in the third region.

In another example, the addition may be an addition of one or more amino acids having a negative charge to the N-terminal and/or C-terminal position(s) of one or more amino acids present in the selected one or more regions.

For example, the addition may be to add one aspartic acid to the N-terminus of the selected one threonine located in the second region. Alternatively, the addition may be to add three amino acids, glutamic acid-aspartic acid-glutamic acid, to the C-terminus of the selected histidine located in the fourth region.

In still another example, the addition may be an addition of one or more amino acids having no charge to the N-terminal and/or C-terminal position(s) of the one or more amino acids present in selected one or more regions.

For example, the addition may be to add two amino acids, serine-valine, to the C-terminus of the selected one cysteine located in the second region. Alternatively, the addition may be to add five amino acids, glycine-proline-glutamine-phenylalanine-leucine, to the N-terminus of the selected lysine located in the third region.

In another example, the addition may be an addition of one or more amino acids selected from positively-charged amino acids, negatively-charged amino acids and non-charged amino acids to the N-terminal and/or C-terminal position(s) of the one or more amino acids present in the selected one or more regions.

For example, the addition may be to add six amino acids, histidine-arginine-glycine-serine-alanine-glutamic acid, to the C-terminus of the selected one arginine located in the first region. Alternatively, the addition may be to add ten amino acids, lysine-lysine-alanine-phenylalanine-glutamine-threonine-methionine-cysteine-aspartic acid-serine, to the N-terminus of the selected one glycine located in the fourth region.

The addition may be an addition of one or more functional domains to the N-terminal and/or C-terminal position(s) of one or more amino acids present in the selected one or more regions.

Here, the functional domain may be a domain having an additional function, in addition to the original functions of the wild-type CRISPR enzyme, which are the first function of cleaving the first strand of the double-stranded DNA and the second function of cleaving the second strand thereof.

Alternatively, the functional domain may be a domain having a function similar to the original functions of the wild-type CRISPR enzyme, such as the first function of cleaving the first strand of the double-stranded DNA and the second function of cleaving the second strand thereof.

In one example, the functional domain may be a domain having methylase activity, demethylase activity, transcription activation activity, transcription repression activity, transcription release factor activity, histone modification activity, RNA cleavage activity or nucleic acid binding activity.

In another example, the functional domain may be a tag or a reporter gene for isolation and purification of a protein (including a peptide). Here, the tag includes a histidine (His) tag, a V5 tag, a FLAG tag, an influenza hemagglutinin (HA) tag, a Myc tag, a VSV-G tag and a thioredoxin (Trx) tag, etc., and the reporter gene includes glutathione-S-transferase (GST), horseradish peroxidase (HRP), chloramphenicol acetyltransferase (CAT), beta-galactosidase, beta-glucuronidase, luciferase, and autofluorescent proteins including a green fluorescent protein (GFP), HcRed, DsRed, a cyan fluorescent protein (CFP), a yellow fluorescent protein (YFP) and a blue fluorescent protein (BFP), but the present invention is not limited thereto.

In still another example, the functional domain may be a deaminase. Here, the deaminase may be a adenine deaminase and/or a cytidine deaminase.

In another example, the functional domain may be a nuclear localization sequence or signal (NLS) or a nuclear export sequence or signal (NES).

In one exemplary embodiment of the disclosure disclosed herein, the artificially engineered CRISPR enzyme may be an artificially engineered Cas9.

The artificially engineered Cas9 may be a Cas9 variant formed by modifying at least one amino acid in the amino acid sequence of a specific region of wild-type Cas9.

The artificially engineered Cas9 may be a Cas9 variant formed by adding at least one amino acid into a specific region of the wild-type Cas9.

Here, the specific region of the wild-type Cas9 may be one or more regions selected from a first region, a second region, a third region and a fourth region.

The first region may be a part of the wild-type Cas9 interacting with a gRNA.

The first region may be a part of the wild-type Cas9 interacting with a target sequence.

The first region may be a part of the wild-type Cas9 interacting with a gRNA-target sequence heteroduplex.

The first region may be a part of the wild-type Cas9 interacting with a PAM distal end of the gRNA-target sequence heteroduplex.

Here, the PAM distal end of the gRNA-target sequence heteroduplex may mean 6 to 10 base pairs at the end of the gRNA-target sequence heteroduplex far from the PAM location, which is a sequence of 6 to 10 bases of the gRNA and a 6 to 10 bases sequence of a target sequence complementarily binding thereto.

The first region may be a region located in a REC lobe of the wild-type Cas9.

The first region may be all or a part of a REC domain of the wild-type Cas9.

The first region may be a region consisting of 300 amino acids at the C-terminus of the REC domain of the wild-type Cas9.

The first region may be a region consisting of 220 amino acids at the N-terminus of the REC domain of the wild-type Cas9.

In one example, when the wild-type Cas9 is wild-type SpCas9 (SEQ ID NO: 1), the first region may be all or a part of the amino acid sequence from aspartic acid at $94^{th}$ position (D94) to glycine at $717^{th}$ position (G717) of the wild-type SpCas9.

In one exemplary embodiment, the first region may be the amino acid sequence (region 1-1, SEQ ID NO: 2) from phenylalanine at $196^{th}$ position (F196) to isoleucine at $282^{th}$ position (I282) of the wild-type SpCas9.

In another exemplary embodiment, the first region may be the amino acid sequence (region 1-2, SEQ ID NO: 3) from proline at $316^{th}$ position (P316) to asparagine at $394^{th}$ position (N394) of the wild-type SpCas9.

In still another exemplary embodiment, the first region may be the amino acid sequence (region 1-3, SEQ ID NO: 4) from lysine at $510^{th}$ position (K510) to asparagine at $612^{th}$ position (N612) of the wild-type SpCas9.

In yet another exemplary embodiment, the first region may be the amino acid sequence (region 1-4, SEQ ID NO: 5) from threonine at 678$^{th}$ position (T678) to histidine at 698$^{th}$ position (H698) of the wild-type SpCas9.

In one exemplary embodiment, the first region may be two regions selected from the amino acid sequence from phenylalanine at 196$^{th}$ position (F196) to isoleucine at 282$^{th}$ position (1282) of the wild-type SpCas9 (region 1-1), the amino acid sequence from proline at 316$^{th}$ position (P316) to asparagine at 394$^{th}$ position (N394) of the wild-type SpCas9 (region 1-2), the amino acid sequence from lysine at 510$^{th}$ position (K510) to asparagine at 612$^{th}$ position (N612) of the wild-type SpCas9 (region 1-3), and the amino acid sequence from threonine at 678th position (T678) to histidine at 698$^{th}$ position (H698) of the wild-type SpCas9 (region 1-4).

In another exemplary embodiment, the first region may be three regions selected from the amino acid sequence from phenylalanine at 196$^{th}$ position (F196) to isoleucine at 282th position (1282) of the wild-type SpCas9 (region 1-1), the amino acid sequence from proline at 316$^{th}$ position (P316) to asparagine at 394$^{th}$ position (N394) of the wild-type SpCas9 (region 1-2), the amino acid sequence from lysine at 510$^{th}$ position (K510) to asparagine at 612$^{th}$ position (N612) of the wild-type SpCas9 (region 1-3), and the amino acid sequence from threonine at 678th position (T678) to histidine at 698$^{th}$ position (H698) of the wild-type SpCas9 (region 1-4).

In still another exemplary embodiment, the first region may be the amino acid sequence from phenylalanine at 196$^{th}$ position (F196) to isoleucine at 282$^{th}$ position (1282) of the wild-type SpCas9 (region 1-1), the amino acid sequence from proline at 316$^{th}$ position (P316) to asparagine at 394$^{th}$ position (N394) of the wild-type SpCas9 (region 1-2), the amino acid sequence from lysine at 510$^{th}$ position (K510) to asparagine at 612$^{th}$ position (N612) of the wild-type SpCas9 (region 1-3), and the amino acid sequence from threonine at 678$^{th}$ position (T678) to histidine at 698$^{th}$ position (H698) of the wild-type SpCas9 (region 1-4).

In another example, when the wild-type Cas9 is wild-type SaCas9, the first region may be all or a part of the amino acid sequence from asparagine at 75$^{th}$ position (N75) to lysine at 426$^{th}$ position (K426) of the wild type SaCas9.

In one exemplary embodiment, the first region may be the amino acid sequence from threonine at 207$^{th}$ position (T207) to lysine at 426$^{th}$ position (K426) of the wild-type SaCas9.

The second region may be a part of the wild-type Cas9 having the first function or the second function of the wild-type Cas9.

The second region may be a region located in an NUC lobe of the wild-type Cas9.

The second region may be all or a part of a RuvC domain of the wild-type Cas9.

The second region may be a part of the RuvC domain including a metal dependent nucleic acid cleaving region of the wild-type Cas9.

Here, the metal dependent nucleic acid cleaving region of the RuvC domain may mean a region capable of cleaving the binding between nucleic acids at a target location by interacting with a metal in the RuvC domain.

The metal dependent nucleic acid cleaving region may consist of a part interacting with a metal and a part of cleaving the binding between nucleic acids at a target location.

In one example, when the wild-type Cas9 is wild-type SpCas9, the second region may be all or a part of the amino acid sequence (RuvC I region) from methionine at 1$^{st}$ position (M1) to alanine at 59$^{th}$ position (A59) of the wild-type SpCas9.

The second region may be all or a part of the amino acid sequence (RuvC II region) from aspartic acid at 718$^{th}$ position (D718) to glutamine at 774$^{th}$ position (Q774) of the wild-type SpCas9.

The second region may be all or a part of the amino acid sequence (RuvC III region) from serine at 909$^{th}$ position (S909) to threonine at 1098$^{th}$ position (T1098) of the wild-type SpCas9.

The second region may be the RuvC I region, the RuvC II region and/or the RuvC III region of the wild-type SpCas9.

In one exemplary embodiment, the second region may be the amino acid sequence (region 2-1, SEQ ID NO: 6) from methionine at 1$^{st}$ position (M1) to threonine at 22$^{th}$ position (T22) of the wild-type SpCas9.

In another exemplary embodiment, the second region may be the amino acid sequence (region 2-2, SEQ ID NO: 7) from proline at 731$^{th}$ position (P731) to threonine at 770th position (T770) of the wild-type SpCas9.

In still another exemplary embodiment, the second region may be the amino acid sequence (region 2-3, SEQ ID NO: 8) from glutamine at 926$^{th}$ position (Q926) to serine at 1040th position (S1040) of the wild-type SpCas9.

In exemplary embodiment, the second region may be the amino acid sequence from methionine at 1$^{st}$ position (M1) to threonine at 22$^{th}$ position (T22) of the wild-type SpCas9 (region 2-1) and the amino acid sequence from proline at 731$^{th}$ position (P731) to threonine at 770th position (T770) of the wild-type SpCas9 (region 2-2).

In another exemplary embodiment, the second region may be the amino acid sequence from methionine at 1$^{st}$ position (M1) to threonine at 22$^{th}$ position (T22) of the wild-type SpCas9 (region 2-1) and the amino acid sequence from glutamine at 926$^{th}$ position (Q926) to serine at 1040$^{th}$ position (S1040) of the wild-type SpCas9 (region 2-3).

In still another exemplary embodiment, the second region may be the amino acid sequence from proline at 731$^{th}$ position (P731) to threonine at 770$^{th}$ position (T770) of the wild-type SpCas9 (region 2-2) and the amino acid sequence from glutamine at 926$^{th}$ position (Q926) to serine at 1040$^{th}$ position (S1040) of the wild-type SpCas9 (region 2-3).

In yet another exemplary embodiment, the second region may be the amino acid sequence from methionine at 1$^{st}$ position (M1) to threonine at 22$^{th}$ position (T22) of the wild-type SpCas9 (region 2-1), the amino acid sequence from proline at 731$^{th}$ position (P731) to threonine at 770$^{th}$ position (T770) of the wild-type SpCas9 (region 2-2), and the amino acid sequence from glutamine at 926$^{th}$ position (Q926) to serine at 1040$^{th}$ position (S1040) of the wild-type SpCas9 (region 2-3).

In another example, when the wild-type Cas9 is a wild-type SaCas9, the second region may be all or a part of the amino acid sequence (RuvC I region) from methionine at 1st position (M1) to valine at 41$^{th}$ position (V41) of the wild type SaCas9.

The second region may be all or a part of the amino acid sequence (RuvC 11 region) from isoleucine at 436$^{th}$ position (1436) to glutamic acid at 481$^{th}$ position (E481) of the wild-type SaCas9.

The second region may be all or a part of the amino acid sequence (RuvC III region) from tyrosine at 651$^{th}$ position (Y651) to valine at 775$^{th}$ position (V775) of the wild type SaCas9.

The second region may be the RuvC I region, the RuvC 11 region and/or the RuvC III region of the wild-type SaCas9.

In one exemplary embodiment, the second region may be the amino acid sequence (region 2-1) from methionine at 1st position (M1) to threonine at 25$^{th}$ position (T25) of the wild type SaCas9.

In another exemplary embodiment, the second region may be the amino acid sequence (region 2-2) from proline at 471$^{th}$ position (P471) to glutamic acid at 481$^{th}$ position (E481) of the amino acid sequence of the wild-type SaCas9.

In still another exemplary embodiment, the second region may be the amino acid sequence (region 2-3) from asparagine at 667$^{th}$ position (N667) to serine at 740$^{th}$ position (S740) of the wild-type SaCas9.

The third region may be a part of the wild-type Cas9 having the first function or the second function thereof.

The third region may be a region located in an NUC lobe of the wild-type Cas9.

The third region may be all or a part of an HNH domain of the wild-type Cas9.

The third region may be all or a part of an HNH domain including a metal dependent nucleic acid cleaving region of the wild-type Cas9.

Here, the metal dependent nucleic acid cleaving region of the HNH domain may mean a region that can cleave nucleic acids at a target location by interacting with a metal in the HNH domain.

In one example, when the wild-type Cas9 is a wild-type SpCas9, the third region may be all or a part of the amino acid sequence from lysine at 775$^{th}$ position (K775) to leucine at 908$^{th}$ position (L908) of the wild-type SpCas9.

In one exemplary embodiment, the third region may be the amino acid sequence (region 3-1, SEQ ID NO: 9) from lysine at 775$^{th}$ position (K775) to leucine at 900$^{th}$ position (L900) of the wild-type SpCas9.

In another example, when the wild-type Cas9 is a wild-type SaCas9, the third region may be all or a part of the amino acid sequence from isoleucine at 521$^{th}$ position (I521) to glutamic acid at 629$^{th}$ position (E629) of the wild-type SaCas9.

In one exemplary embodiment, the third region may be the amino acid sequence (region 3-1) from lysine at 523$^{th}$ position (K523) to leucine at 627$^{th}$ position (L627) of the wild type SaCas9.

The fourth region may be a part of the wild-type Cas9 which can recognize a specific nucleotide sequence, that is, PAM, in a target gene or nucleic acid.

The fourth region may be a part of the wild-type Cas9 interacting with a specific nucleotide sequence, that is, PAM, in a target gene or nucleic acid.

The fourth region may be a part of the wild-type Cas9 interacting with a part of the nucleotide sequence of gRNA.

The fourth region may be a region located in an NUC lobe of the wild-type Cas9.

The fourth region may be all or a part of a PI domain of the wild-type Cas9.

In one example, when the wild-type Cas9 is a wild-type SpCas9, the fourth region may be all or a part of the amino acid sequence from glutamic acid at 1099$^{th}$ position (E1099) to aspartic acid at 1368$^{th}$ position (D1368) of the wild-type SpCas9.

In one exemplary embodiment, the fourth region may be the amino acid sequence (region 4-1, SEQ ID NO: 10) from glutamic acid at 1099$^{th}$ position (E1099) to valine at 1139$^{th}$ position (V1139) of the wild-type SpCas9.

In another example, when the wild-type Cas9 is a wild-type SaCas9, the fourth region may be all or a part of the amino acid sequence from lysine at 910$^{th}$ position (K910) to glycine at 1053$^{th}$ position (G1053) of the wild type SaCas9.

In one exemplary embodiment, the fourth region may be the amino acid sequence (region 4-1) from lysine at 910$^{th}$ position (K910) to aspartic acid at 970$^{th}$ position (D970) of the wild type SaCas9.

The artificially engineered Cas9 may be a Cas9 variant formed by modifying at least one amino acid in the amino acid sequence of one or more regions selected from the first region, the second region, the third region and the fourth region of the wild-type Cas9.

The Cas9 variant may be in a form in which one or more amino acids selected from the amino acid sequence of the first region of the wild-type Cas9 are modified.

In one example, when the wild-type Cas9 is a wild-type SpCas9, a SpCas9 variant may be in a form in which one or more amino acids selected from the amino acid sequence of the first region of the wild-type SpCas9 is modified.

In one exemplary embodiment, the SpCas9 variant may be in a form in which one or more amino acids selected from the amino acid sequence of the region 1-1 of the wild-type SpCas9 are modified.

For example, the SpCas9 variant may be a form with a modification of one or more amino acids selected from N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281 and I282 which are amino acids having an aliphatic or amide-based functional group of the region 1-1 of the wild-type SpCas9.

In another exemplary embodiment, the SpCas9 variant may be in a form in which one or more amino acids selected from the amino acid sequence of the region 1-2 of the wild-type SpCas9 are modified.

For example, the SpCas9 variant may be a form with a modification of one or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 which are non-polar amino acids of the region 1-2 of the wild-type SpCas9.

In one exemplary embodiment, the SpCas9 variant may be in a form in which one or more amino acids selected from the amino acid sequence of the region 1-3 of the wild-type SpCas9 are modified.

For example, the SpCas9 variant may be a form with a modification of one or more amino acids selected from the group consisting of K510, Y515, F539, G582, V583, E584, D585, N588 and I601 of the region 1-3 of the wild-type SpCas9.

For example, the SpCas9 variant may be a form with a modification of one or more amino acids selected from the group consisting of L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606 and L607 which are non-polar amino acids of the region 1-3 of the wild-type SpCas9.

In another exemplary embodiment, the SpCas9 variant may be in a form in which one or more amino acids selected from the amino acid sequence of the region 1-4 of the wild-type SpCas9 are modified.

For example, the SpCas9 variant may be a form with a modification of one or more amino acids selected from the group consisting of N692, M694, Q695 and H698 of the region 1-4 of the wild-type SpCas9.

For example, the SpCas9 variant may be a form with a modification of one or more amino acids selected from the group consisting of non-polar amino acids, that is, I679, L680, F682, L683, G687, F688, A689, F693, M694, L696 and I697 of the region 1-4 of the wild-type SpCas9.

In still another exemplary embodiment, the SpCas9 variant may be in a form in which two or more amino acids selected from the amino acid sequences of the region 1-1, the region 1-2, the region 1-3 and the region 1-4 of the wild-type SpCas9 are modified. Here, the selected two or more amino acids may be located in different regions, respectively. Alternatively, the selected two or more amino acids may be located in the same region.

For example, the SpCas9 variant may be a form with a modification of two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the region 1-1, the region 1-2, the region 1-3 and the region 1-4 of the wild-type SpCas9.

For example, the SpCas9 variant may be a form with a modification of two or more amino acids selected from the group consisting of A203, N277, G366, K510, Y515, F539, G582, V583, E584, D585, N588, I601, N692, M694, Q695 and H698 of the region 1-1, the region 1-2, the region 1-3 and the region 1-4 of the wild-type SpCas9.

For example, the SpCas9 variant may be a form with a modification of two or more amino acids selected from the group consisting of K510, Y515, F539, G582, V583, E584, D585, N588, I601, N692, M694, Q695 and H698 of the region 1-3 and the region 1-4 of the wild-type SpCas9.

For example, the SpCas9 variant may be a form with a modification of two or more amino acids selected from the group consisting of non-polar amino acids, that is, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the region 1-3 and the region 1-4 of the wild-type SpCas9.

In another exemplary embodiment, the SpCas9 variant may be in a form in which three or more amino acids selected from the amino acid sequences of the region 1-1, the region 1-2, the region 1-3 and the region 1-4 of the wild-type SpCas9 are modified. Here, the selected three or more amino acids may be located in different regions, respectively. Alternatively, the selected three or more amino acids may be located in the same region. Alternatively, the selected three or more amino acids may be located in the same or different regions, respectively.

For example, the SpCas9 variant may be a form with a modification of three or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9.

For example, the SpCas9 variant may be a form with a modification of three or more amino acids selected from the group consisting of A203, N277, G366, K510, Y515, F539, G582, V583, E584, D585, N588, I601, N692, M694, Q695 and H698 of the region 1-1, the region 1-2, the region 1-3 and the region 1-4 of the wild-type SpCas9.

For example, the SpCas9 variant may be a form with a modification of three or more amino acids selected from the group consisting of A203, N277, K510, Y515, F539, G582, V583, E584, D585, N588, I601, N692, M694, Q695 and H698 of the region 1-1, the region 1-3 and the region 1-4 of the wild-type SpCas9.

For example, the SpCas9 variant may be a form with a modification of three or more amino acids selected from the group consisting of G366, K510, Y515, F539, G582, V583, E584, D585, N588, I601, N692, M694, Q695 and H698 of the region 1-2, the region 1-3 and the region 1-4 of the wild-type SpCas9.

The Cas9 variant may be in a form in which one or more amino acids selected from the amino acid sequence of the second region of the wild-type Cas9 are modified.

In one example, when the wild-type Cas9 is a wild-type SpCas9, a SpCas9 variant may be in a form in which one or more amino acids selected from the amino acid sequence of the second region of the wild-type SpCas9 are modified.

In one exemplary embodiment, the SpCas9 variant may be in a form in which one or more amino acids selected from the amino acid sequence of the region 2-1 of the wild-type SpCas9 are modified.

For example, the SpCas9 variant may be a form with a modification of one or more amino acids selected from the group consisting of I7, G8, L9, D10, I11 and G12 of the region 2-1 of the wild-type SpCas9.

For example, the SpCas9 variant may be a form with a modification of one or more amino acids selected from the group consisting of the non-polar amino acids, that is, I7, G8, L9, I11, G12, V16, G17, W18, A19, V20 and I21 of the region 2-1 of the wild-type SpCas9.

In another exemplary embodiment, the SpCas9 variant may be in a form in which one or more amino acids selected from the amino acid sequence of the region 2-2 of the wild-type SpCas9 are modified.

For example, the SpCas9 variant may be a form with a modification of one or more amino acids selected from the group consisting of I761, E762, M763, R765, E766 and N767 of the region 2-2 of the wild-type SpCas9.

For example, the SpCas9 variant may be a form with a modification of one or more amino acids selected from the group consisting of the non-polar amino acids, that is, P731, A732, I733, G736, I737, L738, V741, V743, V744, L747, V748, V750, M751, G752, P756, I759, V760, I761, M763 and A764 in the region 2-2 of the wild-type SpCas9.

In still another exemplary embodiment, the SpCas9 variant may be in a form in which one or more amino acids selected from the amino acid sequence of the region 2-3 of the wild-type SpCas9 are modified.

For example, the SpCas9 variant may be a form with a modification of one or more amino acids selected from the group consisting of D965, Y981, H982, H983, A984, H985, D986, A987, Y988, Y1036, F1037, F1038 and Y1039 of the region 2-3 of the wild-type SpCas9.

For example, the SpCas9 variant may be a form with a modification of one or more amino acids selected from the group consisting of the non-polar amino acids, that is, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-3 of the wild-type SpCas9.

In one exemplary embodiment, the SpCas9 variant may be in a form in which two or more amino acids selected from the amino acid sequences of the region 2-1 and the region 2-2 of the wild-type SpCas9 are modified. Here, the selected two or more amino acids may be located in the region 2-1 and the region 2-2, respectively.

For example, the SpCas9 variant may be a form with modifications of two or more amino acids selected from the group consisting of I7, G8, L9, D10, I11, G12, I761, E762, M763, R765, E766 and N767 of the region 2-1 and the region 2-2 of the wild-type SpCas9.

For example, the SpCas9 variant may be a form with modifications of two or more amino acids selected from the group consisting of the non-polar amino acids, that is, I7, G8, L9, I11, G12, V16, G17, W18, A19, V20, I21, P731, A732, I733, G736, I737, L738, V741, V743, V744, L747, V748, V750, M751, G752, P756, I759, V760, I761, M763 and A764 of the region 2-1 and the region 2-2 of the wild-type SpCas9.

In another exemplary embodiment, the SpCas9 variant may be in a form in which two or more amino acids selected from the amino acid sequence of the region 2-1 and the region 2-3 of the wild-type SpCas9 are modified. Here, the selected two or more amino acids may be located in the region 2-1 and the region 2-3, respectively.

For example, the SpCas9 variant may be a form including modifications of two or more amino acids selected from the group consisting of I7, G8, L9, D10, I11, G12, D965, Y981, H982, H983, A984, H985, D986, A987, Y988, Y1036, F1037, F1038 and Y1039 of the region 2-1 and the region 2-3 of the wild-type SpCas9.

For example, the SpCas9 variant may be a form with modifications of two or more amino acids selected from the group consisting of non-polar amino acids, that is, I7, G8, L9, I11, G12, V16, G17, W18, A19, V20, I21, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-1 and the region 2-3 of the wild-type SpCas9.

In still another exemplary embodiment, the SpCas9 variant may be in a form in which two or more amino acids selected from the amino acid sequences of the regions 2-2 and 2-3 of the wild-type SpCas9 are modified. Here, the selected two or more amino acids may be located in the region 2-2 and the region 2-3, respectively.

For example, the SpCas9 variant may be a form with modifications of two or more amino acids selected from the group consisting of I761, E762, M763, R765, E766, N767, D965, Y981, H982, H983, A984, H985, D986, A987, Y988, Y1036, F1037, F1038 and Y1039 of the region 2-2 and the region 2-3 of the wild-type SpCas9.

For example, the SpCas9 variant may be a form including modifications of two or more amino acids selected from the group consisting of the non-polar amino acids, that is, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-2 and the region 2-3 of the wild-type SpCas9.

In another exemplary embodiment, the SpCas9 variant may be in a form in which three or more amino acids selected from the amino acid sequences of the region 2-1, the region 2-2 and the region 2-3 of the wild-type SpCas9 are modified. Here, the selected three or more amino acids may be located in the region 2-1, the region 2-2 and the region 2-3 of the wild-type SpCas9, respectively.

For example, the SpCas9 variant may be a form with modifications of three or more amino acids selected from the group consisting of I7, G8, L9, D10, I11, G12, I761, E762, M763, R765, E766, N767, D965, Y981, H982, H983, A984, H985, D986, A987, Y988, Y1036, F1037, F1038 and Y1039 of the region 2-1, the region 2-2 and the region 2-3 of the wild-type SpCas9.

For example, the SpCas9 variant may be a form including modifications of three or more amino acids selected from the group consisting of the non-polar amino acids, that is, I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-1, the region 2-2 and the region 2-3 of the wild-type SpCas9.

The Cas9 variant may be in a form in which at least one amino acid of the amino acid sequence of the third region of the wild-type Cas9 is modified.

In one example, when the wild-type Cas9 is a wild-type SpCas9, a SpCas9 variant may be in a form in which one or more amino acids selected from the amino acid sequence in the third region of the wild-type SpCas9 are modified.

In one exemplary embodiment, the SpCas9 variant may be in a form in which one or more amino acids selected from the amino acid sequence of the region 3-1 of the wild-type SpCas9 are modified.

For example, the SpCas9 variant may be a form including a modification of one or more amino acids selected from the group consisting of V838, D839, H840, D853, N854, K855, K862, N863, R864, A889, K890 and L891 of the region 3-1 of the wild-type SpCas9.

For example, the SpCas9 variant may be a form with a modification of one or more amino acids selected from the group consisting of charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 in the region 3-1 of the wild-type SpCas9.

The Cas9 variant may be in a form in which one or more amino acids selected from the amino acid sequence of the fourth region of the wild-type Cas9 are modified.

In one example, when the wild-type Cas9 is a wild-type SpCas9, a SpCas9 variant may be in a form in which one or more amino acids selected from the amino acid sequence of the fourth region of the wild-type SpCas9 are modified.

In one exemplary embodiment, the SpCas9 variant may be in a form in which one or more amino acids selected from the amino acid sequence in the region 4-1 of the wild-type SpCas9 are modified.

For example, the SpCas9 variant may be a form with a modification of one or more amino acids selected from the group consisting of T1102, S1106, E1108, S1116, D1117, D1125, D1127, D1135, S1136 and T1138 of the region 4-1 of the wild-type SpCas9.

The Cas9 variant may be in a form in which two or more amino acids selected from the amino acid sequence in the first region and the second region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence in the first region and the second region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 1-1 and the region 2-1 of the wild-type SpCas9 are modified.

For example, the SpCas9 variant may be a form with modifications of two or more amino acids selected from the group consisting of I7, G8, L9, D10, I11, G12, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281 and I282 of the region 1-1 and the region 2-1 of the wild-type SpCas9.

In another exemplary embodiment, the SpCas9 variant may be in a form in which two or more amino acids selected from the amino acid sequence of the region 1-1 and the region 2-2 of the wild-type SpCas9 are modified.

For example, the SpCas9 variant may be a form including modifications of two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, I761, E762, M763, R765, E766 and N767 of the region 1-1 and the region 2-2 of the wild-type SpCas9.

In still another exemplary embodiment, the SpCas9 variant may be in a form in which two or more amino acids selected from the amino acid sequence of the region 1-1 and the region 2-3 of the wild-type SpCas9 are modified.

For example, the SpCas9 variant may be a form with modifications of two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, D965, Y981, H982, H983, A984, H985, D986, A987, Y988, Y1036, F1037, F1038 and Y1039 of the region 1-1 and the region 2-3 of the wild-type SpCas9.

In one exemplary embodiment, the SpCas9 variant may be in a form in which two or more amino acids selected from the amino acid sequence of the region 1-2 and the region 2-1 of the wild-type SpCas9 are modified.

For example, the SpCas9 variant may be a form with modifications of two or more amino acids selected from the group consisting of I7, G8, L9, D10, I11, G12, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 of the region 1-2 and the region 2-1 of the wild-type SpCas9.

For example, the SpCas9 variant may be a form including modifications of two or more amino acids selected from the group consisting of the non-polar amino acids, that is, I7, G8, L9, I11, G12, V16, G17, W18, A19, V20, I21, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 of the region 1-2 and the region 2-1 of the wild-type SpCas9.

In another exemplary embodiment, the SpCas9 variant may be in a form in which two or more amino acids selected from the amino acid sequence of the region 1-2 and the region 2-2 of the wild-type SpCas9 are modified.

For example, the SpCas9 variant may be a form with modifications of two or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, I761, E762, M763, R765, E766 and N767 of the region 1-2 and the region 2-2 of the wild-type SpCas9.

In still another exemplary embodiment, the SpCas9 variant may be in a form in which two or more amino acids selected from the amino acid sequence of the region 1-2 and the region 2-3 of the wild-type SpCas9 are modified.

For example, the SpCas9 variant may be a form with modifications of two or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, D965, Y981, H982, H983, A984, H985, D986, A987, Y988, Y1036, F1037, F1038 and Y1039 of the region 1-2 and the region 2-3 of the wild-type SpCas9.

In one exemplary embodiment, the SpCas9 variant may be in a form in which two or more amino acids selected from the amino acid sequence of the region 1-3 and the region 2-1 of the wild-type SpCas9 are modified.

For example, the SpCas9 variant may be a form including modifications of two or more amino acids selected from the group consisting of I7, G8, L9, D10, I11, G12, K510, Y515, F539, G582, V583, E584, D585, N588 and I601 of the region 1-3 and the region 2-1 of the wild-type SpCas9.

For example, the SpCas9 variant may be a form with modifications of two or more amino acids selected from the group consisting of the non-polar amino acids, that is, I7, G8, L9, I11, G12, V16, G17, W18, A19, V20, I21, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606 and L607 of the region 1-3 and the region 2-1 of the wild-type SpCas9.

In another exemplary embodiment, the SpCas9 variant may be in a form in which two or more amino acids selected from the amino acid sequence of the region 1-3 and the region 2-2 of the wild-type SpCas9 are modified.

For example, the SpCas9 variant may be a form with modifications of two or more amino acids selected from the group consisting of K510, Y515, F539, G582, V583, E584, D585, N588, I601, I761, E762, M763, R765, E766 and N767 of the region 1-3 and the region 2-2 of the wild-type SpCas9.

For example, the SpCas9 variant may be a form including modifications of two or more amino acids selected from the group consisting of the non-polar amino acids, that is, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, P731, A732, I733, G736, I737, L738, V741, V743, V744, L747, V748, V750, M751, G752, P756, I759, V760, I761, M763 and A764 of the region 1-3 and the region 2-2 of the wild-type SpCas9.

In still another exemplary embodiment, the SpCas9 variant may be in a form in which two or more amino acids selected from the amino acid sequence of the region 1-3 and the region 2-3 of the wild-type SpCas9 are modified.

For example, the SpCas9 variant may be a form with modifications of two or more amino acids selected from the group consisting of K510, Y515, F539, G582, V583, E584, D585, N588, I601, D965, Y981, H982, H983, A984, H985, D986, A987, Y988, Y1036, F1037, F1038 and Y1039 of the region 1-3 and the region 2-3 of the wild-type SpCas9.

For example, the SpCas9 variant may be a form including modifications of two or more amino acids selected from the group consisting of the non-polar amino acids, that is, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 1-3 and the region 2-3 of the wild-type SpCas9.

In one exemplary embodiment, the SpCas9 variant may be in a form in which two or more amino acids selected from the amino acid sequence of the region 1-4 and the region 2-1 of the wild-type SpCas9 are modified.

For example, the SpCas9 variant may be a form including modifications of two or more amino acids selected from the group consisting of I7, G8, L9, D10, I11, G12, N692, M694, Q695 and H698 of the region 1-4 and the region 2-1 of the wild-type SpCas9.

For example, the SpCas9 variant may be a form with modifications of two or more amino acids selected from the group consisting of the non-polar amino acids, that is, I7, G8, L9, I11, G12, V16, G17, W18, A19, V20, I21, I679, L680, F682, L683, G687, F688, A689, F693, M694, L696 and I697 of the region 1-4 and the region 2-1 of the wild-type SpCas9.

In another exemplary embodiment, the SpCas9 variant may be in a form in which two or more amino acids selected from the amino acid sequence of the region 1-4 and the region 2-2 of the wild-type SpCas9 are modified.

For example, the SpCas9 variant may be a form including modifications of two or more amino acids selected from the group consisting of N692, M694, Q695, H698, I761, E762, M763, R765, E766 and N767 of the region 1-4 and the region 2-2 of the wild-type SpCas9.

For example, the SpCas9 variant may be a form with modifications of two or more amino acids selected from the group consisting of the non-polar amino acids, that is, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763 and A764 of the region 1-4 and the region 2-2 of the wild-type SpCas9.

In still another exemplary embodiment, the SpCas9 variant may be in a form in which two or more amino acids selected from the amino acid sequence of the region 1-4 and the region 2-3 of the wild-type SpCas9 are modified.

For example, the SpCas9 variant may be a form including modifications of two or more amino acids selected from the group consisting of N692, M694, Q695, H698, D965, Y981, H982, H983, A984, H985, D986, A987, Y988, Y1036, F1037, F1038 and Y1039 of the region 1-4 and the region 2-3 of the wild-type SpCas9.

For example, the SpCas9 variant may be a form with modifications of two or more amino acids selected from the group consisting of the non-polar amino acids, that is, 1679, L680, F682, L683, G687, F688, A689, F693, M694, L696, I697, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 1-4 and the region 2-3 of the wild-type SpCas9.

In one exemplary embodiment, the SpCas9 variant may be in a form in which two or more amino acids selected from the amino acid sequence of the first region and the second region of the wild-type SpCas9 are modified.

Here, the first region may be the region 1-1, the region 1-2, the region 1-3 and the region 1-4.

Here, the second region may be the region 2-1, the region 2-2 and the region 2-3.

For example, the SpCas9 variant may be a form with modifications of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, D965, Y981, H982, H983, A984, H985, D986, A987, Y988, Y1036, F1037, F1038 and Y1039 of the first region and the second region of the wild-type SpCas9.

For example, the SpCas9 variant may be a form with modifications of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the first region and the second region of the wild-type SpCas9.

The Cas9 variant may be in a form in which two or more amino acids selected from the amino acid sequence of the first region and the third region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence of the first region and the third region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 1-1 and the region 3-1 of the wild-type SpCas9 are modified.

For example, the SpCas9 variant may be a form with modifications of two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, V838, D839, H840, D853, N854, K855, K862, N863, R864, A889, K890 and L891 of the region 1-1 and the region 3-1 of the wild-type SpCas9.

In one exemplary embodiment, the SpCas9 variant may be in a form in which two or more amino acids selected from the amino acid sequence of the region 1-2 and the region 3-1 of the wild-type SpCas9 are modified.

For example, the SpCas9 variant may be a form with modifications of two or more amino acids selected from the group consisting of the non-polar amino acids, that is, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 of the region 1-2 of the wild-type SpCas9; and charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In one exemplary embodiment, the SpCas9 variant may be in a form in which two or more amino acids selected from the amino acid sequence of the region 1-3 and the region 3-1 of the wild-type SpCas9 are modified.

For example, the SpCas9 variant may be a form with modifications of two or more amino acids selected from the group consisting of K510, Y515, F539, G582, V583, E584, D585, N588, I601, V838, D839, H840, D853, N854, K855, K862, N863, R864, A889, K890 and L891 of the region 1-3 and the region 3-1 of the wild-type SpCas9.

For example, the SpCas9 variant may be a form with modifications of two or more amino acids selected from the group consisting of the non-polar amino acids, that is, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606 and L607 of the region 1-3 of the wild-type SpCas9; and the charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In another exemplary embodiment, the SpCas9 variant may be in a form in which two or more amino acids selected from the amino acid sequence of the region 1-4 and the region 3-1 of the wild-type SpCas9 are modified.

For example, the SpCas9 variant may be a form with modifications of two or more amino acids selected from the group consisting of N692, M694, Q695, H698, V838, D839, H840, D853, N854, K855, K862, N863, R864, A889, K890 and L891 of the region 1-4 and the region 3-1 of the wild-type SpCas9.

For example, the SpCas9 variant may be a form with modifications of two or more amino acids selected from the group consisting of the non-polar amino acids, that is, I679, L680, F682, L683, G687, F688, A689, F693, M694, L696 and I697 of the region 1-4 of the wild-type SpCas9; and the charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In one exemplary embodiment, the SpCas9 variant may be in a form in which two or more amino acids selected from the amino acid sequence of the first region and the third region of the wild-type SpCas9 are modified.

Here, the first region may be the region 1-1, the region 1-2, the region 1-3 and the region 1-4.

Here, the third region may be the region 3-1.

For example, the SpCas9 variant may be a form with modifications of two or more amino acids selected from the group consisting of A203, N277, G366, K510, Y515, F539, G582, V583, E584, D585, N588, I601, N692, M694, Q695, H698, V838, D839, H840, D853, N854, K855, K862, N863, R864, A889, K890 and L891 of the first region and the third region of the wild-type SpCas9.

For example, the SpCas9 variant may be a form with modifications of two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the first region and the third region of the wild-type SpCas9.

The Cas9 variant may be in a form in which two or more amino acids selected from the amino acid sequence of the first region and the fourth region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence of the first region and the fourth region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 1-1 and the region 4-1 of the wild-type SpCas9 are modified.

For example, the SpCas9 variant may be a form with modifications of two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, T1102, S1106, E1108, S1116, D1117, D1125, D1127, D1135, S1136 and T1138 of the region 1-1 and the region 4-1 of the wild-type SpCas9.

In one exemplary embodiment, the SpCas9 variant may be in a form in which two or more amino acids selected from the amino acid sequence of the region 1-2 and the region 4-1 of the wild-type SpCas9 are modified.

For example, the SpCas9 variant may be a form with modifications of two or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, T1102, S1106, E1108, S1116, D1117, D1125, D1127, D1135, S1136 and T1138 of the region 1-2 and the region 4-1 of the wild-type SpCas9.

In one exemplary embodiment, the SpCas9 variant may be in a form in which two or more amino acids selected from the amino acid sequence of the region 1-3 and the region 4-1 of the wild-type SpCas9 are modified.

For example, the SpCas9 variant may be a form with modifications of two or more amino acids selected from the group consisting of K510, Y515, F539, G582, V583, E584, D585, N588, I601, T1102, S1106, E1108, S1116, D1117, D1125, D1127, D1135, S1136 and T1138 of the region 1-3 and the region 4-1 of the wild-type SpCas9.

For example, the SpCas9 variant may be a form with modifications of two or more amino acids selected from the group consisting of the non-polar amino acids, that is, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606 and L607 of the region 1-3 of the wild-type SpCas9; and T1102, S1106, E1108, S1116, D1117, D1125, D1127, D1135, S1136 and T1138 of the region 4-1 of the wild-type SpCas9.

In another exemplary embodiment, the SpCas9 variant may be in a form in which two or more amino acids selected from the amino acid sequence of the region 1-4 and the region 4-1 of the wild-type SpCas9 are modified.

For example, the SpCas9 variant may be a form with modifications of two or more amino acids selected from the group consisting of N692, M694, Q695, H698, T1102, S1106, E1108, S1116, D1117, D1125, D1127, D1135, S1136 and T1138 of the region 1-4 and the region 4-1 of the wild-type SpCas9.

For example, the SpCas9 variant may be a form with modifications of two or more amino acids selected from the group consisting of the non-polar amino acids, that is, I679, L680, F682, L683, G687, F688, A689, F693, M694, L696 and I697 of the regions 1-4 of the wild-type SpCas9; and T1102, S1106, E1108, S1116, D1117, D1125, D1127, D1135, S1136 and T1138 of the region 4-1 of the wild-type SpCas9.

In one exemplary embodiment, the SpCas9 variant may be in a form in which two or more amino acids selected from the amino acid sequence of the first region and the fourth region of the wild-type SpCas9 are modified.

Here, the first region may be the region 1-1, the region 1-2, the region 1-3 and the region 1-4.

Here, the fourth region may be the region 4-1.

For example, the SpCas9 variant may be a form with modifications of two or more amino acids selected from the group consisting of A203, N277, G366, K510, Y515, F539, G582, V583, E584, D585, N588, I601, N692, M694, Q695, H698, T1102, S1106, E1108, S1116, D1117, D1125, D1127, D1135, S1136 and T1138 of the first region and the fourth region of the wild-type SpCas9.

For example, the SpCas9 variant may be a form with modifications of two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, T1102, S1106, E1108, S1116, D1117, D1125, D1127, D1135, S1136 and T1138 of the first region and the fourth region of the wild-type SpCas9.

The Cas9 variant may be in a form in which two or more amino acids selected from the amino acid sequence of the second region and the third region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence of the second region and the third region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 2-1 and the region 3-1 of the wild-type SpCas9 are modified.

For example, the SpCas9 variant may be a form with modifications of two or more amino acids selected from the group consisting of I7, G8, L9, D10, I11, G12, V838, D839, H840, D853, N854, K855, K862, N863, R864, A889, K890 and L891 of the region 2-1 and the region 3-1 of the wild-type SpCas9.

For example, the SpCas9 variant may be a form with modifications of two or more amino acids selected from the group consisting of the non-polar amino acids, that is, I7, G8, L9, I11, G12, V16, G17, W18, A19, V20 and I21 of the region 2-1 of the wild-type SpCas9; and charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In another exemplary embodiment, the SpCas9 variant may be in a form in which two or more amino acids selected from the amino acid sequence of the region 2-2 and the region 3-1 of the wild-type SpCas9 are modified.

For example, the SpCas9 variant may be a form with modifications of two or more amino acids selected from the group consisting of I761, E762, M763, R765, E766, N767, V838, D839, H840, D853, N854, K855, K862, N863, R864, A889, K890 and L891 of the region 2-2 and the region 3-1 of the wild-type SpCas9.

For example, the SpCas9 variant may be a form with modifications of two or more amino acids selected from the group consisting of the non-polar amino acids, that is, P731, A732, I733, G736, I737, L738, V741, V743, V744, L747, V748, V750, M751, G752, P756, I759, V760, I761, M763 and A764 of the region 2-2 of the wild-type SpCas9; and the charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In still another exemplary embodiment, the SpCas9 variant may be in a form in which two or more amino acids selected from the amino acid sequence of the region 2-3 and the region 3-1 of the wild-type SpCas9 are modified.

For example, the SpCas9 variant may be a form with modifications of two or more amino acids selected from the group consisting of V838, D839, H840, D853, N854, K855, K862, N863, R864, A889, K890, L891, D965, Y981, H982, H983, A984, H985, D986, A987, Y988, Y1036, F1037, F1038 and Y1039 of the region 2-3 and the region 3-1 of the wild-type SpCas9.

For example, the SpCas9 variant may be a form with modifications of two or more amino acids selected from the group consisting of the non-polar amino acids, that is, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-3 of the wild-type SpCas9; and charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the region 3-1 of the wild-type SpCas9.

In one exemplary embodiment, the SpCas9 variant may be in a form in which two or more amino acids selected from the amino acid sequence of the second region and the third region of the wild-type SpCas9 are modified.

Here, the second region may be the region 2-1, the region 2-2 and the region 2-3.

Here, the third region may be the region 3-1.

For example, the SpCas9 variant may be a form with modifications of two or more amino acids selected from the group consisting of I7, G8, L9, D10, I11, G12, I761, E762, M763, R765, E766, N767, V838, D839, H840, D853, N854, K855, K862, N863, R864, A889, K890, L891, Y981, H982, H983, A984, H985, D965, D986, A987, Y988, Y1036, F1037, F1038 and Y1039 of the second region and the third region of the wild-type SpCas9.

For example, the SpCas9 variant may be a form with modifications of two or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the second region and the third region of the wild-type SpCas9.

The Cas9 variant may be in a form in which two or more amino acids selected from the amino acid sequence of the second region and the fourth region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence of the second region and the fourth region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 2-1 and the region 4-1 of the wild-type SpCas9 are modified.

For example, the SpCas9 variant may be a form with modifications of two or more amino acids selected from the group consisting of I7, G8, L9, D10, I11, G12, T1102, S1106, E1108, S1116, D1117, D1125, D1127, D1135, S1136 and T1138 of the region 2-1 and the region 4-1 of the wild-type SpCas9.

For example, the SpCas9 variant may be a form with modifications of two or more amino acids selected from the group consisting of the non-polar amino acids, that is, I7, G8, L9, I11, G12, V16, G17, W18, A19, V20 and I21 of the region 2-1 of the wild-type SpCas9; and T1102, S1106, E1108, S1116, D1117, D1125, D1127, D1135, S1136 and T1138 of the region 4-1 of the wild-type SpCas9.

In another exemplary embodiment, the SpCas9 variant may be in a form in which two or more amino acids selected from the amino acid sequence of the region 2-2 and the region 4-1 of the wild-type SpCas9 are modified.

For example, the SpCas9 variant may be a form with modifications of two or more amino acids selected from the group consisting of I761, E762, M763, R765, E766, N767, T1102, S1106, E1108, S1116, D1117, D1125, D1127, D1135, S1136 and T1138 of the region 2-2 and the region 4-1 of the wild-type SpCas9.

For example, the SpCas9 variant may be a form with modifications of two or more amino acids selected from the group consisting of the non-polar amino acids, that is, P731, A732, I733, G736, I737, L738, V741, V743, V744, L747, V748, V750, M751, G752, P756, I759, V760, I761, M763 and A764 of the region 2-2 of the wild-type SpCas9; and T1102, S1106, E1108, S1116, D1117, D1125, D1127, D1135, S1136 and T1138 of the region 4-1 of the wild-type SpCas9.

In still another exemplary embodiment, the SpCas9 variant may be in a form in which two or more amino acids selected from the amino acid sequence of the region 2-3 and the region 4-1 of the wild-type SpCas9 are modified.

For example, the SpCas9 variant may be a form with modifications of two or more amino acids selected from the group consisting of D965, Y981, H982, H983, A984, H985, D986, A987, Y988, Y1036, F1037, F1038, Y1039, T1102, S1106, E1108, S1116, D1117, D1125, D1127, D1135, S1136 and T1138 of the region 2-3 and the region 4-1 of the wild-type SpCas9.

For example, the SpCas9 variant may be a form with modifications of two or more amino acids selected from the group consisting of the non-polar amino acids, that is, I927, V931, A932, I934, L935, M939, L949, I950, V953, V955, I956, L958, L962, V963, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the region 2-3 of the wild-type SpCas9; and T1102, S1106, E1108, S1116, D1117, D1125, D1127, D1135, S1136 and T1138 of the region 4-1 of the wild-type SpCas9.

In one exemplary embodiment, the SpCas9 variant may be in a form in which two or more amino acids selected from the amino acid sequence of the second region and the fourth region of the wild-type SpCas9 are modified.

Here, the second region may be the region 2-1, the region 2-2 and the region 2-3.

Here, the fourth region may be the region 4-1.

For example, the SpCas9 variant may be a form with modifications of two or more amino acids selected from the group consisting of I7, G8, L9, D10, I11, G12, I761, E762, M763, R765, E766, N767, D965, Y981, H982, H983, A984, H985, D986, A987, Y988, Y1036, F1037, F1038, Y1039, T1102, S1106, E1108, S1116, D1117, D1125, D1127, D1135, S1136 and T1138 of the second region and the fourth region of the wild-type SpCas9.

For example, the SpCas9 variant may be a form with modifications of two or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1038, Y1039, T1102, S1106, E1108, S1116, D1117, D1125, D1127, D1135, S1136 and T1138 of the second region and the fourth region of the wild-type SpCas9.

The Cas9 variant may be in a form in which two or more amino acids selected from the amino acid sequence of the third region and the fourth region of the wild-type Cas9 are modified. Here, the two or more amino acids may be present in different regions, respectively.

In one example, when the wild-type Cas9 is a wild-type SpCas9, a SpCas9 variant may be in a form in which two or more amino acids selected from the amino acid sequence of the third region and the fourth region of the wild-type SpCas9 are modified. Here, the two or more amino acids may be present in different regions, respectively.

In one exemplary embodiment, the SpCas9 variant may be in a form in which two or more amino acids selected from the amino acid sequence of the region 3-1 and the region 4-1 of the wild-type SpCas9 are modified.

For example, the SpCas9 variant may be a form with modifications of two or more amino acids selected from the group consisting of V838, D839, H840, D853, N854, K855, K862, N863, R864, A889, K890, L891, T1102, S1106, E1108, S1116, D1117, D1125, D1127, D1135, S1136 and T1138 in the region 3-1 and the region 4-1 of the wild-type SpCas9.

For example, the SpCas9 variant may be a form with modifications of two or more amino acids selected from the group consisting of the charged amino acids, that is, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 in the region 3-1 of the wild-type SpCas9; and T1102, S1106, E1108, S1116, D1117, D1125, D1127, D1135, S1136 and T1138 of the region 4-1 of the wild-type SpCas9.

The Cas9 variant may be in a form in which three or more amino acids selected from the amino acid sequence(s) of the first region, the second region, the third region and/or the fourth region of the wild-type Cas9 are modified. Here, the three or more amino acids may be present in different regions, respectively.

In one example, when the wild-type Cas9 is a wild-type SpCas9, a SpCas9 variant may be in a form in which three or more amino acids selected from the amino acid sequence(s) of the first region, the second region, the third region and/or the fourth region of the wild-type SpCas9 are modified. Here, the three or more amino acids may be present in different regions, respectively.

In one exemplary embodiment, the SpCas9 variant may be in a form in which three or more amino acids selected from the amino acid sequence(s) of the first region, the second region and the third region of the wild-type SpCas9 are modified.

Here, the first region may be the region 1-1, the region 1-2, the region 1-3 and the region 1-4.

Here, the second region may be the region 2-1, the region 2-2 and the region 2-3.

Here, the third region may be the region 3-1.

For example, the SpCas9 variant may be a form with modifications of three or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038 and Y1039 of the first region, the second region and third region of the wild-type SpCas9.

For example, the SpCas9 variant may be a form with modifications of three or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the first region, the second region and the third region of the wild-type SpCas9.

In another exemplary embodiment, the SpCas9 variant may be in a form in which three or more amino acids selected from the amino acid sequence(s) of the first region, the second region and the fourth region of the wild-type SpCas9 are modified.

Here, the first region may be the region 1-1, the region 1-2, the region 1-3 and the region 1-4.

Here, the second region may be the region 2-1, the region 2-2 and the region 2-3.

Here, the fourth region may be the region 4-1.

For example, the SpCas9 variant may be a form with modifications of three or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, D965, Y981, H982, H983, A984, H985, D986, A987, Y988, Y1036, F1037, F1038, Y1039, T1102 and D1127 of the first region, the second region and the fourth region of the wild-type SpCas9.

For example, the SpCas9 variant may be a form with modifications of three or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the first region, the second region and the fourth region of the wild-type SpCas9.

In still another exemplary embodiment, the SpCas9 variant may be in a form in which three or more amino acids selected from the amino acid sequence(s) of the first region, the third region and the fourth region of the wild-type SpCas9 are modified.

Here, the first region may be the region 1-1, the region 1-2, the region 1-3 and the region 1-4.

Here, the third region may be the region 3-1.

Here, the fourth region may be the region 4-1.

For example, the SpCas9 variant may be a form with modifications of three or more amino acids selected from the group consisting of A203, N277, G366, K510, Y515, F539, G582, V583, E584, D585, N588, I601, N692, M694, Q695, H698, V838, D839, H840, D853, N854, K855, K862, N863, R864, A889, K890, L891, T1102 and D1127 of the first region, the third region and the fourth region of the wild-type SpCas9.

For example, the SpCas9 variant may be a form with modifications of three or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, T1102, S1106, E1108, S1116, D1117, D1125, D1127, D1135, S1136 and T1138 of the first region, the third region and the fourth region of the wild-type SpCas9.

In another exemplary embodiment, the SpCas9 variant may be in a form in which three or more amino acids selected from the amino acid sequence(s) of the second region, the third region and the fourth region of the wild-type SpCas9 are modified.

Here, the second region may be the region 2-1, the region 2-2 and the region 2-3.

Here, the third region may be the region 3-1.

Here, the fourth region may be the region 4-1.

For example, the SpCas9 variant may be a form with modifications of three or more amino acids selected from the group consisting of I7, G8, L9, D10, I11, G12, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the second region, the third region and the fourth region of the wild-type SpCas9.

For example, the SpCas9 variant may be a form with modifications of three or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the second region, the third region and the fourth region of the wild-type SpCas9.

The Cas9 variant may be in a form in which four or more amino acids selected from the amino acid sequences of the first region, the second region, the third region and the fourth region of the wild-type Cas9 are modified. Here, the four or more amino acids may be present in different regions, respectively.

In one example, when the wild-type Cas9 is a wild-type SpCas9, a SpCas9 variant may be in a form in which four or more amino acids selected from the amino acid sequences of the first region, the second region, the third region and the fourth region of the wild-type SpCas9 are modified. Here, the four or more amino acids may be present in different regions, respectively.

In one exemplary embodiment, the SpCas9 variant may be in a form in which three or more amino acids selected from the amino acid sequences of the first region, the second region, the third region and the fourth region of the wild-type SpCas9 are modified.

Here, the first region may be the region 1-1, the region 1-2, the region 1-3 and the region 1-4.

Here, the second region may be the region 2-1, the region 2-2 and the region 2-3.

Here, the third region may be the region 3-1.

Here, the fourth region may be the region 4-1.

For example, the SpCas9 variant may be a form with modifications of three or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the first region, the second region, the third region and the fourth region of the wild-type SpCas9.

For example, the SpCas9 variant may be a form with modifications of three or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the first region, the second region, the third region and the fourth region of the wild-type SpCas9.

The Cas9 variant may include a modification of at least one amino acid selected from the one or more regions.

Here, the modification may be a deletion of the selected one or more amino acids.

In one example, when the wild-type Cas9 is a wild-type SpCas9, the modification may be a deletion of one or more amino acids selected from the amino acid sequence of the first region of the wild-type SpCas9.

In one exemplary embodiment, the modification may be a deletion of one or more amino acids selected from the amino acid sequence(s) of the region 1-1, the region 1-2, the region 1-3 and/or the region 1-4 of the wild-type SpCas9.

For example, the modification may be a deletion of one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9.

The modification may be a deletion of one or more amino acids selected from the amino acid sequence of the second region of the wild-type SpCas9.

In one exemplary embodiment, the modification may be a deletion of one or more amino acids selected from the amino acid sequence(s) in the region 2-1, the region 2-2 and/or the region 2-3 of the wild-type SpCas9.

For example, the modification may be a deletion of one or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the wild-type SpCas9.

The modification may be a deletion of one or more amino acids selected from the amino acid sequence of the third region of the wild-type SpCas9.

In one exemplary embodiment, the modification may be a deletion of one or more amino acids selected from the amino acid sequence of the region 3-1 of the wild-type SpCas9.

For example, the modification may be a deletion of one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the wild-type SpCas9.

The modification may be a deletion of one or more amino acids selected from the amino acid sequence of the fourth region of the wild-type SpCas9.

In one exemplary embodiment, the modification may be a deletion of one or more amino acids selected from the amino acid sequence of the region 4-1 of the wild-type SpCas9.

For example, the modification may be a deletion of one or more amino acids selected from the group consisting of T1102, S1106, E1108, S1116, D1117, D1125, D1127, D1135, S1136 and T1138 of the region 4-1 of the wild-type SpCas9.

The modification may be a deletion of two or more amino acids selected from the amino acid sequence(s) of the first region, the second region, the third region and/or the fourth region of the wild-type SpCas9.

In one exemplary embodiment, the modification may be a deletion of two or more amino acids selected from the amino acid sequence in the region 1-1, the region 1-2, the region 1-3, the region 1-4, the region 2-1, the region 2-2, the region 2-3, the region 3-1 and/or the region 4-1 of the wild-type SpCas9.

For example, the modification may be a deletion of two or more amino acids selected from the group consisting of I7, G8, L9, D10, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9.

Here, the modification may be a substitution of the selected one or more amino acids with different amino acid(s).

In one example, when the wild-type Cas9 is a wild-type SpCas9, the modification may be a substitution of one or more amino acids selected from the amino acid sequence of the first region of the wild-type SpCas9 with different amino acid(s).

In one exemplary embodiment, the modification may be a substitution of one or more amino acids selected from the amino acid sequence(s) of the region 1-1, the region 1-2, the region 1-3 and/or the region 1-4 of the wild-type SpCas9 with stereoisomer(s).

For example, the modification may be a substitution of one or more amino acids selected from the group consisting of A203, N277, G366, K510, Y515, F539, G582, V583, E584, D585, N588, I601, N692, M694, Q695 and H698 of the wild-type SpCas9 with stereoisomer(s). For example, when lysine at 510$^{th}$ position (K510) of the wild-type SpCas9 is L-lysine, the modification may be to substitute the lysine at 510$^{th}$ position (K510) of the wild-type SpCas9 with D-lysine.

In one exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having a relatively low hydropathy index.

For example, the modification may be a substitution of one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9 with amino acid(s) having a relatively low hydropathy index. For example, the modification may be to substitute phenylalanine at 539$^{th}$ position (F539, hydropathy index: 2.8) of the wild-type SpCas9 with serine (hydropathy index: −0.8) having a relatively low hydropathy index. Alternatively, the modification may be to substitute isoleucine at 601$^{th}$ position (I601, hydropathy index: 4.5) of the wild-type SpCas9 with asparagine (hydropathy index: −3.5) having a relatively low hydropathy index.

In another exemplary embodiment, the modification may be a substitution of one or more amino acids selected from the amino acid sequence of the region 1-1, the region 1-2, the region 1-3 and/or the region 1-4 of the wild-type SpCas9 with amino acid(s) having a relatively high hydropathy index.

For example, the modification may be a substitution of one or more amino acids selected from the group consisting of A203, N277, G366, K510, Y515, F539, G582, V583, E584, D585, N588, I601, N692, M694, Q695 and H698 of the wild-type SpCas9 with an amino acid having a relatively high hydropathy index. For example, the modification may be to substitute asparagine at 277$^{th}$ position (N277, hydropathy index: −3.5) of the wild-type SpCas9 with histidine (hydropathy index: −3.2) having a relatively high hydropathy index.

In still another exemplary embodiment, the modification may be a substitution of one or more amino acids selected from the amino acid sequence of the region 1-1, the region 1-2, the region 1-3 and/or the region 1-4 of the wild-type SpCas9 with amino acid(s) having a relatively high or low hydropathy index.

In one exemplary embodiment, the modification may be a substitution of one or more amino acids selected from the amino acid sequence of the region 1-1, the region 1-2, the region 1-3 and/or the region 1-4 of the wild-type SpCas9 with amino acid(s) having a relatively small functional group.

For example, the modification may be a substitution of one or more amino acids selected from the group consisting of A203, N277, G366, K510, Y515, F539, G582, V583, E584, D585, N588, I601, N692, M694, Q695 and H698 of the wild-type SpCas9 with an amino acid having a relatively small functional group. For example, the modification may be to substitute phenylalanine at 539$^{th}$ position (F539) of the wild-type SpCas9 with serine having a relatively small functional group.

In another exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having a relatively large functional group.

For example, the modification may be a substitution of one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9 with an amino acid having a relatively large functional group. For example, the modification may be to substitute alanine at 203$^{th}$ position (A203) of the wild-type SpCas9 with aspartic acid having a relatively large functional group. For example, the modification may be to substitute glycine at 366$^{th}$ position (G366) of the wild-type SpCas9 with serine having a relatively large functional group.

In still another exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having a relatively large or small functional group.

In one exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having relatively low hydrophobicity.

For example, the modification may be a substitution of one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9 with an amino acid having relatively low hydrophobicity. For example, the modification may be to substitute phenylalanine at 539$^{th}$ position (F539, Kyte-Doolittle hydrophobicity: 2.8) and isoleucine at 601$^{th}$ position (I601, Kyte-Doolittle hydrophobicity: 4.5) of the wild-type SpCas9 with serine (Kyte-Doolittle hydrophobicity: −0.8) and asparagine (Kyte-Doolittle hydrophobicity: −3.5), which have relatively further low hydrophobicity, respectively.

In another exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having relatively high hydrophobicity.

For example, the modification may be a substitution of one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 of the wild-type SpCas9 with an amino acid having relatively high hydrophobicity. For example, the modification may be to substitute asparagine at 277th position (N277, Kyte-Doolittle hydrophobicity: −3.5) and phenylalanine at 682$^{th}$ position (F682, Kyte-Doolittle hydrophobicity: 2.8) of the wild-type SpCas9 with histidine (Kyte-Doolittle hydrophobicity: −3.2) and valine (Kyte-Doolittle hydrophobicity: 4.2), which have relatively high hydrophobicity, respectively.

In still another exemplary embodiment, the modification may be a substitution of one or more amino acids selected from the amino acid sequence(s) of the region 1-1, the region 1-2, the region 1-3 and/or the region 1-4 of the wild-type SpCas9 with amino acid(s) having relatively low or high hydrophobicity.

The modification may be a substitution of one or more amino acids selected from the amino acid sequence(s) of the second region of the wild-type SpCas9 with different amino acid(s).

In one exemplary embodiment, the modification may be a substitution of one or more amino acids selected from the amino acid sequence(s) of the region 2-1, the region 2-2 and/or the region 2-3 of the wild-type SpCas9 with stereoisomer(s).

For example, the modification may be a substitution of one or more amino acids selected from the group consisting of I7, G8, L9, D10, I11, G12, I761, E762, M763, R765, E766, N767, D965, Y981, H982, H983, A984, H985, D986, A987, Y988, Y1036, F1037, F1038 and Y1039 of the wild-type SpCas9 with stereoisomer(s). For example, when glycine at 12$^{th}$ position (G12) of the wild-type SpCas9 is L-glycine, the modification may be to substitute glycine at 12$^{th}$ position (G12) of the wild-type SpCas9 with D-glycine.

In one exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively low hydropathy index.

For example, the modification may be a substitution of one or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the wild-type SpCas9 with an amino acid having a relatively low hydropathy index. For example, the modification may be to substitute phenylalanine at 1038$^{th}$ position (F1038, hydropathy index: 2.8) of the wild-type SpCas9 with tyrosine (hydropathy index: −1.3) having a relatively low hydropathy index.

In another exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively high hydropathy index.

For example, the modification may be a substitution of one or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the wild-type SpCas9 with an amino acid having a relatively high hydropathy index. For example, the modification may be to substitute methionine at 763$^{th}$ position (M763, hydropathy index: 1.9) of the wild-type SpCas9 with isoleucine (hydropathy index: 4.5) having a relatively high hydropathy index. For example, the modification may be to substitute aspartic acid at 965$^{th}$ position (D965, hydropathy index: −3.5) of the wild-type SpCas9 with tyrosine (hydropathy index: −1.3) having a relatively high hydropathy index.

In still another exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively high or low hydropathy index.

In one exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively small functional group.

For example, the modification may be a substitution of one or more amino acids selected from the group consisting of I7, G8, L9, D10, I11, G12, I761, E762, M763, R765, E766, N767, D965, Y981, H982, H983, A984, H985, D986, A987, Y988, Y1036, F1037, F1038 and Y1039 of the wild-type SpCas9 with an amino acid having a relatively small functional group. For example, the modification may be to substitute methionine at 763$^{th}$ position (M763) of the wild-type SpCas9 with isoleucine having a relatively small functional group.

In another exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively large functional group.

For example, the modification may be a substitution of one or more amino acids selected from the group consisting of I7, G8, L9, D10, I11, G12, I761, E762, M763, R765, E766, N767, D965, Y981, H982, H983, A984, H985, D986, A987, Y988, Y1036, F1037, F1038 and Y1039 of the wild-type SpCas9 with an amino acid having a relatively large functional group. For example, the modification may be to substitute phenylalanine at 1038$^{th}$ position (F1038) of the wild-type SpCas9 with tyrosine having a relatively large functional group.

In still another exemplary embodiment, the modification may be a substitution of one or more amino acids selected from the amino acid sequence(s) of the region 2-1, the region 2-2 and/or the region 2-3 of the wild-type SpCas9 with amino acid(s) having a relatively large or small functional group.

In one exemplary embodiment, the modification may be a substitution of one or more amino acids selected from the amino acid sequence(s) of the region 2-1, the region 2-2 and/or the region 2-3 of the wild-type SpCas9 with amino acid(s) having relatively low hydrophobicity.

For example, the modification may be a substitution of one or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the wild-type SpCas9 with an amino acid having relatively low hydrophobicity. For example, the modification may be to substitute isoleucine at 761$^{th}$ position (I761, Kyte-Doolittle hydrophobicity: 4.5) and phenylalanine at 1038th position (F1038, Kyte-Doolittle hydrophobicity: 2.8) of the wild-type SpCas9 with methionine (Kyte-Doolittle hydrophobicity: 1.9) and tyrosine (Kyte-Doolittle hydrophobicity: −1.3), which have relatively low hydrophobicity, respectively.

In another exemplary embodiment, the modification may be a substitution of one or more amino acids selected from the amino acid sequence(s) of the region 2-1, the region 2-2 and/or the region 2-3 of the wild-type SpCas9 with amino acid(s) having relatively high hydrophobicity.

For example, the modification may be a substitution of one or more amino acids selected from the group consisting of I7, G8, L9, I11, G12, V16, G17, W18, A19, V20, I21, P731, A732, I733, G736, I737, L738, V741, V743, V744, L747, V748, V750, M751, G752, P756, I759, V760, I761, M763, A764, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037 and F1038 of the wild-type SpCas9 with an amino acid having relatively high hydrophobicity. For example, the modification may be to substitute methionine at 763$^{th}$ position (M763, Kyte-Doolittle hydrophobicity: 1.9) and alanine at 932th position (A932, Kyte-Doolittle hydrophobicity: 1.8) of the wild-type SpCas9 with isoleucine (Kyte-Doolittle hydrophobicity: 4.5) and cysteine (Kyte-Doolittle hydrophobicity: 2.5), which have relatively high hydrophobicity, respectively.

In still another exemplary embodiment, the modification may be a substitution of one or more amino acids selected from the amino acid sequence(s) of the region 2-1, the region 2-2 and/or the region 2-3 of the wild-type SpCas9 with amino acid(s) having relatively low or high hydrophobicity.

The modification may be a substitution of one or more amino acids selected from the amino acid sequence of the third region of the wild-type SpCas9 with a different amino acid.

In one exemplary embodiment, the modification may be a substitution of one or more amino acids selected from the amino acid sequence of the region 3-1 of the wild-type SpCas9 with stereoisomer(s).

For example, the modification may be a substitution of one or more amino acids selected from the group consisting of V838, D839, H840, D853, N854, K855, K862, N863, R864, A889, K890 and L891 of the wild-type SpCas9 with a stereoisomer. For example, when aspartic acid at 853$^{th}$ position (D853) of the wild-type SpCas9 is L-aspartic acid, the modification may be to substitute aspartic acid at 853$^{th}$ position (D853) of the wild-type SpCas9 with D-aspartic acid.

In one exemplary embodiment, the modification may be a substitution of one or more amino acids selected from the amino acid sequence of the region 3-1 of the wild-type SpCas9 with an amino acid having a relatively low hydropathy index.

For example, the modification may be a substitution of one or more amino acids selected from the group consisting of V838, D839, H840, D853, N854, K855, K862, N863, R864, A889, K890 and L891 of the wild-type SpCas9 with an amino acid having a relatively low hydropathy index. For example, the modification may be to substitute lysine at 862$^{th}$ position (K862, hydropathy index: −3.9) of the wild-type SpCas9 with arginine (hydropathy index: −4.5) having a relatively low hydropathy index.

In another exemplary embodiment, the modification may be a substitution of one or more amino acids selected from the amino acid sequence of the region 3-1 of the wild-type SpCas9 with an amino acid having a relatively high hydropathy index.

For example, the modification may be a substitution of one or more amino acids selected from the group consisting of V838, D839, H840, D853, N854, K855, K862, N863, R864, A889, K890 and L891 of the wild-type SpCas9 with an amino acid having a relatively high hydropathy index. For example, the modification may be to substitute lysine at 890$^{th}$ position (K890, hydropathy index: −3.9) of the wild-type SpCas9 with asparagine (hydropathy index: −3.5) having a relatively high hydropathy index.

In still another exemplary embodiment, the modification may be a substitution of one or more amino acids selected from the amino acid sequence of the region 3-1 of the wild-type SpCas9 with amino acid(s) having a relatively high or low hydropathy index.

In one exemplary embodiment, the modification may be a substitution of one or more amino acids selected from the amino acid sequence of the region 3-1 of the wild-type SpCas9 with amino acid(s) having a relatively small functional group.

For example, the modification may be a substitution of one or more amino acids selected from the group consisting of V838, D839, H840, D853, N854, K855, K862, N863, R864, A889, K890 and L891 of the wild-type SpCas9 with an amino acid having a relatively small functional group. For example, the modification may be to substitute lysine at 890$^{th}$ position (K890) of the wild-type SpCas9 with asparagine having a relatively small functional group.

In another exemplary embodiment, the modification may be a substitution of one or more amino acids selected from the amino acid sequence of the region 3-1 of the wild-type SpCas9 with amino acid(s) having a relatively large functional group.

For example, the modification may be a substitution of one or more amino acids selected from the group consisting of V838, D839, H840, D853, N854, K855, K862, N863, R864, A889, K890 and L891 of the wild-type SpCas9 with an amino acid having a relatively large functional group. For example, the modification may be to substitute asparagine at 863$^{th}$ position (N863) of the wild-type SpCas9 with arginine having a relatively large functional group.

In still another exemplary embodiment, the modification may be a substitution of one or more amino acids selected from the amino acid sequence of the region 3-1 of the wild-type SpCas9 with amino acid(s) having a relatively large or small functional group.

In one exemplary embodiment, the modification may be a substitution of one or more amino acids selected from the amino acid sequence of the region 3-1 of the wild-type SpCas9 with amino acid(s) having relatively low hydrophobicity.

For example, the modification may be a substitution of one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the wild-type SpCas9 with an amino acid having relatively low hydrophobicity. For example, the modification may be to substitute glutamic acid at 779$^{th}$ position (E779, Kyte-Doolittle hydrophobicity: −3.5) and lysine at 862th position (K862, Kyte-Doolittle hydrophobicity: −3.9) of the wild-type SpCas9 with lysine (Kyte-Doolittle hydrophobicity: −3.9) and arginine (Kyte-Doolittle hydrophobicity: −4.5), which have relatively low hydrophobicity, respectively.

In another exemplary embodiment, the modification may be a substitution of one or more amino acids selected from the amino acid sequence of the region 3-1 of the wild-type SpCas9 with amino acid(s) having relatively high hydrophobicity.

For example, the modification may be a substitution of one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 of the wild-type SpCas9 with an amino acid having relatively high hydrophobicity. For example, the modification may be to substitute glutamic acid at 827$^{th}$ position (E827, Kyte-Doolittle hydrophobicity: −3.5) and lysine at 890$^{th}$ position (K890, Kyte-Doolittle hydrophobicity: −3.9) of the wild-type SpCas9 with methionine (Kyte-Doolittle hydrophobicity: 1.9) and asparagine (Kyte-Doolittle hydrophobicity: −3.5), which have relatively high hydrophobicity, respectively.

In still another exemplary embodiment, the modification may be a substitution of one or more amino acids selected from the amino acid sequence of the region 3-1 of the wild-type SpCas9 with amino acid(s) having relatively low or high hydrophobicity.

The modification may be a substitution of one or more amino acids selected from the amino acid sequence of the fourth region of the wild-type SpCas9 with a different amino acid.

In one exemplary embodiment, the modification may be a substitution of one or more amino acids selected from the amino acid sequence of the region 4-1 of the wild-type SpCas9 with stereoisomer(s).

For example, the modification may be a substitution of one or more amino acids selected from the group consisting of T1102, S1106, E1108, S1116, D1117, D1125, D1127, D1135, S1136 and T1138 of the wild-type SpCas9 with a stereoisomer. For example, when aspartic acid at 1127$^{th}$ position (D1127) of the wild-type SpCas9 is L-aspartic acid, the modification may be to substitute aspartic acid at 1127$^{th}$ position (D1127) of the wild-type SpCas9 with D-aspartic acid.

In one exemplary embodiment, the modification may be a substitution of one or more amino acids selected from the amino acid sequence of the region 4-1 of the wild-type SpCas9 with amino acid(s) having a relatively low hydropathy index.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having a relatively low hydropathy index. For example, the modification may be to substitute threonine at 1102$^{th}$ position (T1102, hydropathy index: −0.7) of the wild-type SpCas9 with proline (hydropathy index: −1.6) having a relatively low hydropathy index.

In another exemplary embodiment, the modification may be a substitution of one or more amino acids selected from the amino acid sequence of the region 4-1 of the wild-type SpCas9 with amino acid(s) having a relatively high hydropathy index.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having a relatively high hydropathy index. For example, the modification may be to substitute serine at 1106$^{th}$ position (S1106, hydropathy index: −0.8) of the wild-type SpCas9 with glycine (hydropathy index: −0.4) having a relatively high hydropathy index.

In still another exemplary embodiment, the modification may be a substitution of one or more amino acids selected from the amino acid sequence of the region 4-1 of the wild-type SpCas9 with amino acid(s) having a relatively high or low hydropathy index.

In one exemplary embodiment, the modification may be a substitution of one or more amino acids selected from the amino acid sequence of the region 4-1 of the wild-type SpCas9 with amino acid(s) having a relatively small functional group.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having a relatively small functional group. For example, the modification may be to substitute threonine at 1102$^{th}$ position (T1102) of the wild-type SpCas9 with proline having a relatively small functional group.

In another exemplary embodiment, the modification may be a substitution of one or more amino acids selected from the amino acid sequence of the region 4-1 of the wild-type SpCas9 with amino acid(s) having a relatively large functional group.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having a relatively large functional group. For example, the modification may be to substitute aspartic acid at 1127$^{th}$ position (D1127) of the wild-type SpCas9 with glutamic acid having a relatively large functional group.

In still another exemplary embodiment, the modification may be a substitution of one or more amino acids selected from the amino acid sequence of the region 4-1 of the wild-type SpCas9 with amino acid(s) having a relatively large or small functional group.

In one exemplary embodiment, the modification may be a substitution of one or more amino acids selected from the amino acid sequence of the region 4-1 of the wild-type SpCas9 with amino acid(s) having relatively low hydrophobicity.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having a relatively low hydrophobicity. For example, the modification may be to substitute threonine at 1102$^{th}$ position (T1102, Kyte-Doolittle hydrophobicity: −0.7) of the wild-type SpCas9 with proline (Kyte-Doolittle hydrophobicity: −1.6) having relatively low hydrophobicity.

In another exemplary embodiment, the modification may be a substitution of one or more amino acids selected from the amino acid sequence of the region 4-1 of the wild-type SpCas9 with amino acid(s) having relatively high hydrophobicity.

For example, the modification may be a substitution of one or more amino acids selected from the group consisting of T1102, S1106, E1108, S1116, D1117, D1125, D1127, D1135, S1136 and T1138 of the wild-type SpCas9 with an amino acid having relatively high hydrophobicity. For example, the modification may be to substitute glutamic acid at $1108^{th}$ position (E1108, Kyte-Doolittle hydrophobicity: −3.5) of the wild-type SpCas9 with methionine (Kyte-Doolittle hydrophobicity: 1.9) having a relatively high hydrophobicity.

In still another exemplary embodiment, the modification may be a substitution of one or more amino acids selected from the amino acid sequence of the region 4-1 of the wild-type SpCas9 with amino acid(s) having relatively low or high hydrophobicity.

The modification may be a substitution of two or more amino acids selected from the amino acid sequence in the first region, the second region, the third region and/or the fourth region of the wild-type SpCas9 with different amino acids.

In one exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with stereoisomers, respectively.

For example, the modification may be a substitution of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the wild-type SpCas9 with stereoisomers, respectively. For example, when glycine at $8^{th}$ position (G8) of the wild-type SpCas9 is L-glycine, and asparagine at $767^{th}$ position (N767) is L-asparagine, the modification may be to substitute glycine at $8^{th}$ position (G8) and asparagine at $767^{th}$ position (N767) of the wild-type SpCas9 with D-glycine and D-asparagine, respectively.

In one exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively small hydropathy index, respectively.

For example, the modification may be a substitution of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the wild-type SpCas9 with amino acids having a relatively small hydropathy index, respectively. For example, the modification may be to substitute alanine at $203^{th}$ position (A203, hydropathy index: 1.8) and phenylalanine at $539^{th}$ position (F539, hydropathy index: 2.8) of the wild-type SpCas9 with aspartic acid (hydropathy index: −3.5) and serine (hydropathy index: −0.8), which have a relatively low hydropathy index, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having a relatively small hydropathy index, respectively. For example, the modification may be to substitute isoleucine at $601^{th}$ position (I601, hydropathy index: 4.5) and threonine at $1102^{th}$ position (T1102, hydropathy index: −0.7) of the wild-type SpCas9 with asparagine (hydropathy index: −3.5) and proline (hydropathy index: −1.6), which have a relatively low hydropathy index, respectively.

In another exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively high hydropathy index, respectively.

For example, the modification may be a substitution of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the wild-type SpCas9 with amino acids having a relatively high hydropathy index, respectively. For example, the modification may be to substitute asparagine at $277^{th}$ position (N277, hydropathy index: −3.5) and histidine at $840^{th}$ position (H840, hydropathy index: −3.2) of the wild-type SpCas9 with histidine (hydropathy index: −3.2) and alanine (hydropathy index: 1.8), which have a relatively high hydropathy index, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having a relatively high hydropathy index, respectively. For example, the modification may be to substitute methionine at 763$^{th}$ position (M763, hydropathy index: 1.9) and lysine at 890$^{th}$ position (K890, hydropathy index: −3.9) of the wild-type SpCas9 with isoleucine (hydropathy index: 4.5) and asparagine (hydropathy index: −3.5), which have a relatively high hydropathy index, respectively.

In still another exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively high or low hydropathy index, respectively.

For example, the modification may be a substitution of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the wild-type SpCas9 with amino acids having a relatively high or low hydropathy index, respectively. For example, the modification may be to substitute aspartic acid at 10$^{th}$ position (D10, hydropathy index: −3.5) and histidine at 840$^{th}$ position (H840, hydropathy index: −3.2) of the wild-type SpCas9 with alanine (hydropathy index: 1.8) having a relatively high hydropathy index, respectively, and to substitute phenylalanine at 539$^{th}$ position (F539, hydropathy index: 2.8) of the wild-type SpCas9 with serine (hydropathy index: −0.8) having a relatively small hydropathy index.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having a relatively high or low hydropathy index, respectively. For example, the modification may be to substitute methionine at 763$^{th}$ position (M763, hydropathy index: 1.9) and lysine at 890$^{th}$ position (K890, hydropathy index: −3.9) of the wild-type SpCas9 with isoleucine (hydropathy index: 4.5) and asparagine (hydropathy index: −3.5), which have a relatively high hydropathy index, respectively, and to substitute phenylalanine at 539$^{th}$ position (F539, hydropathy index: 2.8) of the wild-type SpCas9 with serine (hydropathy index: −0.8) having a relatively low hydropathy index.

In one examplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively small functional group, respectively.

For example, the modification may be a substitution of two or more amino acids selected from the group consisting of I7, G8, L9, D10, I11, G12, A203, N277, G366, K510, Y515, F539, G582, V583, E584, D585, N588, I601, N692, M694, Q695, H698, I761, E762, M763, R765, E766, N767, V838, D839, H840, D853, N854, K855, K862, N863, R864, A889, K890, L891, D965, Y981, H982, H983, A984, H985, D986, A987, Y988, Y1036, F1037, F1038, Y1039, T1102 and D1127 of the wild-type SpCas9 with amino acids having a relatively small functional group, respectively. For example, the modification may be to substitute phenylalanine at 539$^{th}$ position (F539), methionine at 763$^{th}$ position (M763) and threonine at 1102$^{th}$ position (T1102) of wild-type SpCas9 with serine, isoleucine and proline, which have a relatively small functional group, respectively.

In another one exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively large functional group, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having a relatively large functional group, respectively. For example, the modification may be to substitute isoleucine at 601$^{th}$ position (I601), phenylalanine at 1038$^{th}$ position (F1038) and aspartic acid at 1127$^{th}$ position (D1127) of the wild-type SpCas9 with asparagine, tyrosine and glutamic acid, which have a relatively large functional group, respectively.

In still another exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having a relatively large or small functional group, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having a relatively large or small functional group. For example, the modification may be to substitute phenylalanine at 539$^{th}$ position (F539), methionine at 763$^{th}$ position (M763) and lysine at 890th position (K890) of the wild-type SpCas9 with serine, isoleucine and asparagine having a relatively small functional group, respectively, and to substitute isoleucine at 601$^{th}$ position (I601) and phenylalanine at 1038$^{th}$ position (F1038) with asparagine and tyrosine, which have a relatively large functional group.

In one exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having relatively low hydrophobicity, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having relatively low hydrophobicity, respectively. For example, the modification may be to substitute phenylalanine at 539$^{th}$ position (F539, Kyte-Doolittle hydrophobicity: 2.8), isoleucine at 601$^{th}$ position (I601, Kyte-Doolittle hydrophobicity: 4.5) and threonine at 1102$^{th}$ position (T1102, Kyte-Doolittle hydrophobicity: −0.7) of the wild-type SpCas9 with serine (Kyte-Doolittle hydrophobicity: −0.8), asparagine (Kyte-Doolittle hydrophobicity: −3.5) and proline (Kyte-Doolittle hydrophobicity: −1.6), which have relatively low hydrophobicity, respectively.

In another exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having relatively high hydrophobicity, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having relatively high hydrophobicity, respectively. For example, the modification may be to substitute aspartic acid at 10$^{th}$ position (D10, Kyte-Doolittle hydrophobicity: −3.5), methionine at 763th position (M763, Kyte-Doolittle hydrophobicity: 1.9), histidine at 840$^{th}$ position (H840, Kyte-Doolittle hydrophobicity: −3.2) and lysine at 890$^{th}$ position (K890, Kyte-Doolittle hydrophobicity: −3.9) of the wild-type SpCas9 with alanine (Kyte-Doolittle hydrophobicity: 1.8), isoleucine (Kyte-Doolittle hydrophobicity: 4.5), alanine (Kyte-Doolittle hydrophobicity: 1.8) and asparagine (Kyte-Doolittle hydrophobicity: −3.5), which have relatively high hydrophobicity, respectively.

In still another exemplary embodiment, the modification may be a substitution of two or more amino acids selected from the amino acid sequence of the region 1-1, the region 1-2, the region 1-3, the region 1-4, the region 2-1, the region 2-2, the region 2-3, the region 3-1 and/or the region 4-1 of the wild-type SpCas9 with amino acids having relatively low or high hydrophobicity, respectively.

For example, the modification may be a substitution of two or more amino acids selected from the group consisting of I7, G8, L9, I11, G12, V16, G17, W18, A19, V20, I21, N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696, I697, P731, A732, I733, G736, I737, L738, V741, V743, V744, L747, V748, V750, M751, G752, P756, I759, V760, I761, M763, A764, K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896, D898, I927, V931, A932, I934, L935, M939, L949, I950, V953, V955, I956, L958, L962, V963, D965, F966, F970, F972, V975, U978, A984, A987, L989, A991, V992, V993, G994, A996, L997, I998, P1002, L1004, F1008, V1009, G1011, V1015, V1018, M1021, I1022, A1023, I1029, G1030, A1032, A1034, F1037, F1038, T1102, S1106, E1108, S1116, D1117, D1125, D1127, D1135, S1136 and T1138 of the wild-type SpCas9 with amino acids having relatively low or high hydrophobicity, respectively. For example, the modification may be to substitute methionine at 763$^{th}$ position (M763, Kyte-Doolittle hydrophobicity: 1.9) and lysine at 890$^{th}$ position (K890, Kyte-Doolittle hydrophobicity: −3.9) of the wild-type SpCas9 with isoleucine (Kyte-Doolittle hydrophobicity: 4.5) and asparagine (Kyte-Doolittle hydrophobicity: −3.5), which have relatively high hydrophobicity, respectively, and to substitute phenylalanine at 539$^{th}$ position (F539, Kyte-Doolittle hydrophobicity: 2.8) of the wild-type SpCas9 with serine (Kyte-Doolittle hydrophobicity: −0.8) having relatively low hydrophobicity.

The modification may be a substitution of the selected one or more amino acids with the same number of other amino acids.

For example, the modification may be to substitute one isoleucine located in the first region of the wild-type SpCas9 with one asparagine. Alternatively, the modification may be to substitute one phenylalanine located in the first region of the wild-type SpCas9 and one lysine located in the third region with one serine (first region) and one asparagine (third region), respectively. Alternatively, the modification may be to substitute one methionine and one phenylalanine, which are located in the second region, and one lysine located in the third region of the wild-type SpCas9, with one isoleucine, one tyrosine (second region) and one asparagine (third region), respectively.

The modification may be a substitution of the selected one or more amino acids with a different number of other amino acids.

For example, the modification may be to substitute one threonine located in the second region of the wild-type SpCas9 with cysteine-alanine-alanine, that is, a total of three amino acids. Alternatively, the modification may be to substitute one glutamine located in the first region and two contiguous amino acids, glycine-serine, located in the third region of the wild-type SpCas9 with methionine-valine (first region) and proline (third region), respectively. Alternatively, the modification may be to substitute one serine located in the first region, three contiguous amino acids, lysine-lysine-tyrosine, located in the second region and two contiguous amino acids, serine-isoleucine, located in the third region of the wild-type SpCas9 with alanine (first region), methionine-proline (second region) and cysteine-alanine-threonine-valine (third region), respectively.

The artificially engineered Cas9 may be a Cas9 variant with an addition of at least one amino acid to one or more regions selected from the first region, the second region, the third region and the fourth region of the wild-type Cas9.

Here, the addition may be the addition of one or more amino acids to the N-terminal and/or C-terminal position(s) of one or more amino acids present in the selected one or more regions.

In one example, when the wild-type Cas9 is a wild-type SpCas9, the addition may be the addition of one or more amino acids to the N-terminal and/or C-terminal position(s) present in the first region, the second region, the third region and/or the fourth region of the wild-type SpCas9.

In one exemplary embodiment, the addition may be the addition of one or more positive charged amino acids to the N-terminal and/or C-terminal position(s) of one or more amino acids present in the first region, the second region, the third region and/or the fourth region of the wild-type SpCas9.

For example, the addition may be to add one arginine to the C-terminus of selected one alanine located in the region 1-1 of the wild-type SpCas9. Alternatively, the addition may be to add two amino acids, arginine-lysine, to the N-terminus of selected glutamic acid located in the region 2-2 of the wild-type SpCas9. Alternatively, the addition may be to add two amino acids, arginine-histidine, to the N-terminus of selected leucine located in the region 3-1 of the wild-type SpCas9. Alternatively, the addition may be to add two amino acids, lysine-histidine, to the C-terminus of selected leucine located in the region 3-1 of the wild-type SpCas9, and to add one lysine to the C-terminus of selected tyrosine located in the region 4-1 of the wild-type SpCas9.

In another exemplary embodiment, the addition may be the addition of one or more negatively-charged amino acids to N-terminal and/or C-terminal position(s) of the one or more amino acids present in the first region, the second region, the third region and/or the fourth region of the wild-type SpCas9.

For example, the addition may be to add one aspartic acid to the N-terminus of selected one glycine located in the region 1-2 of the wild-type SpCas9. Alternatively, the addition may be to add three amino acids, glutamic acid-aspartic acid-glutamic acid, to the C-terminus of selected methionine located in the region 2-3 of the wild-type SpCas9. Alternatively, the addition may be to add two amino acids, glutamic acid-glutamic acid, to the N-terminus of selected isoleucine located in the region 3-1 of the wild-type SpCas9. Alternatively, the addition may be to add two amino acids, glutamic acid-aspartic acid, to the C-terminus of selected phenylalanine located in the region 1-1 of the wild-type SpCas9, and to add one aspartic acid to the N-terminus of selected glutamine located in the region 2-1 of the wild-type SpCas9.

In still another exemplary embodiment, the addition may be the addition of one or more non-charged amino acids to the N-terminal and/or C-terminal position(s) present in the first region, the second region, the third region and/or the fourth region of the wild-type SpCas9.

For example, the addition may be to add two amino acids, serine-valine, to the C-terminus of selected one phenylalanine located in the region 1-1 of the wild-type SpCas9. Alternatively, the addition may be to add five amino acids, glycine-proline-glutamine-phenylalanine-leucine, to the N-terminus of selected histidine located in the region 2-1 of the wild-type SpCas9. Alternatively, the addition may be to add two amino acids, alanine-alanine, to the N-terminus of selected asparagine located in the region 3-1 of the wild-type SpCas9. Alternatively, the addition may be to add two amino acids, phenylalanine-leucine, to the C-terminus of selected aspartic acid located in the region 1-1 of the wild-type SpCas9, and to add one serine to the N-terminus of selected glutamine located in the region 1-2 of the wild-type SpCas9.

In another exemplary embodiment, the addition may be the addition of one or more amino acids selected from positively-charged amino acids, negatively-charged amino acids and non-charged amino acids to the N-terminal and/or C-terminal position(s) of one or more amino acids present in the first region, the second region, the third region and/or the fourth region of the wild-type SpCas9.

For example, the addition may be to add six amino acids, histidine-arginine-glycine-serine-alanine-glutamic acid, to the C-terminus of selected one arginine located in the region 1-2 of the wild-type SpCas9. Alternatively, the addition may be to add ten amino acids, lysine-lysine-alanine-phenylalanine-glutamine-threonine-methionine-cysteine-aspartic acid-serine, to the N-terminus of selected one glycine located in the region 3-1 of the wild-type SpCas9. Alternatively, the addition may be to add two amino acids, phenylalanine-histidine, to the C-terminus of selected methionine located in the region 2-1 of the wild-type SpCas9, and to add one lysine to the N-terminus of selected glutamine located in the region 2-3 of the wild-type SpCas9. Alternatively, the addition may be to add two amino acids, aspartic acid-serine, to the C-terminus of selected lysine located in the region 1-1 of the, to add six amino acids, glutamine-threonine-methionine-cysteine-aspartic acid-lysine, to the N-terminus of selected threonine located in the region 2-2 of the wild-type SpCas9, and to add two amino acids, arginine-glycine, to the C-terminus of selected glutamine located in the region 4-1 of the wild-type SpCas9.

Here, the addition may be the addition of one or more functional domains to the N-terminal and/or C-terminal position(s) of one or more amino acids present in the selected one or more regions.

The functional domain may be a domain having an additional function, in addition to the original functions of the wild-type Cas9, that is, a first function of cleaving a first strand of double-stranded DNA and a second function of cleaving a second strand of the double-stranded DNA.

Alternatively, the functional domain may be a domain having a function similar to the original functions of the wild-type Cas9, that is, a first function of cleaving a first strand of double-stranded DNA and/or a second function of cleaving a second strand of the double-stranded DNA.

Descriptions related to the functional domain are the same as described above.

In one example, when the wild-type Cas9 is a wild-type SpCas9, the addition may be the addition of one or more functional domain to the N-terminal and/or C-terminal position(s) of one or more amino acids present in the first region, the second region, the third region and/or the fourth region of the wild-type SpCas9.

In one exemplary embodiment of the disclosure disclosed herein, the artificially engineered Cas9 may be target-specific Cas9.

The "target-specific Cas9 (TS-Cas9)" refers to a Cas9 variant produced through artificial manipulation to relatively increase target specificity, compared to wild-type Cas9.

Here, the "target specificity" means that Cas9 forms a gRNA-Cas9 complex through the interaction with gRNA such that Cas9 specifically acts on a target sequence complementarily binding to gRNA when the gRNA-Cas9 complex approaches or is localized to a target gene or nucleic acid, that is, a subject (nucleic acid) to be manipulated using Cas9. Here, a target sequence completely complementary binding (100%) with gRNA is called an "on-target," and a target sequence having incomplete complementary binding (less than 100%), that is, one or more non-complementary bonds, with gRNA is called an "off-target."

The target specificity may vary according to the degree of complementary binding between gRNA and the target sequence.

In one example, in the case in which a target sequence complementarily binding to gRNA is an on-target, that is, complementary binding between gRNA and the target sequence are full complementary binding (100%), the target specificity is at the highest level.

In another example, in the case in which the target sequence complementarily binding to gRNA is an off-target, that is, complementary binding between gRNA and the target sequence are less than 100% and include one or more non-complementary bonds between them, the target specificity may be lower than that of the on-target, and the higher the number of the non-complementary bonds, the lower the target specificity.

For example, when complementary binding between gRNA and the target sequence is complete complementary binding (100%), the target specificity may be 100%, and when there is one non-complementary bond between gRNA and the target sequence, that is, complementary binding between gRNA and the target sequence is incomplete complementary binding (95%), the target specificity may be 95%. In addition, when there are four non-complementary bonds between gRNA and the target sequence, that is, complementary binding between gRNA and the target sequence is incomplete complementary binding (80%), the target specificity may be 80%.

In still another example, when the target sequence complementarily binding to gRNA is an off-target, that is, the degree of complementary binding between gRNA and the target sequence is less than 100%, that is, there are one or more non-complementary bonds, the target specificity may vary according to the location of the non-complementary bond.

For example, when there is one non-complementary bond between gRNA and the target sequence, and the non-complementary bond becomes closer to PAM adjacent to the target sequence, the target specificity may be lower than that when the non-complementary bond is spaced far from PAM.

The target specificity may vary according to the degree of interaction of gRNA which complementary binds with the target sequence, and Cas9.

In one example, when the interaction of gRNA which complementary binds with the target sequence, and Cas9 may be reduced, the smaller the number of non-complementary bonds between gRNA and the target sequence, the higher target specificity.

For example, when the interaction of gRNA which complementarily bind to the target sequence, and Cas9 is reduced, the target specificity when there is one non-complementary bond between gRNA and the target sequence may be higher than that when there are three non-complementary bonds between gRNA and the target sequence.

In another example, when the interaction of gRNA which complementarily bind to the target sequence, and Cas9 is reduced, the Cas9 may have target specificity only when the complementary binding between gRNA and the target sequence is complete complementary binding (100%).

For example, in the case in which the interaction of gRNA complementarily binding to the target sequence and Cas9 is reduced, only when the target sequence is an on-target, the Cas9 may have target specificity.

The target specificity may vary according to the degree of interaction between the target sequence complementarily binding to gRNA and Cas9.

In one example, when the interaction between a target sequence complementarily binding to gRNA and Cas9 is reduced, the lower the number of non-complementary bonds between gRNA and the target sequence, the higher the target specificity.

For example, when the interaction between a target sequence complementarily binding to gRNA and Cas9 is reduced, compared to the case in which there are four non-complementary bonds between gRNA and the target sequence, in the case in which there are two non-complementary bonds therebetween, target specificity may relatively increase.

In another example, when the interaction between a target sequence complementarily binding to gRNA and Cas9 is reduced, only in the case in which complementary binding between gRNA and the target sequence is complete complementary binding (100%), the Cas9 may have target specificity.

For example, when the interaction between a target sequence complementarily binding to gRNA and Cas9 is reduced, only when the target sequence is an on-target, the Cas9 may have target specificity.

The target-specific Cas9 may be a Cas9 variant manipulating an on-target.

Here, the manipulation may be to cleave the nucleotide sequence of the on-target using the Cas9 variant, or to modify the nucleotide sequence of an on-target such that one or more nucleotides may be deleted from and/or inserted into the nucleotide sequence of the on-target.

The target-specific Cas9 may be a Cas9 variant which has a target specificity for the on-target, which is the same as or higher than that of the wild-type Cas9.

The target-specific Cas9 may be a Cas9 variant that does not manipulate an off-target.

Here, the manipulation may be to cleave the nucleotide sequence of the off-target using the Cas9 variant, or to modify the nucleotide sequence of the off-target such that one or more nucleotides may be deleted from and/or inserted into the nucleotide sequence of the off-target.

The target-specific Cas9 may be a Cas9 variant which is decreased in target specificity for the on-target, compared to the wild-type Cas9.

The target-specific Cas9 may be a Cas9 variant which has the same target specificity for the on-target and lower target specificity for the off-target, compared to the wild-type Cas9.

The target-specific Cas9 may be a Cas9 variant which has the same target specificity for the off-target and higher target specificity for the on-target, compared to the wild-type Cas9.

The target-specific Cas9 may be a Cas9 variant which has higher target specificity for the on-target and lower target specificity for the off-target, compared to the wild-type Cas9.

The target-specific Cas9 may be a Cas9 variant which has lower target specificity for the on-target and lower target specificity for the off-target, compared to the wild-type Cas9.

In one exemplary embodiment of the disclosure disclosed herein, the target-specific Cas9 may be a target-specific SpCas9.

The "target-specific SpCas9 (TS-SpCas9)" refers to a SpCas9 variant produced by artificial manipulation to relatively increase target specificity, compared to the wild-type SpCas9.

The TS-SpCas9 may be a SpCas9 variant manipulating the on-target.

Here, the manipulation may be to cleave the nucleotide sequence of the on-target using the SpCas9 variant, or to modify the nucleotide sequence of the on-target such that one or more nucleotides may be deleted from and/or inserted into the nucleotide sequence of the on-target.

The TS-SpCas9 may be a SpCas9 variant which has the same or higher target specificity for the on-target, compared to the wild-type SpCas9.

The TS-SpCas9 may be a SpCas9 variant that does not manipulate the off-target.

Here, the manipulation may be to cleave the nucleotide sequence of the off-target using the SpCas9 variant, or to modify the nucleotide sequence of the off-target such that one or more nucleotides may be deleted from and/or inserted into the nucleotide sequence of the off-target.

The TS-SpCas9 may be a SpCas9 variant having reduced target specificity for the off-target, compared to the wild-type SpCas9.

The TS-SpCas9 may be a SpCas9 variant which has the same target specificity for the on-target and lower target specificity for the off-target, compared to the wild-type SpCas9.

The TS-SpCas9 may be a SpCas9 variant which has the same target specificity for the off-target and higher target specificity for the on-target, compared to the wild-type SpCas9.

The TS-SpCas9 may be a SpCas9 variant which has higher target specificity for the on-target and lower target specificity for the off-target, compared to the wild-type SpCas9.

The TS-SpCas9 may be a SpCas9 variant which has lower target specificity for the on-target and lower target specificity for the off-target, compared to the wild-type SpCas9.

The TS-SpCas9 may be a SpCas9 variant in which at least one amino acid in the amino acid sequence of one or more regions selected from the first region, the second region, the third region and the fourth region of the wild-type SpCas9 is modified.

The first region may be the amino acid sequence (region 1-1) from phenylalanine at $196^{th}$ position (F196) to isoleucine at $282^{th}$ position (I282) of the wild-type SpCas9.

The first region may be the amino acid sequence (region 1-2) from proline at 316th position (P316) to asparagine at $394^{th}$ position (N394) of the wild-type SpCas9.

The first region may be the amino acid sequence (region 1-3) from lysine at 510th position (K510) to asparagine at $612^{th}$ position (N612) of the wild-type SpCas9.

The first region may be the amino acid sequence (region 1-4) from threonine at $678^{th}$ position (T678) to histidine at $698^{th}$ position (H698) of the wild-type SpCas9.

The first region may be two regions selected from the amino acid sequence (region 1-1) from phenylalanine at $196^{th}$ position (F196) to isoleucine at $282^{th}$ position (I282), the amino acid sequence (region 1-2) from proline at $316^{th}$ position (P316) to asparagine at $394^{th}$ position (N394), the amino acid sequence (region 1-3) from lysine at $510^{th}$ position (K510) to asparagine at $612^{th}$ position (N612), and the amino acid sequence (region 1-4) from threonine at $678^{th}$ position (T678) to histidine at $698^{th}$ position (H698) of the wild-type SpCas9.

The first region may be three regions selected from the amino acid sequence (region 1-1) from phenylalanine at $196^{th}$ position (F196) to isoleucine at $282^{th}$ position (I282), the amino acid sequence (region 1-2) from proline at $316^{th}$ position (P316) to asparagine at $394^{th}$ position (N394), the amino acid sequence (region 1-3) from lysine at $510^{th}$ position (K510) to asparagine at $612^{th}$ position (N612), and the amino acid sequence (region 1-4) from threonine at $678^{th}$ position (T678) to histidine at $698^{th}$ position (H698) of the wild-type SpCas9.

The first region may be the amino acid sequence (region 1-1) from phenylalanine at $196^{th}$ position (F196) to isoleucine at $282^{th}$ position (I282), the amino acid sequence (region 1-2) from proline at $316^{th}$ position (P316) to asparagine at $394^{th}$ position (N394), the amino acid sequence (region 1-3) from lysine at $510^{th}$ position (K510) to asparagine at $612^{th}$ position (N612), and the amino acid sequence (region 1-4) from threonine at $678^{th}$ position (T678) to histidine at $698^{th}$ position (H698) of the wild-type SpCas9.

The second region may be the amino acid sequence (region 2-1) from methionine at 1st position (M1) to threonine at $22^{th}$ position (T22) of the wild-type SpCas9.

The second region may be the amino acid sequence (region 2-2) from proline at $731^{th}$ position (P731) to threonine at $770^{th}$ position (T770) of the wild-type SpCas9.

The second region may be the amino acid sequence (region 2-3) from glutamine at $926^{th}$ position (Q926) to serine at $1040^{th}$ position (S1040) of the wild-type SpCas9.

The second region may be the amino acid sequence (region 2-1) from methionine at $1^{st}$ position (M1) to threonine at $22^{th}$ position (T22) and the amino acid sequence (region 2-2) from proline at $731^{th}$ position (P731) to threonine at $770^{th}$ position (T770) of the wild-type SpCas9.

The second region may be the amino acid sequence (region 2-1) from methionine at $1^{st}$ position (M1) to threonine at $22^{th}$ position (T22) and the amino acid sequence (region 2-3) from glutamine at $926^{th}$ position (Q926) to serine at $1040^{th}$ position (S1040) of the wild-type SpCas9.

The second region may be the amino acid sequence (region 2-2) from proline at $731^{th}$ position (P731) to threonine at $770^{th}$ position (T770) and the amino acid sequence (region 2-3) from glutamine at $926^{th}$ position (Q926) to serine at $1040^{th}$ position (S1040) of the wild-type SpCas9.

The second region may be the amino acid sequence (region 2-1) from methionine at $1^{st}$ position (M1) to threonine at $22^{th}$ position (T22), the amino acid sequence (region 2-2) from proline at $731^{th}$ position (P731) to threonine at $770^{th}$ position (T770) and the amino acid sequence (region 2-3) from glutamine at $926^{th}$ position (Q926) to serine at $1040^{th}$ position (S1040) of the wild-type SpCas9.

The third region may be the amino acid sequence (region 3-1) from lysine at 775th position (K775) to leucine at $900^{th}$ position (L900) of the wild-type SpCas9.

The fourth region may be the amino acid sequence (region 4-1) from glutamic acid at 1099$^{th}$ position (E1099) to valine at 1139$^{th}$ position (V1139) of the wild-type SpCas9.

The TS-SpCas9 may be a SpCas9 variant formed by modifying one or more amino acids selected from the amino acid sequence of the first region of the wild-type SpCas9.

The TS-SpCas9 may be a SpCas9 variant formed by modifying one or more amino acids selected from the amino acid sequence of the region 1-1 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281 and I282 in the region 1-1 of the wild-type SpCas9.

The TS-SpCas9 may be a SpCas9 variant formed by modifying one or more amino acids selected from the amino acid sequence of the region 1-2 of the wild-type SpCas9.

The TS-SpCas9 may be a SpCas9 variant formed by modifying one or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 in the region 1-2 of the wild-type SpCas9.

The TS-SpCas9 may be a SpCas9 variant formed by modifying one or more amino acids selected from the amino acid sequence of the region 1-3 of the wild-type SpCas9.

The TS-SpCas9 may be a SpCas9 variant formed by modifying one or more amino acids selected from K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606 and L607 in the region 1-3 of the wild-type SpCas9.

The TS-SpCas9 may be a SpCas9 variant formed by modifying one or more amino acids selected from the amino acid sequence of the region 1-4 of the wild-type SpCas9.

The TS-SpCas9 may be a SpCas9 variant formed by modifying one or more amino acids selected from the group consisting of I679, L680, F682, L683, G687, F688, A689, N692, F693, M694, Q695, L696, I697 and H698 in the region 1-4 of the wild-type SpCas9.

The TS-SpCas9 may be a SpCas9 variant formed by modifying two or more amino acids selected from the amino acid sequences of the region 1-1 and the region 1-2 of the wild-type SpCas9.

The TS-SpCas9 may be a SpCas9 variant formed by modifying two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391 and L393 in the region 1-1 and the region 1-2 of the wild-type SpCas9.

The TS-SpCas9 may be a SpCas9 variant formed by modifying two or more amino acids selected from the amino acid sequences of the region 1-1 and the region 1-3 of the wild-type SpCas9.

The TS-SpCas9 may be a SpCas9 variant formed by modifying two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606 and L607 in the region 1-1 and the region 1-3 of the wild-type SpCas9.

The TS-SpCas9 may be a SpCas9 variant formed by modifying two or more amino acids selected from the amino acid sequences of the region 1-1 and the region 1-4 of the wild-type SpCas9.

The TS-SpCas9 may be a SpCas9 variant formed by modifying two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, I679, L680, F682, L683, G687, F688, A689, N692, F693, M694, Q695, L696, I697 and H698 in the region 1-1 and the region 1-4 of the wild-type SpCas9.

The TS-SpCas9 may be a SpCas9 variant formed by modifying two or more amino acids selected from the amino acid sequences of the region 1-2 and the region 1-3 of the wild-type SpCas9.

The TS-SpCas9 may be a SpCas9 variant formed by modifying two or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606 and L607 in the region 1-2 and the region 1-3 of the wild-type SpCas9.

The TS-SpCas9 may be a SpCas9 variant formed by modifying two or more amino acids selected from the amino acid sequences of the region 1-2 and the region 1-4 of the wild-type SpCas9.

The TS-SpCas9 may be a SpCas9 variant formed by modifying two or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, I679, L680, F682, L683, G687, F688, A689, N692, F693, M694, Q695, L696, I697 and H698 in the region 1-2 and the region 1-4 of the wild-type SpCas9.

The TS-SpCas9 may be a SpCas9 variant formed by modifying two or more amino acids selected from the amino acid sequences of the region 1-3 and the region 1-4 of the wild-type SpCas9.

The TS-SpCas9 may be a SpCas9 variant formed by modifying two or more amino acids selected from the group consisting of K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606, L607, I679, L680, F682, L683, G687, F688, A689, N692, F693, M694, Q695, L696, I697 and H698 in the region 1-3 and the region 1-4 of the wild-type SpCas9.

The TS-SpCas9 may be a SpCas9 variant formed by modifying three or more amino acids selected from the amino acid sequences of the region 1-1, the region 1-2 and the region 1-3 of the wild-type SpCas9.

The TS-SpCas9 may be a SpCas9 variant formed by modifying three or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606 and L607 in the region 1-1, the region 1-2 and the region 1-3 of the wild-type SpCas9.

The TS-SpCas9 may be a SpCas9 variant formed by modifying three or more amino acids selected from the amino acid sequences of the region 1-1, the region 1-2 and the region 1-4 of the wild-type SpCas9.

The TS-SpCas9 may be a SpCas9 variant formed by modifying three or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, I679, L680, F682, L683, G687, F688, A689, N692, F693, M694, Q695, L696, I697 and H698 in the region 1-1, the region 1-2 and the region 1-4 of the wild-type SpCas9.

The TS-SpCas9 may be a SpCas9 variant formed by modifying three or more amino acids selected from the amino acid sequences of the region 1-1, the region 1-3 and the region 1-4 of the wild-type SpCas9.

The TS-SpCas9 may be a SpCas9 variant formed by modifying three or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606, L607, I679, L680, F682, L683, G687, F688, A689, N692, F693, M694, Q695, L696, I697 and H698 in the region 1-1, the region 1-3 and the region 1-4 of the wild-type SpCas9.

The TS-SpCas9 may be a SpCas9 variant formed by modifying three or more amino acids selected from the amino acid sequences of the region 1-2, the region 1-3 and the region 1-4 of the wild-type SpCas9.

The TS-SpCas9 may be a SpCas9 variant formed by modifying three or more amino acids selected from the group consisting of P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606, L607, I679, L680, F682, L683, G687, F688, A689, N692, F693, M694, Q695, L696, I697 and H698 in the region 1-2, the region 1-3 and the region 1-4 of the wild-type SpCas9.

The TS-SpCas9 may be a SpCas9 variant formed by modifying four or more amino acids selected from the amino acid sequences of the region 1-1, the region 1-2, the region 1-3 and the region 1-4 of the wild-type SpCas9.

The TS-SpCas9 may be a SpCas9 variant formed by modifying four or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, K510, L513, L514, Y515, F518, V520, L524, V527, V530, G533, M534, P537, A538, F539, L540, G542, A547, I548, V549, L551, L552, F553, V559, V561, L564, F569, I572, C574, F575, V578, I580, G582, V583, E584, D585, F587, N588, A589, L591, G592, L597, L598, I600, I601, F606, L607, I679, L680, F682, L683, G687, F688, A689, N692, F693, M694, Q695, L696, I697 and H698 in the region 1-1, the region 1-2, the region 1-3 and the region 1-4 of the wild-type SpCas9.

In one exemplary embodiment, the TS-SpCas9 may be a SpCas9 variant formed by modifying A203; N277; G366; F539; or I601 of the wild-type SpCas9.

In another exemplary embodiment, the TS-SpCas9 may be a SpCas9 variant formed by modifying A203/N277 (A203 and N277); A203/G366; A203/F539; or A203/I601 of the wild-type SpCas9.

In still another exemplary embodiment, the TS-SpCas9 may be a SpCas9 variant formed by modifying N277/G366; N277/F539; or N277/I601 of the wild-type SpCas9.

In one exemplary embodiment, the TS-SpCas9 may be a SpCas9 variant formed by modifying G366/F539; G366/I601; or F539/I601 of the wild-type SpCas9.

In another exemplary embodiment, the TS-SpCas9 may be a SpCas9 variant formed by modifying A203/N277/G366; A203/N277/F539; A203/N277/I601; A203/G366/F539; A203/G366/I601; A203/F539/I601; N277/G366/F539; N277/G366/I601; or G366/F539/I601 of the wild-type SpCas9.

In still another exemplary embodiment, the TS-SpCas9 may be a SpCas9 variant formed by modifying A203/N277/G366/F539; A203/N277/G366/I601; A203/N277/F539/I601; A203/G366/F539/I601; or N277/G366/F539/I601 of the wild-type SpCas9.

In yet another exemplary embodiment, the TS-SpCas9 may be a SpCas9 variant formed by modifying A203/N277/G366/F539/I601 of the wild-type SpCas9.

The TS-SpCas9 may be a SpCas9 variant formed by modifying one or more amino acids selected from the amino acid sequence of the second region of the wild-type SpCas9.

The TS-SpCas9 may be a SpCas9 variant formed by modifying one or more amino acids selected from the amino acid sequence of the region 2-1 of the wild-type SpCas9.

The TS-SpCas9 may be a SpCas9 variant formed by modifying one or more amino acids selected from the group consisting of I7, G8, L9, D10, I11, G12, V16, G17, W18, A19, V20 and I21 in the region 2-1 of the wild-type SpCas9.

The TS-SpCas9 may be a SpCas9 variant formed by modifying one or more amino acids selected from the amino acid sequence of the region 2-2 of the wild-type SpCas9.

The TS-SpCas9 may be a SpCas9 variant formed by modifying one or more amino acids selected from the group consisting of P731, A732, I733, G736, I737, L738, V741, V743, V744, L747, V748, V750, M751, G752, P756, I759, V760, I761, E762, M763, A764, R765, E766 and N767 in the region 2-2 of the wild-type SpCas9.

The TS-SpCas9 may be a SpCas9 variant formed by modifying one or more amino acids selected from the amino acid sequence of the region 2-3 of the wild-type SpCas9.

The TS-SpCas9 may be a SpCas9 variant formed by modifying one or more amino acids selected from the group consisting of I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-3 of the wild-type SpCas9.

The TS-SpCas9 may be a SpCas9 variant formed by modifying two or more amino acids selected from the amino acid sequences of the region 2-1 and the region 2-2 of the wild-type SpCas9.

The TS-SpCas9 may be a SpCas9 variant formed by modifying two or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766 and N767 in the region 2-1 and the region 2-2 of the wild-type SpCas9.

The TS-SpCas9 may be a SpCas9 variant formed by modifying two or more amino acids selected from the amino acid sequences of the region 2-1 and the region 2-3 of the wild-type SpCas9.

The TS-SpCas9 may be a SpCas9 variant formed by modifying two or more amino acids selected from the group consisting of I7, G8, L9, D10, I11, G12, V16, G17, W18, A19, V20, I21, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1 and the region 2-3 of the wild-type SpCas9.

The TS-SpCas9 may be a SpCas9 variant formed by modifying two or more amino acids selected from the amino acid sequences of the region 2-2 and the region 2-3 of the wild-type SpCas9.

The TS-SpCas9 may be a SpCas9 variant formed by modifying two or more amino acids selected from the group consisting of P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-2 and the region 2-3 of the wild-type SpCas9.

The TS-SpCas9 may be a SpCas9 variant formed by modifying three or more amino acids selected from the amino acid sequences of the region 2-1, the region 2-2 and the region 2-3 of the wild-type SpCas9.

The TS-SpCas9 may be a SpCas9 variant formed by modifying three or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and the region 2-3 of the wild-type SpCas9.

In one exemplary embodiment, the TS-SpCas9 may be a SpCas9 variant formed by modifying M763; D965; or F1038 of the wild-type SpCas9.

In another exemplary embodiment, the TS-SpCas9 may be a SpCas9 variant formed by modifying M763/D965; M763/F1038; or D965/F1038 of the wild-type SpCas9.

In still another exemplary embodiment, the TS-SpCas9 may be a SpCas9 variant formed by modifying M763/D965/F1038 of the wild-type SpCas9.

The TS-SpCas9 may be a SpCas9 variant formed by modifying one or more amino acids selected from the amino acid sequence of the third region of the wild-type SpCas9.

The TS-SpCas9 may be a SpCas9 variant formed by modifying one or more amino acids selected from the amino acid sequence of the region 3-1 of the wild-type SpCas9.

The TS-SpCas9 may be a SpCas9 variant formed by modifying one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9.

In one exemplary embodiment, the TS-SpCas9 may be a SpCas9 variant formed by modifying K890 of the wild-type SpCas9.

The TS-SpCas9 may be a SpCas9 variant formed by modifying one or more amino acids selected from the amino acid sequence of the fourth region of the wild-type SpCas9.

The TS-SpCas9 may be a SpCas9 variant formed by modifying one or more amino acids selected from the amino acid sequence of the region 4-1 of the wild-type SpCas9.

The TS-SpCas9 may be a SpCas9 variant formed by modifying one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying T1102 or D1127 of the wild-type SpCas9.

In another exemplary embodiment, the TS-SpCas9 may be a SpCas9 variant formed by modifying T1102/D1127 of the wild-type SpCas9.

The TS-SpCas9 may be a SpCas9 variant formed by modifying two or more amino acids selected from the amino acid sequences of the first region and the second region of the wild-type SpCas9. Here, the two or more amino acids may be present in different regions, respectively.

The TS-SpCas9 may be a SpCas9 variant formed by modifying one or more amino acids selected from the amino acid sequence(s) of the region 1-1, the region 1-2, the region 1-3 and/or the region 1-4; and one or more amino acids selected from the amino acid sequence(s) of the region 2-1, the region 2-2 and/or the region 2-3 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4; and one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 or the region 2-3 of the wild-type SpCas9, respectively.

In one exemplary embodiment, the TS-SpCas9 may be a SpCas9 variant formed by modifying A203/M763; A203/D965; A203/F1038; A203/M763/D965; A203/M763/F1038; A203/D965/F1038; A203/M763/D965/F1038; N277/M763; N277/D965; N277/F1038; N277/M763/D965; N277/M763/F1038; N277/D965/F1038; N277/M763/D965/F1038; G366/M763; G366/D965; G366/F1038; G366/M763/D965; G366/M763/F1038; G366/D965/F1038; G366/M763/D965/F1038; F539/M763; F539/D965; F539/F1038; F539/M763/D965; F539/M763/F1038; F539/D965/F1038; F539/M763/D965/F1038; I601/M763; I601/D965; I601/F1038; I601/M763/D965; I601/M763/F1038; I601/D965/F1038; or I601/M763/D965/F1038 of the wild-type SpCas9.

In another exemplary embodiment, the TS-SpCas9 may be a SpCas9 variant formed by modifying A203/N277/M763; A203/N277/D965; A203/N277/F1038; A203/N277/M763/D965; A203/N277/M763/F1038; A203/N277/D965/F1038; A203/N277/M763/D965/F1038; A203/G366/M763; A203/G366/D965; A203/G366/F1038; A203/G366/M763/D965; A203/G366/M763/F1038; A203/G366/D965/F1038; A203/G366/M763/D965/F1038; A203/F539/M763; A203/F539/D965; A203/F539/F1038; A203/F539/M763/D965; A203/F539/M763/F1038; A203/F539/D965/F1038; A203/F539/M763/D965/F1038; A203/I601/M763; A203/I601/D965; A203/I601/F1038; A203/I601/M763/D965; A203/I601/M763/F1038; A203/I601/D965/F1038; A203/I601/M763/D965/F1038; N277/G366/M763; N277/G366/D965; N277/G366/F1038; N277/G366/M763/D965; N277/G366/M763/F1038; N277/G366/D965/F1038; N277/G366/M763/D965/F1038; N277/F539/M763; N277/F539/D965; N277/F539/F1038; N277/F539/M763/D965; N277/F539/M763/F1038; N277/F539/D965/F1038; N277/F539/M763/D965/F1038; N277/I601/M763; N277/I601/D965; N277/I601/F1038; N277/I601/M763/D965; N277/I601/M763/F1038; N277/I601/D965/F1038; N277/I601/M763/D965/F1038; G366/F539/M763; G366/F539/D965; G366/F539/F1038; G366/F539/M763/D965; G366/F539/M763/F1038; G366/F539/D965/F1038; G366/F539/M763/D965/F1038; G366/I601/M763; G366/I601/D965; G366/I601/F1038; G366/I601/M763/D965; G366/I601/M763/F1038; G366/I601/D965/F1038; G366/I601/M763/D965/F1038; F539/I601/M763; F539/I601/D965; F539/I601/F1038; F539/I601/M763/D965; F539/I601/M763/F1038; F539/I601/D965/F1038; or F539/I601/M763/D965/F1038 of the wild-type SpCas9.

In still another exemplary embodiment, the TS-SpCas9 may be a SpCas9 variant formed by modifying A203/N277/G366/M763; A203/N277/G366/D965; A203/N277/G366/F1038; A203/N277/G366/M763/D965; A203/N277/G366/M763/F1038; A203/N277/G366/D965/F1038; A203/N277/G366/M763/D965/F1038; A203/N277/F539/M763; A203/N277/F539/D965; A203/N277/F539/F1038; A203/N277/F539/M763/D965; A203/N277/F539/M763/F1038; A203/N277/F539/D965/F1038; A203/N277/F539/M763/D965/F1038; A203/N277/I601/M763; A203/N277/I601/D965; A203/N277/I601/F1038; A203/N277/I601/M763/D965; A203/N277/I601/M763/F1038; A203/N277/I601/D965/F1038; A203/N277/I601/M763/D965/F1038; A203/G366/F539/M763; A203/G366/F539/D965; A203/G366/F539/F1038; A203/G366/F539/M763/D965; A203/G366/F539/M763/F1038; A203/G366/F539/D965/F1038; A203/G366/F539/M763/D965/F1038; A203/G366/I601/M763; A203/G366/I601/D965; A203/G366/I601/F1038; A203/G366/I601/M763/D965; A203/G366/I601/M763/F1038; A203/G366/I601/D965/F1038; A203/G366/I601/M763/D965/F1038; A203/F539/I601/M763; A203/F539/I601/D965; A203/F539/I601/F1038; A203/F539/I601/M763/D965; A203/F539/I601/M763/F1038; A203/F539/I601/D965/F1038; A203/F539/I601/M763/D965/F1038; N277/G366/F539/M763; N277/G366/F539/D965; N277/G366/F539/F1038; N277/G366/F539/M763/D965; N277/G366/F539/M763/F1038; N277/G366/F539/D965/F1038; N277/G366/F539/M763/D965/F1038; N277/G366/I601/M763; N277/G366/I601/D965; N277/G366/I601/F1038; N277/G366/I601/M763/D965; N277/G366/I601/M763/F1038; N277/G366/I601/D965/F1038; N277/G366/I601/M763/D965/F1038; G366/F539/I601/M763; G366/F539/I601/D965;

G366/F539/I601/F1038; G366/F539/I601/M763/D965; G366/F539/I601/M763/F1038; G366/F539/I601/D965/F1038; or G366/F539/I601/M763/D965/F1038 of the wild-type SpCas9.

In one exemplary embodiment, the TS-SpCas9 may be a SpCas9 variant formed by modifying A203/N277/G366/F539/M763; A203/N277/G366/F539/D965; A203/N277/G366/F539/F1038; A203/N277/G366/F539/M763/D965; A203/N277/G366/F539/M763/F1038; A203/N277/G366/F539/D965/F1038; A203/N277/G366/F539/M763/D965/F1038; A203/N277/G366/I601/M763; A203/N277/G366/I601/D965; A203/N277/G366/I601/F1038; A203/N277/G366/I601/M763/D965; A203/N277/G366/I601/M763/F1038; A203/N277/G366/I601/D965/F1038; A203/N277/G366/I601/M763/D965/F1038; N277/G366/F539/I601/M763; N277/G366/F539/I601/D965; N277/G366/F539/I601/F1038; N277/G366/F539/I601/M763/D965; N277/G366/F539/I601/M763/F1038; N277/G366/F539/I601/D965/F1038; N277/G366/F539/I601/M763/D965/F1038; A203/N277/G366/F539/I601/M763; A203/N277/G366/F539/I601/D965; A203/N277/G366/F539/I601/F1038; A203/N277/G366/F539/I601/M763/D965; A203/N277/G366/F539/I601/M763/F1038; A203/N277/G366/F539/I601/D965/F1038; or A203/N277/G366/F539/I601/M763/D965/F1038 of the wild-type SpCas9.

The TS-SpCas9 may be a SpCas9 variant formed by modifying two or more amino acids selected from the amino acid sequences of the first region and the third region of the wild-type SpCas9. Here, the two or more amino acids may be present in different regions, respectively.

The TS-SpCas9 may be a SpCas9 variant formed by modifying one or more amino acids selected from the amino acid sequence(s) of the region 1-1, the region 1-2, the region 1-3 and/or the region 1-4; and one or more amino acids selected from the amino acid sequence of the region 3-1 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4; and one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9.

In one exemplary embodiment, the TS-SpCas9 may be a SpCas9 variant formed by modifying A203/K890; N277/K890; G366/K890; F539/K890; or I601/K890 of the wild-type SpCas9.

In another exemplary embodiment, the TS-SpCas9 may be a SpCas9 variant formed by modifying A203/N277/K890; A203/G366/K890; A203/F539/K890; A203/I601/K890; N277/G366/K890; N277/F539/K890; N277/I601/K890; G366/F539/K890; G366/I601/K890; or F539/I601/K890 of the wild-type SpCas9.

In still another exemplary embodiment, the TS-SpCas9 may be a SpCas9 variant formed by modifying A203/N277/G366/K890; A203/N277/F539/K890; A203/N277/I601/K890; A203/G366/F539/K890; A203/G366/I601/K890; A203/F539/I601/K890; N277/G366/F539/K890; N277/G366/I601/K890; or G366/F539/I601/K890 of the wild-type SpCas9.

In one exemplary embodiment, the TS-SpCas9 may be a SpCas9 variant formed by modifying A203/N277/G366/F539/K890; A203/N277/G366/I601/K890; or N277/G366/F539/I601/K890 of the wild-type SpCas9.

In another exemplary embodiment, the TS-SpCas9 may be a SpCas9 variant formed by modifying A203/N277/G366/F539/I601/K890 of the wild-type SpCas9.

The TS-SpCas9 may be a SpCas9 variant formed by modifying two or more amino acids selected from the amino acid sequences of the first region and the fourth region of the wild-type SpCas9. Here, the two or more amino acids may be present in different regions, respectively.

The TS-SpCas9 may be a SpCas9 variant formed by modifying one or more amino acids selected from the amino acid sequence(s) of the region 1-1, the region 1-2, the region 1-3 and/or the region 1-4; and one or more amino acids selected from the amino acid sequence of the region 4-1 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4; and one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying A203/T1102; N277/T1102; G366/T1102; F539/T1102; I601/T1102; A203/D1127; N277/D1127; G366/D1127; F539/D1127; I601/D1127; A203/T1102/D1127; N277/T1102/D1127; G366/T1102/D1127; F539/T1102/D1127; or I601/T1102/D1127 of the wild-type SpCas9.

In another exemplary embodiment, the TS-SpCas9 may be a SpCas9 variant formed by modifying A203/N277/T1102; A203/G366/T1102; A203/F539/T1102; A203/I601/T1102; N277/G366/T1102; N277/F539/T1102; N277/I601/T1102; G366/F539/T1102; G366/I601/T1102; F539/I601/T1102; A203/N277/D1127; A203/G366/D1127; A203/F539/D1127; A203/I601/D1127; N277/G366/D1127; N277/

F539/D1127; N277/I601/D1127; G366/F539/D1127; G366/ I601/D1127; F539/I601/D1127; A203/N277/T1102/D1127; A203/G366/T1102/D1127; A203/F539/T1102/D1127; A203/I601/T1102/D1127; N277/G366/T1102/D1127; N277/F539/T1102/D1127; N277/I601/T1102/D1127; G366/ F539/T1102/D1127; G366/I601/T1102/D1127; or F539/ I601/T1102/D1127 of the wild-type SpCas9.

In still another exemplary embodiment, the TS-SpCas9 may be a SpCas9 variant formed by modifying A203/N277/ G366/T1102; A203/N277/F539/T1102; A203/N277/I601/ T1102; A203/G366/F539/T1102; A203/G366/I601/T1102; A203/F539/I601/T1102; N277/G366/F539/T1102; N277/ G366/I601/T1102; G366/F539/I601/T1102; A203/N277/ G366/D1127; A203/N277/F539/D1127; A203/N277/I601/ D1127; A203/G366/F539/D1127; A203/G366/I601/D1127; A203/F539/I601/D1127; N277/G366/F539/D1127; N277/ G366/I601/D1127; G366/F539/I601/D1127; A203/N277/ G366/T1102/D1127; A203/N277/F539/T1102/D1127; A203/N277/I601/T1102/D1127; A203/G366/F539/T1102/ D1127; A203/G366/I601/T1102/D1127; A203/F539/I601/ T1102/D1127; N277/G366/F539/T1102/D1127; N277/ G366/I601/T1102/D1127; or G366/F539/I601/T1102/ D1127 of the wild-type SpCas9.

In one exemplary embodiment, the TS-SpCas9 may be a SpCas9 variant formed by modifying A203/N277/G366/ F539/T1102; A203/N277/G366/I601/T1102; N277/G366/ F539/I601/T1102; A203/N277/G366/F539/D1127; A203/ N277/G366/I601/D1127; N277/G366/F539/I601/D1127; A203/N277/G366/F539/T1102/D1127; A203/N277/G366/ I601/T1102/D1127; or N277/G366/F539/I601/T1102/ D1127 of the wild-type SpCas9.

In another exemplary embodiment, the TS-SpCas9 may be a SpCas9 variant formed by modifying A203/N277/ G366/F539/I601/T1102; A203/N277/G366/F539/I601/ D1127; or A203/N277/G366/F539/I601/T1102/D1127 of the wild-type SpCas9.

The TS-SpCas9 may be a SpCas9 variant formed by modifying two or more amino acids selected from the amino acid sequences of the second region and the third region of the wild-type SpCas9. Here, the two or more amino acids may be present in different regions, respectively.

The TS-SpCas9 may be a SpCas9 variant formed by modifying one or more amino acids selected from the amino acid sequences of the region 2-1, the region 2-2 and/or the region 2-3; and one or more amino acids selected from the amino acid sequence of the region 3-1 of the wild-type SpCas9.

The TS-SpCas9 may be a SpCas9 variant formed by modifying one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3; and one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9.

In one exemplary embodiment, the TS-SpCas9 may be a SpCas9 variant formed by modifying M763/K890; K890/ D965; or K890/F1038 of the wild-type SpCas9.

In another exemplary embodiment, the TS-SpCas9 may be a SpCas9 variant formed by modifying M763/K890/ D965; M763/K890/F1038; or K890/D965/F1038 of the wild-type SpCas9.

In still another exemplary embodiment, the TS-SpCas9 may be a SpCas9 variant formed by modifying M763/K890/ D965/F1038 of the wild-type SpCas9.

The TS-SpCas9 may be a SpCas9 variant formed by modifying two or more amino acids selected from the amino acid sequences of the second region and the fourth region of the wild-type SpCas9. Here, the two or more amino acids may be present in different regions, respectively.

The TS-SpCas9 may be a SpCas9 variant formed by modifying one or more amino acids selected from the amino acid sequence(s) of the region 2-1, the region 2-2 and/or the region 2-3; and one or more amino acids selected from the amino acid sequence of the region 4-1 of the wild-type SpCas9.

The TS-SpCas9 may be a SpCas9 variant formed by modifying one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3; and one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying M763/T1102; D965/ T1102; F1038/T1102; M763/D1127; D965/D1127; F1038/ D1127; M763/T1102/D1127; D965/T1102/D1127; or F1038/T1102/D1127 of the wild-type SpCas9.

In another exemplary embodiment, the TS-SpCas9 may be a SpCas9 variant formed by modifying M763/D965/ T1102; M763/F1038/T1102; D965/F1038/T1102; M763/ D965/D1127; M763/F1038/D1127; D965/F1038/D1127; M763/D965/T1102/D1127; M763/F1038/T1102/D1127; or D965/F1038/T1102/D1127 of the wild-type SpCas9.

In still another exemplary embodiment, the TS-SpCas9 may be a SpCas9 variant formed by modifying M763/D965/ F1038/T1102; M763/D965/F1038/D1127; or M763/D965/ F1038/T1102/D1127 of the wild-type SpCas9.

The TS-SpCas9 may be a SpCas9 variant formed by modifying two or more amino acids selected from the amino acid sequences of the third region and the fourth region of the wild-type SpCas9. Here, the two or more amino acids may be present in different regions, respectively.

The TS-SpCas9 may be a SpCas9 variant formed by modifying one or more amino acids selected from the amino acid sequence in the region 3-1; and one or more amino acids selected from the amino acid sequence in the region 4-1 of the wild-type SpCas9.

The TS-SpCas9 may be a SpCas9 variant formed by modifying one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 in the region 3-1; and one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying K890/T1102; K890/D1127; or K890/T1102/D1127 of the wild-type SpCas9.

The TS-SpCas9 may be a SpCas9 variant formed by modifying three or more amino acids selected from the amino acid sequences of the first region, the second region and the third region of the wild-type SpCas9. Here, the three or more amino acids may be present in different regions, respectively.

The TS-SpCas9 may be a SpCas9 variant formed by modifying one or more amino acids selected from the amino acid sequence(s) of the region 1-1, the region 1-2, the region 1-3 and/or the region 1-4; one or more amino acids selected from the amino acid sequences of the region 2-1, the region 2-2 and/or the region 2-3; and one or more amino acids selected from the amino acid sequence of the region 3-1 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4; one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3; and one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9.

In one exemplary embodiment, the TS-SpCas9 may be a SpCas9 variant formed by modifying A203/M763/K890; A203/K890/D965; A203/K890/F1038; A203/M763/K890/D965; A203/M763/K890/F1038; A203/K890/D965/F1038; A203/M763/K890/D965/F1038; N277/M763/K890; N277/K890/D965; N277/K890/F1038; N277/M763/K890/D965; N277/M763/K890/F1038; N277/K890/D965/F1038; N277/M763/K890D965/F1038; G366/M763/K890; G366/K890/D965; G366/K890/F1038; G366/M763/K890/D965; G366/M763/K890/F1038; G366/K890/D965/F1038; G366/M763/K890/D965/F1038; F539/M763/K890; F539/K890/D965; F539/K890/F1038; F539/M763/K890/D965; F539/M763/K890/F1038; F539/K890/D965/F1038; F539/M763/K890/D965/F1038; I601/M763/K890; I601/K890/D965; I601/K890/F1038; I601/M763/K890/D965; I601/M763/K890/F1038; I601/K890/D965/F1038; or I601/M763/K890/D965/F1038 of the wild-type SpCas9.

In another exemplary embodiment, the TS-SpCas9 may be a SpCas9 variant formed by modifying A203/N277/M763/K890; A203/N277/K890/D965; A203/N277/K890/F1038; A203/N277/M763/K890/D965; A203/N277/M763/K890/F1038; A203/N277/K890/D965/F1038; A203/N277/M763/K890/D965/F1038; A203/G366/M763/K890; A203/G366/K890/D965; A203/G366/K890/F1038; A203/G366/M763/K890/D965; A203/G366/M763/K890/F1038; A203/G366/K890/D965/F1038; A203/G366/M763/K890/D965/F1038; A203/F539/M763/K890; A203/F539/K890/D965; A203/F539/K890/F1038; A203/F539/M763/K890/D965; A203/F539/M763/K890/F1038; A203/F539/K890/D965/F1038; A203/F539/M763/K890/D965/F1038; A203/I601/M763/K890; A203/I601/K890/D965; A203/I601/K890/F1038; A203/I601/M763/K890/D965; A203/I601/M763/K890/F1038; A203/I601/K890/D965/F1038; A203/I601/M763/K890/D965/F1038; N277/G366/M763/K890; N277/G366/K890/D965; N277/G366/K890/F1038; N277/G366/M763/K890/D965; N277/G366/M763/K890/F1038; N277/G366/K890/D965/F1038; N277/G366/M763/K890/D965/F1038; N277/F539/M763/K890; N277/F539/K890/D965; N277/F539/K890/F1038; N277/F539/M763/K890/D965; N277/F539/M763/K890/F1038; N277/F539/K890/D965/F1038; N277/F539/M763/K890/D965/F1038; N277/I601/M763/K890; N277/I601/K890/D965; N277/I601/K890/F1038; N277/I601/M763/K890/D965; N277/I601/M763/K890/F1038; N277/I601/K890/D965/F1038; N277/I601/M763/K890/D965/F1038; G366/F539/M763/K890; G366/F539/K890/D965; G366/F539/K890/F1038; G366/F539/M763/K890/D965; G366/F539/M763/K890/F1038; G366/F539/K890/D965/F1038; G366/F539/M763/K890/D965/F1038; G366/I601/M763/K890; G366/I601/K890/D965; G366/I601/K890/F1038; G366/I601/M763/K890/D965; G366/I601/M763/K890/F1038; G366/I601/K890/D965/F1038; G366/I601/M763/K890/D965/F1038; F539/I601/M763/K890; F539/I601/K890/D965; F539/I601/K890/F1038; F539/I601/M763/K890/D965; F539/I601/M763/K890/F1038; F539/I601/K890/D965/F1038; or F539/I601/M763/K890/D965/F1038 of the wild-type SpCas9.

In still another exemplary embodiment, the TS-SpCas9 may be a SpCas9 variant formed by modifying A203/N277/G366/M763/K890; A203/N277/G366/K890/D965; A203/N277/G366/K890/F1038; A203/N277/G366/M763/K890/D965; A203/N277/G366/M763/K890/F1038; A203/N277/G366/K890/D965/F1038; A203/N277/G366/M763/K890/D965/F1038; A203/N277/F539/M763/K890; A203/N277/F539/K890/D965; A203/N277/F539/K890/F1038; A203/

N277/F539/M763/K890/D965; A203/N277/F539/M763/ K890/F1038; A203/N277/F539/K890/D965/F1038; A203/ N277/F539/M763/K890/D965/F1038; A203/N277/I601/ M763/K890; A203/N277/I601/K890/D965; A203/N277/ I601/K890/F1038; A203/N277/I601/M763/K890/D965; A203/N277/I601/M763/K890/F1038; A203/N277/I601/ K890/D965/F1038; A203/N277/I601/M763/K890/D965/ F1038; A203/G366/F539/M763/K890; A203/G366/F539/ K890/D965; A203/G366/F539/K890/F1038; A203/G366/ F539/M763/K890/D965; A203/G366/F539/M763/K890/ F1038; A203/G366/F539/K890/D965/F1038; A203/G366/ F539/M763/K890/D965/F1038; A203/G366/I601/M763/ K890; A203/G366/I601/K890/D965; A203/G366/I601/ K890/F1038; A203/G366/I601/M763/K890/D965; A203/ G366/I601/M763/K890/F1038; A203/G366/I601/K890/ D965/F1038; A203/G366/I601/M763/K890/D965/F1038; A203/F539/I601/M763/K890; A203/F539/I601/K890/ D965; A203/F539/I601/K890/F1038; A203/F539/I601/ M763/K890/D965; A203/F539/I601/M763/K890/F1038; A203/F539/I601/K890/D965/F1038; A203/F539/I601/ M763/K890/D965/F1038; N277/G366/F539/M763/K890; N277/G366/F539/K890/D965; N277/G366/F539/K890/ F1038; N277/G366/F539/M763/K890/D965; N277/G366/ F539/M763/K890/F1038; N277/G366/F539/K890/D965/ F1038; N277/G366/F539/M763/K890/D965/F1038; N277/ G366/I601/M763/K890; N277/G366/I601/K890/D965; N277/G366/I601/K890/F1038; N277/G366/I601/M763/ K890/D965; N277/G366/I601/M763/K890/F1038; N277/ G366/I601/K890/D965/F1038; N277/G366/I601/M763/ K890/D965/F1038; G366/F539/I601/M763/K890; G366/ F539/I601/K890/D965; G366/F539/I601/K890/F1038; G366/F539/I601/M763/K890/D965; G366/F539/I601/ M763/K890/F1038; G366/F539/I601/K890/D965/F1038; or G366/F539/I601/M763/K890/D965/F1038 of the wild-type SpCas9.

In one exemplary embodiment, the TS-SpCas9 may be a SpCas9 variant formed by modifying A203/N277/G366/ F539/M763/K890; A203/N277/G366/F539/K890/D965; A203/N277/G366/F539/K890/F1038; A203/N277/G366/ F539/M763/K890/D965; A203/N277/G366/F539/M763/ K890/F1038; A203/N277/G366/F539/K890/D965/F1038; A203/N277/G366/F539/M763/K890/D965/F1038; A203/ N277/G366/I601/M763/K890; A203/N277/G366/I601/ K890/D965; A203/N277/G366/I601/K890/F1038; A203/ N277/G366/I601/M763/K890/D965; A203/N277/G366/ I601/M763/K890/F1038; A203/N277/G366/I601/K890/ D965/F1038; A203/N277/G366/I601/M763/K890/D965/ F1038; N277/G366/F539/I601/M763/K890; N277/G366/ F539/I601/K890/D965; N277/G366/F539/I601/K890/ F1038; N277/G366/F539/I601/M763/K890/D965; N277/ G366/F539/I601/M763/K890/F1038; N277/G366/F539/ I601/K890/D965/F1038; N277/G366/F539/I601/M763/ K890/D965/F1038; A203/N277/G366/F539/I601/M763/ K890; A203/N277/G366/F539/I601/K890/D965; A203/ N277/G366/F539/I601/K890/F1038; A203/N277/G366/ F539/I601/M763/K890/D965; A203/N277/G366/F539/ I601/M763/K890/F1038; A203/N277/G366/F539/I601/ K890/D965/F1038; or A203/N277/G366/F539/I601/M763/ K890/D965/F1038 of the wild-type SpCas9.

The TS-SpCas9 may be a SpCas9 variant formed by modifying three or more amino acids selected from amino acid sequences of the first region, the second region and the fourth region of the wild-type SpCas9. Here, the three or more amino acids may be present in different regions, respectively.

The TS-SpCas9 may be a SpCas9 variant formed by modifying one or more amino acids selected from the amino acid sequence(s) of the region 1-1, the region 1-2, the region 1-3 and/or the region 1-4; one or more amino acids selected from the amino acid sequence(s) of the region 2-1, the region 2-2 and/or the region 2-3; and one or more amino acids selected from the amino acid sequence of the region 4-1 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4; one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3; and one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying A203/M763/T1102; A203/D965T1102; A203/F1038T1102; A203/M763/D965/ T1102; A203/M763/F1038/T1102; A203/D965/F1038/ T1102; A203/M763/D965/F1038/T1102; N277/M763/ T1102; N277/D965/T1102; N277/F1038/T1102; N277/ M763/D965/T1102; N277/M763/F1038/T1102; N277/ D965/F1038/T1102; N277/M763/D965/F1038/T1102; G366/M763/T1102; G366/D965/T1102; G366/F1038/ T1102; G366/M763/D965/T1102; G366/M763/F1038/ T1102; G366/D965/F1038/T1102; G366/M763/D965/ F1038/T1102; F539/M763/T1102; F539/D965/T1102; F539/F1038/T1102; F539/M763/D965/T1102; F539/M763/ F1038/T1102; F539/D965/F1038/T1102; F539/M763/ D965/F1038/T1102; I601/M763/T1102; I601/D965/T1102; I601/F1038/T1102; I601/M763/D965/T1102; I601/M763/ F1038/T1102; I601/D965/F1038/T1102; I601/M763/D965/ F1038/T1102; A203/M763/D1127; A203/D965/D1127; A203/F1038/D1127; A203/M763/D965/D1127; A203/ M763/F1038/D1127; A203/D965/F1038/D1127; A203/ M763/D965/F1038/D1127; N277/M763/D1127; N277/ D965/D1127; N277/F1038/D1127; N277/M763/D965/ D1127; N277/M763/F1038/D1127; N277/D965/F1038/ D1127; N277/M763/D965/F1038/D1127; G366/M763/ D1127; G366/D965/D1127; G366/F1038/D1127; G366/ M763/D965/D1127; G366/M763/F1038/D1127; G366/ D965/F1038/D1127; G366/M763/D965/F1038/D1127;

F539/M763/D1127; F539/D965/D1127; F539/F1038/D1127; F539/M763/D965/D1127; F539/M763/F1038/D1127; F539/D965/F1038/D1127; F539/M763/D965/F1038/D1127; I601/M763/D1127; I601/D965/D1127; I601/F1038/D1127; I601/M763/D965/D1127; I601/M763/F1038D1127; I601/D965/F1038/D1127; or I601/M763/D965/F1038/D1127 of the wild-type SpCas9.

In another exemplary embodiment, the TS-SpCas9 may be a SpCas9 variant formed by modifying A203/M763/T1102/D1127; A203/D965/T1102/D1127; A203/F1038/T1102/D1127; A203/M763/D965/T1102/D1127; A203/M763/F1038/T1102/D1127; A203/D965/F1038/T1102/D1127; A203/M763/D965/F1038/T1102/D1127; N277/M763/T1102/D1127; N277/D965/T1102/D1127; N277/F1038/T1102/D1127; N277/M763/D965/T1102/D1127; N277/M763/F1038/T1102/D1127; N277/D965/F1038/T1102/D1127; N277/M763/D965/F1038/T1102/D1127; G366/M763/T1102/D1127; G366/D965/T1102/D1127; G366/F1038/T1102/D1127; G366/M763/D965/T1102/D1127; G366/M763/F1038/T1102/D1127; G366/D965/F1038/T1102/D1127; G366/M763/D965/F1038/T1102/D1127; F539/M763/T1102/D1127; F539/D965/T1102/D1127; F539/F1038/T1102/D1127; F539/M763/D965/T1102/D1127; F539/M763/F1038/T1102/D1127; F539/D965/F1038/T1102/D1127; F539/M763/D965/F1038/T1102/D1127; I601/M763/T1102/D1127; I601/D965/T1102/D1127; I601/F1038/T1102/D1127; I601/M763/D965/T1102/D1127; I601/M763/F1038T1102/D1127; I601/D965/F1038/T1102/D1127; or I601/M763/D965/F1038/T1102/D1127 of the wild-type SpCas9.

In one exemplary embodiment, the TS-SpCas9 may be a SpCas9 variant formed by modifying A203/N277/M763/T1102; A203/N277/D965/T1102; A203/N277/F1038/T1102; A203/N277/M763/D965/T1102; A203/N277/M763/F1038/T1102; A203/N277/D965/F1038/T1102; A203/N277/M763/D965/F1038/T1102; A203/G366/M763/T1102; A203/G366/D965/T1102; A203/G366/F1038/T1102; A203/G366/M763/D965/T1102; A203/G366/M763/F1038/T1102; A203/G366/D965/F1038/T1102; A203/G366/M763/D965/F1038/T1102; A203/F539/M763/T1102; A203/F539/D965/T1102; A203/F539/F1038/T1102; A203/F539/M763/D965/T1102; A203/F539/M763/F1038/T1102; A203/F539/D965/F1038/T1102; A203/F539/M763/D965/F1038/T1102; A203/I601/M763/T1102; A203/I601/D965/F1038/T1102; A203/I601/F1038/T1102; A203/I601/M763/D965/T1102; A203/I601/M763/F1038/T1102; A203/I601/D965/F1038/T1102; A203/I601/M763/D965/F1038/T1102; N277/G366/M763/T1102; N277/G366/D965/T1102; N277/G366/F1038/T1102; N277/G366/M763/D965/T1102; N277/G366/M763/F1038/T1102; N277/G366/D965/F1038/T1102; N277/G366/M763/D965/F1038/T1102; N277/F539/M763/T1102; N277/F539/D965/T1102; N277/F539/F1038/T1102; N277/F539/M763/D965/T1102; N277/F539/M763/F1038/T1102; N277/F539/D965/F1038/T1102; N277/F539/M763/D965/F1038/T1102; N277/I601/M763/T1102; N277/I601/D965/T1102; N277/I601/F1038/T1102; N277/I601/M763/D965/T1102; N277/I601/M763/F1038/T1102; N277/I601/D965/F1038/T1102; G366/F539/M763/T1102; G366/F539/D965/T1102; G366/F539/F1038/T1102; G366/F539/M763/D965/T1102; G366/F539/M763/F1038/T1102; G366/F539/D965/F1038/T1102; G366/F539/M763/D965/F1038/T1102; G366/I601/M763/T1102; G366/I601/D965/T1102; G366/I601/F1038/T1102; G366/I601/M763/D965/T1102; G366/I601/M763/F1038/T1102; G366/I601/D965/F1038/T1102; G366/I601/M763/D965/F1038/T1102; F539/I601/M763/T1102; F539/I601/D965/T1102; F539/I601/F1038/T1102; F539/I601/M763/D965/T1102; F539/I601/M763/F1038/T1102; F539/I601/D965/F1038/T1102; F539/I601/M763/F1038/T1102; F539/I601/M763/D965/T1102; F539/I601/M763/F1038/D1127; A203/N277/F1038/D1127; A203/N277/M763/D965/D1127; A203/N277/M763/F1038/D1127; A203/N277/D965/F1038/D1127; A203/N277/M763/D965/F1038/D1127; A203/G366/M763/D1127; A203/G366/D965/D1127; A203/G366/F1038/D1127; A203/G366/M763/D965/D1127; A203/G366/M763/F1038/D1127; A203/G366/D965/F1038/D1127; A203/G366/M763/D965/F1038/D1127; A203/F539/M763/D1127; A203/F539/D965/D1127; A203/F539/F1038/D1127; A203/F539/M763/D965/D1127; A203/F539/M763/F1038/D1127; A203/F539/D965/F1038/D1127; A203/F539/M763/D965/F1038/D1127; A203/I601/M763/D1127; A203/I601/D965/D1127; A203/I601/F1038/D1127; A203/I601/M763/D965/D1127; A203/I601/M763/F1038/D1127; A203/I601/D965/F1038/D1127; A203/I601/M763/D965/F1038/D1127; N277/G366/M763/D1127; N277/G366/D965/D1127; N277/G366/F1038/D1127; N277/G366/M763/D965/D1127; N277/G366/M763/F1038/D1127; N277/G366/D965/F1038/D1127; N277/G366/M763/D965/F1038/D1127; N277/F539/M763/D1127; N277/F539/D965/D1127; N277/F539/F1038/D1127; N277/F539/M763/D965/D1127; N277/F539/M763/F1038/D1127; N277/F539/D965/F1038/D1127; N277/F539/M763/D965/F1038/D1127; N277/I601/M763/D1127; N277/I601/D965/D1127; N277/I601/F1038/D1127; N277/I601/M763/D965/D1127; N277/I601/M763/F1038/D1127; N277/I601/D965/F1038/D1127; N277/I601/M763/D965/F1038/D1127; G366/F539/M763/D1127; G366/F539/D965/D1127; G366/F539/F1038/D1127; G366/F539/M763/D965/D1127; G366/F539/M763/F1038/D1127; G366/F539/D965/F1038/D1127; G366/F539/M763/D965/F1038/D1127; G366/I601/M763/D1127; G366/I601/D965/D1127; G366/I601/F1038/D1127; G366/I601/M763/D965/D1127; G366/I601/M763/F1038/D1127; G366/I601/D965/F1038/D1127; G366/I601/M763/D965/F1038/D1127; F539/I601/M763/D1127; F539/I601/D965/D1127; F539/I601/F1038/D1127; F539/I601/M763/D965/D1127; F539/I601/M763/F1038/D1127; F539/I601/D965/F1038/D1127; or F539/I601/M763/D965/F1038/D1127 of the wild-type SpCas9.

In another exemplary embodiment, the TS-SpCas9 may be a SpCas9 variant formed by modifying A203/N277/M763/T1102/D1127; A203/N277/D965/T1102/D1127; A203/N277/F1038/T1102/D1127; A203/N277/M763/D965/T1102/D1127; A203/N277/M763/F1038/T1102/D1127; A203/N277/D965/F1038/T1102/D1127; A203/N277/M763/D965/F1038/T1102/D1127; A203/G366/M763/T1102/D1127; A203/G366/D965/T1102/D1127; A203/G366/F1038/T1102/D1127; A203/G366/M763/D965/T1102/D1127; A203/G366/M763/F1038/T1102/D1127; A203/G366/D965/F1038/T1102/D1127; A203/G366/M763/D965/F1038/T1102/D1127; A203/F539/M763/T1102/D1127; A203/F539/D965/T1102/D1127; A203/F539/F1038/T1102/D1127; A203/F539/M763/D965/T1102/D1127; A203/F539/M763/F1038/T1102/D1127; A203/F539/D965/F1038/T1102/D1127; A203/F539/M763/D965/F1038/T1102/D1127; A203/I601/M763/T1102/D1127; A203/I601/D965/T1102/D1127; A203/I601/F1038/T1102/D1127; A203/I601/M763/D965/T1102/D1127; A203/I601/M763/F1038/T1102/D1127; A203/I601/D965/F1038/T1102/D1127; A203/I601/M763/D965/F1038/T1102/D1127; N277/G366/M763/T1102/D1127; N277/G366/D965/T1102/D1127; N277/G366/F1038/T1102/D1127; N277/G366/M763/D965/T1102/D1127; N277/G366/M763/F1038/T1102/D1127; N277/G366/D965/F1038/T1102/D1127; N277/G366/M763/D965/F1038/T1102/D1127; N277/F539/

M763/T1102/D1127; N277/F539/D965/T1102/D1127; N277/F539/F1038/T1102/D1127; N277/F539/D965/T1102/D1127; N277/F539/M763/F1038/T1102/D1127; N277/F539/D965/F1038/T1102/D1127; N277/F539/M763/D965/F1038/T1102/D1127; N277/I601/M763/T1102/D1127; N277/I601/D965/T1102/D1127; N277/I601/F1038/T1102/D1127; N277/I601/M763/D965/T1102/D1127; N277/I601/M763/F1038/T1102/D1127; N277/I601/D965/F1038/T1102/D1127; N277/I601/M763/D965/F1038/T1102/D1127; G366/F539/M763/T1102/D1127; G366/F539/D965/T1102/D1127; G366/F539/F1038/T1102/D1127; G366/F539/M763/D965/T1102/D1127; G366/F539/M763/F1038/T1102/D1127; G366/F539/D965/F1038/T1102/D1127; G366/F539/M763/D965/F1038/T1102/D1127; G366/I601/M763/T1102/D1127; G366/I601/D965/T1102/D1127; G366/I601/F1038/T1102/D1127; G366/I601/M763/D965/T1102/D1127; G366/I601/M763/F1038/T1102/D1127; G366/I601/D965/F1038/T1102/D1127; G366/I601/M763/D965/F1038/T1102/D1127; F539/I601/M763/T1102/D1127; F539/I601/D965/T1102/D1127; F539/I601/F1038/T1102/D1127; F539/I601/M763/D965/T1102/D1127; F539/I601/M763/F1038/T1102/D1127; F539/I601/D965/F1038/T1102/D1127; or F539/I601/M763/D965/F1038/T1102/D1127 of the wild-type SpCas9.

In one exemplary embodiment, the TS-SpCas9 may be a SpCas9 variant formed by modifying A203/N277/G366/M763/T1102; A203/N277/G366/D965/T1102; A203/N277/G366/F1038/T1102; A203/N277/G366/M763/D965/T1102; A203/N277/G366/M763/F1038/T1102; A203/N277/G366/D965/F1038/T1102; A203/N277/G366/M763/D965/F1038/T1102; A203/N277/F539/M763/T1102; A203/N277/F539/D965/T1102; A203/N277/F539/F1038/T1102; A203/N277/F539/M763/D965/T1102; A203/N277/F539/M763/F1038/T1102; A203/N277/F539/D965/F1038/T1102; A203/N277/F539/M763/D965/F1038/T1102; A203/N277/I601/M763/T1102; A203/N277/I601/D965/T1102; A203/N277/I601/F1038/T1102; A203/N277/I601/M763/D965/T1102; A203/N277/I601/M763/F1038/T1102; A203/N277/I601/D965/F1038/T1102; A203/N277/I601/M763/D965/F1038/T1102; A203/G366/F539/M763/T1102; A203/G366/F539/D965/T1102; A203/G366/F539/F1038/T1102; A203/G366/F539/M763/D965/T1102; A203/G366/F539/M763/F1038/T1102; A203/G366/F539/D965/F1038/T1102; A203/G366/F539/M763/D965/F1038/T1102; A203/G366/I601/M763/T1102; A203/G366/I601/D965/T1102; A203/G366/I601/F1038/T1102; A203/G366/I601/M763/D965/T1102; A203/G366/I601/M763/F1038/T1102; A203/G366/I601/D965/F1038/T1102; A203/G366/I601/M763/D965/F1038/T1102; A203/F539/I601/M763/T1102; A203/F539/I601/D965/T1102; A203/F539/I601/F1038/T1102; A203/F539/I601/M763/D965/T1102; A203/F539/I601/M763/F1038/T1102; A203/F539/I601/D965/F1038/T1102; A203/F539/I601/M763/D965/F1038/T1102; N277/G366/F539/M763/T1102; N277/G366/F539/D965/T1102; N277/G366/F539/F1038/T1102; N277/G366/F539/M763/D965/T1102; N277/G366/F539/M763/F1038/T1102; N277/G366/F539/D965/F1038/T1102; N277/G366/F539/M763/D965/F1038/T1102; N277/G366/I601/M763/T1102; N277/G366/I601/D965/T1102; N277/G366/I601/F1038/T1102; N277/G366/I601/M763/D965/T1102; N277/G366/I601/M763/F1038/T1102; N277/G366/I601/D965/F1038/T1102; N277/G366/I601/M763/D965/F1038/T1102; G366/F539/I601/M763/T1102; G366/F539/I601/D965/T1102; G366/F539/I601/F1038/T1102; G366/F539/I601/M763/D965/T1102; G366/F539/I601/M763/F1038/T1102; G366/F539/I601/D965/F1038/T1102; G366/F539/I601/M763/D965/F1038/T1102; A203/N277/G366/M763/D1127; A203/N277/G366/D965/D1127; A203/N277/G366/F1038/D1127; A203/N277/G366/M763/D965/D1127; A203/N277/G366/M763/F1038/D1127; A203/N277/G366/D965/F1038/D1127; A203/N277/G366/M763/D965/F1038/D1127; A203/N277/F539/M763/D1127; A203/N277/F539/D965/D1127; A203/N277/F539/F1038/D1127; A203/N277/F539/M763/D965/D1127; A203/N277/F539/M763/F1038/D1127; A203/N277/F539/D965/F1038/D1127; A203/N277/F539/M763/D965/F1038/D1127; A203/N277/I601/M763/D1127; A203/N277/I601/D965/D1127; A203/N277/I601/F1038/D1127; A203/N277/I601/M763/D965/D1127; A203/N277/I601/M763/F1038/D1127; A203/N277/I601/D965/F1038/D1127; A203/N277/I601/M763/D965/F1038/D1127; A203/G366/F539/M763/D1127; A203/G366/F539/D965/D1127; A203/G366/F539/F1038/D1127; A203/G366/F539/M763/D965/D1127; A203/G366/F539/M763/F1038/D1127; A203/G366/F539/D965/F1038/D1127; A203/G366/F539/M763/D965/F1038/D1127; A203/G366/I601/M763/D1127; A203/G366/I601/D965/D1127; A203/G366/I601/F1038/D1127; A203/G366/I601/M763/D965/D1127; A203/G366/I601/M763/F1038/D1127; A203/G366/I601/D965/F1038/D1127; A203/G366/I601/M763/D965/F1038/D1127; A203/F539/I601/M763/D1127; A203/F539/I601/D965/D1127; A203/F539/I601/F1038/D1127; A203/F539/I601/M763/D965/D1127; A203/F539/I601/M763/F1038/D1127; A203/F539/I601/D965/F1038/D1127; A203/F539/I601/M763/D965/F1038/D1127; N277/G366/F539/M763/D1127; N277/G366/F539/D965/D1127; N277/G366/F539/F1038/D1127; N277/G366/F539/M763/D965/D1127; N277/G366/F539/M763/F1038/D1127; N277/G366/F539/D965/F1038/D1127; N277/G366/F539/M763/D965/F1038/D1127; N277/G366/I601/M763/D1127; N277/G366/I601/D965/D1127; N277/G366/I601/F1038/D1127; N277/G366/I601/M763/D965/D1127; N277/G366/I601/M763/F1038/D1127; N277/G366/I601/D965/F1038/D1127; N277/G366/I601/M763/D965/F1038/D1127; G366/F539/I601/M763/D1127; G366/F539/I601/D965/D1127; G366/F539/I601/F1038/D1127; G366/F539/I601/M763/D965/D1127; G366/F539/I601/M763/F1038/D1127; G366/F539/I601/D965/F1038/D1127; or G366/F539/I601/M763/D965/F1038/D1127 of the wild-type SpCas9.

In another exemplary embodiment, the TS-SpCas9 may be a SpCas9 variant formed by modifying A203/N277/G366/M763/T1102/D1127; A203/N277/G366/D965/T1102/D1127; A203/N277/G366/F1038/T1102/D1127; A203/N277/G366/M763/D965/T1102/D1127; A203/N277/G366/M763/F1038/T1102/D1127; A203/N277/G366/D965/F1038/T1102/D1127; A203/N277/G366/M763/D965/F1038/T1102/D1127; A203/N277/F539/M763/T1102/D1127; A203/N277/F539/D965/T1102/D1127; A203/N277/F539/F1038/T1102/D1127; A203/N277/F539/M763/D965/T1102/D1127; A203/N277/F539/M763/F1038/T1102/D1127; A203/N277/F539/D965/F1038/T1102/D1127; A203/N277/F539/M763/D965/F1038/T1102/D1127; A203/N277/I601/M763/T1102/D1127; A203/N277/I601/D965/T1102/D1127; A203/N277/I601/F1038/T1102/D1127; A203/N277/I601/M763/D965/T1102/D1127; A203/N277/I601/M763/F1038/T1102/D1127; A203/N277/I601/D965/F1038/T1102/D1127; A203/N277/I601/M763/D965/F1038/T1102/D1127; A203/G366/F539/M763/T1102/D1127; A203/G366/F539/D965/T1102/D1127; A203/G366/F539/F1038/T1102/D1127; A203/G366/F539/M763/D965/T1102/D1127; A203/G366/F539/M763/F1038/T1102/D1127; A203/G366/F539/D965/F1038/T1102/D1127; A203/G366/F539/M763/D965/F1038/T1102/D1127; A203/G366/I601/M763/T1102/D1127; A203/G366/I601/D965/

T1102/D1127; A203/G366/I601/F1038/T1102/D1127; A203/G366/I601/M763/D965/T1102/D1127; A203/G366/I601/M763/F1038/T1102/D1127; A203/G366/I601/M763/D965/F1038/T1102/D1127; A203/G366/I601/M763/D965/F1038/T1102/D1127; A203/F539/I601/M763/T1102/D1127; A203/F539/I601/D965/T1102/D1127; A203/F539/I601/F1038/T1102/D1127; A203/F539/I601/M763/D965/T1102/D1127; A203/F539/I601/M763/F1038/T1102/D1127; A203/F539/I601/D965/F1038/T1102/D1127; A203/F539/I601/M763/D965/F1038/T1102/D1127; N277/G366/F539/M763/T1102/D1127; N277/G366/F539/D965/T1102/D1127; N277/G366/F539/F1038/T1102/D1127; N277/G366/F539/M763/D965/T1102/D1127; N277/G366/F539/M763/F1038/T1102/D1127; N277/G366/F539/D965/F1038/T1102/D1127; N277/G366/F539/M763/D965/F1038/T1102/D1127; N277/G366/I601/M763/T1102/D1127; N277/G366/I601/D965/T1102/D1127; N277/G366/I601/F1038/T1102/D1127; N277/G366/I601/M763/D965/T1102/D1127; N277/G366/I601/M763/F1038/T1102/D1127; N277/G366/I601/D965/F1038/T1102/D1127; N277/G366/I601/M763/D965/F1038/T1102/D1127; G366/F539/I601/M763/T1102/D1127; G366/F539/I601/D965/T1102/D1127; G366/F539/I601/F1038/T1102/D1127; G366/F539/I601/M763/D965/T1102/D1127; G366/F539/I601/M763/F1038/T1102/D1127; G366/F539/I601/D965/F1038/T1102/D1127; or G366/F539/I601/M763/D965/F1038/T1102/D1127 of the wild-type SpCas9.

In one exemplary embodiment, the TS-SpCas9 may be a SpCas9 variant formed by modifying A203/N277/G366/F539/M763/T1102; A203/N277/G366/F539/D965/T1102; A203/N277/G366/F539/F1038/T1102; A203/N277/G366/F539/M763/D965/T1102; A203/N277/G366/F539/M763/F1038/T1102; A203/N277/G366/F539/D965/F1038/T1102; A203/N277/G366/F539/M763/D965/F1038/T1102; A203/N277/G366/I601/M763/T1102; A203/N277/G366/I601/D965/T1102; A203/N277/G366/I601/F1038/T1102; A203/N277/G366/I601/M763/D965/T1102; A203/N277/G366/I601/M763/F1038/T1102; A203/N277/G366/I601/D965/F1038/T1102; A203/N277/G366/I601/M763/D965/F1038/T1102; N277/G366/F539/I601/M763/T1102; N277/G366/F539/I601/D965/T1102; N277/G366/F539/I601/F1038/T1102; N277/G366/F539/I601/M763/D965/T1102; N277/G366/F539/I601/M763/F1038/T1102; N277/G366/F539/I601/D965/F1038/T1102; A203/N277/G366/F539/I601/M763/T1102; A203/N277/G366/F539/I601/D965/T1102; A203/N277/G366/F539/I601/F1038/T1102; A203/N277/G366/F539/I601/M763/D965/T1102; A203/N277/G366/F539/I601/M763/F1038/T1102; A203/N277/G366/F539/I601/D965/F1038/T1102; A203/N277/G366/F539/M763/D965/D1127; A203/N277/G366/F539/D965/D1127; A203/N277/G366/F539/F1038/D1127; A203/N277/G366/F539/M763/D965/D1127; A203/N277/G366/F539/M763/F1038/D1127; A203/N277/G366/F539/D965/F1038/D1127; A203/N277/G366/F539/M763/D965/F1038/D1127; A203/N277/G366/I601/M763/D1127; A203/N277/G366/I601/D965/D1127; A203/N277/G366/I601/F1038/D1127; A203/N277/G366/I601/M763/D965/D1127; A203/N277/G366/I601/M763/F1038/D1127; A203/N277/G366/I601/D965/F1038/D1127; A203/N277/G366/I601/M763/D965/F1038/D1127; N277/G366/F539/I601/M763/D1127; N277/G366/F539/I601/D965/D1127; N277/G366/F539/I601/F1038/D1127; N277/G366/F539/I601/M763/D965/D1127; N277/G366/F539/I601/M763/F1038/D1127; N277/G366/F539/I601/D965/F1038/D1127; N277/G366/F539/I601/M763/D965/F1038/D1127; A203/N277/G366/F539/I601/D965/D1127; A203/N277/G366/F539/I601/F1038/D1127; A203/N277/G366/F539/I601/M763/F1038/D1127; A203/N277/G366/F539/I601/D965/F1038/D1127; or A203/N277/G366/F539/I601/M763/D965/F1038/D1127 of the wild-type SpCas9.

In another exemplary embodiment, the TS-SpCas9 may be a SpCas9 variant formed by modifying A203/N277/G366/F539/M763/T1102/D1127; A203/N277/G366/F539/D965/T1102/D1127; A203/N277/G366/F539/F1038/T1102/D1127; A203/N277/G366/F539/M763/D965/T1102/D1127; A203/N277/G366/F539/M763/F1038/T1102/D1127; A203/N277/G366/F539/D965/F1038/T1102/D1127; A203/N277/G366/F539/M763/D965/F1038/T1102/D1127; A203/N277/G366/I601/M763/T1102/D1127; A203/N277/G366/I601/D965/T1102/D1127; A203/N277/G366/I601/F1038/T1102/D1127; A203/N277/G366/I601/M763/D965/T1102/D1127; A203/N277/G366/I601/M763/F1038/T1102/D1127; A203/N277/G366/I601/D965/F1038/T1102/D1127; A203/N277/G366/I601/M763/D965/F1038/T1102/D1127; N277/G366/F539/I601/M763/T1102/D1127; N277/G366/F539/I601/D965/T1102/D1127; N277/G366/F539/I601/F1038/T1102/D1127; N277/G366/F539/I601/M763/D965/T1102/D1127; N277/G366/F539/I601/M763/F1038/T1102/D1127; N277/G366/F539/I601/D965/F1038/T1102/D1127; N277/G366/F539/I601/M763/D965/F1038/T1102/D1127; A203/N277/G366/F539/I601/M763/T1102/D1127; A203/N277/G366/F539/I601/D965/T1102/D1127; A203/N277/G366/F539/I601/F1038/T1102/D1127; A203/N277/G366/F539/I601/M763/D965/T1102/D1127; A203/N277/G366/F539/I601/M763/F1038/T1102/D1127; A203/N277/G366/F539/I601/D965/F1038/T1102/D1127; or A203/N277/G366/F539/I601/M763/D965/F1038/T1102/D1127 of the wild-type SpCas9.

The TS-SpCas9 may be a SpCas9 variant formed by modifying three or more amino acids selected from the amino acid sequences of the second region, the third region and the fourth region of the wild-type SpCas9. Here, the three or more amino acids may be present in different regions, respectively.

The TS-SpCas9 may be a SpCas9 variant formed by modifying one or more amino acids selected from the amino acid sequence(s) of the region 2-1, the region 2-2 and/or the region 2-3; one or more amino acids selected from the amino acid sequence of the region 3-1; and one or more amino acids selected from the amino acid sequence of the region 4-1 of the wild-type SpCas9.

The TS-SpCas9 may be a SpCas9 variant formed by modifying one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3; one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, K880, R884, K890, R895, K896 and D898 in the region 3-1;

and one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying M763/K890/T1102; K890/D965/T1102; K890/F1038/T1102; M763/K890/D1127; K890/D965/D1127; K890/F1038/D1127; M763/K890/T1102/D1127; K890/D965/T1102/D1127; or K890/F1038/T1102/D1127 of the wild-type SpCas9.

In another exemplary embodiment, the TS-SpCas9 may be a SpCas9 variant formed by modifying M763/K890/D965/T1102; M763/K890/F1038/T1102; K890/D965/F1038/T1102; M763/K890/D965/D1127; M763/K890/F1038/D1127; K890/D965/F1038/D1127; M763/K890/D965/T1102/D1127; M763/K890/F1038/T1102/D1127; or K890/D965/F1038/T1102/D1127 of the wild-type SpCas9.

In still another exemplary embodiment, the TS-SpCas9 may be a SpCas9 variant formed by modifying M763/K890/D965/F1038/T1102; M763/K890/D965/F1038/D1127 or M763/K890/D965/F1038/T1102/D1127 of the wild-type SpCas9.

The TS-SpCas9 may be a SpCas9 variant formed by modifying three or more amino acids selected from the amino acid sequences of the first region, the second region, the third region and the fourth region of the wild-type SpCas9. Here, the three or more amino acids may be present in different regions, respectively.

The TS-SpCas9 may be a SpCas9 variant formed by modifying one or more amino acids selected from the amino acid sequence(s) of the region 2-1, the region 2-2 and/or the region 2-3; one or more amino acids selected from the amino acid sequence of the region 3-1; and one or more amino acids selected from the amino acid sequence of the region 4-1 of the wild-type SpCas9.

The TS-SpCas9 may be a SpCas9 variant formed by modifying one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4; one or more amino acids 17, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3; one or more amino acids selected from the group consisting of K775, R778, E779, R780, K782, R783, E785, E786, K789, E790, K797, E798, H799, E802, E809, K810, R820, D821, D825, E827, D829, R832, D835, D837, D839, H840, K848, D849, D850, D853, K855, R859, D861, K862, R864, K866, D868, E873, E874, K877, K878, D880, R884, K890, R895, K896 and D898 in the region 3-1; and one or more amino acids selected from the group consisting of T1102, S1106, E1108, S1116, D1117, D1125, D1127, D1135, S1136 and T1138 in the region 4-1 of the wild-type SpCas9.

In one exemplary embodiment, the TS-SpCas9 may be a SpCas9 variant formed by modifying A203/M763/K890/T1102; A203/K890/D965/T1102; A203/K890/F1038/T1102; A203/M763/K890/D965/T1102; A203/M763/K890/F1038/T1102; A203/K890/D965/F1038/T1102; A203/M763/K890/D965/F1038/T1102; N277/M763/K890/T1102; N277/K890/D965/T1102; N277/K890/F1038/T1102; N277/M763/K890/D965/T1102; N277/M763/K890/F1038/T1102; N277/K890/D965/F1038/T1102; N277/M763/K890D965/F1038/T1102; G366/M763/K890/T1102; G366/K890/D965/T1102; G366/K890/F1038/T1102; G366/M763/K890/D965/T1102; G366/M763/K890/F1038/T1102; G366/K890/D965/F1038/T1102; G366/M763/K890/D965/F1038/T1102; F539/M763/K890/T1102; F539/K890/D965/T1102; F539/K890/F1038/T1102; F539/M763/K890/D965/T1102; F539/M763/K890/F1038/T1102; F539/K890/D965/F1038/T1102; F539/M763/K890/D965/F1038/T1102; I601/M763/K890/T1102; I601/K890/D965/T1102; I601/K890/F1038/T1102; I601/M763/K890/D965/T1102; I601/M763/K890/F1038/T1102; I601/K890/D965/F1038/T1102; I601/M763/K890/D965/F1038/T1102; A203/M763/K890/D1127; A203/K890/D965/D1127; A203/K890/F1038/D1127; A203/M763/K890/D965/D1127; A203/M763/K890/F1038/D1127; A203/K890/D965/F1038/D1127; A203/M763/K890/D965/F1038/D1127; N277/M763/K890/D1127; N277/K890/D965/D1127; N277/K890/F1038/D1127; N277/M763/K890/D965/D1127; N277/M763/K890/F1038/D1127; N277/K890/D965/F1038/D1127; N277/M763/K890D965/F1038/D1127; G366/M763/K890/D1127; G366/K890/D965/D1127; G366/K890/F1038/D1127; G366/M763/K890/D965/D1127; G366/M763/K890/F1038/D1127; G366/K890/D965/F1038/D1127; G366/M763/K890/D965/F1038/D1127; F539/M763/K890/D1127; F539/K890/D965/D1127; F539/K890/F1038/D1127; F539/M763/K890/D965/D1127; F539/M763/K890/F1038/D1127; F539/K890/D965/F1038/D1127; F539/M763/K890/D965/F1038/D1127; I601/M763/K890/D1127; I601/K890/D965/D1127; I601/K890/F1038/D1127; I601/M763/K890/D965/D1127; I601/M763/K890/F1038/D1127; I601/K890/D965/F1038/D1127; or I601/M763/K890/D965/F1038/D1127 of the wild-type SpCas9.

In another exemplary embodiment, the TS-SpCas9 may be a SpCas9 variant formed by modifying A203/M763/K890/T1102/D1127; A203/K890/D965/T1102/D1127; A203/K890/F1038/T1102/D1127; A203/M763/K890/D965/T1102/D1127; A203/M763/K890/F1038/T1102/D1127; A203/K890/D965/F1038/T1102/D1127; A203/M763/K890/D965/F1038/T1102/D1127; N277/M763/K890/T1102/D1127; N277/K890/D965/T1102/D1127; N277/K890/F1038/T1102/D1127; N277/M763/K890/D965/T1102/D1127; N277/M763/K890/F1038/T1102/D1127; N277/K890/D965/F1038/T1102/D1127; N277/M763/K890D965/F1038/T1102/D1127; G366/M763/K890/T1102/D1127; G366/K890/D965/T1102/D1127; G366/K890/F1038/T1102/D1127; G366/M763/K890/D965/T1102/D1127; G366/M763/K890/F1038/T1102/D1127; G366/K890/D965/F1038/T1102/D1127; G366/M763/K890/D965/F1038/T1102/D1127; F539/M763/K890/T1102/D1127; F539/K890/D965/F1038/T1102/D1127; F539/K890/F1038/T1102/

D1127; F539/M763/K890/D965/T1102/D1127; F539/M763/K890/F1038/T1102/D1127; F539/K890/D965/F1038/T1102/D1127; F539/M763/K890/D965/F1038/T1102/D1127; I601/M763/K890/T1102/D1127; I601/K890/D965/T1102/D1127; I601/K890/F1038/T1102/D1127; I601/M763/K890/D965/T1102/D1127; I601/M763/K890/F1038/T1102/D1127; I601/K890/D965/F1038/T1102/D1127; or I601/M763/K890/D965/F1038/T1102/D1127 of the wild-type SpCas9.

In one exemplary embodiment, the TS-SpCas9 may be a SpCas9 variant formed by modifying A203/N277/M763/K890/T1102; A203/N277/K890/D965/T1102; A203/N277/K890/F1038/T1102; A203/N277/M763/K890/D965/T1102; A203/N277/M763/K890/F1038/T1102; A203/N277/K890/D965/F1038/T1102; A203/N277/M763/K890/D965/F1038/T1102; A203/G366/M763/K890/T1102; A203/G366/K890/D965/T1102; A203/G366/K890/F1038/T1102; A203/G366/M763/K890/D965/T1102; A203/G366/M763/K890/F1038/T1102; A203/G366/K890/D965/F1038/T1102; A203/G366/M763/K890/D965/F1038/T1102; A203/F539/M763/K890/T1102; A203/F539/K890/D965/T1102; A203/F539/K890/F1038/T1102; A203/F539/M763/K890/D965/T1102; A203/F539/M763/K890/F1038/T1102; A203/F539/K890/D965/F1038/T1102; A203/F539/M763/K890/D965/F1038/T1102; A203/I601/M763/K890/T1102; A203/I601/K890/D965/T1102; A203/I601/K890/F1038/T1102; A203/I601/M763/K890/D965/T1102; A203/I601/M763/K890/F1038/T1102; A203/I601/K890/D965/F1038/T1102; A203/I601/M763/K890/D965/F1038/T1102; N277/G366/M763/K890/T1102; N277/G366/K890/D965/T1102; N277/G366/K890/F1038/T1102; N277/G366/M763/K890/D965/T1102; N277/G366/M763/K890/F1038/T1102; N277/G366/K890/D965/F1038/T1102; N277/G366/M763/K890/D965/F1038/T1102; N277/F539/M763/K890/T1102; N277/F539/K890/D965/T1102; N277/F539/K890/F1038/T1102; N277/F539/M763/K890/D965/T1102; N277/F539/M763/K890/F1038/T1102; N277/F539/K890/D965/F1038/T1102; N277/F539/M763/K890/D965/F1038/T1102; N277/I601/M763/K890/T1102; N277/I601/K890/D965/T1102; N277/I601/K890/F1038/T1102; N277/I601/M763/K890/D965/T1102; N277/I601/M763/K890/F1038/T1102; N277/I601/K890/D965/F1038/T1102; N277/I601/M763/K890/D965/F1038/T1102; G366/F539/M763/K890/T1102; G366/F539/K890/D965/T1102; G366/F539/K890/F1038/T1102; G366/F539/M763/K890/D965/T1102; G366/F539/M763/K890/F1038/T1102; G366/F539/K890/D965/F1038/T1102; G366/F539/M763/K890/D965/F1038/T1102; G366/I601/M763/K890/T1102; G366/I601/K890/D965/T1102; G366/I601/K890/F1038/T1102; G366/I601/M763/K890/D965/T1102; G366/I601/M763/K890/F1038/T1102; G366/I601/K890/D965/F1038/T1102; G366/I601/M763/K890/D965/F1038/T1102; F539/I601/M763/K890/T1102; F539/I601/K890/D965/T1102; F539/I601/K890/F1038/T1102; F539/I601/M763/K890/D965/T1102; F539/I601/M763/K890/F1038/T1102; F539/I601/K890/D965/F1038/T1102; F539/I601/M763/K890/D965/F1038/T1102; A203/N277/M763/K890/D1127; A203/N277/K890/D965/D1127; A203/N277/K890/F1038/D1127; A203/N277/M763/K890/D965/D1127; A203/N277/M763/K890/F1038/D1127; A203/N277/K890/D965/F1038/D1127; A203/N277/M763/K890/D965/F1038/D1127; A203/G366/M763/K890/D1127; A203/G366/K890/D965/D1127; A203/G366/K890/F1038/D1127; A203/G366/M763/K890/D965/D1127; A203/G366/M763/K890/F1038/D1127; A203/G366/K890/D965/F1038/D1127; A203/G366/M763/K890/D965/F1038/D1127; A203/F539/M763/K890/D1127; A203/F539/K890/D965/D1127; A203/F539/K890/F1038/D1127; A203/F539/M763/K890/D965/D1127; A203/F539/M763/K890/F1038/D1127; A203/F539/K890/D965/F1038/D1127; A203/F539/M763/K890/D965/F1038/D1127; A203/I601/M763/K890/D1127; A203/I601/K890/D965/D1127; A203/I601/K890/F1038/D1127; A203/I601/M763/K890/D965/D1127; A203/I601/M763/K890/F1038/D1127; A203/I601/K890/D965/F1038/D1127; A203/I601/M763/K890/D965/F1038/D1127; N277/G366/M763/K890/D1127; N277/G366/K890/D965/D1127; N277/G366/K890/F1038/D1127; N277/G366/M763/K890/D965/D1127; N277/G366/M763/K890/F1038/D1127; N277/G366/K890/D965/F1038/D1127; N277/G366/M763/K890/D965/F1038/D1127; N277/F539/M763/K890/D1127; N277/F539/K890/D965/D1127; N277/F539/K890/F1038/D1127; N277/F539/M763/K890/D965/D1127; N277/F539/M763/K890/F1038/D1127; N277/F539/K890/D965/F1038/D1127; N277/F539/M763/K890/D965/F1038/D1127; N277/I601/M763/K890/D1127; N277/I601/K890/D965/D1127; N277/I601/K890/F1038/D1127; N277/I601/M763/K890/D965/D1127; N277/I601/M763/K890/F1038/D1127; N277/I601/K890/D965/F1038/D1127; N277/I601/M763/K890/D965/F1038/D1127; G366/F539/M763/K890/D1127; G366/F539/K890/D965/D1127; G366/F539/K890/F1038/D1127; G366/F539/M763/K890/D965/D1127; G366/F539/M763/K890/F1038/D1127; G366/F539/K890/D965/F1038/D1127; G366/F539/M763/K890/D965/F1038/D1127; G366/I601/M763/K890/D1127; G366/I601/K890/D965/D1127; G366/I601/K890/F1038/D1127; G366/I601/M763/K890/D965/D1127; G366/I601/M763/K890/F1038/D1127; G366/I601/K890/D965/F1038/D1127; G366/I601/M763/K890/D965/F1038/D1127; F539/I601/M763/K890/D1127; F539/I601/K890/D965/D1127; F539/I601/K890/F1038/D1127; F539/I601/M763/K890/D965/D1127; F539/I601/M763/K890/F1038/D1127; F539/I601/K890/D965/F1038/D1127; or F539/I601/M763/K890/D965/F1038/D1127 of the wild-type SpCas9.

In another exemplary embodiment, the TS-SpCas9 may be a SpCas9 variant formed by modifying A203/N277/M763/K890/T1102/D1127; A203/N277/K890/D965/T1102/D1127; A203/N277/K890/F1038/T1102/D1127; A203/N277/M763/K890/D965/T1102/D1127; A203/N277/M763/K890/F1038/T1102/D1127; A203/N277/K890/D965/F1038/T1102/D1127; A203/N277/M763/K890/D965/F1038/T1102/D1127; A203/G366/M763/K890/T1102/D1127; A203/G366/K890/D965/T1102/D1127; A203/G366/K890/F1038/T1102/D1127; A203/G366/M763/K890/D965/T1102/D1127; A203/G366/M763/K890/F1038/T1102/D1127; A203/G366/K890/D965/F1038/T1102/D1127; A203/G366/M763/K890/D965/F1038/T1102/D1127; A203/F539/M763/K890/T1102/D1127; A203/F539/K890/D965/T1102/D1127; A203/F539/K890/F1038/T1102/D1127; A203/F539/M763/K890/D965/T1102/D1127; A203/F539/M763/K890/F1038/T1102/D1127; A203/F539/K890/D965/F1038/T1102/D1127; A203/F539/M763/K890/D965/F1038/T1102/D1127; A203/I601/M763/K890/T1102/D1127; A203/I601/K890/D965/T1102/D1127; A203/I601/K890/F1038/T1102/D1127; A203/I601/M763/K890/D965/T1102/D1127; A203/I601/M763/K890/F1038/T1102/D1127; A203/I601/K890/D965/F1038/T1102/D1127; A203/I601/M763/K890/D965/F1038/T1102/D1127; N277/G366/M763/K890/T1102/D1127; N277/G366/K890/D965/T1102/D1127; N277/G366/K890/F1038/T1102/D1127; N277/G366/M763/K890/D965/T1102/D1127; N277/G366/M763/K890/F1038/T1102/D1127; N277/G366/K890/D965/F1038/T1102/D1127; N277/G366/M763/K890/D965/F1038/T1102/D1127; N277/F539/M763/K890/T1102/D1127; N277/F539/K890/D965/T1102/D1127; N277/F539/K890/F1038/T1102/D1127; N277/F539/M763/

K890/D965/T1102/D1127; N277/F539/M763/K890/F1038/ T1102/D1127; N277/F539/K890/D965/F1038/T1102/ D1127; N277/F539/M763/K890/D965/F1038/T1102/ D1127; N277/I601/M763/K890/T1102/D1127; N277/I601/ K890/D965/T1102/D1127; N277/I601/K890/F1038/T1102/ D1127; N277/I601/M763/K890/D965/T1102/D1127; N277/ I601/M763/K890/F1038/T1102/D1127; N277/I601/K890/ D965/F1038/T1102/D1127; N277/I601/M763/K890/D965/ F1038/T1102/D1127; G366/F539/M763/K890/T1102/ D1127; G366/F539/K890/D965/T1102/D1127; G366/F539/ K890/F1038/T1102/D1127; G366/F539/M763/K890/D965/ T1102/D1127; G366/F539/M763/K890/F1038/T1102/ D1127; G366/F539/K890/D965/F1038/T1102/D1127; G366/F539/M763/K890/D965/F1038/T1102/D1127; G366/ I601/M763/K890/T1102/D1127; G366/I601/K890/D965/ T1102/D1127; G366/I601/K890/F1038/T1102/D1127; G366/I601/M763/K890/D965/T1102/D1127; G366/I601/ M763/K890/F1038/T1102/D1127; G366/I601/K890/D965/ F1038/T1102/D1127; G366/I601/M763/K890/D965/F1038/ T1102/D1127; F539/I601/M763/K890/T1102/D1127; F539/ I601/K890/D965/T1102/D1127; F539/I601/K890/F1038/ T1102/D1127; F539/I601/M763/K890/D965/T1102/D1127; F539/I601/M763/K890/F1038/T1102/D1127; F539/I601/ K890/D965/F1038/T1102/D1127; or F539/I601/M763/ K890/D965/F1038/T1102/D1127 of the wild-type SpCas9.

In one exemplary embodiment, the TS-SpCas9 may be a SpCas9 variant formed by modifying A203/N277/G366/ M763/K890/T1102; A203/N277/G366/K890/D965/T1102; A203/N277/G366/K890/F1038/T1102; A203/N277/G366/ M763/K890/D965/T1102; A203/N277/G366/M763/K890/ F1038/T1102; A203/N277/G366/K890/D965/F1038/ T1102; A203/N277/G366/M763/K890/D965/F103811102; A203/N277/F539/M763/K890/T1102; A203/N277/F539/ K890/D965/T1102; A203/N277/F539/K890/F103811102; A203/N277/F539/M763/K890/D965/T1102; A203/N277/ F539/M763/K890/F1038/T1102; A203/N277/F539/K890/ D965/F1038/T1102; A203/N277/F539/M763/K890/D965/ F1038/T1102; A203/N277/I601/M763/K890/T1102; A203/ N277/I601/K890/D965/T1102; A203/N277/I601/K890/ F1038/T1102; A203/N277/I601/M763/K890/D965/T1102; A203/N277/I601/M763/K890/F1038/T1102; A203/N277/ I601/K890/D965/F1038/T1102; A203/N277/I601/M763/ K890/D965/F1038/T1102; A203/G366/F539/M763/K890/ T1102; A203/G366/F539/K890/D965/T1102; A203/G366/ F539/K890/F1038/T1102; A203/G366/F539/M763/K890/ D965/T1102; A203/G366/F539/M763/K890/F1038/T1102; A203/G366/F539/K890/D965/F1038/T1102; A203/G366/ F539/M763/K890/D965/F1038/T1102; A203/G366/I601/ M763/K890/T1102; A203/G366/I601/K890/D965/T1102; A203/G366/I601/K890/F1038/T1102; A203/G366/I601/ M763/K890/D965/T1102; A203/G366/I601/M763/K890/ F1038/T1102; A203/G366/I601/K890/D965/F1038/T1102; A203/G366/I601/M763/K890/D965/F1038/T1102; A203/ F539/I601/M763/K890/T1102; A203/F539/I601/K890/ D965/T1102; A203/F539/I601/K890/F1038/T1102; A203/ F539/I601/M763/K890/D965/T1102; A203/F539/I601/ M763/K890/F1038/T1102; A203/F539/I601/K890/D965/ F1038/T1102; A203/F539/I601/M763/K890/D965/F1038/ T1102; N277/G366/F539/M763/K890/T1102; N277/G366/ F539/K890/D965/T1102; N277/G366/F539/K890/F1038/ T1102; N277/G366/F539/M763/K890/D965/T1102; N277/ G366/F539/M763/K890/F1038/T1102; N277/G366/F539/ K890/D965/F1038/T1102; N277/G366/F539/M763/K890/ D965/F1038/T1102; N277/G366/I601/M763/K890/T1102; N277/G366/I601/K890/D965/T1102; N277/G366/I601/ K890/F1038/T1102; N277/G366/I601/M763/K890/D965/ T1102; N277/G366/I601/M763/K890/F1038/T1102; N277/ G366/I601/K890/D965/F1038/T1102; N277/G366/I601/ M763/K890/D965/F1038/T1102; N277/G366/F539/I1038/T1102; N277/G366/I601/ M763/K890/D965/F1038/T1102; G366/F539/I601/M763/ K890/T1102; G366/F539/I601/K890/D965/T1102; G366/ F539/I601/K890/F103811102; G366/F539/I601/M763/ K890/D965/T1102; G366/F539/I601/M763/K890/F1038/ T1102; G366/F539/I601/K890/D965/F1038/T1102; G366/ F539/I601/M763/K890/D965/F1038/T1102; A203/N277/ G366/M763/K890/D1127; A203/N277/G366/K890/D965/ D1127; A203/N277/G366/K890/F1038/D1127; A203/ N277/G366/M763/K890/D965/D1127; A203/N277/G366/ M763/K890/F1038/D1127; A203/N277/G366/K890/D965/ F1038/D1127; A203/N277/G366/M763/K890/D965/F1038/ D1127; A203/N277/F539/M763/K890/D1127; A203/N277/ F539/K890/D965/D1127; A203/N277/F539/K890/F1038/ D1127; A203/N277/F539/M763/K890/D965/D1127; A203/ N277/F539/M763/K890/F1038/D1127; A203/N277/F539/ K890/D965/F1038/D1127; A203/N277/F539/M763/K890/ D965/F1038/D1127; A203/N277/I601/M763/K890/D1127; A203/N277/I601/K890/D965/D1127; A203/N277/I601/ K890/F1038/D1127; A203/N277/I601/M763/K890/D965/ D1127; A203/N277/I601/M763/K890/F1038/D1127; A203/ N277/I601/K890/D965/F1038/D1127; A203/N277/I601/ M763/K890/D965/F1038/D1127; A203/G366/F539/M763/ K890/D1127; A203/G366/F539/K890/D965/D1127; A203/ G366/F539/K890/F1038/D1127; A203/G366/F539/M763/ K890/D965/D1127; A203/G366/F539/M763/K890/F1038/ D1127; A203/G366/F539/K890/D965/F1038/D1127; A203/ G366/F539/M763/K890/D965/F1038/D1127; A203/G366/ I601/M763/K890/D1127; A203/G366/I601/K890/D965/ D1127; A203/G366/I601/K890/F1038/D1127; A203/G366/ I601/M763/K890/D965/D1127; A203/G366/I601/M763/ K890/F1038/D1127; A203/G366/I601/K890/D965/F1038/ D1127; A203/G366/I601/M763/K890/D965/F1038/D1127; A203/F539/I601/M763/K890/D1127; A203/F539/I601/ K890/D965/D1127; A203/F539/I601/K890/F1038/D1127; A203/F539/I601/M763/K890/D965/D1127; A203/F539/ I601/M763/K890/F1038/D1127; A203/F539/I601/K890/ D965/F1038/D1127; A203/F539/I601/M763/K890/D965/ F1038/D1127; N277/G366/F539/M763/K890/D1127; N277/G366/F539/K890/D965/D1127; N277/G366/F539/ K890/F1038/D1127; N277/G366/F539/M763/K890/D965/ D1127; N277/G366/F539/M763/K890/F1038/D1127; N277/G366/F539/K890/D965/F1038/D1127; N277/G366/ F539/M763/K890/D965/F1038/D1127; N277/G366/I601/ M763/K890/D1127; N277/G366/I601/K890/D965/D1127; N277/G366/I601/K890/F1038/D1127; N277/G366/I601/ M763/K890/D965/D1127; N277/G366/I601/M763/K890/ F1038/D1127; N277/G366/I601/K890/D965/F1038/D1127; N277/G366/I601/M763/K890/D965/F1038/D1127; G366/ F539/I601/M763/K890/D1127; G366/F539/I601/K890/ D965/D1127; G366/F539/I601/K890/F1038/D1127; G366/ F539/I601/M763/K890/D965/D1127; G366/F539/I601/ M763/K890/F1038/D1127; G366/F539/I601/K890/D965/ F1038/D1127; or G366/F539/I601/M763/K890/D965/ F1038/D1127 of the wild-type SpCas9.

In another exemplary embodiment, the TS-SpCas9 may be a SpCas9 variant formed by modifying A203/N277/ G366/M763/K890/T1102/D1127; A203/N277/G366/K890/ D965/T1102/D1127; A203/N277/G366/K890/F1038/ T1102/D1127; A203/N277/G366/M763/K890/D965/T1102/ D1127; A203/N277/G366/M763/K890/F1038/T1102/ D1127; A203/N277/G366/K890/D965/F1038/T1102/ D1127; A203/N277/G366/M763/K890/D965/F1038/T1102/ D1127; A203/N277/F539/M763/K890/T1102/D1127; A203/N277/F539/K890/D965/T1102/D1127; A203/N277/ F539/K890/F1038/T1102/D1127; A203/N277/F539/M763/ K890/D965/T1102/D1127; A203/N277/F539/M763/K890/

F1038/T1102/D1127; A203/N277/F539/K890/D965/F1038/ T1102/D1127; A203/N277/F539/M763/K890/D965/F1038/ T1102/D1127; A203/N277/I601/M763/K890/T1102/ D1127; A203/N277/I601/K890/D965/T1102/D1127; A203/ N277/I601/K890/F1038/T1102/D1127; A203/N277/I601/ M763/K890/D965/T1102/D1127; A203/N277/I601/M763/ K890/F1038/T1102/D1127; A203/N277/I601/K890/D965/ F1038/T1102/D1127; A203/N277/I601/M763/K890/D965/ F1038/T1102/D1127; A203/G366/F539/M763/K890/ T1102/D1127; A203/G366/F539/K890/D965/T1102/ D1127; A203/G366/F539/K890/F1038/T1102/D1127; A203/G366/F539/M763/K890/D965/T1102/D1127; A203/ G366/F539/M763/K890/F1038/T1102/D1127; A203/G366/ F539/K890/D965/F1038/T1102/D1127; A203/G366/F539/ M763/K890/D965/F1038/T1102/D1127; A203/G366/I601/ M763/K890/T1102/D1127; A203/G366/I601/K890/D965/ T1102/D1127; A203/G366/I601/K890/F1038/T1102/ D1127; A203/G366/I601/M763/K890/D965/T1102/D1127; A203/G366/I601/M763/K890/F1038/T1102/D1127; A203/ G366/I601/K890/D965/F1038/T1102/D1127; A203/G366/ I601/M763/K890/D965/F1038/T1102/D1127; A203/F539/ I601/M763/K890/T1102/D1127; A203/F539/I601/K890/ D965/T1102/D1127; A203/F539/I601/K890/F1038/T1102/ D1127; A203/F539/I601/M763/K890/D965/T1102/D1127; A203/F539/I601/M763/K890/F1038/T1102/D1127; A203/ F539/I601/K890/D965/F1038/T1102/D1127; A203/F539/ I601/M763/K890/D965/F1038/T1102/D1127; N277/G366/ F539/M763/K890/T1102/D1127; N277/G366/F539/K890/ D965/T1102/D1127; N277/G366/F539/K890/F1038/ T1102/D1127; N277/G366/F539/M763/K890/D965/T1102/ D1127; N277/G366/F539/M763/K890/F1038/T1102/ D1127; N277/G366/F539/K890/D965/F1038/T1102/ D1127; N277/G366/F539/M763/K890/D965/F1038/T1102/ D1127; N277/G366/I601/M763/K890/T1102/D1127; N277/ G366/I601/K890/D965/T1102/D1127; N277/G366/I601/ K890/F1038/T1102/D1127; N277/G366/I601/M763/K890/ D965/T1102/D1127; N277/G366/I601/M763/K890/F1038/ T1102/D1127; N277/G366/I601/K890/D965/F1038/T1102/ D1127; N277/G366/I601/M763/K890/D965/F1038/T1102/ D1127; G366/F539/I601/M763/K890/T1102/D1127; G366/ F539/I601/K890/D965/T1102/D1127; G366/F539/I601/ K890/F1038/T1102/D1127; G366/F539/I601/M763/K890/ D965/T1102/D1127; G366/F539/I601/M763/K890/F1038/ T1102/D1127; G366/F539/I601/K890/D965/F1038/ D1127; or G366/F539/I601/M763/K890/D965/F1038/ T1102/D1127 of the wild-type SpCas9.

In one exemplary embodiment, the TS-SpCas9 may be a SpCas9 variant formed by modifying A203/N277/G366/ F539/M763/K890/T1102; A203/N277/G366/F539/K890/ D965/T1102; A203/N277/G366/F539/K890/F1038/T1102; A203/N277/G366/F539/M763/K890/D965/T1102; A203/ N277/G366/F539/M763/K890/F1038/T1102; A203/N277/ G366/F539/K890/D965/F1038/T1102; A203/N277/G366/ F539/M763/K890/D965/F1038/T1102; A203/N277/G366/ I601/M763/K890/T1102; A203/N277/G366/I601/K890/ D965/T1102; A203/N277/G366/I601/K890/F1038/T1102; A203/N277/G366/I601/M763/K890/D965/T1102; A203/ N277/G366/I601/M763/K890/F1038/T1102; A203/N277/ G366/I601/K890/D965/F1038/T1102; A203/N277/G366/ I601/M763/K890/D965/F1038/T1102; N277/G366/F539/ I601/M763/K890/T1102; N277/G366/F539/I601/K890/ D965/T1102; N277/G366/F539/I601/K890/F1038/T1102; N277/G366/F539/I601/M763/K890/D965/T1102; N277/ G366/F539/I601/M763/K890/F1038/T1102; N277/G366/ F539/I601/K890/D965/F1038/T1102; N277/G366/F539/ I601/M763/K890/D965/F1038/T1102; A203/N277/G366/ F539/I601/M763/K890/T1102; A203/N277/G366/F539/ I601/K890/D965/T1102; A203/N277/G366/F539/I601/ K890/F1038/T1102; A203/N277/G366/F539/I601/M763/ K890/D965/T1102; A203/N277/G366/F539/I601/M763/ K890/F1038/T1102; A203/N277/G366/F539/I601/K890/ D965/F1038/T1102; A203/N277/G366/F539/I601/M763/ K890/D965/F1038/T1102; A203/N277/G366/F539/M763/ K890/D1127; A203/N277/G366/F539/K890/D965/D1127; A203/N277/G366/F539/K890/F1038/D1127; A203/N277/ G366/F539/M763/K890/D965/D1127; A203/N277/G366/ F539/M763/K890/F1038/D1127; A203/N277/G366/F539/ K890/D965/F1038/D1127; A203/N277/G366/F539/M763/ K890/D965/F1038/D1127; A203/N277/G366/I601/M763/ K890/D1127; A203/N277/G366/I601/K890/D965/D1127; A203/N277/G366/I601/K890/F1038/D1127; A203/N277/ G366/I601/M763/K890/D965/D1127; A203/N277/G366/ I601/M763/K890/F1038/D1127; A203/N277/G366/I601/ K890/D965/F1038/D1127; A203/N277/ G366/I601/M763/K890/D965/D1127; A203/N277/G366/ I601/M763/K890/F1038/D1127; A203/N277/G366/I601/ K890/D965/F1038/D1127; A203/N277/G366/I601/M763/ K890/D965/F1038/D1127; N277/G366/F539/I601/M763/ K890/D1127; N277/G366/F539/I601/K890/D965/D1127; N277/G366/F539/I601/K890/F1038/D1127; N277/G366/ F539/I601/M763/K890/D965/D1127; N277/G366/F539/ I601/M763/K890/F1038/D1127; N277/G366/F539/I601/ K890/D965/F1038/D1127; N277/G366/F539/I601/M763/ K890/D965/F1038/D1127; A203/N277/G366/F539/I601/ M763/K890/D1127; A203/N277/G366/F539/I601/K890/ D965/D1127; A203/N277/G366/F539/I601/K890/F1038/ D1127; A203/N277/G366/F539/I601/M763/K890/D965/ D1127; A203/N277/G366/F539/I601/M763/K890/F1038/ D1127; A203/N277/G366/F539/I601/K890/D965/F1038/ D1127; or A203/N277/G366/F539/I601/M763/K890/D965/ F1038/D1127 of the wild-type SpCas9.

In another exemplary embodiment, the TS-SpCas9 may be a SpCas9 variant formed by modifying A203/N277/ G366/F539/M763/K890/T1102/D1127; A203/N277/G366/ F539/K890/D965/T1102/D1127; A203/N277/G366/F539/ K890/F1038/T1102/D1127; A203/N277/G366/F539/M763/ K890/D965/T1102/D1127; A203/N277/G366/F539/M763/ K890/F1038/T1102/D1127; A203/N277/G366/F539/K890/ D965/F1038/T1102/D1127; A203/N277/G366/F539/M763/ K890/D965/F1038/T1102/D1127; A203/N277/G366/I601/ M763/K890/T1102/D1127; A203/N277/G366/I601/K890/ D965/T1102/D1127; A203/N277/G366/I601/K890/F1038/ T1102/D1127; A203/N277/G366/I601/M763/K890/D965/ T1102/D1127; A203/N277/G366/I601/M763/K890/F1038/ T1102/D1127; A203/N277/G366/I601/K890/D965/F1038/ T1102/D1127; A203/N277/G366/I601/M763/K890/D965/ F1038/T1102/D1127; N277/G366/F539/I601/M763/K890/ T1102/D1127; N277/G366/F539/I601/K890/D965/T1102/ D1127; N277/G366/F539/I601/K890/F1038/T1102/D1127; N277/G366/F539/I601/M763/K890/D965/T1102/D1127; N277/G366/F539/I601/M763/K890/F1038/T1102/D1127; N277/G366/F539/I601/K890/D965/F1038/T1102/D1127; N277/G366/F539/I601/M763/K890/D965/F1038/T1102/ D1127; A203/N277/G366/F539/I601/M763/K890/T1102/ D1127; A203/N277/G366/F539/I601/K890/D965/T1102/ D1127; A203/N277/G366/F539/I601/K890/F1038/T1102/ D1127; A203/N277/G366/F539/I601/M763/K890/D965/ T1102/D1127; A203/N277/G366/F539/I601/M763/K890/ F1038/T1102/D1127; A203/N277/G366/F539/I601/K890/ D965/F1038/T1102/D1127; or A203/N277/G366/F539/ I601/M763/K890/D965/F1038/T1102/D1127 of the wild-type SpCas9.

The TS-SpCas9 may be a SpCas9 variant formed by removing one or more amino acids selected from the amino acid sequence(s) of the first region, the second region, the third region and/or the fourth region of the wild-type SpCas9.

The TS-SpCas9 may be a SpCas9 variant formed by removing one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the first region; 17, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the second region; K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the third region; and/or T1102, S1106, E1108, S1116, D1117, D1125, D1127, D1135, S1136 and T1138 in the fourth region of the wild-type SpCas9.

The TS-SpCas9 may be a SpCas9 variant formed by substituting one or more amino acids selected from the amino acid sequence(s) of the first region, the second region, the third region and/or the fourth region of the wild-type SpCas9 with different amino acid(s).

The TS-SpCas9 may be a SpCas9 variant formed by substituting one or more amino acids selected from the amino acid sequence of the first region of the wild-type SpCas9 with different amino acid(s).

The TS-SpCas9 may be a SpCas9 variant formed by substituting one or more amino acids selected from N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acid(s) having a relatively low hydropathy index.

In one exemplary embodiment, the TS-SpCas9 may be a SpCas9 variant formed by substituting A203 (hydropathy index: 1.8) in the region 1-1 of the wild-type SpCas9 with one amino acid selected from the group consisting of amino acids having a relatively low hydropathy index, such as arginine, asparagine, aspartic acid, glutamic acid, glutamine, glycine, histidine, lysine, proline, serine, threonine, tryptophan and tyrosine.

For example, the TS-SpCas9 may be a SpCas9 variant formed by substituting A203 (hydropathy index: 1.8) in the region 1-1 of the wild-type SpCas9 with an amino acid having a relatively low hydropathy index, such as aspartic acid (hydropathy index: −3.5).

In another exemplary embodiment, the TS-SpCas9 may be a SpCas9 variant formed by substituting G366 (hydropathy index: −0.4) in the region 1-2 of the wild-type SpCas9 with one amino acid selected from the group consisting of amino acids having a relatively low hydropathy index, such as arginine, asparagine, aspartic acid, glutamic acid, glutamine, histidine, lysine, proline, serine, threonine, tryptophan and tyrosine.

For example, the TS-SpCas9 may be a SpCas9 variant formed by substituting G366 (hydropathy index: −0.4) in the region 1-2 of the wild-type SpCas9 with an amino acid having a relatively low hydropathy index, such as serine (hydropathy index: −0.8).

In one exemplary embodiment, the TS-SpCas9 may be a SpCas9 variant formed by substituting F539 (hydropathy index: 2.8) in the region 1-3 of the wild-type SpCas9 with one amino acid selected from the group consisting of amino acids having a relatively low hydropathy index, such as alanine, arginine, asparagine, aspartic acid, cysteine, glutamic acid, glutamine, glycine, histidine, lysine, methionine, proline, serine, threonine, tryptophan and tyrosine.

For example, the TS-SpCas9 may be a SpCas9 variant formed by substituting F539 (hydropathy index: 2.8) in the region 1-3 of the wild-type SpCas9 with an amino acid having a relatively low hydropathy index such as serine (hydropathy index: −0.8).

In another exemplary embodiment, the TS-SpCas9 may be a SpCas9 variant formed by substituting I601 (hydropathy index: 4.5) in the region 1-3 of the wild-type SpCas9 with one amino acid selected from the group consisting of amino acids having a relatively low hydropathy index, such as alanine, arginine, asparagine, aspartic acid, cysteine, glutamic acid, glutamine, glycine, histidine, leucine, lysine, methionine, phenylalanine, proline, serine, threonine, tryptophan, tyrosine and valine.

For example, the TS-SpCas9 may be a SpCas9 variant formed by substituting I601 (hydropathy index: 4.5) in the region 1-3 of the wild-type SpCas9 with an amino acid having a relatively low hydropathy index such as asparagine (hydropathy index: −3.5).

In still another exemplary embodiment, the TS-SpCas9 may be a SpCas9 variant formed by substituting A203 (hydropathy index: 1.8), G366 (hydropathy index: −0.4), F539 (hydropathy index: 2.8) and I601 (hydropathy index: 4.5) in the region 1-1, the region 1-2, the region 1-3 and/or the region 1-4 of the wild-type SpCas9 with amino acids having a relatively low hydropathy index, respectively.

For example, the TS-SpCas9 may be a SpCas9 variant formed by substituting A203 (hydropathy index: 1.8) in the region 1-1 of the wild-type SpCas9 with an amino acid having a relatively low hydropathy index, such as aspartic acid (hydropathy index: −3.5), substituting G366 (hydropathy index: −0.4) in the region 1-2 thereof with an amino acid having a relatively low hydropathy index, such as serine (hydropathy index: −0.8), substituting F539 (hydropathy index: 2.8) in the region 1-3 thereof with an amino acid having a relatively low hydropathy index, such as serine (hydropathy index: −0.8), and substituting I601 (hydropathy index: 4.5) in the region 1-3 thereof with an amino acid having a relatively low hydropathy index, such as asparagine (hydropathy index: −3.5).

The TS-SpCas9 may be a SpCas9 variant formed by substituting one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acid(s) having a relatively high hydropathy index.

In one exemplary embodiment, the TS-SpCas9 may be a SpCas9 variant formed by substituting N277 (hydropathy index: −3.5) in the region 1-1 of the wild-type SpCas9 with one amino acid selected from the group consisting of amino acids having a relatively high hydropathy index, such as alanine, cysteine, glycine, histidine, isoleucine, leucine, methionine, phenylalanine, proline, serine, threonine, tryptophan, tyrosine and valine.

For example, the TS-SpCas9 may be a SpCas9 variant formed by substituting N277 (hydropathy index: −3.5) in the region 1-1 of the wild-type SpCas9 with an amino acid having a relatively high hydropathy index, such as histidine (hydropathy index: −3.2).

The TS-SpCas9 may be a SpCas9 variant formed by substituting two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acids having a relatively low or high hydropathy index.

In one exemplary embodiment, the TS-SpCas9 may be a SpCas9 variant formed by substituting A203 (hydropathy index: 1.8), N277 (hydropathy index: −3.5), G366 (hydropathy index: −0.4), F539 (hydropathy index: 2.8) and I601 (hydropathy index: 4.5) in the region 1-1, the region 1-2, the region 1-3 and/or the region 1-4 of the wild-type SpCas9 with amino acids having a relatively low or high hydropathy index, respectively.

For example, the TS-SpCas9 may be a SpCas9 variant formed by substituting A203 (hydropathy index: 1.8) in the region 1-1 of the wild-type SpCas9 with aspartic acid (hydropathy index: −3.5), which is an amino acid having a relatively low hydropathy index, substituting N277 (hydropathy index: −3.5) in the region 1-1 of the wild-type SpCas9 with histidine (hydropathy index: −3.2), which is an amino acid having a relatively high hydropathy index, substituting G366 (hydropathy index: −0.4) in the region 1-2 with serine (hydropathy index: −0.8), which is an amino acid having a relatively low hydropathy index, substituting F539 (hydropathy index: 2.8) in the region 1-3 with serine (hydropathy index: −0.8), which is an amino acid having a relatively low hydropathy index, and substituting I601 (hydropathy index: 4.5) in the region 1-3 with asparagine (hydropathy index: −3.5), which is an amino acid having a relatively low hydropathy index.

The TS-SpCas9 may be a SpCas9 variant formed by substituting one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acid(s) having a relatively small functional group.

In one exemplary embodiment, the TS-SpCas9 may be a SpCas9 variant formed by substituting F539 in the region 1-3 of the wild-type SpCas9 with one amino acid selected from the group consisting of alanine, asparagine, aspartic acid, cysteine, glutamic acid, glutamine, glycine, histidine, isoleucine, leucine, lysine, methionine, proline, serine, threonine and valine, which are amino acids having a relatively small functional group.

For example, the TS-SpCas9 may be a SpCas9 variant formed by substituting F539 in the region 1-3 of the wild-type SpCas9 with asparagine, which is an amino acid having a relatively small functional group.

The TS-SpCas9 may be a SpCas9 variant formed by substituting one or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, L246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acid(s) having a relatively large functional group.

In one exemplary embodiment, the TS-SpCas9 may be a SpCas9 variant formed by substituting A203 in the region 1-1 of the wild-type SpCas9 with one amino acid selected from the group consisting of arginine, asparagine, aspartic acid, cysteine, glutamic acid, glutamine, histidine, isoleucine, leucine, lysine, methionine, phenylalanine, proline, serine, threonine, tryptophan, tyrosine and valine, which are amino acids having a relatively large functional group.

For example, the TS-SpCas9 may be a SpCas9 variant formed by substituting A203 in the region 1-1 of the wild-type SpCas9 with aspartic acid, which is an amino acid having a relatively large functional group.

The TS-SpCas9 may be a SpCas9 variant formed by substituting two or more amino acids selected from the group consisting of N199, I201, N202, A203, G205, V206, A208, A210, I211, L212, A214, L216, L222, N224, L225, I226, A227, Q228, L229, G231, N235, G236, L237, G239, N240, L241, I242, A243, L244, I246, G247, L248, N251, N255, L258, A259, A262, L264, Q265, L266, L275, N277, L278, L279, A280, Q281, I282, P316, L317, A319, M321, I322, L332, L334, L335, A337, L338, V339, L343, P344, I350, F351, F352, G358, A360, G361, I363, G365, G366, A367, F372, F375, I376, P378, I379, L380, M383, G385, L389, L390, V391, L393, L513, L514, F518, V520, L524, V527, V530, G533, M534, P537, A538, F539, L540, G542, A547, I548, V549, L551, L552, F553, V559, V561, L564, F569, I572, C574, F575, V578, I580, G582, V583, F587, A589, L591, G592, L597, L598, I600, I601, F606, L607, I679, L680, F682, L683, G687, F688, A689, F693, M694, L696 and I697 in the region 1-1, the region 1-2, the region 1-3 and/or the region 1-4 of the wild-type SpCas9 with amino acid(s) having a relatively small or large functional group.

In one exemplary embodiment, the TS-SpCas9 may be a SpCas9 variant formed by substituting A203, N277, G366, F539 and I601 in the region 1-1, the region 1-2, the region 1-3 and/or the region 1-4 of the wild-type SpCas9 with amino acids having a relatively small or large functional group.

For example, the TS-SpCas9 may be a SpCas9 variant formed by substituting A203 and N277 in the region 1-1, G366 in the region 1-2, and I601 in the region 1-3 of the wild-type SpCas9 with aspartic acid, histidine, serine and asparagine, which are amino acids having a relatively large functional group, respectively, and substituting F539 in the region 1-3 with serine, which has a relatively small functional group.

The TS-SpCas9 may be a SpCas9 variant formed by substituting one or more amino acids selected from the amino acid sequence of the second region of the wild-type SpCas9 with different amino acid(s).

The TS-SpCas9 may be a SpCas9 variant formed by substituting one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3 of the wild-type SpCas9 with amino acid(s) having a relatively high hydropathy index.

In one exemplary embodiment, the TS-SpCas9 may be a SpCas9 variant formed by substituting M763 (hydropathy index: 1.9) in the region 2-2 of the wild-type SpCas9 with one amino acid selected from the group consisting of cysteine, isoleucine, leucine, phenylalanine and valine, which are amino acids having a relatively high hydropathy index.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index.

In another exemplary embodiment, the TS-SpCas9 may be a SpCas9 variant formed by substituting D965 (hydropathy index: −3.5) in the region 2-3 of the wild-type SpCas9 with one amino acid selected from the group consisting of alanine, cysteine, glycine, histidine, isoleucine, leucine, methionine, phenylalanine, proline, serine, threonine, tryptophan, tyrosine and valine, which are amino acids having a relatively high hydropathy index.

For example, the TS-SpCas9 may be a SpCas9 variant formed by substituting D965 (hydropathy index: −3.5) in the 2-3 of the wild-type SpCas9 with tyrosine (hydropathy index: −1.3), which is an amino acid having a relatively high hydropathy index.

In still another exemplary embodiment, the TS-SpCas9 may be a SpCas9 variant formed by substituting M763 (hydropathy index: 1.9) and D965 (hydropathy index: −3.5) in the region 2-1, the region 2-2 and/or the region 2-3 of the wild-type SpCas9 with amino acid(s) having a relatively high hydropathy index.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index, and substituting D965 (hydropathy index: −3.5) in the region 2-3 of the wild-type SpCas9 with tyrosine (hydropathy index: −1.3), which is an amino acid having a relatively high hydropathy index.

The TS-SpCas9 may be a SpCas9 variant formed by substituting one or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3 of the wild-type SpCas9 with amino acids having a relatively low hydropathy index.

In one exemplary embodiment, the TS-SpCas9 may be a SpCas9 variant formed by substituting F1037 and/or F1038 in the region 2-3 of the wild-type SpCas9 with one amino acid selected from the group consisting of arginine, asparagine, aspartic acid, cysteine, glutamic acid, glutamine, glycine, histidine, lysine, methionine, proline, serine, threonine, tryptophan and tyrosine, which are amino acids having a relatively low hydropathy index.

For example, the TS-SpCas9 may be a SpCas9 variant formed by substituting F1038 (hydropathy index: 2.8) in the region 2-3 of the wild-type SpCas9 with tyrosine (hydropathy index: −1.3), which is an amino acid having a relatively low hydropathy index.

For example, the TS-SpCas9 may be a SpCas9 variant formed by substituting F1037 (hydropathy index: 2.8) in the region 2-3 of the wild-type SpCas9 with arginine (hydropathy index: −4.5), which is an amino acid having a relatively low hydropathy index.

The TS-SpCas9 may be a SpCas9 variant formed by substituting two or more amino acids selected from the group consisting of I7, G8, L9, D10, I11, G12, V16, G17, W18, A19, V20, I21, P731, A732, I733, G736, I737, L738, V741, V743, V744, L747, V748, V750, M751, G752, P756, I759, V760, I761, E762, M763, A764, R765, E766, N767, I927, V931, A932, I934, L935, M939, L949, I950, V953, V955, I956, L958, L962, V963, D965, F966, F970, F972, V975, U978, Y981, H982, H983, A984, H985, D986, A987, Y988, L989, A991, V992, V993, G994, A996, L997, I998, P1002, L1004, F1008, V1009, G1011, V1015, V1018, M1021, I1022, A1023, I1029, G1030, A1032, A1034, Y1036, F1037, F1038 and Y1039 in the region 2-1, the region 2-2 and/or the region 2-3 of the wild-type SpCas9 with amino acid(s) having a relatively low or high hydropathy index.

In one exemplary embodiment, the TS-SpCas9 may be a SpCas9 variant formed by substituting M763 (hydropathy index: 1.9), D965 (hydropathy index: −3.5) and F1038 (hydropathy index: 2.8) in the region 2-1, the region 2-2 and/or the region 2-3 of the wild-type SpCas9 with amino acids having a relatively low or high hydropathy index.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index, substituting D965 (hydropathy index: −3.5) in the region 2-3 with tyrosine (hydropathy index: −1.3), which is an amino acid having a relatively high hydropathy index, and substituting F1038 (hydropathy index: 2.8) in the region 2-3 with tyrosine (hydropathy index: −1.3), which is an amino acid having a relatively low hydropathy index.

The TS-SpCas9 may be a SpCas9 variant formed by substituting one or more amino acids selected from the amino acid sequence of the third region of the wild-type SpCas9 with a different amino acid.

The TS-SpCas9 may be a SpCas9 variant formed by substituting one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9 with amino acid(s) having a relatively high hydropathy index.

In one exemplary embodiment, the TS-SpCas9 may be a SpCas9 variant formed by substituting K890 (hydropathy index: −3.9) in the region 3-1 of the wild-type SpCas9 with one amino acid selected from the group consisting of alanine, asparagine, aspartic acid, cysteine, glutamic acid, glutamine, glycine, histidine, isoleucine, leucine, methionine, phenylalanine, proline, serine, threonine, tryptophan, tyrosine and valine, which are amino acids having a relatively high hydropathy index.

For example, the TS-SpCas9 may be a SpCas9 variant formed by substituting K890 (hydropathy index: −3.9) in the region 3-1 of the wild-type SpCas9 with asparagine (hydropathy index: −3.5), which is an amino acid having a relatively high hydropathy index.

The TS-SpCas9 may be a SpCas9 variant formed by substituting one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9 with uncharged amino acid(s).

In one exemplary embodiment, the TS-SpCas9 may be a SpCas9 variant formed by substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting K890 in the region 3-1 of the wild-type SpCas9 with glutamine, which is an uncharged amino acid.

For example, the TS-SpCas9 may be a SpCas9 variant formed by substituting K890 in the region 3-1 of the wild-type SpCas9 with asparagine, which is an uncharged amino acid.

The TS-SpCas9 may be a SpCas9 variant formed by substituting one or more amino acids selected from the group consisting of K775, R778, E779, R780, K782, R783, E785, E786, K789, E790, K797, E798, H799, E802, E809, K810, R820, D821, D825, E827, D829, R832, D835, D837, V838, D839, H840, K848, D849, D850, D853, N854, K855, R859, D861, K862, N863, R864, K866, D868, E873, E874, K877, K878, K880, R884, A889, K890, L891, R895, K896 and D898 in the region 3-1 of the wild-type SpCas9 with amino acid(s) having a relatively small functional group.

In one exemplary embodiment, the TS-SpCas9 may be a SpCas9 variant formed by substituting K890 and/or K896 in the region 3-1 of the wild-type SpCas9 with one amino acid selected from the group consisting of alanine, asparagine, aspartic acid, cysteine, glycine, isoleucine, leucine, proline, serine, threonine and valine, which are amino acids having a relatively small functional group.

For example, the TS-SpCas9 may be a SpCas9 variant formed by substituting K890 in the region 3-1 of the wild-type SpCas9 with aspartic acid, which is an amino acid having a relatively small functional group.

For example, the TS-SpCas9 may be a SpCas9 variant formed by substituting K896 in the region 3-1 of the wild-type SpCas9 with asparagine, which is an amino acid having a relatively small functional group.

The TS-SpCas9 may be a SpCas9 variant formed by substituting one or more amino acids selected from the amino acid sequence in the fourth region of the wild-type SpCas9 with different amino acids.

The TS-SpCas9 may be a SpCas9 variant formed by substituting one or more amino acids selected from the group consisting of T1102, S1106, E1108, S1116, D1117, D1125, D1127, D1135, S1136 and T1138 in the region 4-1 of the wild-type SpCas9 with amino acid(s) having a relatively low hydropathy index.

In one exemplary embodiment, the TS-SpCas9 may be a SpCas9 variant formed by substituting T1102 in the region 4-1 of the wild-type SpCas9 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting T1102 (hydropathy index: −0.7) in the region 4-1 of the wild-type SpCas9 with proline (hydropathy index: −1.6) having a relatively low hydropathy index.

The TS-SpCas9 may be a SpCas9 variant formed by substituting one or more amino acids selected from the group consisting of T1102, S1106, E1108, S1116, D1117, D1125, D1127, D1135, S1136 and T1138 in the region 4-1 of the wild-type SpCas9 with amino acid(s) having a relatively high hydropathy index.

In one exemplary embodiment, the TS-SpCas9 may be a SpCas9 variant formed by substituting S1106 in the region 4-1 of the wild-type SpCas9 with one amino acid selected from the group consisting of alanine, cysteine, glycine, isoleucine, leucine, methionine, phenylalanine, threonine and valine, which are amino acids having a relatively high hydropathy index.

For example, the TS-SpCas9 may be a SpCas9 variant formed by substituting S1106 (hydropathy index: −0.8) in the region 4-1 of the wild-type SpCas9 with glycine (hydropathy index: −0.4), which is a relatively high hydropathy index.

The TS-SpCas9 may be a SpCas9 variant formed by substituting two or more amino acids selected from the group consisting of T1102, S1106, E1108, S1116, D1117, D1125, D1127, D1135, S1136 and T1138 in the region 4-1 of the wild-type SpCas9 with amino acids having a relatively low or high hydropathy index.

For example, the TS-SpCas9 may be a SpCas9 variant formed by substituting T1102 and S1136 in the region 4-1 of the wild-type SpCas9 with amino acids having a relatively low or high hydropathy index.

For example, the TS-SpCas9 may be a SpCas9 variant formed by substituting T1102 (hydropathy index: −0.7) in the region 4-1 of the wild-type SpCas9 with proline (hydropathy index: −1.6), which has a relatively low hydropathy index, and substituting S1106 (hydropathy index: −0.8) of the wild-type SpCas9 with glycine (hydropathy index: −0.4) having a relatively high hydropathy index.

The TS-SpCas9 may be a SpCas9 variant formed by substituting one or more amino acids selected from the group consisting of T1102, S1106, E1108, S1116, D1117, D1125, D1127, D1135, S1136 and T1138 in the region 4-1 of the wild-type SpCas9 with amino acid(s) having a relatively small functional group.

In one exemplary embodiment, the TS-SpCas9 may be a SpCas9 variant formed by substituting T1102 in the region 4-1 of the wild-type SpCas9 with an amino acid having a relatively small functional group.

For example, the TS-SpCas9 may be a SpCas9 variant formed by substituting T1102 in the region 4-1 of the wild-type SpCas9 with proline having a relatively small functional group.

The TS-SpCas9 may be a SpCas9 variant formed by substituting one or more amino acids selected from the group consisting of T1102, S1106, E1108, S1116, D1117, D1125, D1127, D1135, S1136 and T1138 in the region 4-1 of the wild-type SpCas9 with an amino acid having a relatively large functional group.

In one exemplary embodiment, the TS-SpCas9 may be a SpCas9 variant formed by substituting D1127 in the region 4-1 of the wild-type SpCas9 with an amino acid having a relatively large functional group.

For example, the TS-SpCas9 may be a SpCas9 variant formed by substituting D1127 in the region 4-1 of the wild-type SpCas9 with glutamic acid having a relatively large functional group.

The TS-SpCas9 may be a SpCas9 variant formed by substituting two or more amino acids selected from the group consisting of T1102, S1106, E1108, S1116, D1117, D1125, D1127, D1135, S1136 and T1138 in the region 4-1 of the wild-type SpCas9 with amino acids having a relatively small or large functional group.

In one exemplary embodiment, the TS-SpCas9 may be a SpCas9 variant formed by substituting T1102 and D1127 in the region 4-1 of the wild-type SpCas9 with amino acids having a relatively small or large functional group.

For example, the TS-SpCas9 may be a SpCas9 variant formed by substituting T1102 in the region 4-1 of the wild-type SpCas9 with proline having a relatively small functional group, and substituting D1127 in the region 4-1 of the wild-type SpCas9 with glutamic acid having a relatively large functional group.

The TS-SpCas9 may be a SpCas9 variant formed by substituting two or more amino acids selected from the amino acid sequences of the first region, the second region, the third region and/or the fourth region of the wild-type SpCas9 with different amino acids. Here, the two or more amino acids may be present in different regions, respectively.

Here, descriptions on the substitution of the one or more amino acids selected in the different regions are the same as described above.

The TS-SpCas9 may be a SpCas9 variant formed by substituting one or more amino acids selected from the amino acid sequence of the first region; and one or more amino acids selected from the amino acid sequence of the second region of the wild-type SpCas9 with different amino acids, respectively.

In one exemplary embodiment, the TS-SpCas9 may be a SpCas9 variant formed by substituting F539 (hydropathy index: 2.8) in the region 1-3 of the wild-type SpCas9 with one amino acid selected from the group consisting of alanine, arginine, asparagine, aspartic acid, cysteine, glutamic acid, glutamine, glycine, histidine, lysine, methionine, proline, serine, threonine, tryptophan and tyrosine, which are amino acids having a relatively low hydropathy index; and substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acids having a relatively high hydropathy index.

For example, the TS-SpCas9 may be a SpCas9 variant formed by substituting F539 (hydropathy index: 2.8) in the region 1-3 of the wild-type SpCas9 with serine (hydropathy index: −0.8), which is an amino acid having a relatively low hydropathy index, and substituting M763 (hydropathy index: 1.9) in the region 2-2 of the wild-type SpCas9 with isoleucine (hydropathy index: 4.5) having an amino acid having a relatively high hydropathy index.

In another exemplary embodiment, the TS-SpCas9 may be a SpCas9 variant formed by substituting I601 (hydropathy index: 4.5) in the region 1-3 of the wild-type SpCas9 with one amino acid selected from the group consisting of alanine, arginine, asparagine, aspartic acid, cysteine, glutamic acid, glutamine, glycine, histidine, leucine, lysine, methionine, phenylalanine, proline, serine, threonine, tryptophan, tyrosine and valine, which are amino acids having a relatively low hydropathy index; and substituting D965 (hydropathy index: −3.5) in the region 2-3 of the wild-type SpCas9 with one amino acid selected from the group consisting of alanine, cysteine, glycine, histidine, isoleucine, leucine, methionine, phenylalanine, proline, serine, threonine, tryptophan, tyrosine and valine, which are amino acids having a relatively high hydropathy index.

For example, the TS-SpCas9 may be a SpCas9 variant formed by substituting I601 (hydropathy index: 4.5) in the region 1-3 of the wild-type SpCas9 with asparagine (hydropathy index: −3.5), which is an amino acid having a relatively low hydropathy index, and substituting D965 (hydropathy index: −3.5) in the region 2-3 of the wild-type SpCas9 with tyrosine (hydropathy index: −1.3), which is an amino acid having a relatively high hydropathy index.

In still another exemplary embodiment, the TS-SpCas9 may be a SpCas9 variant formed by substituting A203 (hydropathy index: 1.8) in the region 1-1 of the wild-type SpCas9 with one amino acid selected from the group consisting of arginine, asparagine, aspartic acid, glutamic acid, glutamine, glycine, histidine, lysine, proline, serine, threonine, tryptophan and tyrosine, which are amino acids having a relatively low hydropathy index; and substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acids having a relatively high hydropathy index.

For example, the TS-SpCas9 may be a SpCas9 variant formed by substituting A203 (hydropathy index: 1.8) in the region 1-1 of the wild-type SpCas9 with aspartic acid (hydropathy index: −3.5), which is an amino acid having a relatively low hydropathy index, and M763 (hydropathy index: 1.9) in the region 2-2 of the wild-type SpCas9 with isoleucine (hydropathy index: 4.5), which is an amino acid having a relatively high hydropathy index.

The TS-SpCas9 may be a SpCas9 variant formed by substituting one or more amino acids selected form the amino acid sequence of the first region of the wild-type SpCas9; and one or more amino acids selected form the amino acid sequence of the third region of the wild-type SpCas9 with different amino acids, respectively.

In one exemplary embodiment, the TS-SpCas9 may be a SpCas9 variant formed by substituting F539 (hydropathy index: 2.8) in the region 1-3 of the wild-type SpCas9 with one amino acid selected from the group consisting of alanine, arginine, asparagine, aspartic acid, cysteine, glutamic acid, glutamine, glycine, histidine, lysine, methionine, proline, serine, threonine, tryptophan and tyrosine, which are amino acids having a relatively low hydropathy index; and substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting F539 (hydropathy index: 2.8) in the region 1-3 of the wild-type SpCas9 with serine (hydropathy index: −0.8), which is an amino acid having a relatively low hydropathy index, and substituting K890 in the region 3-1 of the wild-type SpCas9 with asparagine, which is an uncharged amino acid.

In another exemplary embodiment, the TS-SpCas9 may be a SpCas9 variant formed by substituting F539 and/or I601 in the region 1-3 of the wild-type SpCas9 with one amino acid selected from the group consisting of arginine, asparagine, aspartic acid, glutamic acid, glutamine, histidine, lysine, serine, threonine and tyrosine, which are polar amino acids; and substituting K890 (hydropathy index: −3.9) in the region 3-1 of the wild-type SpCas9 with one amino acid selected from the group consisting of alanine, asparagine, aspartic acid, cysteine, glutamic acid, glutamine, glycine, histidine, isoleucine, leucine, methionine, phenylalanine, proline, serine, threonine, tryptophan, tyrosine and valine, which are amino acids having a relatively high hydropathy index.

For example, the TS-SpCas9 may be a SpCas9 variant formed by substituting F539 and I601 in the region 1-3 of the wild-type SpCas9 with threonine and glutamic acid, which are polar amino acids, respectively, and substituting K890 (hydropathy index: −3.9) in the region 3-1 of the wild-type SpCas9 with asparagine (hydropathy index: −3.5), which is an amino acid having a relatively high hydropathy index.

The TS-SpCas9 may be a SpCas9 variant formed by substituting one or more amino acids selected from the amino acid sequence in the first region of the wild-type SpCas9 and one or more amino acids selected from the amino acid sequence in the fourth region of the wild-type SpCas9 with different amino acids, respectively.

In one exemplary embodiment, the TS-SpCas9 may be a SpCas9 variant formed by substituting A203 (hydropathy index: 1.8) in the region 1-1 of the wild-type SpCas9 with one amino acid selected from the group consisting of arginine, asparagine, aspartic acid, glutamic acid, glutamine, glycine, histidine, lysine, proline, serine, threonine, tryptophan and tyrosine, which are amino acids having a relatively low hydropathy index; and substituting T1102 in the region 4-1 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting A203 (hydropathy index: 1.8) in the region 1-1 of the wild-type SpCas9 with aspartic acid (hydropathy index: −3.5), which is an amino acid having a relatively low hydropathy index, and substituting T1102 (hydropathy index: −0.7) in the region 4-1 of the wild-type SpCas9 with proline (hydropathy index: −1.6) having a relatively low hydropathy index.

In one exemplary embodiment, the TS-SpCas9 may be a SpCas9 variant formed by substituting F539 (hydropathy index: 2.8) in the region 1-3 of the wild-type SpCas9 with one amino acid selected from the group consisting of alanine, arginine, asparagine, aspartic acid, cysteine, glutamic acid, glutamine, glycine, histidine, lysine, methionine, proline, serine, threonine, tryptophan and tyrosine, which are amino acids having a relatively low hydropathy index; and substituting D1127 in the region 4-1 of the wild-type SpCas9 with an amino acid having a relatively large functional group.

For example, the TS-SpCas9 may be a SpCas9 variant formed by substituting F539 (hydropathy index: 2.8) in the region 1-3 of the wild-type SpCas9 with serine (hydropathy index: −0.8), which is an amino acid having a relatively low hydropathy index, and substituting D1127 in the region 4-1 of the wild-type SpCas9 with glutamic acid having a relatively large functional group.

The TS-SpCas9 may be a SpCas9 variant formed by substituting one or more amino acids selected from the amino acid sequence in the second region of the wild-type SpCas9; and one or more amino acids selected from the amino acid sequence in the third region of the wild-type SpCas9 with different amino acids, respectively.

In one exemplary embodiment, the TS-SpCas9 may be a SpCas9 variant formed by substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acids having a relatively high hydropathy index; and substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index, and substituting K890 in the region 3-1 of the wild-type SpCas9 with asparagine, which is an uncharged amino acid.

In another exemplary embodiment, the TS-SpCas9 may be a SpCas9 variant formed by substituting F1037 and/or F1038 in the region 2-3 of the wild-type SpCas9 with one amino acid selected from the group consisting of arginine, asparagine, aspartic acid, glutamic acid, glutamine, histidine, lysine, serine, threonine and tyrosine, which are polar amino acids; and substituting K890 (hydropathy index: −3.9) in the region 3-1 with one amino acid selected from the group consisting of alanine, asparagine, aspartic acid, cysteine, glutamic acid, glutamine, glycine, histidine, isoleucine, leucine, methionine, phenylalanine, proline, serine, threonine, tryptophan, tyrosine and valine, which are amino acids having a relatively high hydropathy index.

For example, the TS-SpCas9 may be a SpCas9 variant formed by substituting F1038 in the region 2-3 of the wild-type SpCas9 with tyrosine, which is a polar amino acid, and substituting K890 (hydropathy index: −3.9) in the region 3-1 of the wild-type SpCas9 with asparagine (hydropathy index: −3.5), which is an amino acid having a high hydropathy index.

In another exemplary embodiment, the TS-SpCas9 may be a SpCas9 variant formed by substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which is an amino acid having a relatively high hydropathy index; substituting F1037 and/or F1038 in the region 2-3 of the wild-type SpCas9 with one amino acid selected from the group consisting of arginine, asparagine, aspartic acid, glutamic acid, glutamine, histidine, lysine, serine, threonine and tyrosine, which are polar amino acids; and substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index, substituting F1038 in the region 2-3 with tyrosine, which is a polar amino acid, and substituting K890 in the region 3-1 of the wild-type SpCas9 with asparagine, which is an uncharged amino acid.

The TS-SpCas9 may be a SpCas9 variant formed by substituting one or more amino acids selected from the amino acid sequence of the second region of the wild-type SpCas9; and one or more amino acids selected from the amino acid sequence of the fourth region of the wild-type SpCas9 with different amino acids, respectively.

In one exemplary embodiment, the TS-SpCas9 may be a SpCas9 variant formed by substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acids having a relatively high hydropathy index; and substituting T1102 in the region 4-1 of the wild-type SpCas9 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting M763 (hydropathy index: 1.9) in the region 2-2 of the wild-type SpCas9 with isoleucine (hydropathy index: 4.5), which is an amino acid having a relatively high hydropathy index, and substituting T1102 (hydropathy index: −0.7) in the region 4-1 of the wild-type SpCas9 with proline (hydropathy index: −1.6) having a relatively low hydropathy index.

In another exemplary embodiment, the TS-SpCas9 may be a SpCas9 variant formed by substituting F1037 and/or F1038 in the region 2-3 of the wild-type SpCas9 with one amino acid selected from the group consisting of arginine, asparagine, aspartic acid, glutamic acid, glutamine, histidine, lysine, serine, threonine and tyrosine, which are polar amino acids; and substituting D1127 in the region 4-1 of the wild-type SpCas9 with an amino acid having a relatively large functional group.

For example, the TS-SpCas9 may be a SpCas9 variant formed by substituting F1038 in the region 2-3 of the wild-type SpCas9 with tyrosine, which is a polar amino acid, and substituting D1127 in the region 4-1 of the wild-type SpCas9 with glutamic acid having a relatively large functional group.

The TS-SpCas9 may be a SpCas9 variant formed by substituting one or more amino acids selected from the amino acid sequence of the third region of the wild-type SpCas9; and one or more amino acids selected from the amino acid sequence of the fourth region with different amino acids, respectively.

In one exemplary embodiment, the TS-SpCas9 may be a SpCas9 variant formed by substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids; and substituting T1102 in the region 4-1 of the wild-type SpCas9 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting K890 in the region 3-1 of the wild-type SpCas9 with asparagine, which is an uncharged amino acid, and substituting T1102 (hydropathy index: −0.7) in the region 4-1 of the wild-type SpCas9 with proline (hydropathy index: −1.6) having a relatively low hydropathy index.

In another exemplary embodiment, the TS-SpCas9 may be a SpCas9 variant formed by substituting K890 (hydropathy index: −3.9) in the region 3-1 of the wild-type SpCas9 with one amino acid selected from the group consisting of alanine, asparagine, aspartic acid, cysteine, glutamic acid, glutamine, glycine, histidine, isoleucine, leucine, methionine, phenylalanine, proline, serine, threonine, tryptophan, tyrosine and valine, which are amino acids having a relatively high hydropathy index; and substituting D1127 in the region 4-1 of the wild-type SpCas9 with an amino acid having a relatively large functional group.

For example, the TS-SpCas9 may be a SpCas9 variant formed by substituting K890 (hydropathy index: −3.9) in the region 3-1 of the wild-type SpCas9 with asparagine (hydropathy index: −3.5), which is an amino acid having a relatively high hydropathy index, and substituting D1127 in the region 4-1 of the wild-type SpCas9 with glutamic acid having a relatively large functional group.

The TS-SpCas9 may be a SpCas9 variant formed by substituting one or more amino acids selected from the amino acid sequence of the first region of the wild-type SpCas9; one or more amino acids selected in the amino acid sequence of the second region of the wild-type SpCas9; and/or one or more amino acids selected in the amino acid sequence of the third region of the wild-type SpCas9 with different amino acids, respectively.

In one exemplary embodiment, the TS-SpCas9 may be a SpCas9 variant formed by substituting F539 (hydropathy index: 2.8) in the region 1-3 of the wild-type SpCas9 with one amino acid selected from the group consisting of alanine, arginine, asparagine, aspartic acid, cysteine, glutamic acid, glutamine, glycine, histidine, lysine, methionine, proline, serine, threonine, tryptophan and tyrosine, which are amino acids having a relatively low hydropathy index; substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acid having a relatively high hydropathy index; and substituting K890 (hydropathy index: −3.9) in the region 3-1 of the wild-type SpCas9 with one amino acid selected from the group consisting of alanine, asparagine, aspartic acid, cysteine, glutamic acid, glutamine, glycine, histidine, isoleucine, leucine, methionine, phenylalanine, proline, serine, threonine, tryptophan, tyrosine and valine, which are amino acid having a relatively high hydropathy index.

For example, the TS-SpCas9 may be a SpCas9 variant formed by substituting F539 (hydropathy index: 2.8) in the region 1-3 of the wild-type SpCas9 with serine (hydropathy index: −0.8), which is an amino acid having a relatively low hydropathy index, substituting M763 (hydropathy index: 1.9) in the region 2-2 of the wild-type SpCas9 with isoleucine (hydropathy index: 4.5), which is an amino acid having a relatively high hydropathy index, and substituting K890 (hydropathy index: −3.9) in the region 3-1 of the wild-type SpCas9 with asparagine (hydropathy index: −3.5), which is an amino acid having a relatively high hydropathy index.

In another exemplary embodiment, the TS-SpCas9 may be a SpCas9 variant formed by substituting F539 and/or I601 in the region 1-3 of the wild-type SpCas9; and F1037 and/or F1038 in the region 2-3 of the wild-type SpCas9 with one amino acid selected from the group consisting of arginine, asparagine, aspartic acid, glutamic acid, glutamine, histidine, lysine, serine, threonine and tyrosine, which are polar amino acids, respectively; substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids; and substituting T1102 in the region 4-1 of the wild-type SpCas9 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting F539 in the region 1-3 of the wild-type SpCas9 with serine, which is a polar amino acid, substituting F1038 in the region 2-3 of the wild-type SpCas9 with tyrosine, which is a polar amino acid, substituting K890 in the region 3-1 of the wild-type SpCas9 with asparagine, which is an uncharged amino acid, and substituting T1102 in the region 4-1 of the wild-type SpCas9 with proline (hydropathy index: −1.6), which is an amino acid having a relatively low hydropathy index.

For example, the TS-SpCas9 may be a SpCas9 variant formed by substituting I601 in the region 1-3 of the wild-type SpCas9 with glutamic acid, which is a polar amino acid, substituting F1038 in the region 2-3 of the wild-type SpCas9 with tyrosine, which is a polar amino acid, K890 in the region 3-1 of the wild-type SpCas9 with asparagine, which is an uncharged amino acid, and substituting T1102 in the region 4-1 of the wild-type SpCas9 with proline (hydropathy index: −1.6), which is an amino acid having a relatively low hydropathy index.

For example, the TS-SpCas9 may be a SpCas9 variant formed by substituting F539 and I601 in the region 1-3 of the wild-type SpCas9 with serine and asparagine, which are polar amino acids, respectively, substituting F1038 in the region 2-3 of the wild-type SpCas9 with tyrosine, which is a polar amino acid, substituting K890 in the region 3-1 of the wild-type SpCas9 with asparagine, which is an uncharged amino acid, and substituting T1102 in the region 4-1 of the wild-type SpCas9 with proline (hydropathy index: −1.6), which is an amino acid having a relatively low hydropathy index.

In still another exemplary embodiment, the TS-SpCas9 may be a SpCas9 variant formed by substituting F539 and/or I601 in the region 1-3 of the wild-type SpCas9 with one amino acid selected from the group consisting of arginine, asparagine, aspartic acid, glutamic acid, glutamine, histidine, lysine, serine, threonine and tyrosine, which are polar amino acids, respectively; substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acid having a relatively high hydropathy index; and substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting I601 in the region 1-3 of the wild-type SpCas9 with asparagine, which is a polar amino acid, substituting M763 (hydropathy index: 1.9) in the region 2-2 of the wild-type SpCas9 with isoleucine (hydropathy index: 4.5), which is an amino acid having a relatively high hydropathy index, and substituting K890 in the region 3-1 of the wild-type SpCas9 with asparagine, which is an uncharged amino acid.

For example, the TS-SpCas9 may be a SpCas9 variant formed by substituting F539 and I601 in the region 1-3 of the wild-type SpCas9 with serine and asparagine, which are polar amino acids, respectively, substituting M763 (hydropathy index: 1.9) in the region 2-2 of the wild-type SpCas9 with isoleucine (hydropathy index: 4.5), which is an amino acid having a relatively high hydropathy index, and substituting K890 in the region 3-1 of the wild-type SpCas9 with asparagine, which is an uncharged amino acid.

In another exemplary embodiment, the TS-SpCas9 may be a SpCas9 variant formed by substituting A203 (hydropathy index: 1.8) in the region 1-1 of the wild-type SpCas9 with one amino acid selected from the group consisting of arginine, asparagine, aspartic acid, glutamic acid, glutamine, glycine, histidine, lysine, proline, serine, threonine, tryptophan and tyrosine, which are amino acids having a relatively low hydropathy index; substituting M763 (hydropathy index: 1.9) and/or A764 (hydropathy index: 1.8) in the region 2-2 of the wild-type SpCas9 with one amino acid selected from the group consisting of cysteine, isoleucine, leucine, phenylalanine and valine, which are amino acids having a relatively high hydropathy index; and substituting K890 in the region 3-1 of the wild-type SpCas9 with one amino acid selected from the group consisting of alanine, asparagine, cysteine, glutamine, glycine, isoleucine, leucine, methionine, phenylalanine, proline, serine, threonine, tryptophan, tyrosine and valine, which are uncharged amino acids.

For example, the TS-SpCas9 may be a SpCas9 variant formed by substituting A203 (hydropathy index: 1.8) in the region 1-1 of the wild-type SpCas9 with aspartic acid (hydropathy index: −3.5), which is an amino acid having a relatively low hydropathy index, substituting M763 (hydropathy index: 1.9) in the region 2-2 of the wild-type SpCas9 with isoleucine (hydropathy index: 4.5), which is an amino acid having a relatively high hydropathy index, substituting F1038 in the region 2-3 with tyrosine, which is a polar amino acid, and substituting K890 in the region 3-1 of the wild-type SpCas9 with asparagine, which is an uncharged amino acid.

In yet another exemplary embodiment, the TS-SpCas9 may be a SpCas9 variant formed by substituting I601 (hydropathy index: 4.5) in the region 1-3 of the wild-type SpCas9 with one amino acid selected from the group consisting of alanine, arginine, asparagine, aspartic acid, cysteine, glutamic acid, glutamine, glycine, histidine, leucine, lysine, methionine, phenylalanine, proline, serine, threonine, tryptophan, tyrosine and valine, which are amino acids having a relatively low hydropathy index; substituting D965 (hydropathy index: −3.5) in the region 2-3 of the wild-type SpCas9 with one amino acid selected from the group consisting of alanine, cysteine, glycine, histidine, isoleucine, leucine, methionine, phenylalanine, proline, serine, threonine, tryptophan, tyrosine and valine, which are amino acids having a relatively high hydropathy index; and substituting T1102 in the region 4-1 of the wild-type SpCas9 with one amino acid selected from the group consisting of arginine, asparagine, aspartic acid, glutamic acid, glutamine, lysine, proline, serine, tryptophan and tyrosine, which are amino acids having a relatively low hydropathy index.

For example, the TS-SpCas9 may be a SpCas9 variant formed by substituting I601 (hydropathy index: 4.5) in the region 1-3 of the wild-type SpCas9 with asparagine (hydropathy index: −3.5), which is an amino acid having a relatively low hydropathy index, substituting M763 (hydropathy index: 1.9) in the region 2-2 of the wild-type SpCas9 with isoleucine (hydropathy index: 4.5), which is an amino acid having a relatively high hydropathy index, substituting D965 (hydropathy index: −3.5) in the region 2-3 of the wild-type SpCas9 with tyrosine (hydropathy index: −1.3), which is an amino acid having a relatively high hydropathy index, and substituting T1102 (hydropathy index: −0.7) in the region 4-1 of the wild-type SpCas9 with proline (hydropathy index: −1.6) having a relatively low hydropathy index.

In one exemplary embodiment, the TS-SpCas9 may be a SpCas9 variant formed by substituting one or more amino acids selected from the group consisting of A203 and N277 in the region 1-1, G366 in the region 1-2, and F539 and I601 in the region 1-3 of the wild-type SpCas9 with amino acid(s) having a relatively small or large functional group; substituting one or more amino acids selected from the group consisting of M763 in the region 2-2 and D956 and F1038 in the region 2-3 of the wild-type SpCas9 with amino acid(s) having a relatively small or large functional group; substituting K890 in the region 3-1 of the wild-type SpCas9 with an uncharged amino acid; and substituting one or more amino acids selected from the group consisting of T1102 and D1127 in the region 4-1 of the wild-type SpCas9 with amino acid(s) having a relatively small or large functional group.

For example, the TS-SpCas9 may be a SpCas9 variant formed by substituting G366 in the region 1-2, and F539 and I601 in the region 1-3 of the wild-type SpCas9 with serine (amino acid having a relatively large functional group), serine (amino acid having a relatively small functional group) and asparagine (amino acid having a relatively large functional group), respectively, substituting M763 in the region 2-2 and F1038 in the region 2-3 with isoleucine (amino acid having a relatively small functional group) and tyrosine (amino acid having a relatively large functional group), respectively, substituting K890 in the region 3-1 with uncharged asparagine, and substituting D1127 in the region 4-1 with glutamic acid having a relatively large functional group.

For example, the TS-SpCas9 may be a SpCas9 variant formed by substituting A203 and N277 in the region 1-1, G366 in the region 1-2, and F539 and I601 in the region 1-3 of the wild-type SpCas9 with aspartic acid (amino acid having a relatively large functional group), histidine (amino acid having a relatively large functional group), serine (amino acid having a relatively large functional group), serine (amino acid having a relatively small functional group) and asparagine (amino acid having a relatively large functional group), respectively, substituting M763 in the region 2-2 and D956 and F1038 in the region 2-3 of the wild-type SpCas9 with isoleucine (amino acid having a relatively small functional group), tyrosine (amino acid having a relatively large functional group) and tyrosine (amino acid having a relatively large functional group), respectively, substituting K890 in the region 3-1 of the wild-type SpCas9 with uncharged asparagine, and substituting T1102 and D1127 in the region 4-1 with proline (amino acid having a relatively small functional group) and glutamic acid (amino acid having a relatively large functional group), respectively.

As an example of the TS-SpCas9 disclosed herein, the TS-SpCas9 may be a SpCas9 variant formed by substituting F539, M763 and/or K890 of the wild-type SpCas9 with different amino acids.

In one exemplary embodiment, the TS-SpCas9 may be a SpCas9 variant formed by substituting F539 of the wild-type SpCas9 with one amino acid selected from the group consisting of alanine, arginine, asparagine, aspartic acid, cysteine, glutamic acid, glutamine, glycine, histidine, lysine, methionine, proline, serine, threonine, tryptophan and tyrosine.

For example, the TS-SpCas9 may be a SpCas9 variant formed by substituting F539 of the wild-type SpCas9 with serine. Here, the TS-SpCas9 (F539S) formed by substituting F539 with serine may be a SpCas9 variant in which the interaction between the REC domain of SpCas9 (F539S) and a target sequence and/or the PAM distal end of gRNA may be changed, compared to the wild-type SpCas9.

In one exemplary embodiment, the TS-SpCas9 may be a SpCas9 variant formed by substituting M763 of the wild-type SpCas9 with one amino acid selected from the group consisting of cysteine, isoleucine, leucine, phenylalanine and valine.

For example, the TS-SpCas9 may be a SpCas9 variant formed by substituting M763 of the wild-type SpCas9 with isoleucine. Here, the TS-SpCas9 (F539S) formed by substituting M763 with isoleucine may be a SpCas9 variant in which the interaction between the RuvC domain of SpCas9 (M763I) and a metal may be changed, compared to the wild-type SpCas9.

In one exemplary embodiment, the TS-SpCas9 may be a SpCas9 variant formed by substituting K890 of the wild-type SpCas9 with alanine, asparagine, cysteine, glutamine, glycine, isoleucine, leucine, methionine, phenylalanine, proline, serine, threonine, tryptophan, tyrosine and valine.

For example, the SpCas9 may be a SpCas9 variant formed by substituting K890 of the wild-type SpCas9 with asparagine. Here, the TS-SpCas9 (K890N) formed by substituting K890 with asparagine may be a SpCas9 variant in which the interaction between the HNH domain of SpCas9 (K890N) and a metal is changed, compared to the wild-type SpCas9.

In another exemplary embodiment, the TS-SpCas9 may be a SpCas9 variant formed by substituting F539 and M763 of the wild-type SpCas9 with amino acids different from the original ones, respectively.

Here, the amino acids different from the original ones may be amino acids selected from the group consisting of alanine, arginine, asparagine, aspartic acid, cysteine, glutamic acid, glutamine, glycine, histidine, lysine, methionine, proline, serine, threonine, tryptophan, tyrosine, isoleucine, leucine, phenylalanine and valine.

For example, the TS-SpCas9 may be a SpCas9 variant formed by substituting F539 and M763 of the wild-type SpCas9 with serine and isoleucine, respectively. Here, the TS-SpCas9 (F539S, M763I) in which the F539 and M763 are substituted with serine and isoleucine, respectively, may be a SpCas9 variant in which the interaction between the REC domain of SpCas9 (F539S, M763I) and a target sequence and/or the PAM distal end of gRNA and the interaction between the RuvC domain of the SpCas9 (F539S, M763I) and a metal are changed, compared to the wild-type SpCas9.

In still another exemplary embodiment, the TS-SpCas9 may be a SpCas9 variant formed by substituting F539 and K890 of the wild-type SpCas9 with amino acids different form the original amino acids.

Here, the amino acids different form the original amino acids may be amino acids selected from the group consisting of alanine, arginine, asparagine, aspartic acid, cysteine, glutamic acid, glutamine, glycine, histidine, lysine, methionine, proline, serine, threonine, tryptophan, tyrosine, isoleucine, leucine, phenylalanine and valine.

For example, the TS-SpCas9 may be a SpCas9 variant formed by substituting F539 and K890 of the wild-type SpCas9 with serine and asparagine, respectively. Here, the TS-SpCas9 (F539S, K890N) formed by substituting F539 and K890 with serine and asparagine, respectively, may be a SpCas9 variant in which the interaction between the REC domain of SpCas9 (F539S, K890N) and a target sequence and/or the PAM distal end of gRNA, and the interaction between the HNH domain of the SpCas9 (F539S, K890N) and a metal are changed, compared to the wild-type SpCas9.

In another one exemplary embodiment, the TS-SpCas9 may be a SpCas9 variant formed by substituting M763 and K890 of the wild-type SpCas9 with amino acids different from the original ones.

Here, the amino acids different from the original ones may be amino acids selected from the group consisting of alanine, asparagine, cysteine, glutamine, glycine, isoleucine, leucine, methionine, phenylalanine, proline, serine, threonine, tryptophan, tyrosine and valine.

For example, the TS-SpCas9 may be a SpCas9 variant formed by substituting M763 and K890 of the wild-type SpCas9 with isoleucine and asparagine, respectively. Here, TS-SpCas9 (M763I, K890N) formed by substituting the M763 and K890 with isoleucine and asparagine, respectively, may be a SpCas9 variant in which the interaction between the RuvC domain of SpCas9 (M763I, K890N) and a metal, and the interaction between the HNH domain of SpCas9 (M763I, K890N) and a metal are changed, compared to the wild-type SpCas9.

In one exemplary embodiment, the TS-SpCas9 may be a SpCas9 variant formed by substituting F539, M763 and K890 of the wild-type SpCas9 with amino acids different from the original ones.

Here, the amino acids different from the original ones may be amino acids selected from the group consisting of alanine, arginine, asparagine, aspartic acid, cysteine, glutamic acid, glutamine, glycine, histidine, lysine, methionine, proline, serine, threonine, tryptophan, tyrosine, isoleucine, leucine, phenylalanine and valine.

For example, the TS-SpCas9 may be a SpCas9 variant (SEQ ID NO: 11) formed by substituting F539, M763 and K890 of the wild-type SpCas9 with serine, isoleucine and asparagine, respectively. Here, the TS-SpCas9 (F539S, M763I, K890N) formed by substituting F539, M763 and K890 with serine, isoleucine and asparagine, respectively, may be a SpCas9 variant in which the interaction between the REC domain of SpCas9 (F539S, M763I, K890N) and a target sequence and/or the PAM distal end of gRNA, and the interaction between the RuvC domain of the SpCas9 (F539S, M763I, K890N) and a metal, and the interaction between the HNH domain of SpCas9 (F539S, M763I, K890N) and a metal are changed, compared to the wild-type SpCas9.

In one exemplary embodiment of the disclosure disclosed herein, the artificially engineered Cas9 may be a fusion protein.

The fusion protein may be an artificially produced protein including target-specific Cas9 and one or more functional domains.

The descriptions of the target-specific Cas9 have been provided above.

The descriptions of the functional domains have been provided above.

For example, the fusion protein may be an artificially produced protein including TS-SpCas9 and a deaminase.

Here, the TS-SpCas9 may be a SpCas9 variant formed by substituting D10, F539, M763 and K890 of the wild-type SpCas9 with amino acids different from the original ones, respectively.

Alternatively, the TS-SpCas9 may be a SpCas9 variant formed by substituting F539, M763, H840 and K890 of the wild-type SpCas9 with amino acids different from the original ones, respectively.

Alternatively, the TS-SpCas9 may be a SpCas9 variant formed by substituting D10, F539, M763, H840 and K890 of the wild-type SpCas9 with amino acids different from the original ones, respectively.

Here, the deaminase may be an adenine deaminase and/or a cytidine deaminase.

Here, the fusion protein may be an artificially produced protein in the form in which a deaminase is fused to the N-terminus of TS-SpCas9.

Alternatively, the fusion protein may be an artificially produced protein in the form in which a deaminase is fused to the C-terminus of TS-SpCas9.

Alternatively, the fusion protein may be an artificially produced protein in the form in which the same or different deaminases are fused to the N-terminus and the C-terminus of TS-SpCas9, respectively.

A CRISPR enzyme, artificially engineered CRISPR enzyme, CRISPR enzyme variant, Cas9, artificially engineered Cas9, Cas9 variant or target-specific Cas9 disclosed herein may be a polypeptide or protein.

A CRISPR enzyme, artificially engineered CRISPR enzyme, CRISPR enzyme variant, Cas9, artificially engineered Cas9, Cas9 variant or target-specific Cas9 disclosed herein may be a nucleic acid having a nucleotide sequence encoding the polypeptide or protein.

The CRISPR enzyme, artificially engineered CRISPR enzyme, CRISPR enzyme variant, Cas9, artificially engineered Cas9, Cas9 variant or target-specific Cas9 may be codon-optimized for a subject to be introduced.

The term "codon optimization" refers to a process of modifying a nucleic acid sequence by maintaining a native amino acid sequence while replacing at least one codon of the native sequence with a codon more frequently or the most frequently used in host cells so as to improve expression in the host cells. A variety of species have a specific bias to a specific codon of a specific amino acid, and the codon bias (the difference in codon usage between organisms) is frequently correlated with efficiency of the translation of mRNA, which is considered to be dependent on the characteristic of a translated codon and availability of a specific tRNA molecule. The dominance of tRNA selected in cells generally reflects codons most frequently used in peptide synthesis. Therefore, a gene may be customized by optimal gene expression in a given organism based on codon optimization.

The nucleic acid having the nucleotide sequence encoding the polypeptide or protein may be a form of a non-vector.

The non-vector may be naked DNA, a DNA complex or mRNA.

The nucleic acid having the nucleotide sequence encoding the polypeptide or protein may be included in a vector.

Here, the nucleic acid having the nucleotide sequence encoding the polypeptide or protein may be included in one vector, or divided and included in several vectors.

The vector may be a plasmid.

The vector may be a viral vector or a non-viral vector.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding a guide nucleic acid or editor protein).

For example, a promoter useful for the CRISPR enzyme may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The guide nucleic acid and/or editor protein may be introduced into a subject using a virus having such a characteristic. The guide nucleic acid and/or editor protein introduced using the virus may be temporarily expressed in the subject (e.g., cells). Alternatively, the guide nucleic acid and/or editor protein introduced using the virus may be continuously expressed in a subject (e.g., cells) for a long time (e.g., 1, 2 or 3 weeks, 1, 2, 3, 6 or 9 months, 1 or 2 years, or permanently).

The packaging capacity of a virus may vary from at least 2 to 50 kb depending on the type of virus. According to the packaging capacity, a viral vector only including a CRISPR enzyme or a viral vector including a CRISPR enzyme and gRNA may be designed. Alternatively, a viral vector including a CRISPR enzyme, gRNA and an additional component may be designed.

In one example, a nucleic acid encoding a CRISPR enzyme may be included in a recombinant lentivirus vector.

In another example, the nucleic acid encoding a CRISPR enzyme may be included in a recombinant adenovirus vector.

In still another example, the nucleic acid encoding a CRISPR enzyme may be included in a recombinant AAV vector.

In yet another example, the nucleic acid encoding a CRISPR enzyme may be included in a hybrid vector, for example, one or more hybrid vectors among viruses disclosed herein.

In one exemplary embodiment disclosed herein, a nucleic acid encoding a CRISPR enzyme variant and/or Cas9 variant may be expressed to use the CRISPR enzyme variant and/or the Cas9 variant. Expression may be performed in various methods. For example, the nucleic acid encoding the CRISPR enzyme variant and/or the Cas9 variant may be cloned into an intermediate virus for transduction into prokaryotic or eukaryotic cells for cloning and/or expression. For storage or manipulation of the nucleic acid encoding the CRISPR enzyme variant and/or the Cas9 variant to produce the CRISPR enzyme variant and/or Cas9 variant, the intermediate vector is typically a prokaryotic vector such as a plasmid, a shuttle vector or an insect vector. In addition, the nucleic acid of the CRISPR enzyme variant and/or the Cas9 variant may be cloned into an expression vector for introduction into plant cells, animal cells, preferably, mammalian cells or human cells, fungal cells, bacterial cells, or protozoan cells.

To accomplish expression, typically, a sequence encoding a CRISPR enzyme variant and/or Cas9 variant is subcloned into an expression vector containing a promoter directing transcription. A bacteria expression system for expressing a engineered protein may be obtained from, for example, *E. coli, Bacillus* sp. and *Salmonella* sp. A kit for the expression system is commercially available. A eukaryotic cell-expressing system for mammalian, yeast and insect cells are widely known in the art, and also commercially available.

A promoter used to direct nucleic acid expression depends on a specific application. For example, a typically strong constitutive promoter is used to express and proliferate a fusion protein. In contrast, when a CRISPR enzyme variant and/or Cas9 variant is introduced into a living body for gene regulation, a constitutive or inducible promoter may be used according to a specific application of the CRISPR enzyme variant and/or Cas9 variant. In addition, a preferable promoter for introducing the CRISPR enzyme variant and/or Cas9 variant may be a weak promoter, for example, HSV TK or a promoter having a similar activity. The promoter may also include transcription activation-response elements, for example, a hypoxia-response element, a Gal4-response element, a lac inhibitor-response element, and small molecule-controlled systems, for example, a tetracycline-regulated system and a RU-486 system.

In addition to the promoter, typically, an expression vector includes a transcription unit or expression cassette containing additional elements required for nucleic acid expression in host cells such as prokaryotic or eukaryotic cells. Therefore, the typical expression cassette may include, for example, a promoter operably linked to a nucleic acid sequence encoding a CRISPR enzyme variant and/or Cas9 variant, and a random signal required for, for example, effective polyadenylation of a transcript, transcription termination, ribosome-binding sites, or translation termination. Additional elements of the cassette may include, for example, an enhancer and spliced heterologous intron signals.

A specific expression vector for transferring genetic information to cells is selected in regard to a desired use of a CRISPR enzyme variant and/or Cas9 variant, for example, expression in plants, animals, bacteria, fungi, protozoa or the like. Standard bacteria expression vectors include plasmids, for example, a pBR322-based plasmid, pSKF and pET23D, and commercially-available tag-fused expression systems, for example, GST and LacZ.

An expression vector containing a regulatory element derived from a eukaryotic cell virus is frequently used in a eukaryotic expression vector, for example, a SV40 vector, a papilloma virus vector, or a vector derived from Epstein-Barr virus. Other exemplary eukaryotic vectors include pMSG, pAV009/A+, pMTO10/A+, pMAMneo-5, baculovirus, pDSVE, and other vectors allowing protein expression under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

A vector for expressing a CRISPR enzyme variant and/or Cas9 variant may include the RNA Pol III promoter for inducing the expression of guide RNA, for example, the H1, U6 or 7SK promoter. Such a human promoter allows the expression of a CRISPR enzyme variant and/or Cas9 variant in mammalian cells after plasmid transfection.

Some expression systems have markers for selecting a stably transfected cell line, for example, thymidine kinase, hygromycin B phosphotransferase, and dihydrofolate reductase. A high yield expression system, for example, using a baculovirus vector in addition to a gRNA-coding sequence under the direction of a polyhedrin promoter or other strong baculovirus promoters in insect cells is also suitable.

Elements typically included in an expression vector also include a replicon functioning in *E. coli*, a gene encoding antibiotic resistance for allowing the selection of bacteria containing a recombinant plasmid, and a unique restriction site in the non-essential region of a plasmid to allow the insertion of a recombinant sequence.

A bacterial, mammalian, yeast or insect cell line expressing a large amount of proteins is produced using a standard transfection method, and purified using a standard technique (For example, refer to Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells is performed according to a standard technique (For example, refer to Morrison, 1977, J. Bacteriol. 132:349-351; Clark-Curtiss & Curtiss, Methods in Enzymology 101:347-362 (Wu et al., eds, 1983)).

Any known procedures for introducing a foreign nucleotide sequence into host cells may be used. These procedures include calcium phosphate transfection, polybrene, protoplast fusion, electroporation, nucleofection, liposomes, microinjection, naked DNA, a plasmid vector, a viral vector, episomal and integrative vectors, and other widely known methods for introducing cloned genome DNA, cDNA, synthetic DNA or other foreign genetic materials into host cells. The specific gene manipulation procedures used herein have to successfully introduce at least one gene into host cells capable of expressing a CRISPR enzyme variant and/or Cas9 variant.

In one exemplary embodiment disclosed herein, a vector capable of expressing a CRISPR enzyme variant and/or Cas9 variant and cells including the vector may be provided.

Examples

Hereinafter, the present invention will be described in detail with reference to examples.

The examples are merely provided to describe the present invention in further detail, and it might be obvious to those of ordinary skill in the art that the scope of the present invention is not limited to the following examples.

Example 1. Cas9 Variant

1. Cas9 Variant Libraries

SpCas9 variant libraries were constructed using three independent protocols. For the first library, a Cas9 library plasmid was transformed into XL1-red competent cells (Agilent), which were cultured according to the instructions in the vendor's manual. For the second and third libraries, error-prone PCR was performed on whole WT-SpCas9 from Cas9 library plasmid sequences using Genemorph II (Agilent) and Diversify PCR random mutagenesis kits (Clontech) under the condition of a low error rate (0-5 mutations/kb) with primers designed for Gibson Assembly. Subsequently, PCR products were gel-purified. The purified randomly mutagenized library and the backbone of the Cas9 library plasmid were Gibson-assembled. The assembled libraries were transformed into Endura™ electrocompetent cells (Lucigen) and incubated on chloramphenicol LB plates (12.5 μg/mL) at 37° C. overnight. After the transformed cells were cultured, each library was isolated and purified using a Midi prep kit (NucleoBond Xtra Midi EF, Macherey-Nagel). The obtained libraries were screened using a target-specific Cas9 screening method (WO 2017217768) with a multi-target system, thereby selecting target-specific Cas9 variants.

2-1. Plasmids Encoding Target-Specific Cas9 Variants

Plasmids encoding wild-type SpCas9 (p3s-Cas9HC; Addgene plasmid #43945) were purchased and used to produce target-specific SpCas9 variants. Constructs for the target-specific SpCas9 variants were produced by Gibson Assembly of a nucleic acid sequence including desired site mutations and the p3s-Cas9HC plasmid backbone. All constructs were confirmed by Sanger sequencing.

2-2. Plasmids Encoding Target-Specific Cas9 Variants

Plasmids encoding wild-type SpCas9 (p3s-Cas9HC; Addgene plasmid #43945) were purchased and used to produce target-specific SpCas9 variants. To produce target-specific SpCas9 variants, constructs including site mutations were produced in wild-type SpCas9-encoded plasmids using a site-directed mutagenesis kit. All constructs were confirmed by Sanger sequencing.

Example 2. Target Gene Manipulation Effect of Cas9 Variant

Experimental Methods

1. Cell Culture and Transfection Conditions

HEK293T cells (ATCC, CRL-11268) were maintained in DMEM medium supplemented with 10% FBS (fetal bovine serum) and 1% antibiotics. For genetic manipulation by Cas9 variants, HEK293T cells were seeded into 48-well plates until 70-80% confluency before transfection. The cells were transfected with Cas9 variant expression plasmids (250 ng) and sgRNA expression plasmids (250 ng) using Lipofectamine 2000 (Invitrogen). Genomic DNA was isolated and extracted using a DNeasy Blood & Tissue Kit (Qiagen) 72 hours after transfection.

2. In-Vitro Cleavage of Genomic DNA

Genomic DNA was purified from HEK293T cells using a DNeasy Blood & Tissue Kit (Qiagen). The genomic DNA (10 μg) was incubated with Cas9 or Sniper1 protein (100 nM) and 4 sgRNAs (75 nM each) in a reaction volume 1 mL for 8h at 37° C. in a buffer (100 mM NaCl, 50 mM Tris-HCl, 10 mM $MgCl_2$, 100 μg/mL BSA, at pH 7.9). Digested genomic DNA was treated with RNase A (50 μg/mL) to degrade sgRNAs and purified again with DNeasy Blood & Tissue Kit (Qiagen).

3. Whole Genome and Digenome Sequencing

Genomic DNA (1 μg) was fragmented into a 400- to 500-bp range using the Covaris system (Life Technologies), and both ends of the fragments were blunt-ended using End Repair Mix (Thermo Fischer). To construct libraries, fragmented DNA was ligated with an adapter, and then subjected to whole-genome sequencing using a HiSeq X Ten Sequencer (Illumina) at Macrogen. Whole genome sequencing was performed at a sequencing depth of 30-40×. DNA cleavage sites were identified using Digenome 1.0 programs.

4. Targeted Deep Sequencing

Target sites and potential off-target sites were analyzed by targeted deep sequencing. Deep-sequencing libraries were generated by PCR. TruSeq HT Dual Index primers were used to label each sample. Pooled libraries were subjected to paired-end sequencing using MiniSeq.

Experimental Results

In this example, to confirm a target gene manipulation effect of SpCas9 variants, the indel (%) effect of the SpCas9 variants according to the target gene was confirmed with various genes used as a target. Here, the effect of the SpCas9 variants was confirmed for each region.

1. First Region Variants of SpCas9

A total of five SpCas9 variants (A203D, N277H, G366S, F539S and I601N) formed by substituting A203, N277, G366, F539 and I601 in the first region of SpCas9 with different amino acids, respectively, were used in the experiment.

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29), a sequence different from the target sequence is shown in lower case), in all SpCas9 variants, compared to the wild-type SpCas9, indel frequencies at the on-target site increased, indel frequencies at the off-target site decreased, which is that the ratio of indel frequency at the off-target site based on the value of the on-target site was low (FIG. 1). Particularly, it was confirmed that, for A203D, F539S and I601N, indel frequencies at on-target sites are similar to those of the wild-type SpCas9, but indel frequencies at off-target sites are lowered below a certain level compared to the wild-type SpCas9.

Figure 2:
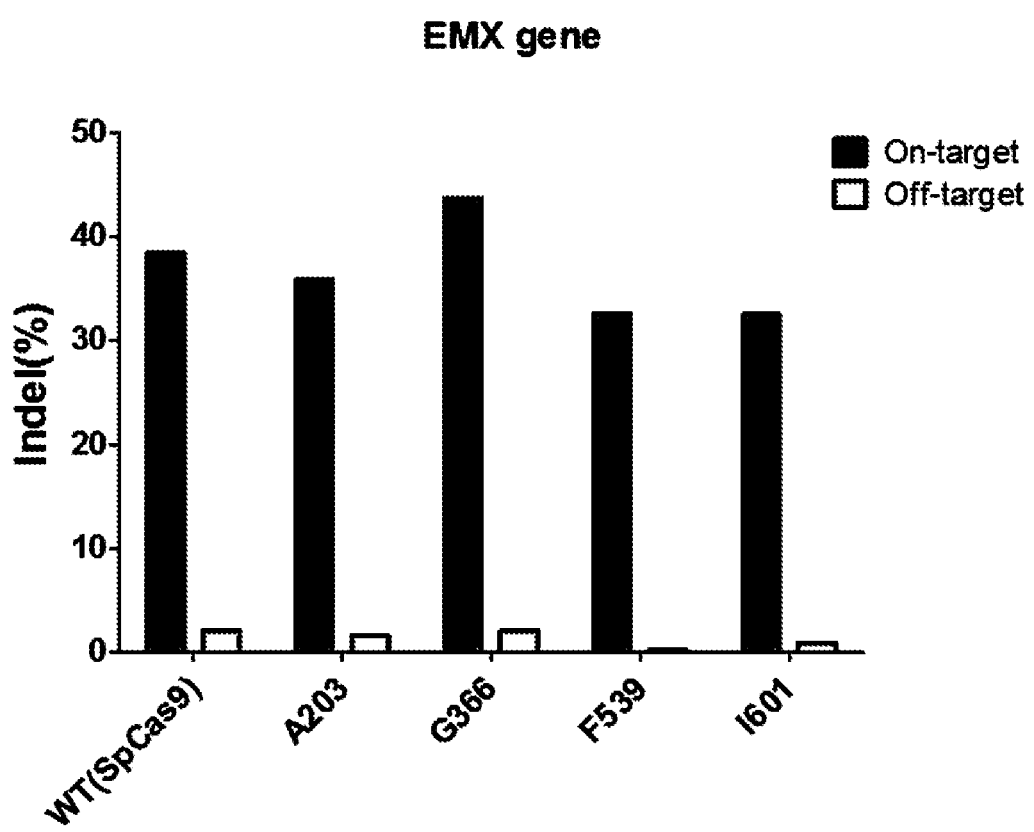
FIG. 2 is a graph showing indel frequencies (%), which represents the manipulation effect of a target gene (EMX gene) by first region variants of SpCas9.

In addition, when an EMX gene was used as a target gene (target sequence: GAGTCCGAGCAGAAGAAGAA (SEQ ID NO: 30)/non-target sequence: GAGT-taGAGCAGAAGAAGAA (SEQ ID NO: 31)), for all SpCas9 variants, compared to the wild-type SpCas9, indel frequencies increased at the on-target site and decreased at the off-target site, which is that the ratio of indel frequency at the off-target site based on the value of the on-target site was low (FIG. 2). Particularly, for G366S, it was confirmed that indel frequencies at the off-target site are similar to those of the wild-type SpCas9, but indel frequencies at the on-target site are higher than those of the wild-type SpCas9. In addition, for F539S and I601N, it was confirmed that indel frequencies at the off-target site are almost not shown or are lowered to half of those of the wild-type SpCas9.

Figure 3:
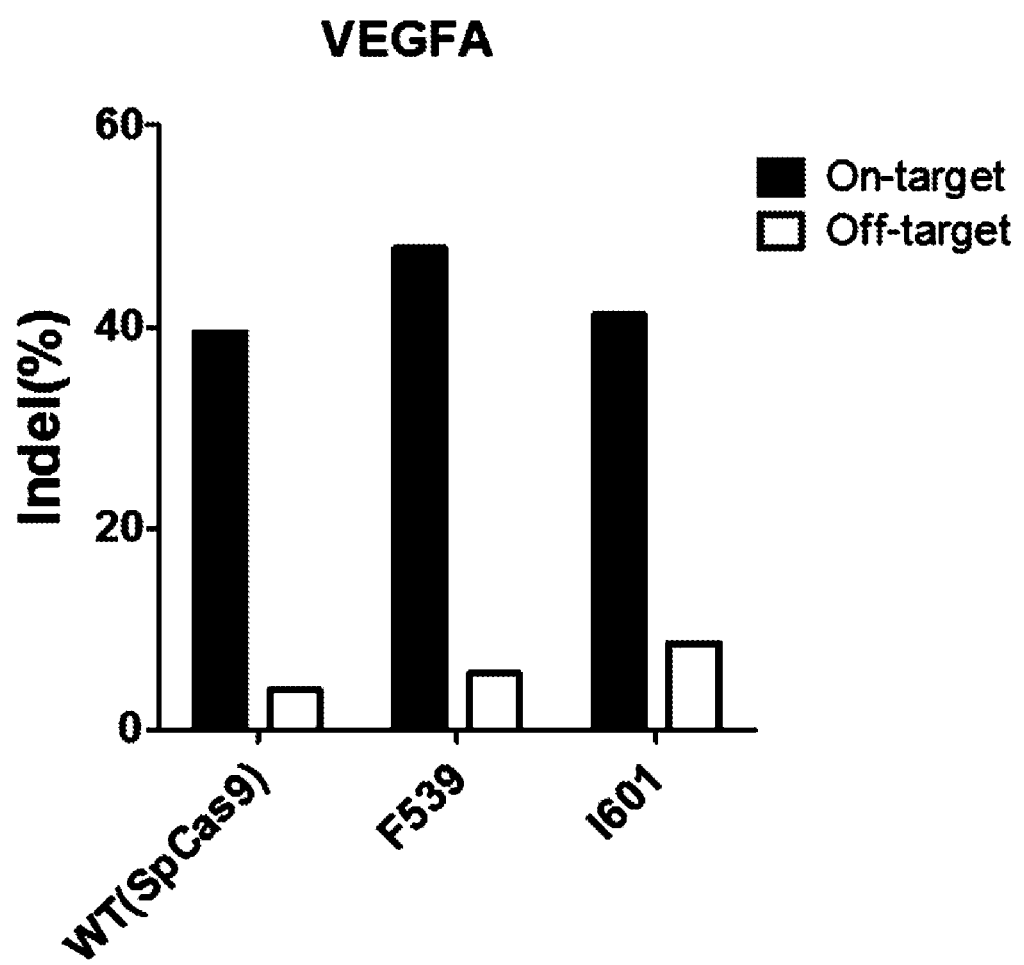
FIG. 3 is a graph showing indel frequencies (%), which represents the manipulation effect of a target gene (VEGFA gene) by first region variants of SpCas9.

When a VEGFA gene was used as a target gene (target sequence: GGTGAGTGAGTGTGTGCGTG (SEQ ID NO: 32)/non-target sequence: GGTGAGTGAGTGTGTGtGTG (SEQ ID NO: 33)), for all SpCas9 variants, compared to the wild-type SpCas9, indel frequencies at the on-target site increased, or were similar to those of the wild-type SpCas9 (FIG. 3). Particularly, for F539S, indel frequencies at the off-target site were similar to those of the wild-type SpCas9, but indel frequencies at the on-target site were 10% or higher than those of the wild-type SpCas9.

From the above-mentioned results, it can be confirmed that a total of five SpCas9 variants formed by substituting A203, N277, G366, F539 and I601 in the first region of SpCas9 with different amino acids are improved in target specificity, compared to the wild-type SpCas9.

2. Second Region Variants of SpCas9

Three SpCas9 variants (M763I, D965Y and F1038Y) formed by substituting M763, D965 and F1038 in the second region of SpCas9 with different amino acids and two SpCas9 variants (M763I/F1038Y and D965Y/F1038Y) formed by substituting M763/F1038 and D965/F1038 in the second region of SpCas9 with different amino acids were used in an experiment.

Figure 4:
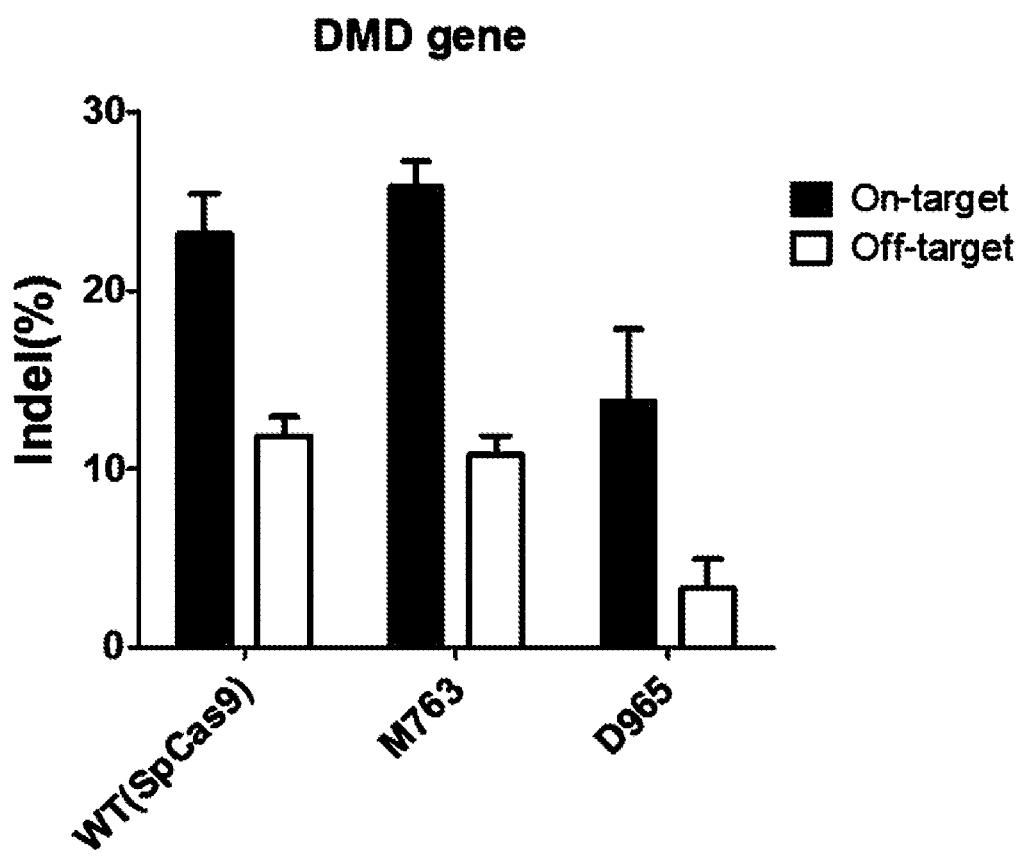
FIGS. 4 and 5 are graphs showing indel frequencies (%), which represents the manipulation effect of a target gene (DMD gene) by second region variants of SpCas9.
Figure 5:
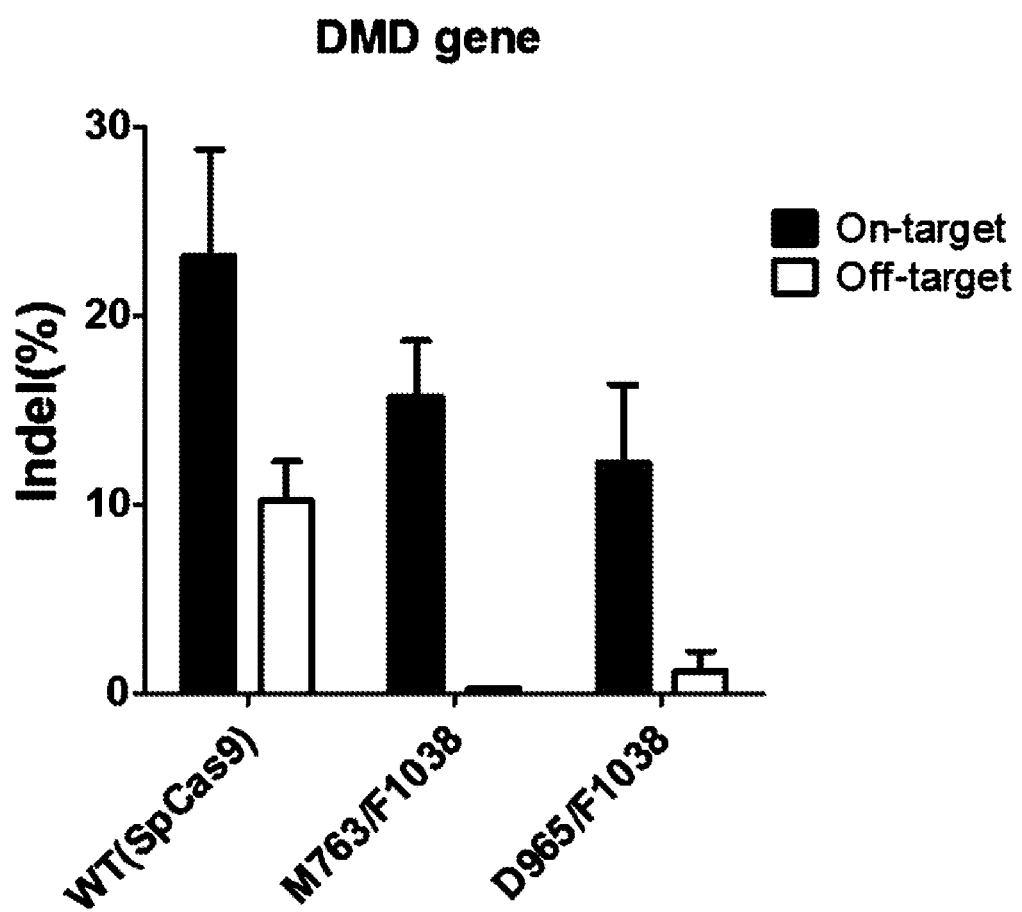

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29)), for all SpCas9 variants, compared to the wild-type SpCas9, indel frequencies at the on-target site increased, indel frequencies at the off-target site decreased, or the indel frequencies at the off-target site were lower than those at the on-target site (FIG. 4). Particularly, for M763I, it was confirmed that indel frequencies at the off-target site were similar to those of wild-type SpCas9, but indel frequencies at the on-target site were higher than those of the wild-type SpCas9. In addition, for M763I/F1038Y and D965Y/F1038Y, it was confirmed that indel frequencies at the on-target site are slightly lower than those of the wild-type SpCas9, but indel frequencies at the off-target site are almost not shown, and thus the ratio of indel frequency at the off-target site based on the value of the on-target site was lower than those of the wild-type SpCas9. Therefore, it was confirmed that the SpCas9 variants have target specificity, compared to the wild-type SpCas9 (FIG. 5).

Figure 6:
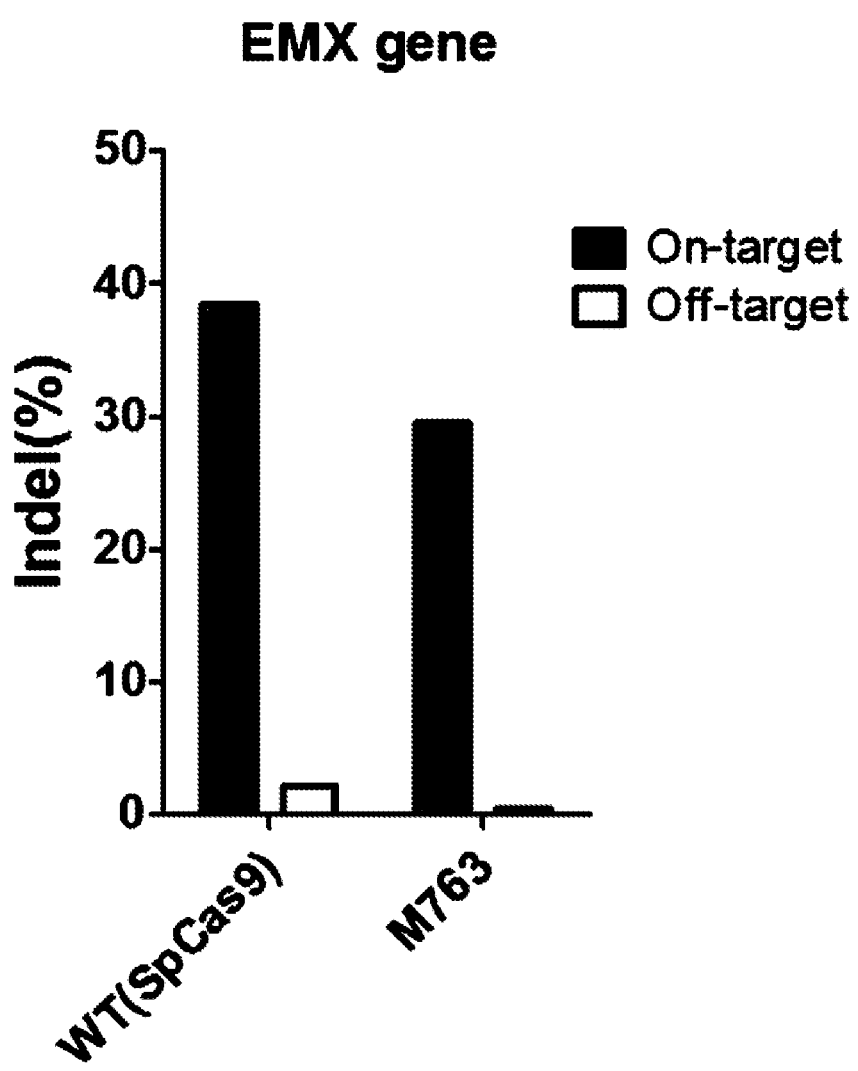
FIGS. 6 and 7 are graphs showing indel frequencies (%), which represents the manipulation effect of a target gene (EMX gene) by second region variants of SpCas9.
Figure 7:
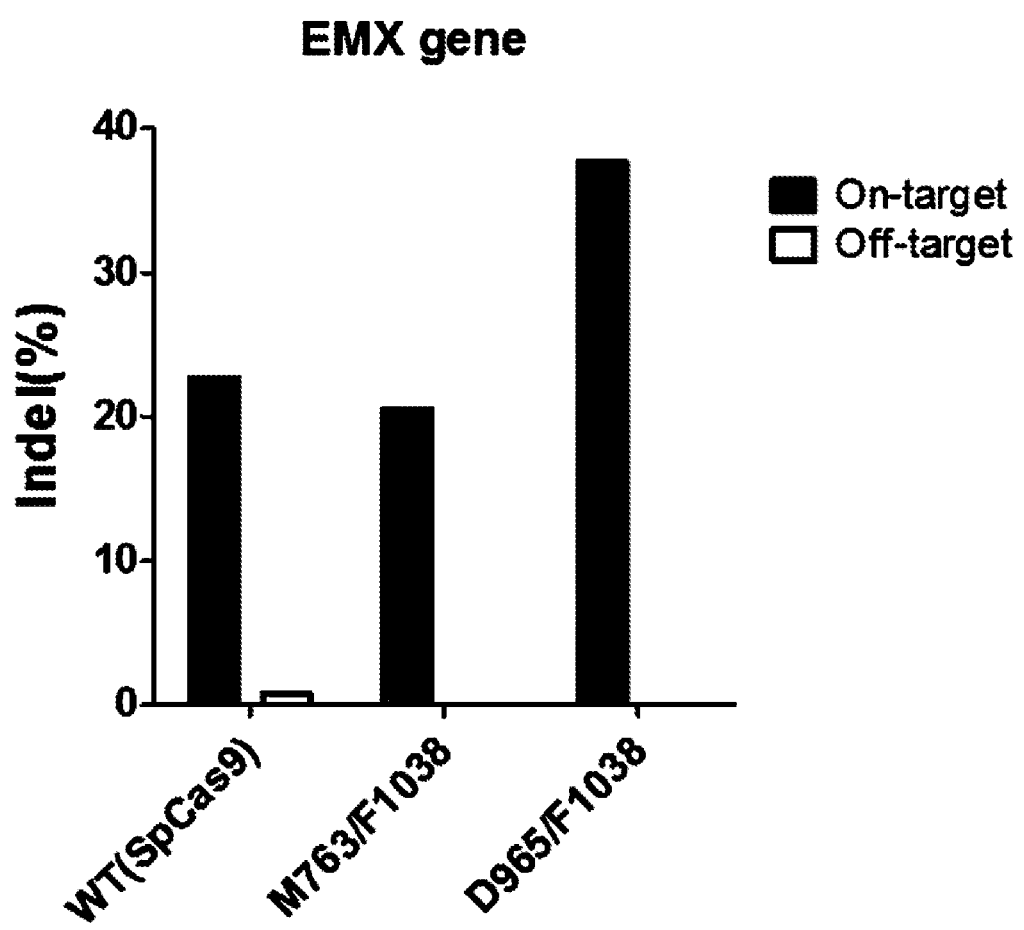

In addition, when an EMX gene was used as a target gene (target sequence: GAGTCCGAGCAGAAGAAGAA (SEQ ID NO: 30)/non-target sequence: GAGT-taGAGCAGAAGAAGAA (SEQ ID NO: 31)), for M763I, compared to the wild-type SpCas9, indel frequencies at the on-target site were slightly lowered, but indel frequencies at the off-target site were almost not shown, and thus the ratio of indel frequency at the off-target site based on the value of the on-target site was low. Therefore, M763I has target specificity, compared to the wild-type SpCas9 (FIG. 6). In addition, for M763I/F1038Y and D965Y/F1038Y, indel frequencies at the off-target site were almost not shown, and indel frequencies at the on-target site were similar to or significantly higher, compared to the wild-type SpCas9 (FIG. 7).

Figure 8:
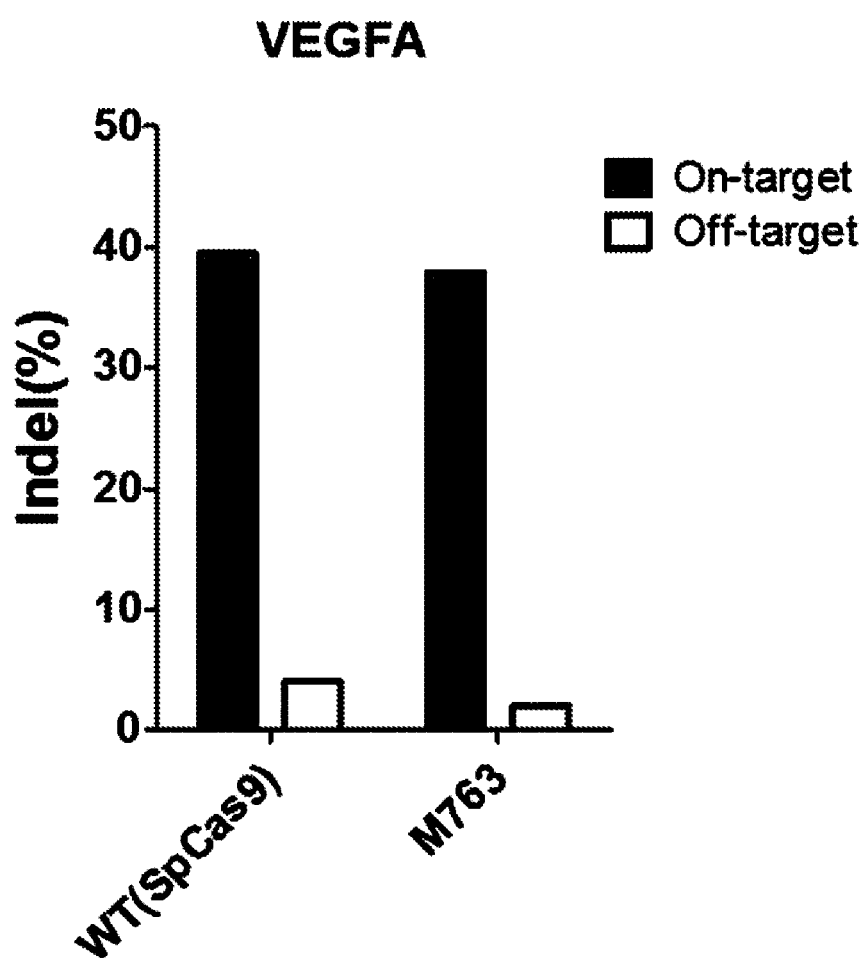
FIG. 8 is a graph showing indel frequencies (%), which represents the manipulation effect of a target gene (VEGFA gene) by second region variants of SpCas9.

When a VEGFA gene was used as a target gene (target sequence: GGTGAGTGAGTGTGTGCGTG (SEQ ID NO: 32)/non-target sequence: GGTGAGTGAGTGTGTGtGTG (SEQ ID NO: 33)), for M763I, compared to the wild-type SpCas9, indel frequencies at the on-target site were similar, but indel frequencies at the off-target site were almost not shown, and thus it can be confirmed that for M763I, compared to the wild-type SpCas9, which is that the ratio of indel frequency at the off-target site based on the value of the on-target site was low, and thus M763I has target specificity, compared to the wild-type SpCas9 (FIG. 8).

Figure 9:
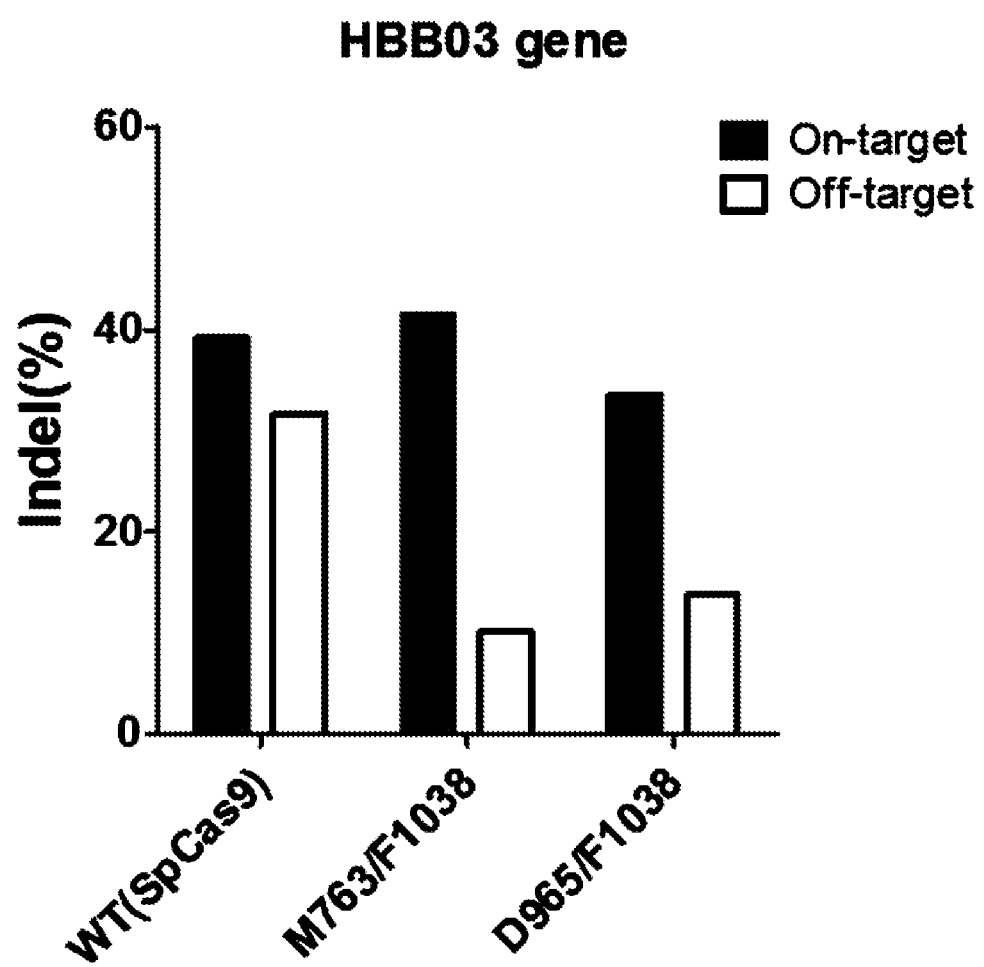
FIG. 9 is a graph showing indel frequencies (%), which represents the manipulation effect of a target gene (HBB03 gene) by second region variants of SpCas9.

When an HBB03 gene was used as a target gene (target sequence: CACGTTCACCTTGCCCCACA (SEQ ID NO: 34)/non-target sequence: CACGTTCActTTGCCCCACA (SEQ ID NO: 35)), it was confirmed that, for M763I/F1038Y and D965Y/F1038Y, compared to the wild-type SpCas9, indel frequencies at the off-target site decrease by half or less, but indel frequencies at the on-target site increase or slightly decrease (FIG. 9).

Figure 10:
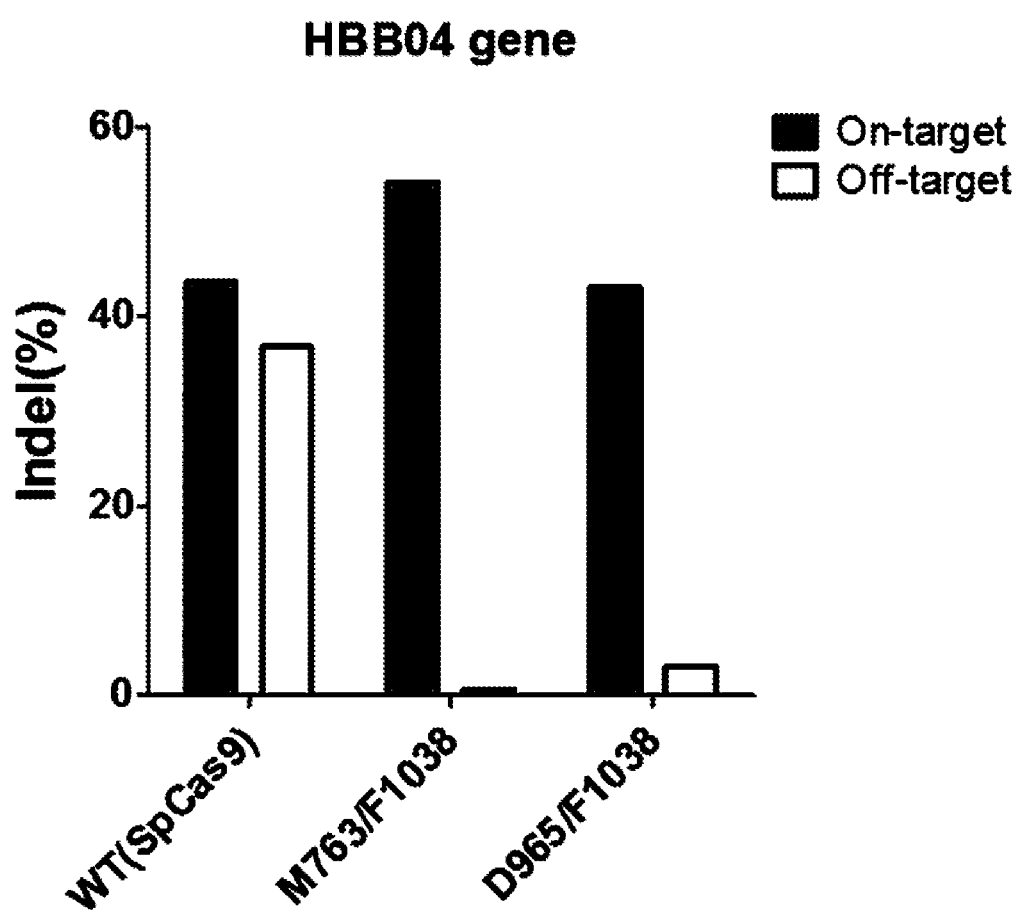
FIG. 10 is a graph showing indel frequencies (%), which represents the manipulation effect of a target gene (HBB04 gene) by second region variants of SpCas9.

When an HBB04 gene was used as a target gene (target sequence: CCACGTTCACCTTGCCCCAC (SEQ ID NO: 36)/non-target sequence: CCACaTTCACCTTGCCCCAC (SEQ ID NO: 37)), it was confirmed that, for M763I/F1038Y and D965Y/F1038Y, compared to the wild-type SpCas9, indel frequencies at the off-target site are almost not shown, and indel frequencies at the on-target site increase or similar (FIG. 10).

From the above-mentioned results, it can be confirmed that the three SpCas9 variants (M763I, D965Y and F1038Y) formed by substituting M763, D965 and F1038 in the second region of SpCas9 with different amino acids and two SpCas9 variants (M763I/F1038Y and D965Y/F1038Y) formed by substituting M763/F1038 and D965/F1038 in the second region of SpCas9 with different amino acids were improved in target specificity, compared to the wild-type SpCas9.

3. Third Region Variants of SpCas9

A SpCas9 variant (K890N) formed by substituting K890 in the third region of SpCas9 with different amino acid were used in the experiment.

Figure 11:
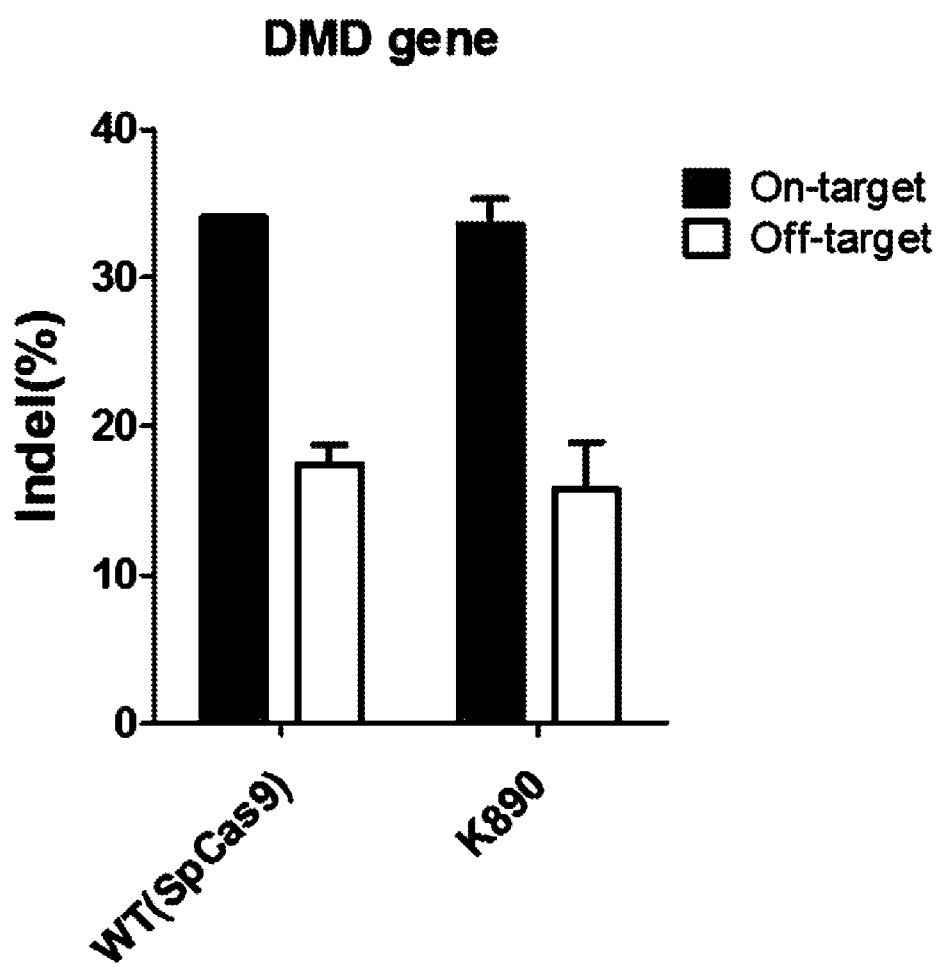
FIG. 11 is a graph showing indel frequencies (%), which represents the manipulation effect of a target gene (DMD gene) by third region variants of SpCas9.

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29)), it was confirmed that, for K890N, compared to the wild-type SpCas9, indel frequencies at the on-target site are similar, but indel frequencies at the off-target site slightly decrease (FIG. 11).

Form the above-mentioned results, it can be confirmed that the SpCas9 variant (K890N) formed by substituting K890 in the third region of SpCas9 with a different amino acid shows similar or slightly increased target specificity, compared to the wild-type SpCas9.

4. Fourth Region Variants of SpCas9

SpCas9 variants (T1102P and D1127E) formed by substituting T1102 and D1127 in the fourth region of SpCas9 with different amino acids were used in the experiment.

Figure 12:
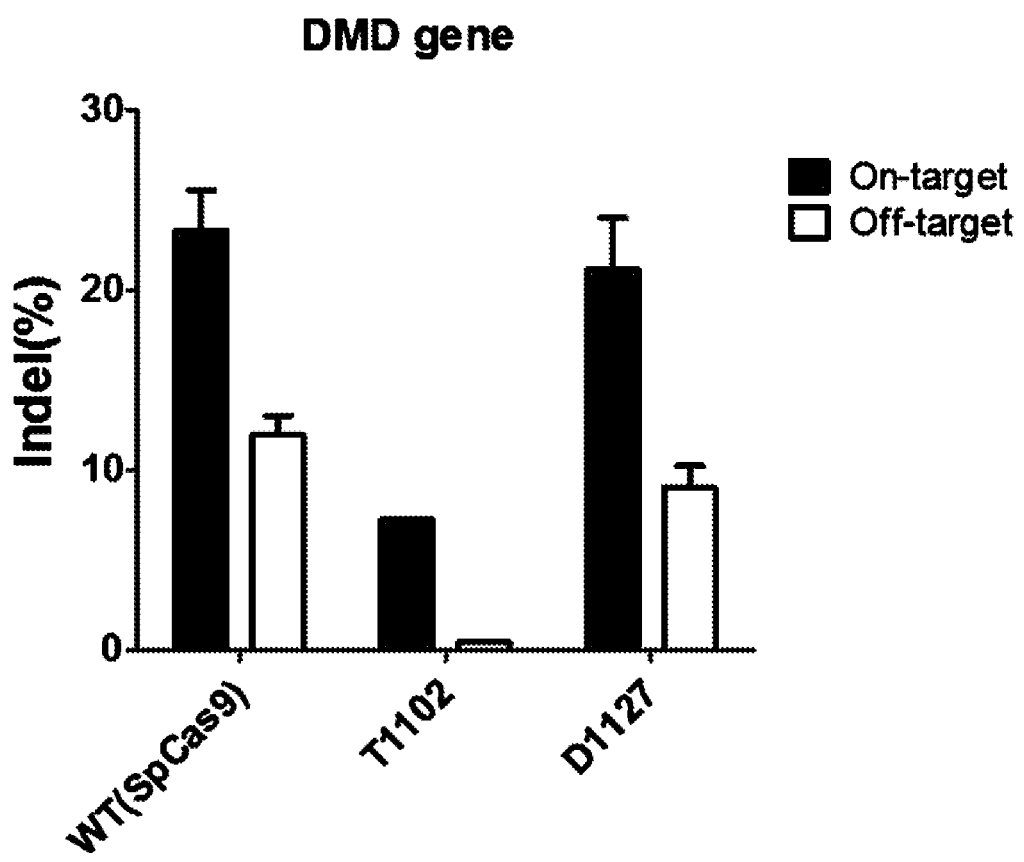
FIG. 12 is a graph showing indel frequencies (%), which represents the manipulation effect of a target gene (DMD gene) by fourth region variants of SpCas9.

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29)), it was confirmed that, for T1102P, compared to the wild-type SpCas9, almost no indel frequencies at the off-target site are shown, and for D1127E, compared to the wild-type SpCas9, indel frequencies at the on-target site are similar, but indel frequencies at the off-target site decrease (FIG. 12).

Figure 13:
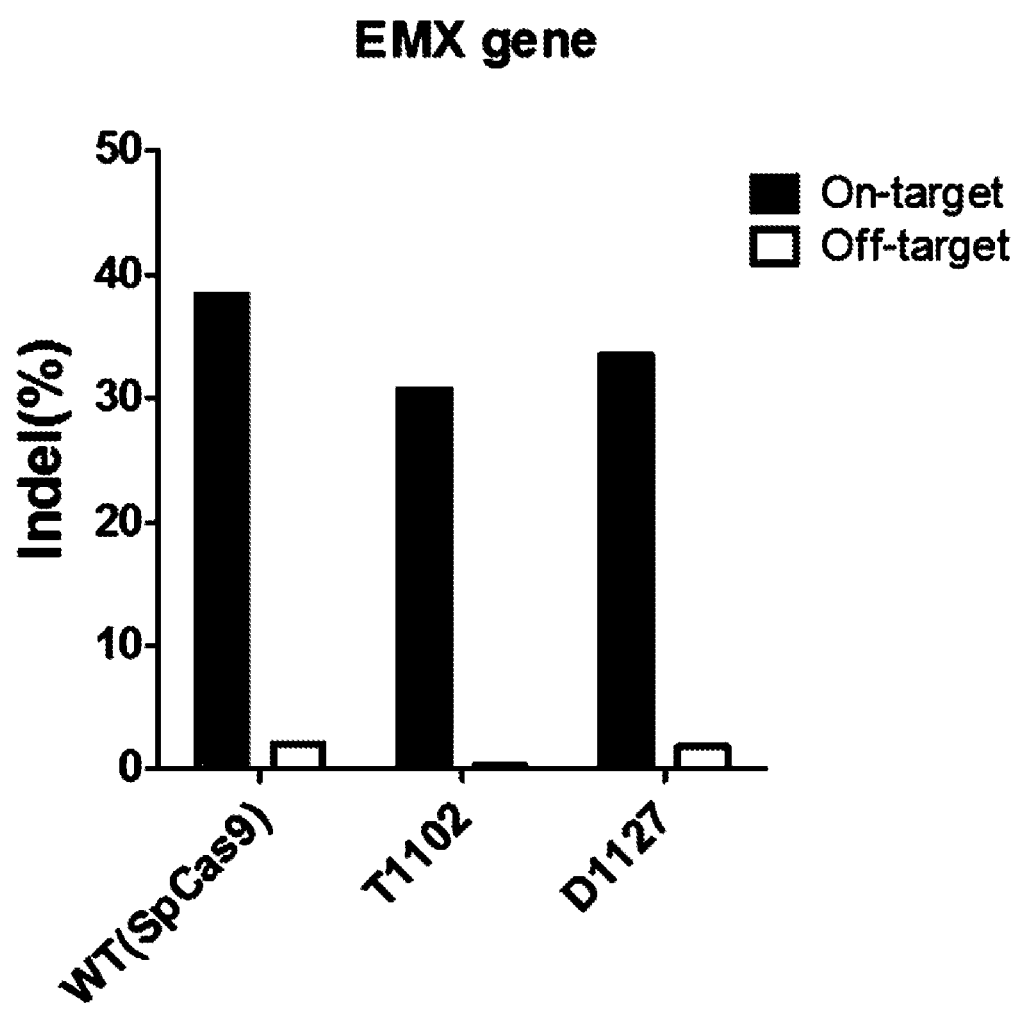
FIG. 13 is a graph showing indel frequencies (%), which represents the manipulation effect of a target gene (EMX gene) by fourth region variants of SpCas9.

In addition, when an EMX gene was used as a target gene (target sequence: GAGTCCGAGCAGAAGAAGAA (SEQ ID NO: 30)/non-target sequence: GAGT-taGAGCAGAAGAAGAA (SEQ ID NO: 31)), both T1102 and D1127 showed similar indel frequencies at the on-target site, but almost no indel frequencies at the off-target site, compared to the wild-type SpCas9 (FIG. 13).

Form the above-mentioned results, it can be confirmed that the SpCas9 variants (T1102P and D1127E) formed by substituting T1102 and D1127 in the fourth region of SpCas9 with different amino acids show similar or slightly improved target specificity, compared to the wild-type SpCas9.

5. SpCas9 Variants Having Mutations in Two Regions

SpCas9 variants having mutations in two regions of the four regions of SpCas9 are used in an experiment. Here, F539S/F1038Y, F539S/M763I, I601N/D965Y and F539S/M763I/F1038Y having mutations in the first and second regions; F539S/K890N having mutations in the first and third regions; and M763I/K890N having mutations in the second and third regions were used as SpCas9 variants.

Figure 14:
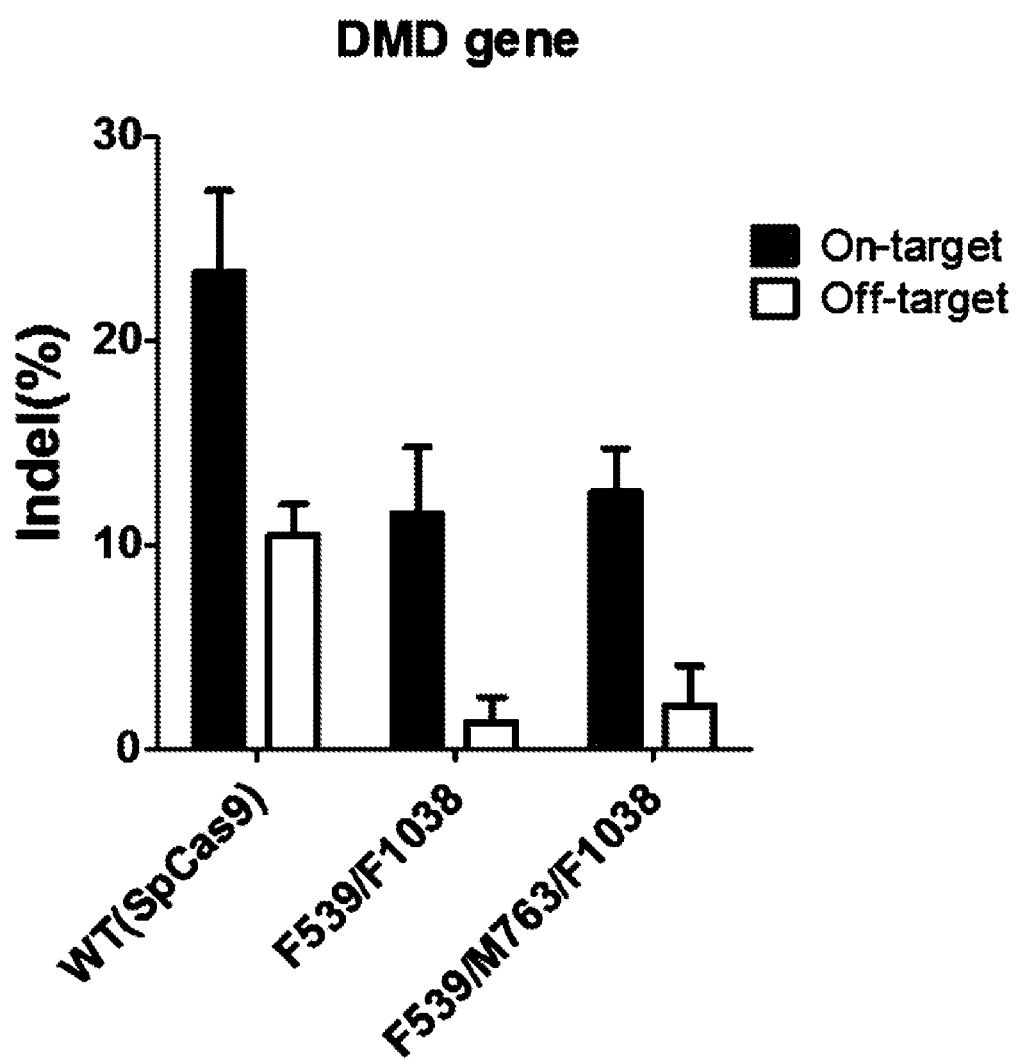
FIG. 14 is a graph showing indel frequencies (%), which represents the manipulation effect of a target gene (DMD gene) by SpCas9 variants having mutations in two regions of the four regions of SpCas9.

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29)), it was confirmed that, for F539S/F1038Y and F539S/M763I/F1038Y, compared to the wild-type SpCas9, indel frequencies at the on-target site decreased, but indel frequencies at the off-target site decreased by approximately 70 to 80%, and thus the ratio of indel frequency at the off-target site based on the value of the on-target site was low. Therefore, it was confirmed that F539S/F1038Y and F539S/M763I/F1038Y have target specificity, compared to the wild-type SpCas9 (FIG. 14).

Figure 15:
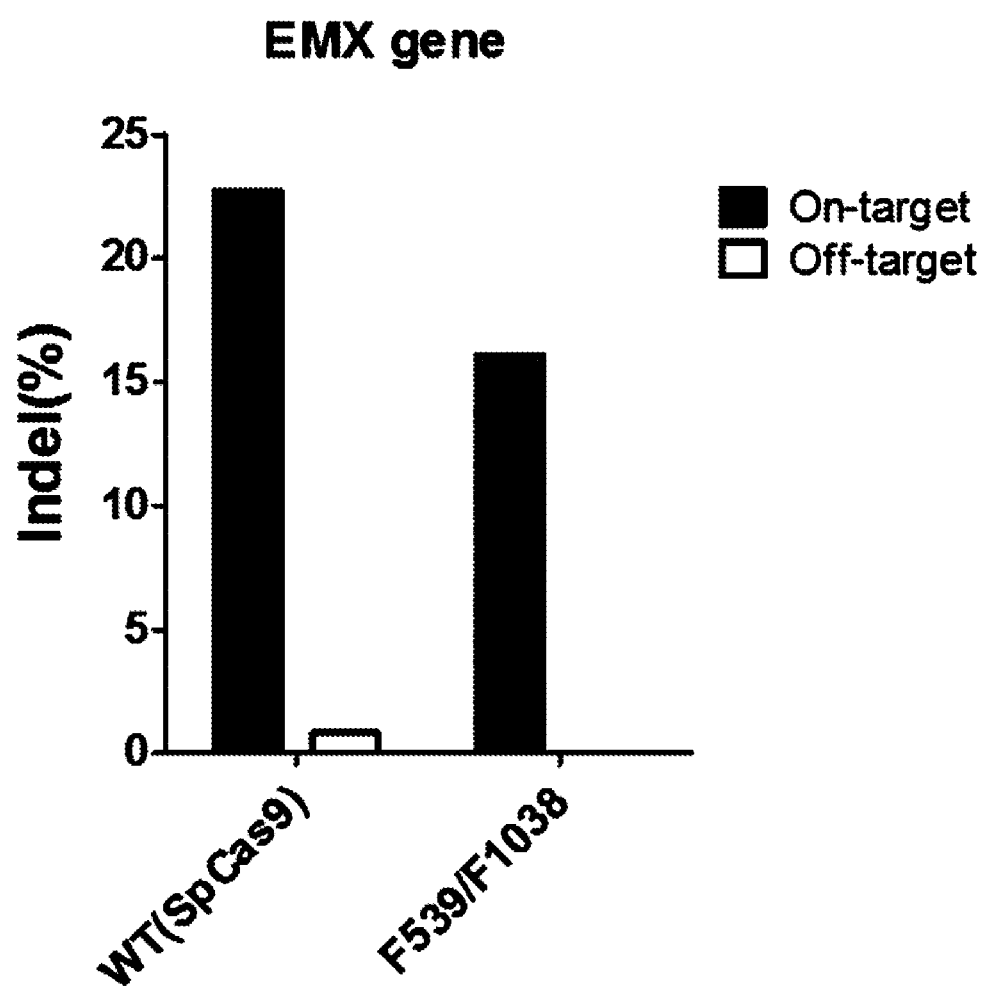
FIG. 15 is a graph showing indel frequencies (%), which represents the manipulation effect of a target gene (EMX gene) by SpCas9 variants having mutations in two regions of the four regions of SpCas9.

In addition, when an EMX gene was used as a target gene (target sequence: GAGTCCGAGCAGAAGAAGAA (SEQ ID NO: 30)/non-target sequence: GAGTtaGAGCAGAAGAAGAA (SEQ ID NO: 31)), for F539S/F1038Y, compared to the wild-type SpCas9, indel frequencies at the on-target site slightly decreased, but indel frequencies at the off-target site were almost not shown, and thus the ratio of indel frequency at the off-target site based on the value of the on-target site was low. Therefore, it was confirmed that F539S/F1038Y has target specificity, compared to the wild-type SpCas9 (FIG. 15).

Figure 16:
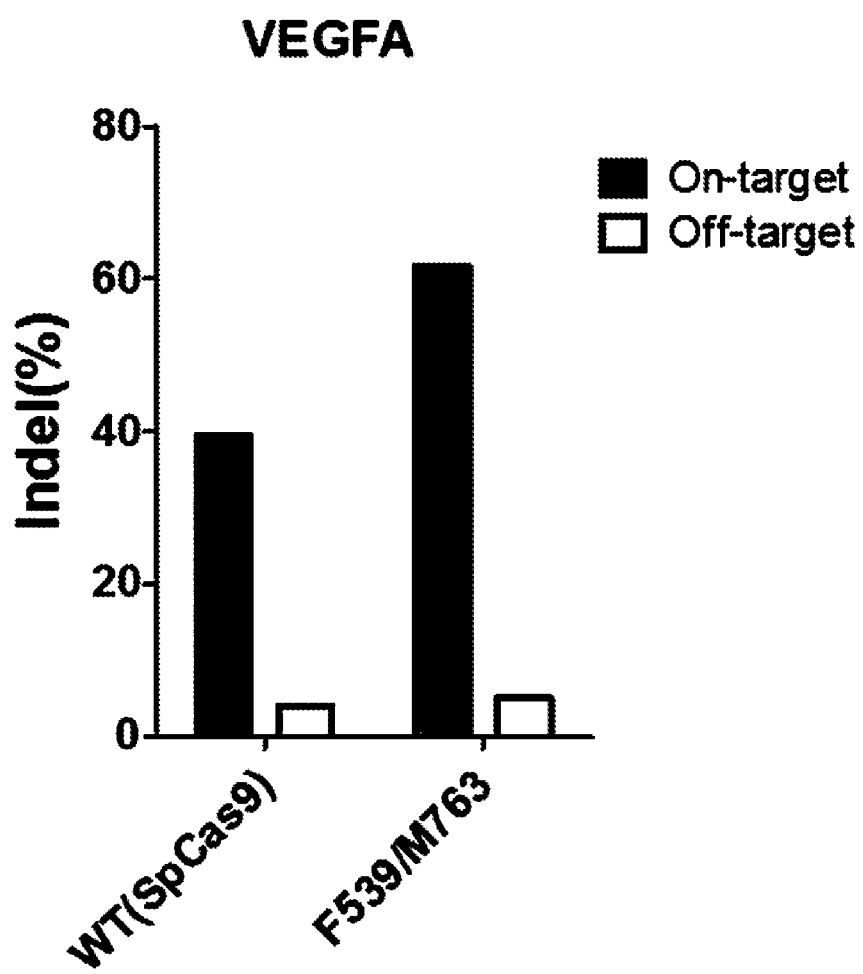
FIG. 16 is a graph showing indel frequencies (%), which represents the manipulation effect of a target gene (VEGFA gene) by SpCas9 variants having mutations in two regions of the four regions of SpCas9.

When a VEGFA gene was used as a target gene (target sequence: GGTGAGTGAGTGTGTGCGTG (SEQ ID NO: 32)/non-target sequence: GGTGAGTGAGTGTGTGtGTG (SEQ ID NO: 33)), it was confirmed that, for F539S/M763I, compared to the wild-type SpCas9, indel frequencies at the off-target site are similar, but indel frequencies at the on-target site significantly increase (FIG. 16).

Figure 17:
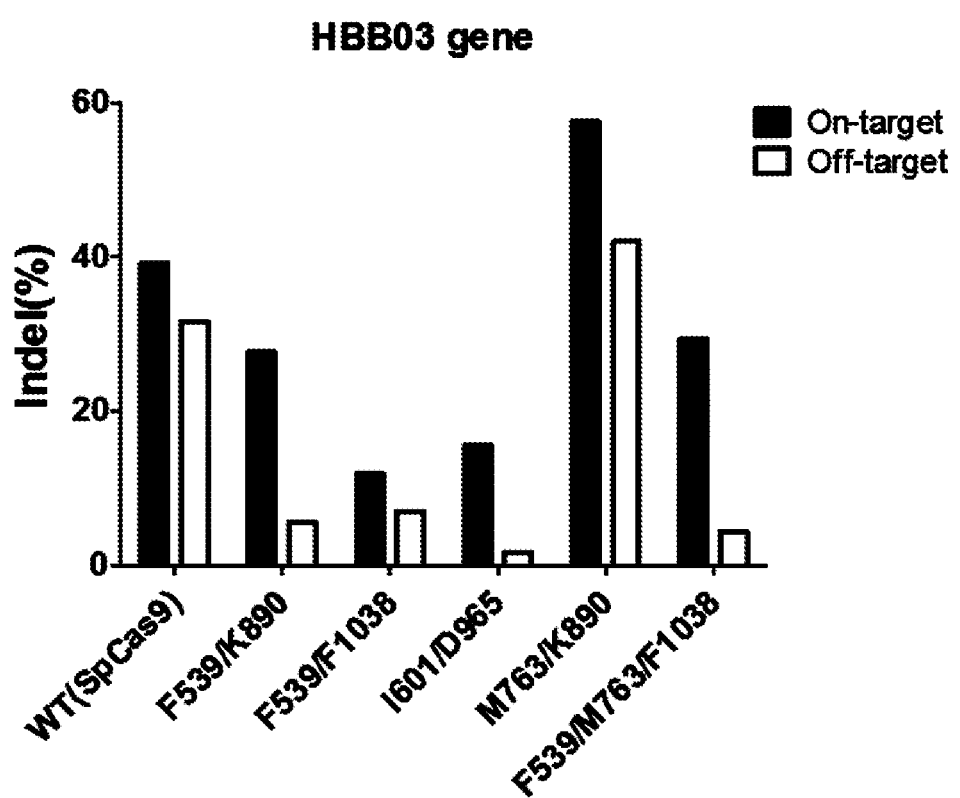
FIG. 17 is a graph showing indel frequencies (%), which represents the manipulation effect of a target gene (HBB03 gene) by SpCas9 variants having mutations in two regions of the four regions of SpCas9.

When an HBB03 gene was used as a target gene (target sequence: CACGTTCACCTTGCCCCACA (SEQ ID NO: 34)/non-target sequence: CACGTTCACtTTGCCCCACA (SEQ ID NO: 35)), it was confirmed that, for F539S/K890N and F539S/M763I/F1038Y, compared to the wild-type SpCas9, indel frequencies at the on-target site slightly decrease, but indel frequencies at the off-target site decrease by 70% or more, and thus the ratio of indel frequency at the off-target site based on the value of the on-target site was low. Therefore, it was confirmed that F539S/K890N and F539S/M763I/F1038Y have target specificity, compared to the wild-type SpCas9 (FIG. 17). In addition, it was confirmed that, for M763I/K890N, compared to the wild-type SpCas9, indel frequencies at the off-target site slightly increase, but indel frequencies at the on-target site increase by approximately 30 to 40%, and thus the ratio of indel frequency at the off-target site based on the value of the on-target site was low. Therefore, it was confirmed that M763I/K890N has target specificity, compared to the wild-type SpCas9 (FIG. 17).

Figure 18:
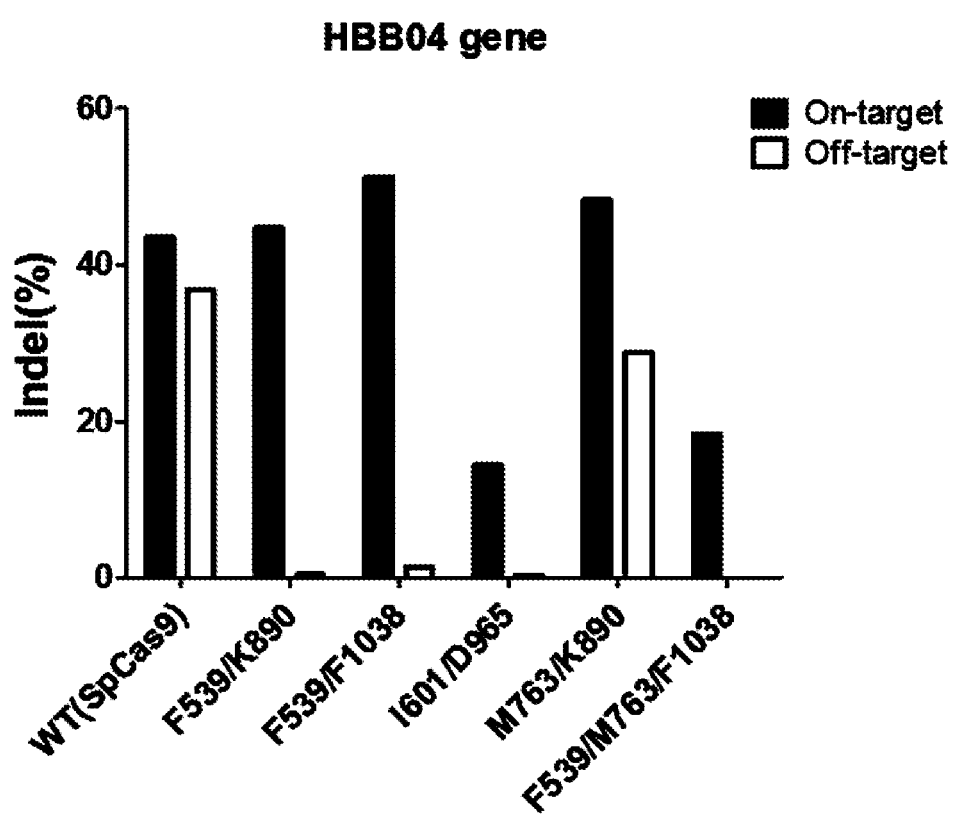
FIG. 18 is a graph showing indel frequencies (%), which represents the manipulation effect of a target gene (HBB04 gene) by SpCas9 variants having mutations in two regions of the four regions of SpCas9.

When an HBB04 gene was used as a target gene (target sequence: CCACGTTCACCTTGCCCCAC (SEQ ID NO: 36)/non-target sequence: CCACaTTCACCTTGCCCCAC (SEQ ID NO: 37)), it was confirmed that, for F539S/K890N and F539S/F1038Y, compared to the wild-type SpCas9, indel frequencies at the on-target site are similar or increase, and indel frequencies at the off-target site are almost not shown (FIG. 18). In addition, it was confirmed that, for M763I/K890N, compared to the wild-type SpCas9, indel frequencies at the on-target site slightly increase, and indel frequencies at the off-target site decrease by approximately 30% (FIG. 18).

Form the above-mentioned results, it can be confirmed that the SpCas9 variants (F539S/K890N, F539S/F1038Y, F539S/M763I, I601N/D965Y, M763I/K890N and F539S/M763I/F1038Y) having mutations in two regions of the four regions of SpCas9 are improved in target specificity, compared to the wild-type SpCas9.

6. SpCas9 Variants Having Mutations in Three or More Regions

SpCas9 variants having mutations in three or more regions of the four regions of SpCas9 were used in the experiment. Here, F539S/M763I/K890N, F539S/M763I/D965Y/K890N and F539S/M763I/K890N/F1038Y having mutations in the first, second and third regions; and A203D/N277H/G366S/M763I/F1038Y/T1102P/D1127E having mutations in the first, second and fourth regions were used as SpCas9 variants.

Figure 19:
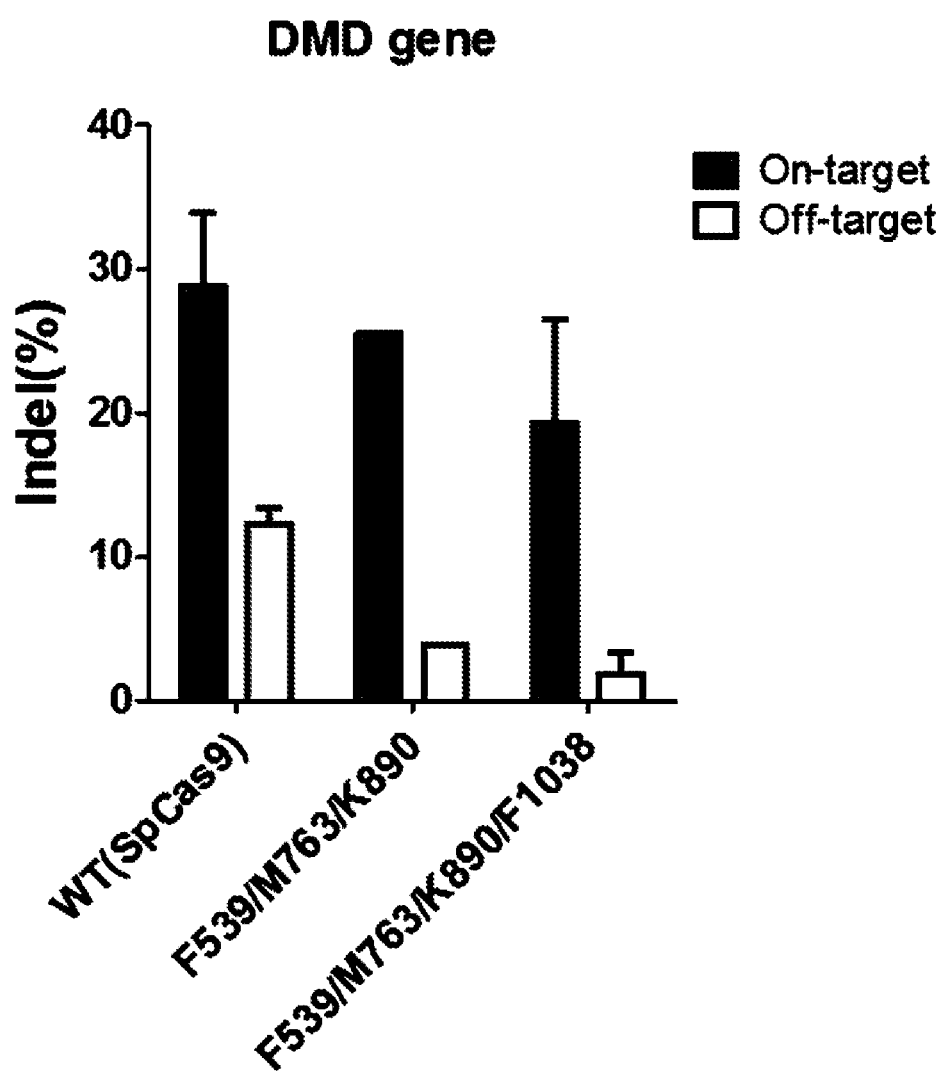
FIG. 19 is a graph showing indel frequencies (%), which represents the manipulation effect of a target gene (DMD gene) by SpCas9 variants having mutations in three regions of the four regions of SpCas9.
Figure 23:
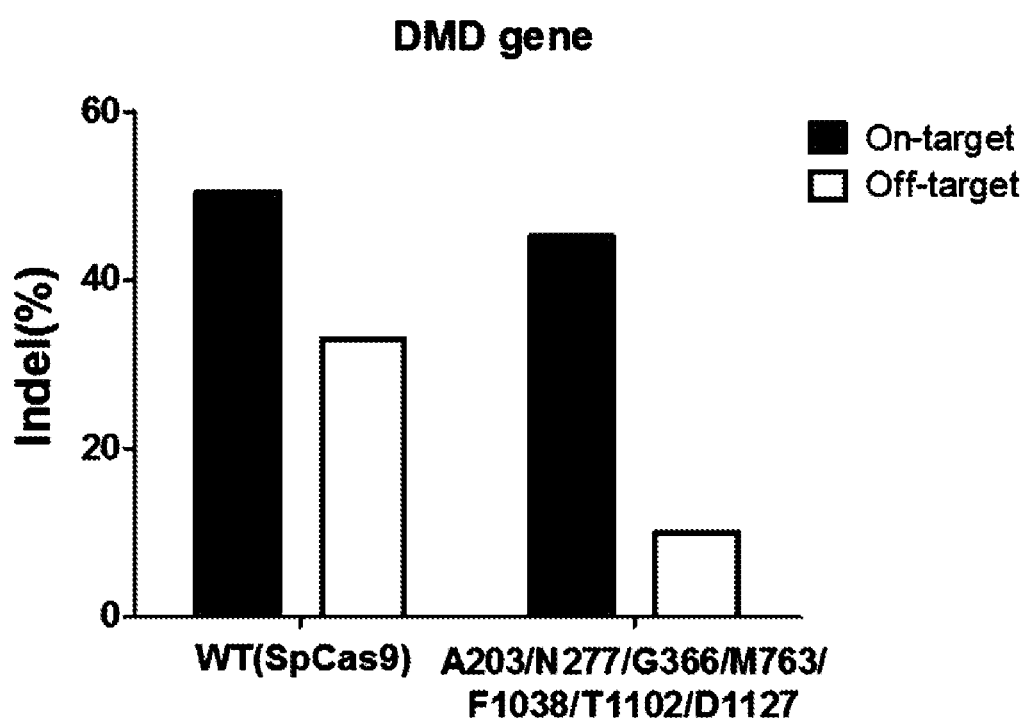
FIG. 23 is a graph showing indel frequencies (%), which represents the manipulation effect of a target gene (DMD gene) by SpCas9 variants having mutations in three regions of the four regions of SpCas9.

As a result, when a DMD gene was used as a target gene (target sequence: CTTTCTACCTACTGAGTCTG (SEQ ID NO: 28)/non-target sequence: CTTTCTACC-TACcGAGTCTG (SEQ ID NO: 29)), it was confirmed that, for F539S/M763I/K890N and F539S/M763I/K890N/F1038Y, compared to the wild-type SpCas9, indel frequencies at the on-target site slightly decrease, but indel frequencies at the off-target site decrease by half or less, and thus the ratio of indel frequency at the off-target site based on the value of the on-target site was low. Therefore, it was confirmed that for F539S/M763I/K890N and F539S/M763I/K890N/F1038Y have target specificity, compared to the wild-type SpCas9 (FIG. 19). In addition, for A203D/N277H/G366S/M763I/F1038Y/T1102P/D1127E, compared to the wild-type SpCas9, indel frequencies at the on-target site slightly decrease, but indel frequencies at the off-target site decrease by approximately 60 to 70%, and thus the ratio of indel frequency at the off-target site based on the value of the on-target site was low. Therefore, it was confirmed that A203D/N277H/G366S/M763I/F1038Y/T1102P/D1127E has target specificity, compared to the wild-type SpCas9 (FIG. 23).

Figure 20:
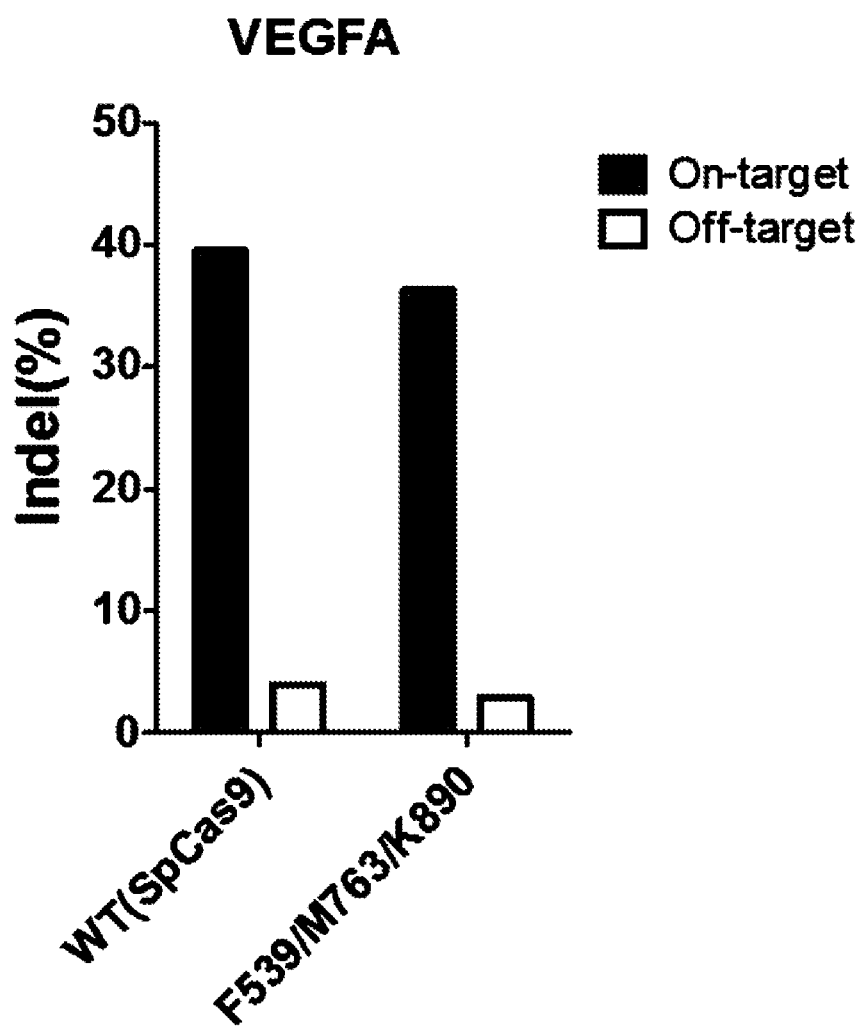
FIG. 20 is a graph showing indel frequencies (%), which represents the manipulation effect of a target gene (VEGFA gene) by SpCas9 variants having mutations in three regions of the four regions of SpCas9.

When a VEGFA gene was used as a target gene (target sequence: GGTGAGTGAGTGTGTGCGTG (SEQ ID NO: 32)/non-target sequence: GGTGAGTGAGTGTGTGtGTG (SEQ ID NO: 33)), it was confirmed that, for F539S/M763I/K890N, compared to the wild-type SpCas9, indel frequencies at the on-target site slightly decrease, but indel frequencies at the off-target site decrease by half, and thus the ratio of indel frequency at the off-target site based on the value of the on-target site was low. Therefore, it was confirmed that F539S/M763I/K890N has target specificity, compared to the wild-type SpCas9 (FIG. 20).

Figure 21:
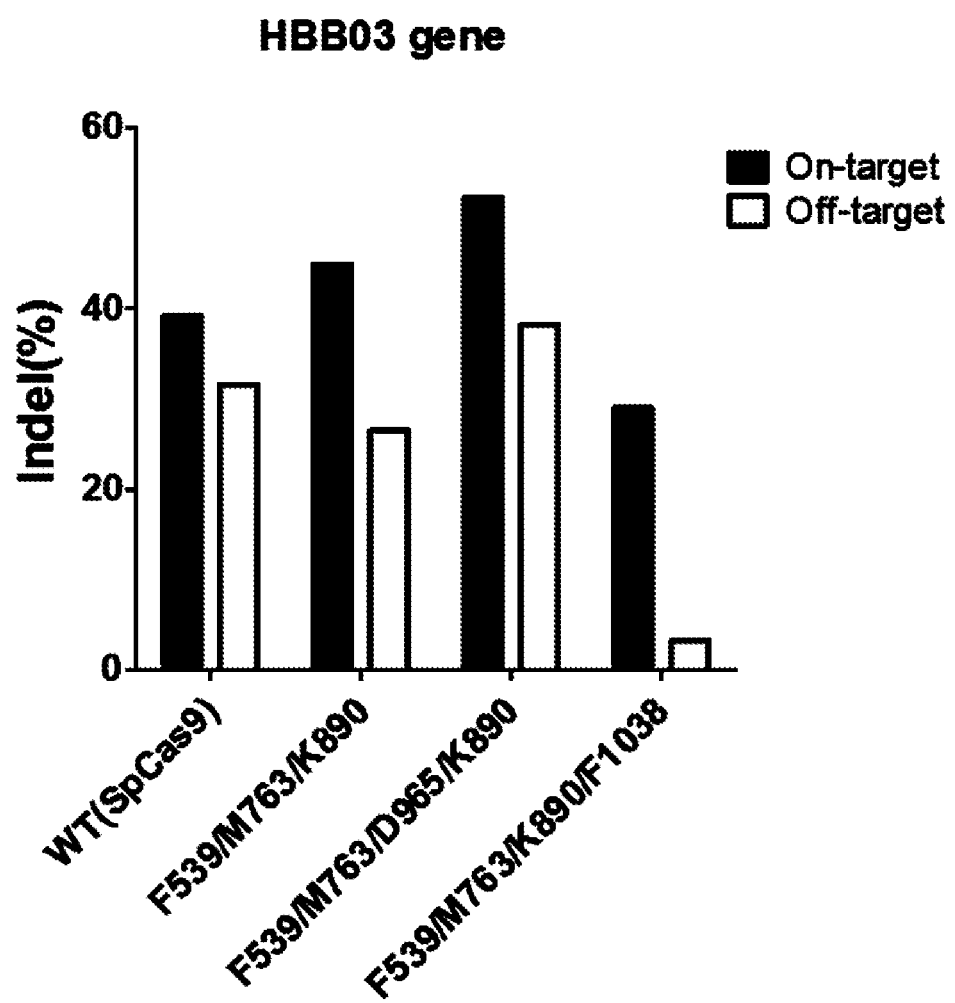
FIG. 21 is a graph showing indel frequencies (%), which represents the manipulation effect of a target gene (HBB03 gene) by SpCas9 variants having mutations in three regions of the four regions of SpCas9.

When an HBB03 gene was used as a target gene (target sequence: CACGTTCACCTTGCCCCACA (SEQ ID NO: 34)/non-target sequence: CACGTTCACtTTGCCCCACA (SEQ ID NO: 35)), it was confirmed that, for F539S/M763I/K890N, compared to the wild-type SpCas9, indel frequencies at the on-target site increase, but indel frequencies at the off-target site decrease, for F539S/M763I/K890N/F1038Y, compared to the wild-type SpCas9, indel frequencies at the on-target site slightly decrease, but indel frequencies at the off-target site decrease by approximately 70% or more, and thus the ratio of indel frequency at the off-target site based on the value of the on-target site was low. Therefore, it was confirmed that F539S/M763I/K890N and F539S/M763I/K890N/F1038Y have target specificity, compared to the wild-type SpCas9 (FIG. 21). In addition, it was confirmed that, compared to the wild-type SpCas9, for F539S/M763I/D965Y/K890N, indel frequencies at the off-target site slightly increase, but indel frequencies at the on-target sites increase by approximately 10 to 20%, and thus the ratio of indel frequency at the off-target site based on the value of the on-target site was low. Therefore, it can be confirmed that F539S/M763I/D965Y/K890N has target specificity, compared to the wild-type SpCas9 (FIG. 21).

Figure 22:
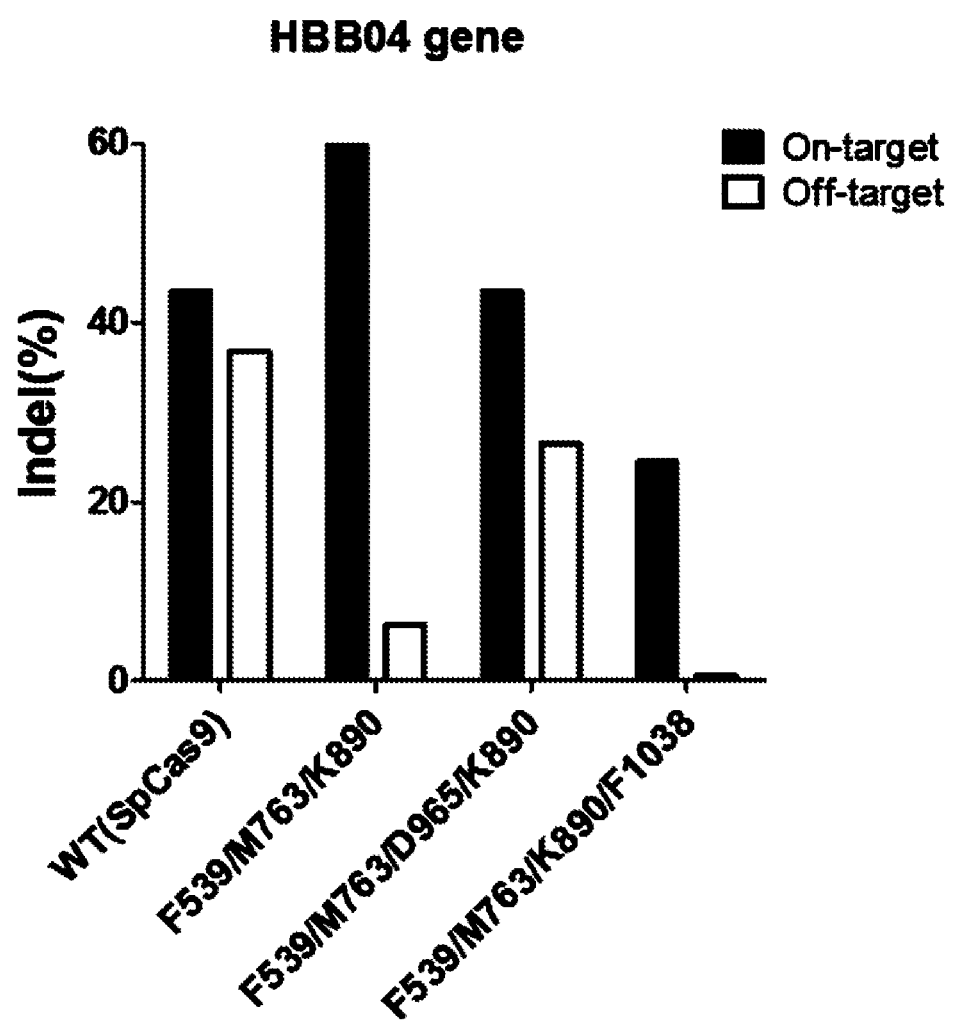
FIG. 22 is a graph showing indel frequencies (%), which represents the manipulation effect of a target gene (HBB04 gene) by SpCas9 variants having mutations in three regions of the four regions of SpCas9.

When an HBB04 gene was used as a target gene (target sequence: CCACGTTCACCTTGCCCCAC (SEQ ID NO: 36)/non-target sequence: CCACaTTCACCTTGCCCCAC (SEQ ID NO: 37)), it was confirmed that, compared to the wild-type SpCas9, for F539S/M763I/K890N, indel frequencies at the on-target site increase, indel frequencies at the off-target site significantly decrease, and for F539S/M763I/D965Y/K890N, indel frequencies at the on-target site are similar, but indel frequencies at the off-target site decrease by approximately 10 to 20% (FIG. 22). In addition, it was confirmed that, for F539S/M763I/K890N/F1038Y, compared to the wild-type SpCas9, indel frequencies at the on-target site decrease by approximately 40%, indel frequencies at the off-target site are almost not shown, and thus the ratio of indel frequency at the off-target site based on the value of the on-target site was lower compared to the wild-type SpCas9. Therefore, it was confirmed that F539S/M763I/K890N has target specificity, compared to the wild-type SpCas9 (FIG. 22).

Form the above-mentioned results, it can be confirmed that the SpCas9 variants (F539S/M763I/K890N, F539S/M763I/D965Y/K890N, F539S/M763I/K890N/F1038Y and A203D/N277H/G366S/M763I/F1038Y/T1102P/D1127E) having mutations in three or more regions of the four regions of SpCas9 are improved in target specificity, compared to the wild-type SpCas9.

Form the above-mentioned results, it was confirmed that the SpCas9 variants having mutations in one or more amino acids selected from the four regions of SpCas9 were improved in target specificity, compared to the wild-type SpCas9.

INDUSTRIAL APPLICABILITY

In the present invention, a CRISPR-Cas system improved in target specificity using an artificially engineered CRISPR enzyme can be used in genome and/or epigenome manipulation or modification, genome targeting, genome editing, and in vitro diagnosis, etc.

[Sequence Listing Free Text]

Amino acid sequence of wild-type SpCas9, amino acid sequence of each region and amino acid sequence of target-specific SpCas9 variant according to one exemplary embodiment This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A SpCas9 (*Streptococcus pyogenes* Cas9) variant comprising all of SEQ ID NO: 1 except for (i) a serine at the position corresponding to position 539 of the polypeptide of SEQ ID NO: 1; (ii) an isoleucine at the position corresponding to position 763 of the polypeptide of SEQ ID NO: 1; and (iii) an asparagine at the position corresponding to position 890 of the polypeptide of SEQ ID NO: 1, and wherein the SpCas9 variant has an endonuclease activity.

2. The SpCas9 variant of claim 1, wherein the SpCas9 variant further comprises one or more functional domains selected from the group consisting of:

a tag for isolation and purification;

a deaminase; and an activity domain having methylase activity, demethylase activity, transcription activation activity, transcription repression activity, transcription release factor activity, histone modification activity, RNA cleavage activity, or nucleic acid binding activity.

3. The SpCas9 variant of claim 2, wherein the SpCas9 variant further comprises a reporter protein, a NLS (nuclear localization sequence or signal), or a NES (nuclear export sequence or signal).

4. A composition for gene modification comprising a Cas9 and a guide RNA, wherein the Cas9 is a *Streptococcus pyogenes* Cas9 (SpCas9) variant comprising all of SEQ ID NO: 1 except for (i) a serine at the position corresponding to position 539 of the polypeptide of SEQ ID NO: 1; (ii) an isoleucine at the position corresponding to position 763 of the polypeptide of SEQ ID NO: 1; and (iii) an asparagine at the position corresponding to position 890 of the polypeptide of SEQ ID NO: 1, and wherein the guide RNA is complementary to a target gene.

5. The composition of claim 4, wherein the guide RNA and the Cas9 form a complex which is a ribonucleoprotein (RNP).

6. The composition of claim 4, wherein the composition further comprises a donor nucleic acid that comprises a gene of interest.

* * * * *

SEQUENCE LISTING

```
<160> NUMBER OF SEQ ID NOS: 37

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205
```

```
Lys Ala Ile Leu Ser Ala Arg Leu Ser Lys Ser Arg Leu Glu Asn
    210                 215                 220

Leu Ile Ala Gln Leu Pro Gly Glu Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
```

-continued

```
            625                 630                 635                 640
        His Leu Phe Asp Asp Lys Val Met Lys Gln Leu Lys Arg Arg Tyr
                        645                 650                 655
        Thr Gly Trp Gly Arg Leu Ser Arg Lys Leu Ile Asn Gly Ile Arg Asp
                        660                 665                 670
        Lys Gln Ser Gly Lys Thr Ile Leu Asp Phe Leu Lys Ser Asp Gly Phe
                        675                 680                 685
        Ala Asn Arg Asn Phe Met Gln Leu Ile His Asp Ser Leu Thr Phe
                        690                 695                 700
        Lys Glu Asp Ile Gln Lys Ala Gln Val Ser Gly Gln Gly Asp Ser Leu
        705                 710                 715                 720
        His Glu His Ile Ala Asn Leu Ala Gly Ser Pro Ala Ile Lys Lys Gly
                        725                 730                 735
        Ile Leu Gln Thr Val Lys Val Val Asp Glu Leu Val Lys Val Met Gly
                        740                 745                 750
        Arg His Lys Pro Glu Asn Ile Val Ile Glu Met Ala Arg Glu Asn Gln
                        755                 760                 765
        Thr Thr Gln Lys Gly Gln Lys Asn Ser Arg Glu Arg Met Lys Arg Ile
        770                 775                 780
        Glu Glu Gly Ile Lys Glu Leu Gly Ser Gln Ile Leu Lys Glu His Pro
        785                 790                 795                 800
        Val Glu Asn Thr Gln Leu Gln Asn Glu Lys Leu Tyr Leu Tyr Tyr Leu
                        805                 810                 815
        Gln Asn Gly Arg Asp Met Tyr Val Asp Gln Glu Leu Asp Ile Asn Arg
                        820                 825                 830
        Leu Ser Asp Tyr Asp Val Asp His Ile Val Pro Gln Ser Phe Leu Lys
                        835                 840                 845
        Asp Asp Ser Ile Asp Asn Lys Val Leu Thr Arg Ser Asp Lys Asn Arg
                        850                 855                 860
        Gly Lys Ser Asp Asn Val Pro Ser Glu Val Val Lys Lys Met Lys
        865                 870                 875                 880
        Asn Tyr Trp Arg Gln Leu Leu Asn Ala Lys Leu Ile Thr Gln Arg Lys
                        885                 890                 895
        Phe Asp Asn Leu Thr Lys Ala Glu Arg Gly Gly Leu Ser Glu Leu Asp
                        900                 905                 910
        Lys Ala Gly Phe Ile Lys Arg Gln Leu Val Glu Thr Arg Gln Ile Thr
                        915                 920                 925
        Lys His Val Ala Gln Ile Leu Asp Ser Arg Met Asn Thr Lys Tyr Asp
                        930                 935                 940
        Glu Asn Asp Lys Leu Ile Arg Glu Val Lys Val Ile Thr Leu Lys Ser
        945                 950                 955                 960
        Lys Leu Val Ser Asp Phe Arg Lys Asp Phe Gln Phe Tyr Lys Val Arg
                        965                 970                 975
        Glu Ile Asn Asn Tyr His His Ala His Asp Ala Tyr Leu Asn Ala Val
                        980                 985                 990
        Val Gly Thr Ala Leu Ile Lys Lys Tyr Pro Lys Leu Glu Ser Glu Phe
                        995                 1000                1005
        Val Tyr Gly Asp Tyr Lys Val Tyr Asp Val Arg Lys Met Ile Ala
                        1010                1015                1020
        Lys Ser Glu Gln Glu Ile Gly Lys Ala Thr Ala Lys Tyr Phe Phe
                        1025                1030                1035
        Tyr Ser Asn Ile Met Asn Phe Phe Lys Thr Glu Ile Thr Leu Ala
                        1040                1045                1050
```

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 87
<212> TYPE: PRT
<213> ORGANISM: Streptococcus pyogenes

<400> SEQUENCE: 2

Phe Glu Glu Asn Pro Ile Asn Ala Ser Gly Val Asp Ala Lys Ala Ile
1               5                   10                  15

Leu Ser Ala Arg Leu Ser Lys Ser Arg Arg Leu Glu Asn Leu Ile Ala
            20                  25                  30

Gln Leu Pro Gly Glu Lys Lys Asn Gly Leu Phe Gly Asn Leu Ile Ala

```
                    35                  40                  45

Leu Ser Leu Gly Leu Thr Pro Asn Phe Lys Ser Asn Phe Asp Leu Ala
         50                  55                  60

Glu Asp Ala Lys Leu Gln Leu Ser Lys Asp Thr Tyr Asp Asp Leu
65                   70                  75                  80

Asp Asn Leu Leu Ala Gln Ile
                85

<210> SEQ ID NO 3
<211> LENGTH: 79
<212> TYPE: PRT
<213> ORGANISM: Streptococcus pyogenes

<400> SEQUENCE: 3

Pro Leu Ser Ala Ser Met Ile Lys Arg Tyr Asp Glu His His Gln Asp
1               5                   10                  15

Leu Thr Leu Leu Lys Ala Leu Val Arg Gln Gln Leu Pro Glu Lys Tyr
                20                  25                  30

Lys Glu Ile Phe Phe Asp Gln Ser Lys Asn Gly Tyr Ala Gly Tyr Ile
            35                  40                  45

Asp Gly Gly Ala Ser Gln Glu Glu Phe Tyr Lys Phe Ile Lys Pro Ile
        50                  55                  60

Leu Glu Lys Met Asp Gly Thr Glu Glu Leu Leu Val Lys Leu Asn
65                  70                  75

<210> SEQ ID NO 4
<211> LENGTH: 103
<212> TYPE: PRT
<213> ORGANISM: Streptococcus pyogenes

<400> SEQUENCE: 4

Lys His Ser Leu Leu Tyr Glu Tyr Phe Thr Val Tyr Asn Glu Leu Thr
1               5                   10                  15

Lys Val Lys Tyr Val Thr Glu Gly Met Arg Lys Pro Ala Phe Leu Ser
                20                  25                  30

Gly Glu Gln Lys Lys Ala Ile Val Asp Leu Leu Phe Lys Thr Asn Arg
            35                  40                  45

Lys Val Thr Val Lys Gln Leu Lys Glu Asp Tyr Phe Lys Lys Ile Glu
        50                  55                  60

Cys Phe Asp Ser Val Glu Ile Ser Gly Val Glu Asp Arg Phe Asn Ala
65                  70                  75                  80

Ser Leu Gly Thr Tyr His Asp Leu Leu Lys Ile Ile Lys Asp Lys Asp
                85                  90                  95

Phe Leu Asp Asn Glu Glu Asn
            100

<210> SEQ ID NO 5
<211> LENGTH: 21
<212> TYPE: PRT
<213> ORGANISM: Streptococcus pyogenes

<400> SEQUENCE: 5

Thr Ile Leu Asp Phe Leu Lys Ser Asp Gly Phe Ala Asn Arg Asn Phe
1               5                   10                  15

Met Gln Leu Ile His
            20

<210> SEQ ID NO 6
```

-continued

```
<211> LENGTH: 22
<212> TYPE: PRT
<213> ORGANISM: Streptococcus pyogenes

<400> SEQUENCE: 6

Met Asp Lys Lys Tyr Ser Ile Gly Leu Asp Ile Gly Thr Asn Ser Val
1               5                   10                  15

Gly Trp Ala Val Ile Thr
            20

<210> SEQ ID NO 7
<211> LENGTH: 40
<212> TYPE: PRT
<213> ORGANISM: Streptococcus pyogenes

<400> SEQUENCE: 7

Pro Ala Ile Lys Lys Gly Ile Leu Gln Thr Val Lys Val Val Asp Glu
1               5                   10                  15

Leu Val Lys Val Met Gly Arg His Lys Pro Glu Asn Ile Val Ile Glu
            20                  25                  30

Met Ala Arg Glu Asn Gln Thr Thr
        35                  40

<210> SEQ ID NO 8
<211> LENGTH: 115
<212> TYPE: PRT
<213> ORGANISM: Streptococcus pyogenes

<400> SEQUENCE: 8

Gln Ile Thr Lys His Val Ala Gln Ile Leu Asp Ser Arg Met Asn Thr
1               5                   10                  15

Lys Tyr Asp Glu Asn Asp Lys Leu Ile Arg Glu Val Lys Val Ile Thr
            20                  25                  30

Leu Lys Ser Lys Leu Val Ser Asp Phe Arg Lys Asp Phe Gln Phe Tyr
        35                  40                  45

Lys Val Arg Glu Ile Asn Asn Tyr His His Ala His Asp Ala Tyr Leu
    50                  55                  60

Asn Ala Val Val Gly Thr Ala Leu Ile Lys Lys Tyr Pro Lys Leu Glu
65                  70                  75                  80

Ser Glu Phe Val Tyr Gly Asp Tyr Lys Val Tyr Asp Val Arg Lys Met
                85                  90                  95

Ile Ala Lys Ser Glu Gln Glu Ile Gly Lys Ala Thr Ala Lys Tyr Phe
            100                 105                 110

Phe Tyr Ser
        115

<210> SEQ ID NO 9
<211> LENGTH: 126
<212> TYPE: PRT
<213> ORGANISM: Streptococcus pyogenes

<400> SEQUENCE: 9

Lys Asn Ser Arg Glu Arg Met Lys Arg Ile Glu Glu Gly Ile Lys Glu
1               5                   10                  15

Leu Gly Ser Gln Ile Leu Lys Glu His Pro Val Glu Asn Thr Gln Leu
            20                  25                  30

Gln Asn Glu Lys Leu Tyr Leu Tyr Tyr Leu Gln Asn Gly Arg Asp Met
        35                  40                  45

Tyr Val Asp Gln Glu Leu Asp Ile Asn Arg Leu Ser Asp Tyr Asp Val
```

```
                    50                  55                  60
Asp His Ile Val Pro Gln Ser Phe Leu Lys Asp Asp Ser Ile Asp Asn
 65                  70                  75                  80

Lys Val Leu Thr Arg Ser Asp Lys Asn Arg Gly Lys Ser Asp Asn Val
                     85                  90                  95

Pro Ser Glu Glu Val Val Lys Lys Met Lys Asn Tyr Trp Arg Gln Leu
                100                 105                 110

Leu Asn Ala Lys Leu Ile Thr Gln Arg Lys Phe Asp Asn Leu
            115                 120                 125

<210> SEQ ID NO 10
<211> LENGTH: 41
<212> TYPE: PRT
<213> ORGANISM: Streptococcus pyogenes

<400> SEQUENCE: 10

Glu Val Gln Thr Gly Gly Phe Ser Lys Glu Ser Ile Leu Pro Lys Arg
  1               5                  10                  15

Asn Ser Asp Lys Leu Ile Ala Arg Lys Lys Asp Trp Asp Pro Lys Lys
                 20                  25                  30

Tyr Gly Gly Phe Asp Ser Pro Thr Val
             35                  40

<210> SEQ ID NO 11
<211> LENGTH: 1368
<212> TYPE: PRT
<213> ORGANISM: Artificial Sequence
<220> FEATURE:
<223> OTHER INFORMATION: Streptococcus pyogenes Cas9 variant

<400> SEQUENCE: 11

Met Asp Lys Lys Tyr Ser Ile Gly Leu Asp Ile Gly Thr Asn Ser Val
  1               5                  10                  15

Gly Trp Ala Val Ile Thr Asp Glu Tyr Lys Val Pro Ser Lys Lys Phe
                 20                  25                  30

Lys Val Leu Gly Asn Thr Asp Arg His Ser Ile Lys Lys Asn Leu Ile
             35                  40                  45

Gly Ala Leu Leu Phe Asp Ser Gly Glu Thr Ala Glu Ala Thr Arg Leu
 50                  55                  60

Lys Arg Thr Ala Arg Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205
```

-continued

```
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
        290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
        370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
        450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Ser Leu Ser Gly Glu Gln
        530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
        610                 615                 620
```

```
Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Ile Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Asn Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
            1010                1015                1020

Lys Ser Glu Gln Glu Ile Gly Lys Ala Thr Ala Lys Tyr Phe Phe
            1025                1030                1035

Tyr Ser Asn Ile Met Asn Phe Phe Lys Thr Glu Ile Thr Leu Ala
```

```
            1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

<210> SEQ ID NO 12
<211> LENGTH: 7
<212> TYPE: PRT
<213> ORGANISM: Artificial Sequence
<220> FEATURE:
<223> OTHER INFORMATION: nuclear localization sequence

<400> SEQUENCE: 12

Pro Lys Lys Lys Arg Lys Val
1               5
```

```
<210> SEQ ID NO 13
<211> LENGTH: 16
<212> TYPE: PRT
<213> ORGANISM: Artificial Sequence
<220> FEATURE:
<223> OTHER INFORMATION: nuclear localization sequence

<400> SEQUENCE: 13

Lys Arg Pro Ala Ala Thr Lys Lys Ala Gly Gln Ala Lys Lys Lys Lys
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: nuclear localization sequence

<400> SEQUENCE: 14

Pro Ala Ala Lys Arg Val Lys Leu Asp
1               5

<210> SEQ ID NO 15
<211> LENGTH: 11
<212> TYPE: PRT
<213> ORGANISM: Artificial Sequence
<220> FEATURE:
<223> OTHER INFORMATION: nuclear localization sequence

<400> SEQUENCE: 15

Arg Gln Arg Arg Asn Glu Leu Lys Arg Ser Pro
1               5                   10

<210> SEQ ID NO 16
<211> LENGTH: 38
<212> TYPE: PRT
<213> ORGANISM: Artificial Sequence
<220> FEATURE:
<223> OTHER INFORMATION: nuclear localization sequence

<400> SEQUENCE: 16

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
                35

<210> SEQ ID NO 17
<211> LENGTH: 42
<212> TYPE: PRT
<213> ORGANISM: Artificial Sequence
<220> FEATURE:
<223> OTHER INFORMATION: nuclear localization sequence

<400> SEQUENCE: 17

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
                35                  40

<210> SEQ ID NO 18
<211> LENGTH: 8
```

```
<212> TYPE: PRT
<213> ORGANISM: Artificial Sequence
<220> FEATURE:
<223> OTHER INFORMATION: nuclear localization sequence

<400> SEQUENCE: 18

Val Ser Arg Lys Arg Pro Arg Pro
1               5

<210> SEQ ID NO 19
<211> LENGTH: 8
<212> TYPE: PRT
<213> ORGANISM: Artificial Sequence
<220> FEATURE:
<223> OTHER INFORMATION: nuclear localization sequence

<400> SEQUENCE: 19

Pro Pro Lys Lys Ala Arg Glu Asp
1               5

<210> SEQ ID NO 20
<211> LENGTH: 8
<212> TYPE: PRT
<213> ORGANISM: Artificial Sequence
<220> FEATURE:
<223> OTHER INFORMATION: nuclear localization sequence

<400> SEQUENCE: 20

Pro Gln Pro Lys Lys Lys Pro Leu
1               5

<210> SEQ ID NO 21
<211> LENGTH: 12
<212> TYPE: PRT
<213> ORGANISM: Artificial Sequence
<220> FEATURE:
<223> OTHER INFORMATION: nuclear localization sequence

<400> SEQUENCE: 21

Ser Ala Leu Ile Lys Lys Lys Lys Lys Met Ala Pro
1               5                   10

<210> SEQ ID NO 22
<211> LENGTH: 5
<212> TYPE: PRT
<213> ORGANISM: Artificial Sequence
<220> FEATURE:
<223> OTHER INFORMATION: nuclear localization sequence

<400> SEQUENCE: 22

Asp Arg Leu Arg Arg
1               5

<210> SEQ ID NO 23
<211> LENGTH: 7
<212> TYPE: PRT
<213> ORGANISM: Artificial Sequence
<220> FEATURE:
<223> OTHER INFORMATION: nuclear localization sequence

<400> SEQUENCE: 23

Pro Lys Gln Lys Lys Arg Lys
1               5

<210> SEQ ID NO 24
<211> LENGTH: 10
<212> TYPE: PRT
```

```
<213> ORGANISM: Artificial Sequence
<220> FEATURE:
<223> OTHER INFORMATION: nuclear localization sequence

<400> SEQUENCE: 24

Arg Lys Leu Lys Lys Ile Lys Lys Leu
1               5                  10

<210> SEQ ID NO 25
<211> LENGTH: 10
<212> TYPE: PRT
<213> ORGANISM: Artificial Sequence
<220> FEATURE:
<223> OTHER INFORMATION: nuclear localization sequence

<400> SEQUENCE: 25

Arg Glu Lys Lys Lys Phe Leu Lys Arg Arg
1               5                  10

<210> SEQ ID NO 26
<211> LENGTH: 20
<212> TYPE: PRT
<213> ORGANISM: Artificial Sequence
<220> FEATURE:
<223> OTHER INFORMATION: nuclear localization sequence

<400> SEQUENCE: 26

Lys Arg Lys Gly Asp Glu Val Asp Gly Val Asp Glu Val Ala Lys Lys
1               5                  10                  15

Lys Ser Lys Lys
            20

<210> SEQ ID NO 27
<211> LENGTH: 17
<212> TYPE: PRT
<213> ORGANISM: Artificial Sequence
<220> FEATURE:
<223> OTHER INFORMATION: nuclear localization sequence

<400> SEQUENCE: 27

Arg Lys Cys Leu Gln Ala Gly Met Asn Leu Glu Ala Arg Lys Thr Lys
1               5                  10                  15

Lys

<210> SEQ ID NO 28
<211> LENGTH: 20
<212> TYPE: DNA
<213> ORGANISM: Homo sapiens

<400> SEQUENCE: 28
ctttctacct actgagtctg                                           20

<210> SEQ ID NO 29
<211> LENGTH: 20
<212> TYPE: DNA
<213> ORGANISM: Artificial Sequence
<220> FEATURE:
<223> OTHER INFORMATION: non-target sequence

<400> SEQUENCE: 29
ctttctacct accgagtctg                                           20

<210> SEQ ID NO 30
<211> LENGTH: 20
<212> TYPE: DNA
```

<213> ORGANISM: Homo sapiens

<400> SEQUENCE: 30
gagtccgagc agaagaagaa                                          20

<210> SEQ ID NO 31
<211> LENGTH: 20
<212> TYPE: DNA
<213> ORGANISM: Artificial Sequence
<220> FEATURE:
<223> OTHER INFORMATION: non-target sequence

<400> SEQUENCE: 31
gagttagagc agaagaagaa                                          20

<210> SEQ ID NO 32
<211> LENGTH: 20
<212> TYPE: DNA
<213> ORGANISM: Homo sapiens

<400> SEQUENCE: 32
ggtgagtgag tgtgtgcgtg                                          20

<210> SEQ ID NO 33
<211> LENGTH: 20
<212> TYPE: DNA
<213> ORGANISM: Artificial Sequence
<220> FEATURE:
<223> OTHER INFORMATION: non-target sequence

<400> SEQUENCE: 33
ggtgagtgag tgtgtgtgtg                                          20

<210> SEQ ID NO 34
<211> LENGTH: 20
<212> TYPE: DNA
<213> ORGANISM: Homo sapiens

<400> SEQUENCE: 34
cacgttcacc ttgccccaca                                          20

<210> SEQ ID NO 35
<211> LENGTH: 20
<212> TYPE: DNA
<213> ORGANISM: Artificial Sequence
<220> FEATURE:
<223> OTHER INFORMATION: non-target sequence

<400> SEQUENCE: 35
cacgttcact ttgccccaca                                          20

<210> SEQ ID NO 36
<211> LENGTH: 20
<212> TYPE: DNA
<213> ORGANISM: Homo sapiens

<400> SEQUENCE: 36
ccacgttcac cttgccccac                                          20

<210> SEQ ID NO 37
<211> LENGTH: 20
<212> TYPE: DNA
<213> ORGANISM: Artificial Sequence
<220> FEATURE:
<223> OTHER INFORMATION: non-target sequence

```
<400> SEQUENCE: 37
ccacattcac cttgccccac                                               20
```